US012679879B2

(12) United States Patent
Lam et al.

(10) Patent No.: US 12,679,879 B2
(45) Date of Patent: Jul. 14, 2026

(54) NR4A-DEFICIENT CELLS EXPRESSING C-JUN AND USES THEREOF

(71) Applicant: Lyell Immunopharma, Inc., South San Francisco, CA (US)

(72) Inventors: Viola Lam, South San Francisco, CA (US); Rachel Christina Lynn, South San Francisco, CA (US)

(73) Assignee: Lyell Immunopharma, Inc., South San Francisco, CA (US)

( * ) Notice: Subject to any disclaimer, the term of this patent is extended or adjusted under 35 U.S.C. 154(b) by 1039 days.

(21) Appl. No.: 17/830,218

(22) Filed: Jun. 1, 2022

(65) Prior Publication Data

US 2023/0052243 A1     Feb. 16, 2023

Related U.S. Application Data

(60) Provisional application No. 63/365,023, filed on May 19, 2022, provisional application No. 63/195,956, filed on Jun. 2, 2021.

(51) Int. Cl.
| | |
|---|---|
| *A61K 35/17* | (2025.01) |
| *A61K 40/11* | (2025.01) |
| *A61K 40/31* | (2025.01) |
| *A61K 40/32* | (2025.01) |
| *A61K 40/42* | (2025.01) |
| *C07K 14/705* | (2006.01) |
| *C07K 14/725* | (2006.01) |
| *C12N 5/0783* | (2010.01) |
| *C12N 15/113* | (2010.01) |

(52) U.S. Cl.
CPC .......... *C07K 14/7051* (2013.01); *A61K 40/11* (2025.01); *A61K 40/31* (2025.01); *A61K 40/32* (2025.01); *A61K 40/4202* (2025.01); *A61K 40/4264* (2025.01); *A61K 40/4269* (2025.01); *C12N 5/0636* (2013.01); *A61K 2239/55* (2023.05); *A61K 2239/57* (2023.05); *C12N 15/113* (2013.01); *C12N 2310/20* (2017.05)

(58) Field of Classification Search
CPC ............ C07K 14/7051; C07K 14/4702; C07K 14/70567; C07K 16/2803; C07K 2317/622; C07K 2317/73; A61K 40/11; A61K 40/31; A61K 40/32; A61K 40/4269; A61K 2239/57; A61K 2039/5156; C12N 5/0636; C12N 15/113; C12N 2310/20; C12N 2510/00; A61P 35/00
See application file for complete search history.

(56) References Cited

U.S. PATENT DOCUMENTS

| | | |
|---|---|---|
| 5,034,506 A | 7/1991 | Summerton et al. |
| 5,356,802 A | 10/1994 | Chandrasegaran |
| 5,436,150 A | 7/1995 | Chandrasegaran |
| 5,487,994 A | 1/1996 | Chandrasegaran |
| 5,489,677 A | 2/1996 | Sanghvi et al. |
| 5,602,240 A | 2/1997 | De et al. |
| 5,709,874 A | 1/1998 | Hanson et al. |
| 5,759,542 A | 6/1998 | Gurewich |
| 5,840,674 A | 11/1998 | Yatvin et al. |
| 5,900,252 A | 5/1999 | Calanchi et al. |
| 5,972,366 A | 10/1999 | Haynes et al. |
| 5,985,307 A | 11/1999 | Hanson et al. |
| 6,004,534 A | 12/1999 | Langer et al. |
| 6,039,975 A | 3/2000 | Shah et al. |
| 6,048,736 A | 4/2000 | Kosak |
| 6,060,082 A | 5/2000 | Chen et al. |
| 6,071,495 A | 6/2000 | Unger et al. |
| 6,120,751 A | 9/2000 | Unger |
| 6,131,570 A | 10/2000 | Schuster et al. |
| 6,139,865 A | 10/2000 | Friend et al. |
| 6,253,872 B1 | 7/2001 | Neumann |
| 6,271,359 B1 | 8/2001 | Norris et al. |
| 6,274,552 B1 | 8/2001 | Tamarkin et al. |
| 6,316,652 B1 | 11/2001 | Steliou |

(Continued)

FOREIGN PATENT DOCUMENTS

| | | |
|---|---|---|
| WO | WO-9712622 A1 | 4/1997 |
| WO | WO-9817815 A1 | 4/1998 |

(Continued)

OTHER PUBLICATIONS

Marofi, F., Motavalli, R., Safonov, V.A., Thangavelu, L., Yumashev, A.V., Alexander, M., Shomali, N., Chartrand, M.S., Pathak, Y., Jarahian, M. and Izadi, S., 2021. CAR T cells in solid tumors: challenges and opportunities. Stem cell research & therapy, 12(1), p. 81. (Year: 2021).*

(Continued)

*Primary Examiner* — Jeremy C Flinders
*Assistant Examiner* — Masudur Rahman
(74) *Attorney, Agent, or Firm* — Sterne, Kessler, Goldstein & Fox P.L.L.C.

(57) ABSTRACT

The present disclosure provides methods of promoting a persistent effector function of immune cells, comprising modifying the cells to overexpress c-Jun and reduced levels of a NR4A gene and/or protein. Also provided are modified cells, e.g., immune cell, which have been modified to overexpress c-Jun and express reduced levels of NR4A gene and/or protein. Overexpressing c-Jun and simultaneously reducing expression levels of a NR4A gene and/or protein leads to exhaustion/dysfunction resistant cells, which are apoptosis resistant and also immune checkpoint resistant, and also to the maintenance of anti-tumor function in tumor microenvironments.

20 Claims, 22 Drawing Sheets

Figure 3:
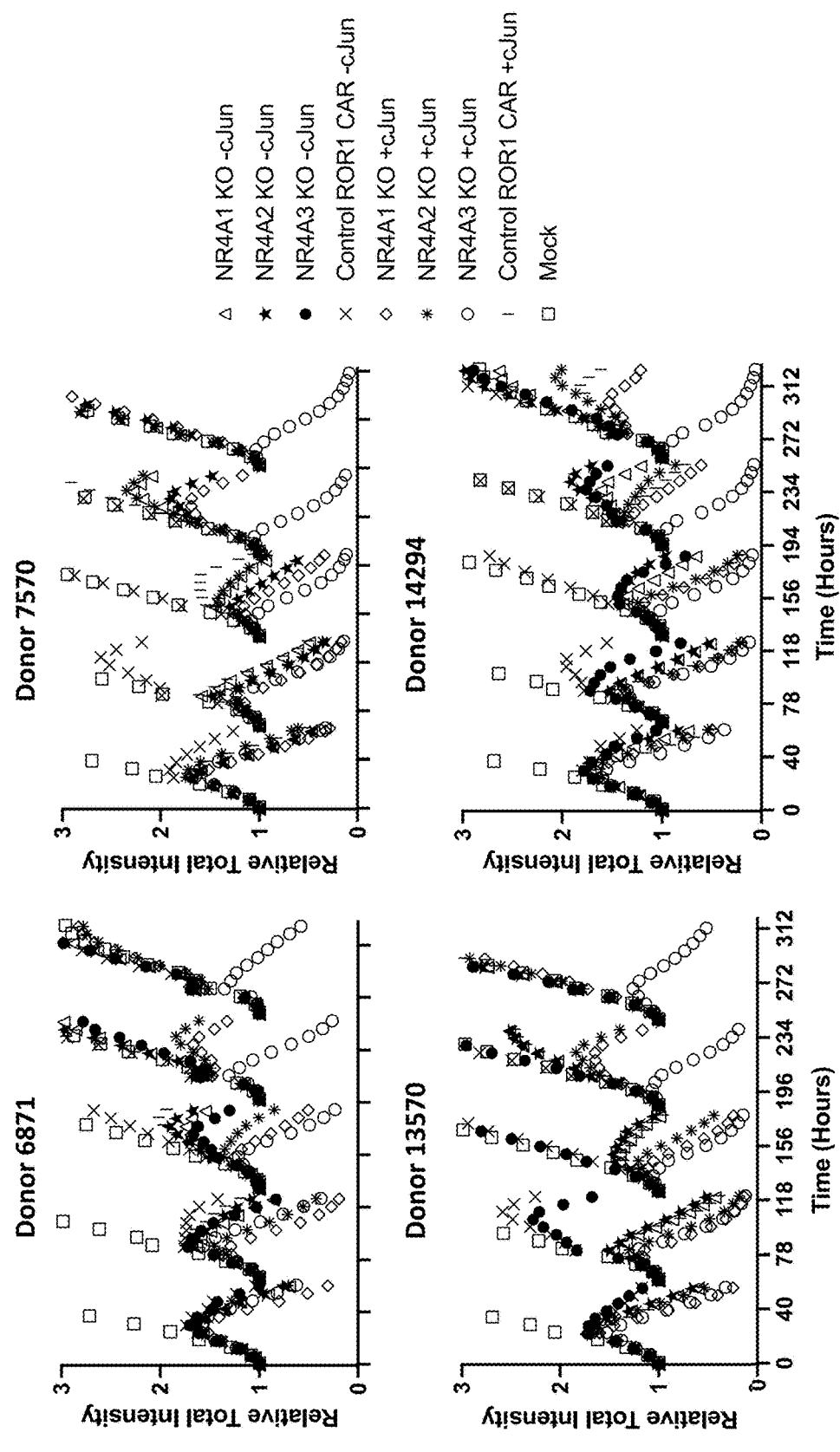

Specification includes a Sequence Listing.

(56) References Cited

U.S. PATENT DOCUMENTS

| | | | |
|---|---|---|---|
| 6,453,242 | B1 | 9/2002 | Eisenberg et al. |
| 7,732,417 | B2 | 6/2010 | Beach et al. |
| 8,202,846 | B2 | 6/2012 | Hannon et al. |
| 8,383,599 | B2 | 2/2013 | Hannon et al. |
| 8,710,200 | B2 | 4/2014 | Schrum et al. |
| 8,999,380 | B2 | 4/2015 | Bancel et al. |
| 9,316,646 | B2 | 4/2016 | Rader et al. |
| 9,758,586 | B2 | 9/2017 | Rader et al. |
| 9,782,437 | B2 | 10/2017 | Holmes et al. |
| 9,970,001 | B2 | 5/2018 | Miller |
| 10,047,355 | B2 | 8/2018 | Yin et al. |
| 10,221,398 | B2 | 3/2019 | Cady et al. |
| 10,822,413 | B2 | 11/2020 | Liu et al. |
| 2003/0232410 | A1 | 12/2003 | Liljedahl et al. |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2006/0063231 | A1 | 3/2006 | Li et al. |
| 2006/0188987 | A1 | 8/2006 | Guschin et al. |
| 2009/0226474 | A1 | 9/2009 | Weidanz et al. |
| 2011/0145940 | A1 | 6/2011 | Voytas et al. |
| 2011/0239315 | A1 | 9/2011 | Bonas et al. |
| 2011/0269234 | A1 | 11/2011 | Doyon |
| 2013/0115272 | A1 | 5/2013 | De Fougerolles et al. |
| 2017/0121693 | A1 | 5/2017 | Liu et al. |
| 2019/0092876 | A1 | 3/2019 | Banham et al. |
| 2019/0183932 | A1 | 6/2019 | Mackall et al. |
| 2019/0275148 | A1 | 9/2019 | Olson et al. |
| 2019/0284553 | A1* | 9/2019 | Benson .................. A61P 35/04 |
| 2020/0030379 | A1 | 1/2020 | Pulé et al. |
| 2020/0172879 | A1 | 6/2020 | Suri et al. |
| 2020/0190487 | A1 | 6/2020 | Zhang et al. |
| 2021/0123046 | A1 | 4/2021 | Huang et al. |

FOREIGN PATENT DOCUMENTS

| | | | |
|---|---|---|---|
| WO | WO-9817816 | A1 | 4/1998 |
| WO | WO-9818934 | A1 | 5/1998 |
| WO | WO-9931251 | A1 | 6/1999 |
| WO | WO-03078619 | A1 | 9/2003 |
| WO | WO-2004031346 | A2 | 4/2004 |
| WO | WO-2005105989 | A1 | 11/2005 |
| WO | WO-2006097784 | A1 | 9/2006 |
| WO | WO-2006097853 | A1 | 9/2006 |
| WO | WO-2006097854 | A1 | 9/2006 |
| WO | WO-2010079430 | A1 | 7/2010 |
| WO | WO-2012135805 | A2 | 10/2012 |
| WO | WO-2013039857 | A1 | 3/2013 |
| WO | WO-2013052523 | A1 | 4/2013 |
| WO | WO-2013142578 | A1 | 9/2013 |
| WO | WO-2013151671 | A1 | 10/2013 |
| WO | WO-2013176772 | A1 | 11/2013 |
| WO | WO-2014065596 | A1 | 5/2014 |
| WO | WO-2014089290 | A1 | 6/2014 |
| WO | WO-2014093622 | A2 | 6/2014 |
| WO | WO-2014093924 | A1 | 6/2014 |
| WO | WO-2014099750 | A2 | 6/2014 |
| WO | WO-2014131833 | A1 | 9/2014 |
| WO | WO-2018013797 | A1 | 1/2018 |
| WO | WO-2019079777 | A1 | 4/2019 |
| WO | WO-2019118902 | A2 | 6/2019 |
| WO | WO-2020028400 | A1 | 2/2020 |
| WO | WO-2020237040 | A1 | 11/2020 |
| WO | WO-2022251644 | A1 | 12/2022 |
| WO | WO-2022256437 | A1 | 12/2022 |

OTHER PUBLICATIONS

Lynn, R.C., Weber, E.W., Sotillo, E et al. c-Jun overexpression in CAR T cells induces exhaustion resistance. Nature 576, 293-300 (2019). https://doi.org/10.1038/s41586-019-1805-z (Year: 2019).*

Aghajanian, C., et al., "Final Overall Survival and Safety Analysis of OCEANS, a Phase 3 Trial of Chemotherapy With or Without Bevacizumab in Patients With Platinum-sensitive Recurrent Ovarian Cancer," Gynecologic Oncology 139(1):10-16, Academic Press, United States (Oct. 2015).

Ahsan, M.K., et al., "Loss of Interleukin-2-dependency in HTLV-I-infected T Cells on Gene Silencing of Thioredoxin-binding Protein-2," Oncogene 25(15):2181-2191, Nature Publishing Group, United Kingdom (Apr. 2006).

Anaya, D., et al., "Development of Ingenui-T, a Novel Vein-to-Vein Solution for Rapid Autologous CAR T-Cell Manufacturing Starting From Whole Blood, for the Treatment of Autoimmune Diseases," bioRxiv 576713, Cold Spring Laboratory Press, United States (Jan. 2024).

Andre, T., et al., "Pembrolizumab in Microsatellite-Instability-High Advanced Colorectal Cancer," New England Journal of Medicine 383(23):2207-2218, Massachusetts Medical Society, United States (Dec. 2020).

Balakrishnan, A., et al., "Analysis of ROR1 Protein Expression in Human Cancer and Normal Tissues," Clinical Cancer Research 23(12):3061-3071, Denville, United States (Jun. 2017).

Bardia, A. et al. LBA17 ASCENT: A Randomized Phase III Study of Sacituzumab Govitecan (SG) vs Treatment of Physician's Choice (TPC) in Patients (pts) with Previously Treated Metastatic Triple-negative Breast Cancer (mTNBC), Annals of Oncology 31(S4):S1149-S1150, Elsevier Inc (Sep. 2020).

Barennes, P., et al., "Benchmarking of T Cell Receptor Repertoire Profiling Methods Reveals Large Systematic Biases," Nature Biotechnology 39(2):236-245, Nature America Publishing, United States (Feb. 2021).

Baskar, S., et al., "Targeting Malignant B Cells with an Immunotoxin Against ROR1," MAbs 4(3):349-361, Taylor & Francis, United States (May-Jun. 2012).

Baur, K., et al., "Dasatinib for Treatment of CAR T-cell Therapy-related Complications," Journal for Immunotherapy of Cancer 10(12):e005956, BMJ Publishing Group Ltd, United Kingdom (Dec. 2022).

Beatty, G.L., and O'Hara, M., "Chimeric Antigen Receptor-modified T Cells for the Treatment of Solid Tumors: Defining the Challenges and Next Steps," Pharmacology & Therapeutics 166:30-39, Pergamon Press, United Kingdom (Oct. 2016).

Bediaga, N.G., et al., "Multi-level Remodelling of Chromatin Underlying Activation of Human T Cells," Scientific Reports 11(1):528, Nature Publishing Group, United Kingdom (Jan. 2021).

Beerli, R.R., and Barbas, C.F., "Engineering Polydactyl Zinc-finger Transcription Factors," Nature Biotechnology 20(2):135-141, Nature America Publishing, United States (Feb. 2002).

Belfort, M. and Roberts, R.J., "Homing Endonucleases: Keeping the House in Order," Nucleic Acids Research 25(17):3379-3388, Oxford University Press, England (Sep. 1997).

Belfort, M., et al., "Mobile Introns: Pathways and Proteins," *Mobile DNA II*, Craig, N., ed., Chapter 31, pp. 761-783, ASM Press, Washington, D.C., United States (2002).

Beltra, J.C., et al., "Developmental Relationships of Four Exhausted CD8+ T Cell Subsets Reveals Underlying Transcriptional and Epigenetic Landscape Control Mechanisms," Immunity 52(5):825-841.e8, Cell Press, United States (May 2020).

Bengsch, B., et al., "Epigenomic-Guided Mass Cytometry Profiling Reveals Disease-Specific Features of Exhausted CD8 T Cells," Immunity 48(5):1029-1045.e5, Cell Press, United States (May 2018).

Berge, V.D., et al., "RNA Sequencing Data: Hitchhiker's Guide to Expression Analysis," Annual Review of Biomedical Data Science 2(1):139-173, Annual Reviews, United States (2019).

Berger, C., et al., "Safety of Targeting ROR1 in Primates with Chimeric Antigen Receptor-modified T Cells," Cancer Immunology Research 3(2):206-216, American Association for Cancer Research, United States (Feb. 2015).

Bisikirska, B., et al., "Tcr Stimulation With Modified Anti-CD3 Mab Expands CD8+ T Cell Population and Induces CD8+CD25+ Tregs," The Journal of Clinical Investigation 115(10):2904-2913, American Society for Clinical Investigation, United States (Oct. 2005).

Bitinaite, J., et al., "FokI Dimerization is Required for DNA Cleavage," Proceedings of the National Academy of Sciences of the

(56)          References Cited

OTHER PUBLICATIONS

United States of America 95(18):10570-10575, National Academy of Sciences, United States (Sep. 1998).

Boettler, T., et al., "Expression of the interleukin-7 receptor alpha chain (CD127) on virus-specific CD8+ T cells identifies functionally and phenotypically defined memory T cells during acute resolving hepatitis B virus infection," Journal of Virology 80(7):3532-3540, American Society For Microbiology, United States (Apr. 2006).

Bohmann, D., et al., "Human Proto-oncogene c-jun Encodes a DNA Binding Protein with Structural and Functional Properties of Transcription Factor AP-1," Science 238(4832):1386-1392, American Association for the Advancement of Science, United States (Dec. 1987).

Borghaei, H., et al., "Nivolumab Versus Docetaxel in Advanced Nonsquamous Non-small-cell Lung Cancer," The New England Journal of Medicine 373(17):1627-1639, Massachusetts Medical Society, United States (Sep. 2015).

Brahmer, J., et al., "Nivolumab versus Docetaxel in Advanced Squamous-Cell Non-Small-Cell Lung Cancer," The New England Journal of Medicine 373(2):123-135, Massachusetts Medical Society, United States (Jul. 2015).

Brehm, M.A., et al., "Lack of Acute Xenogeneic Graft-versus-host Disease, but Retention of T-cell Function Following Engraftment of Human Peripheral Blood Mononuclear Cells in NSG Mice Deficient in MHC Class I and II Expression," FASEB Journal 33(3):3137-3151, Federation of American Societies for Experimental Biology, United States (Mar. 2019).

Brennan, A., et al., "Selective Antagonism of cJUN for Cancer Therapy," Journal of Experimental & Clinical Cancer Research 39(1):184, BioMed Central, England (Sep. 2020).

Bruzzone, R., et al., "Connections with Connexins: The Molecular Basis of Direct Intercellular Signaling," European Journal of Biochemistry, 238(1):1-27, Blackwell Science Ltd. on behalf of the Federation of European Biochemical Societies, United Kingdom (May 1996).

Capecchi, M.R., "High Efficiency Transformation by Direct Microinjection of DNA Into Cultured Mammalian Cells," Cell 22(Pt 2):479-488, Cell Press, United States (Nov. 1980).

Caushi, J.X., et al., "Transcriptional Programs of Neoantigen-specific TIL in Anti-PD-1-treated Lung Cancers," Nature 596(7870):126-132, G27, Nature Publishing Group, United Kingdom (Aug. 2021).

Chames, P., et al., "In Vivo Selection of Engineered Homing Endonucleases Using Double-strand Break Induced Homologous Recombination," Nucleic Acids Research 33(20):e178, Oxford University Press, United Kingdom (Nov. 2005).

Chen, C. and Okayama, H., "High-efficiency Transformation of Mammalian Cells by Plasmid DNA," Molecular and Cellular Biology 7(8):2745-2752, American Society for Microbiology, United States (Aug. 1987).

Chen, G., et al., "Cytomegalovirus Reactivation After CD19 Car T-cell Therapy is Clinically Significant," Haematologica 108(2):615-620, Ferrata Storti Foundation, Italy (Feb. 2023).

Chen, J., et al., "Generation of Normal T and B Lymphocytes by c-jun Deficient Embryonic Stem Cells," Immunity 1(1):65-72, Cell Press, United States (Apr. 1994).

Chen, J., et al., "NR4A Transcription Factors Limit CAR T Cell Function in Solid Tumours," Nature 567(7749):530-534, Nature Publishing Group, United Kingdom (Mar. 2019).

Chen, P., et al., "Metabolic Diversity in Human Non-small Cell Lung Cancer Cells," Molecular Cell 76(5):838-851.e5, Cell Press, United States (Dec. 2019).

Chen, Y., et al., "Transcriptional and Epigenetic Regulation of Effector and Memory CD8 T Cell Differentiation," Frontiers in Immunology 9:2826, 14 pages, Frontiers Research Foundation, Switzerland (Dec. 2018).

Chen, Z. and Zhao, H., "A Highly Sensitive Selection Method for Directed Evolution of Homing Endonucleases," Nucleic Acids Research 33(18):e154, Oxford University Press, United Kingdom (Oct. 2005).

Cheung, A.S., et al., "Scaffolds that Mimic Antigen-presenting Cells Enable Ex Vivo Expansion of Primary T Cells," Nature Biotechnology 36(2):160-169, Nature America Publishing, United States (Feb. 2018).

Chevalier, B.S., et al., "Design, Activity, and Structure of a Highly Specific Artificial Endonuclease," Molecular Cell 10(4):895-905, Cell Press, United States (Oct. 2002).

Chien, H.P., et al., "Expression of ROR1 has Prognostic Significance in Triple Negative Breast Cancer," Virchows Archiv 468(5):589-595, Springer International, Germany (May 2016).

Choo, Y. and Isalan, M., "Advances in Zinc Finger Engineering," Current Opinion in Structural Biology 10(4):411-416, Elsevier Science, United Kingdom (Aug. 2000).

Christian, M., et al., "Targeting DNA Double-Strand Breaks With TAL Effector Nucleases," Genetics 186(2):757-761, Oxford University Press, United States (Oct. 2010).

Cong, L., et al., "Multiplex Genome Engineering using CRISPR/Cas Systems," Science 339(6121):819-823, American Association for the Advancement of Science, United States (Feb. 2013).

Cronican, J.J., et al., "Potent Delivery of Functional Proteins into Mammalian Cells in Vitro and in Vivo Using a Supercharged Protein," ACS Chemical Biology 5(8):747-752, American Chemical Society, United States (2010).

Davila, M.L., et al., "Efficacy and Toxicity Management of 19-28z CAR T Cell Therapy in B Cell Acute Lymphoblastic Leukemia," Science Translational Medicine 6(224):224ra25, American Association for the Advancement of Science, United States (2014).

Deangelo D., et al., "Clinical Outcomes for the Phase 2, Single-arm, Multicenter Trial of JCAR015 in Adult B-ALL (ROCKET Study)," Journal for Immuno Therapy of Cancer 5(Suppl 2):86, BMJ, United States (2017).

Derijard, B., et al., "JNK1: A Protein Kinase Stimulated by UV Light and Ha-Ras that Binds and Phosphorylates the c-Jun Activation Domain," Cell 76(6):1025-1037, Cell Press, United States (Mar. 1994).

Dickinson, M.J., et al., "A Novel Autologous CAR-T Therapy, YTB323, with Preserved T-cell Stemness Shows Enhanced CAR T-cell Efficacy in Preclinical and Early Clinical Development," Cancer Discovery 13(9):1982-1997, American Association for Cancer Research, United States (Sep. 2023).

Dieci, M.V., et al., "Impact of Estrogen Receptor Levels on Outcome in Non-metastatic Triple Negative Breast Cancer Patients Treated With Neoadjuvant/adjuvant Chemotherapy," NPJ Breast Cancer 7(1):101, Nature Publishing Group, United States (Aug. 2021).

Doench, J.G., et al., "Optimized sgRNA Design to Maximize Activity and Minimize Off-target Effects of CRISPR-Cas9," Nature Biotechnology 34(2):184-191, Nature America Publishing, United States (Feb. 2016).

Doench, J.G., et al., "Rational Design of Highly Active sgRNAs for CRISPR-Cas9-mediated Gene Inactivation," Nature Biotechnology 32(12):1262-1267, Nature America Publishing, United States (Dec. 2014).

Dossaji, Z., et al., "A Review of Hepatitis B Reactivation Risk on Immunosuppressants with a Focus on Newer Immunomodulators," Current Hepatology Reports 23:253-267, Springer Nature, Germany (Feb. 2024).

Dressler, L., et al., "Comparative Assessment of Genes Driving Cancer and Somatic Evolution in Non-cancer Tissues: an Update of the Network of Cancer Genes (NCG) Resource," Genome Biology 23(1):35, BioMed Central Ltd, United Kingdom (Jan. 2022).

Durgeau, A., et al., "Recent Advances in Targeting CD8 T-Cell Immunity for More Effective Cancer Immunotherapy," Frontiers in Immunology 9:14, Frontiers Research Foundation, Switzerland (Jan. 2018).

Eastwood, D., et al., "Monoclonal antibody TGN1412 trial failure explained by species differences in CD28 expression on CD4+ effector memory T-cells," British Journal of Pharmacology 161:512-526, The British Pharmacological Society, England (2010).

Eferl, R., et al., "Functions of c-Jun in Liver and Heart Development," Journal of Cell Biology 145(5):1049-1061, Rockefeller University Press, United States (May 1999).

(56)　　　　　　　References Cited

OTHER PUBLICATIONS

Eisenhauer, E.A., et al., "New Response Evaluation Criteria in Solid Tumours: Revised RECIST Guideline (Version 1.1)," European Journal of Cancer 45(2):228-247, Elsevier, Netherlands (Jan. 2009).

Epinat, J.C., et al., "A Novel Engineered Meganuclease Induces Homologous Recombination in Yeast and Mammalian Cells," Nucleic Acids Research 31(11):2952-2962, Oxford University Press, United Kingdom (Jun. 2003).

Etxeberria, I., et al., "Engineering Bionic T Cells: Signal 1, Signal 2, Signal 3, Reprogramming and the Removal of Inhibitory Mechanisms," Cellular & Molecular Immunology 17(6):576-586, Chinese Society of Immunology; Nature Pub. Group, China (Jun. 2020).

Ferrando, A.A., "The role of NOTCH1 signaling in T-ALL," Hematology 2009(1):353-361, American Society of Hematology, United States (2009).

Fire, A., et al., "Potent and Specific Genetic Interference by Double-stranded RNA in Caenorhabditis Elegans," Nature 361:806-811, Nature Portfolio, Germany (1998).

Fraietta, J.A., et al., "Determinants of Response and Resistance to CD19 Chimeric Antigen Receptor (CAR) T Cell Therapy of Chronic Lymphocytic Leukemia," Nature Medicine 24(5):563-571, Nature Publishing Company, United States (May 2018).

Fraietta, J.A., et al., "Disruption of TET2 Promotes the Therapeutic Efficacy of CD19-targeted T Cells," Nature 558(7709):307-312 Nature Publishing Group, United Kingdom (Jun. 2018).

Freeman, W.M., et al., "Quantitative Rt-pcr: Pitfalls and Potential," BioTechniques 26(1):112-122, 124-125, Informa Healthcare USA Inc, England (1999).

Garces De Los Fayos Alonso, I, et al., "The Role of Activator Protein-1 (AP-1) Family Members in CD30-Positive Lymphomas," Cancers 10(4):93, MDPI, Switzerland (Mar. 2018).

Gattinoni, L., et al., "A Human Memory T Cell Subset With Stem Cell-like Properties," Nature Medicine 17:1290-1297, Nature Publishing Company, United States (Sep. 2011).

Gattinoni L., et al., "Acquisition of full effector function in vitro paradoxically impairs the in vivo antitumor efficacy of adoptively transferred CD8+ T cells," Journal of Clinical Investigation 115(6):1616-1626, American Society for Clinical Investigation, United States. (Jun. 2005).

Gattinoni, L., et al., "T Memory Stem Cells in Health and Disease," Nature Medicine 23(1):18-27, Nature Publishing Company, United States (Jan. 2017).

Gattinoni, L., et al., "Wnt Signaling Arrests Effector T Cell Differentiation and Generates CD8 Memory Stem Cells," Nature Medicine 15(7):808-813, Nature Publishing Company, United States (Jul. 2009).

Gebhardt, T., et al., "Stem-like Exhausted and Memory CD8+ T Cells in Cancer," Nature Reviews Cancer 23:780-798, Nature Publishing Group, United Kingdom (Nov. 2023).

GenBank, "*Homo sapiens* chromosome 1, GRCh38.p14 Primary Assembly," Accession No. NC_000001.11, accessed at https://www.ncbi.nlm.nih.gov/nuccore/NC_000001.11/, accessed on Feb. 6, 2023, 3 pages.

GenBank, "*Homo sapiens* chromosome 12, GRCh38.p14 Primary Assembly," Accession No. NC_000012.12, accessed at https://www.ncbi.nlm.nih.gov/nuccore/NC_000012.12/, accessed on Feb. 6, 2023, 3 pages.

GenBank, "*Homo sapiens* chromosome 2, GRCh38.p14 Primary Assembly," Accession No. NC_000002.12, accessed at https://www.ncbi.nlm.nih.gov/nuccore/NC_000002.12/, accessed on Feb. 6, 2023, 3 pages.

GenBank, "*Homo sapiens* Jun proto-oncogene, AP-1 transcription factor subunit (JUN), mRNA," NCBI Reference Sequence: NM_002228.4, accessed at https://www.ncbi.nlm.nih.gov/nuccore/NM_002228.4, 2019, 6 pages.

Geraci, F., et al., "Editorial: RNA-Seq Analysis: Methods, Applications and Challenges," Frontiers in Genetics 11:220, Frontiers Research Foundation, Switzerland (Mar. 2020).

Ghilardi, G., et al., "Bendamustine is Safe and Effective for Lymphodepletion Before Tisagenlecleucel in Patients With Refrac-tory or Relapsed Large B-cell Lymphomas," Annals of Oncology 33(9):916-928, Elsevier, United Kingdom (Sep. 2022).

Giles, J.R., et al., "CD8+ T Cells in the Cancer-immunity Cycle," Immunity 56(10):2231-2253, Cell Press, United States (Oct. 2023).

Gilham, D.E., et al., "CAR-T Cells and Solid Tumors: Tuning T Cells to Challenge an Inveterate Foe," Trends in Molecular Medicine 18(7):377-384, Elsevier Science Ltd, United Kingdom (Jul. 2012).

Gimble, F.S., et al., "Assessing the Plasticity of DNA Target Site Recognition of the PI-SceI Homing Endonuclease Using a Bacterial Two-hybrid Selection System," Journal of Molecular Biology 334(5):993-1008, Elsevier, United Kingdom (Dec. 2003).

Gonzalez, N.M., et al., "Schrödinger's T Cells: Molecular Insights Into Stemness and Exhaustion," Frontiers in immunology 12:725618, Frontiers Research Foundation, Switzerland (Aug. 2021).

Good, C.R., et al., "An NK-like CAR T cell transition in CAR T cell dysfunction," Cell 184:25 6081-6100.e26, CellPress, United States (Dec. 2021).

Gouirand, V., et al., "Influence of the Tumor Microenvironment on Cancer Cells Metabolic Reprogramming," Frontiers in Oncology 8:117, Frontiers Research Foundation, Switzerland (Apr. 2018).

Gruen, M., et al., "An in Vivo Selection System for Homing Endonuclease Activity," Nucleic Acids Research 30(7):e29, Oxford University Press, England (Apr. 2002).

Guhan, N. and Muniyappa, K., "Structural and Functional Characteristics of Homing Endonucleases," Critical Reviews in Biochemistry and Molecular Biology 38(3):199-248, Informa Healthcare, United Kingdom (2003).

Guo, C., et al., "Off-target Effects in CRISPR/Cas9 Gene Editing," Frontiers in Bioengineering and Biotechnology 11:1143157, Frontiers Media S.A., Switzerland (Mar. 2023).

Gupta, B., et al., "Simultaneous Coexpression of Memory-related and Effector-related Genes by Individual Human CD8 T Cells Depends on Antigen Specificity and Differentiation," Journal of Immunotherapy 35(6):488-501, Lippincott Williams & Wilkins, United States (Jul. 2012).

Haas, A.R., et al., "Two Cases of Severe Pulmonary Toxicity From Highly Active Mesothelin-directed CAR T Cells," Molecular Therapy 31(8):2309-2325, Cell Press, United States (Aug. 2023).

Hay, K.A., et al., "Kinetics and Biomarkers of Severe Cytokine Release Syndrome After Cd19 Chimeric Antigen Receptor-modified T-cell Therapy," Blood 130(21):2295-2306, Elsevier, United States (Nov. 2017).

Heiser, W.C., "Optimizing Electroporation Conditions for the Transformation of Mammalian Cells," Methods in Molecular Biology 130:117-134, Humana Press, United States (2000).

Heliste, J., et al., "Receptor Tyrosine Kinase Profiling of Ischemic Heart Identifies RoR1 as a Potential Therapeutic Target," BMC Cardiovascular Disorders 18(1):196, BioMed Central, United Kingdom (Oct. 2018).

Hendel, A., et al., "Chemically Modified Guide rNAs Enhance CrIsPr-Cas Genome Editing in Human Primary Cells," Nature Biotechnology 33(9):985-989, Nature America Publishing, United States (Sep. 2015).

Herbst, R.S., et al., "Pembrolizumab Versus Docetaxel for Previously Treated, PD-L1-positive, Advanced non-small-cell Lung Cancer (KEYNOTE-010): A Randomised Controlled Trial," Lancet 387(10027):1540-1550, Elsevier, United Kingdom (Apr. 2016).

Hibino, S., et al., "Inhibition of Nr4a Receptors Enhances Antitumor Immunity by Breaking Treg-Mediated Immune Tolerance," Cancer Research 78(11):3027-3040, American Association for Cancer Research, United States (Jun. 2018).

Hilberg, F., et al., "c-Jun is Essential for Normal Mouse Development and Hepatogenesis," Nature 365(6442):179-181 Nature Publishing Group, United Kingdom (Sep. 1993).

Hines, M.R., et al., "Immune Effector Cell-associated Hemophagocytic Lymphohistiocytosis-like Syndrome," Transplantation and Cellular Therapy 438.e1-438.e16, Elsevier Inc, United States (Jul. 2023).

Hiwa, R., et al., "NR4A Family Members Regulate T Cell Tolerance to Preserve Immune Homeostasis and Suppress Autoimmunity," JCI Insight 6(17):e151005, American Society for Clinical Investigation, United States (2021).

(56)         References Cited

OTHER PUBLICATIONS

Huang, L.P., et al., "Granulysin-mediated Tumor Rejection in Transgenic Mice," Journal of Immunology 178(1):77-84, American Association of Immunologists, United States (Jan. 2007).

Hudecek, M., et al., "Receptor Affinity and Extracellular Domain Modifications Affect Tumor Recognition by ROR1-specific Chimeric Antigen Receptor T Cells," Clinical Cancer Research 19(12):3153-3164, The Association, United States (Jun. 2013).

Huster, K. M., et al., "Selective expression of IL-7 receptor on memory T cells identifies early CD40L-dependent generation of distinct CD8+ memory T cell subsets," PNAS 101(15):5610-5615 (Mar. 2004).

Hwang, W.Y., et al., "Efficient Genome Editing in Zebrafish Using a CRISPR-Cas System," Nature Biotechnology 31(3):227-229, Nature America Publishing, United States (Mar. 2013).

Innis, M.A., et al., "DNA Sequencing with thermus Aquaticus Dna Polymerase Direct Sequencing of Polymerase Chain Reaction-Amplified DNA," Proceedings of the National Academy of Sciences of the United States of America 85(24):9436-9440, National Academy of Sciences, United States (1988).

International Search Report and Written Opinion for International Application No. PCT/US2022/031818, mailed on Aug. 19, 2022, 14 pages.

Isalan, M., et al., "A Rapid, Generally Applicable Method to Engineer Zinc Fingers Illustrated by Targeting the HIV-1 Promoter," Nature Biotechnology 19(7):656-660, Nature America Publishing, United States (Jul. 2001).

Jansen, C.S., et al., "An Intra-tumoral Niche Maintains and Differentiates Stem-like CD8 T Cells," Nature 576(7787):465-470, Nature Publishing Group, United Kingdom (Dec. 2019).

Jiang, W., et al., "CRISPR-Assisted Editing of Bacterial Genomes," Nature Biotechnology 31(3):233-239, Nature America Publishing, United States (Mar. 2013).

Jinek, M., et al., "A Programmable Dual-RNA-guided DNA Endonuclease in Adaptive Bacterial Immunity," Science 337(6096):816-821, American Association for the Advancement of Science, United States (Aug. 2012).

Jurica, M.S., and Stoddard, B.L., "Homing Endonucleases: Structure, Function and Evolution," Cellular and Molecular Life Sciences 55(10):1304-1326, Springer, Switzerland (Aug. 1999).

Kabadi, A.M., and Gersbach, C.A., "Engineering Synthetic Tale and CRISPR/cas9 Transcription Factors for Regulating Gene Expression," Methods 69(2):188-197, Academic Press, United States (Sep. 2014).

Kaech, S.M., et al., "Transcriptional Control of Effector and Memory CD8+ T Cell Differentiation," Nature Reviews. Immunology 12(11):749-761, Nature Publishng Group, United Kingdom (Nov. 2012).

Kim, Y.G., et al., "Chimeric Restriction Endonuclease," Proceedings of the National Academy of Sciences of the United States of America 91(3):883-887, National Academy of Sciences, United States (Feb. 1994).

Kim, Y.G., et al., "Insertion and Deletion Mutants of FokI Restriction Endonuclease," The Journal of Biological Chemistry 269(50):31978-31982, Elsevier Inc, United States (Dec. 1994).

Kiniwa, Y., et al., "CD8+ Foxp3+ Regulatory T Cells Mediate Immunosuppression in Prostate Cancer," Clinical Cancer Research 13(23):6947-6958, American Association for Cancer Research, United States (Dec. 2007).

Kleinstiver, B.P., et al., "Engineered CRISPR-Cas9 nucleases with altered PAM specificities," Nature, 523:481-485, Macmillan Publishers Limited (Jul. 2015).

Krishna, S., et al., "Stem-like CD8 T Cells Mediate Response of Adoptive cell Immunotherapy Against Human Cancer," Science 370(6522):1328-1334, American Association for the Advancement of Science United States (Dec. 2020).

Kuroki, L., et al., "Treatment of Epithelial Ovarian Cancer," BMJ 371:m3773, British Medical Association, United Kingdom (Nov. 2020).

Lafleur, M.W., et al., "Prevention of CAR-T-cell dysfunction," Nature Biomedical Engineering 4(1):16-17, Springer Nature, United Kingdom (Jan. 2020).

Lakomy, T., et al., "Early Use of Corticosteroids following CAR T-Cell Therapy Correlates with Reduced Risk of High-Grade CRS without Negative Impact on Neurotoxicity or Treatment Outcome," Biomolecules 13(2):382, MDPI, Switzerland (Feb. 2023).

Le, D.T., et al., "Phase II Open-Label Study of Pembrolizumab in Treatment-Refractory, Microsatellite Instability-High/Mismatch Repair-Deficient Metastatic Colorectal Cancer: KEYNOTE-164," Journal of Clinical Oncology 38(1):11-19, American Society of Clinical Oncology, United States (Jan. 2020).

Leenay, R.T., et al., "Large Dataset Enables Prediction of Repair After CRISPR-Cas9 Editing in Primary T Cells," Nature Biotechnology 37(9):1034-1037, Nature America Publishing, United States (Sep. 2019).

Lewis, W.H., et al., "Parameters Governing the Transfer of the Genes for Thymidine Kinase and Dihydrofolate Reductase Into Mouse Cells Using Metaphase Chromosomes or DNA," Somatic Cell Genetics 6(3):333-347, Plenum, United States (May 1980).

Li, A., et al., "Engineering Potent CAR T-Cell Therapies by Controlling T-Cell Activation Signaling Parameters using the Stim-RTM Technology, A Programmable Synthetic Cell-Signaling Platform," Presented at: The Annual Meeting of The Society for Immunotherapy of Cancer (SITC), Boston, MA, (Nov. 8-12, 2022).

Li, F., and Zhang, Y., "Targeting NR4As, A New Strategy to Fine-tune CAR-T cells Against Solid Tumors," Signal Transduction and Targeted Therapy 4:7, Nature Publishing Group, United Kingdom (Mar. 2019).

Li, P., et al., "Risk of HBV Reactivation in Patients With Resolved HBV Infection Receiving Anti-CD19 Chimeric Antigen Receptor T Cell Therapy Without Antiviral Prophylaxis," Frontiers in Immunology 15:12:638678, Frontiers Research Foundation, Switzerland (Jul. 2021).

Li, T., et al., "TAL Nucleases (TALNs): Hybrid Proteins Composed of TAL Effectors and FokI DNA-Cleavage Domain," Nucleic Acids Research 39(1):359-372, Oxford University Press, United Kingdom (Jan. 2011).

Liebmann, M., et al., "Nur77 Serves as a Molecular Brake of the Metabolic Switch During T Cell Activation to Restrict Autoimmunity," Proceedings of the National Academy of Sciences of the United States of America 115(34):E8017-E8026, National Academy of Sciences, United States (Aug. 2018).

Lin, H., et al., "Hepatitis B Virus Reactivation Associated With CAR T-cell Therapy," Holistic Integrative Oncology 3:16, Springer Nature, Germany (Mar. 2024).

Lin, J., et al., "CRISPR-Net: A Recurrent Convolutional Network Quantifies CRISPR Off-Target Activities with Mismatches and Indels," Advanced Science 7(13):1903562, Wiley, United States (May 2020).

Liou, G.Y., and Storz, P., "Reactive Oxygen Species in Cancer," Free Radical Research 44(5):479-496, Informa Healthcare, United Kingdom (May 2010).

Listgarten, J., et al., "Prediction of Off-target Activities for the End-to-end Design of CRISPR Guide RNAs," Nature Biomedical Engineering 2(1):38-47, Springer Nature, United Kingdom (Jan. 2018).

Liu, D., et al., "Author Correction: ROR1 is Upregulated in Endometrial Cancer and Represents a Novel Therapeutic Target," Scientific Reports 12(1):10918, Nature Publishing Group, United Kingdom (Jun. 2022).

Liu, S., et al., "Corticosteroids do not Influence the Efficacy and Kinetics of CAR-T Cells for B-cell Acute Lymphoblastic Leukemia," Blood Cancer Journal 10(2):15, Nature Publish Group, United States (Feb. 2020).

Liu, X., et al., "Genome-wide Analysis Identifies NR4A1 as a Key Mediator of T Cell Dysfunction," Nature 567(7749):525-529, Nature Publishing Group, United Kingdom (Mar. 2019).

Li, L., and Chandrasegaran, S., "Alteration of the Cleavage Distance of Fok I Restriction Endonuclease by Insertion Mutagenesis," Proceedings of the National Academy of Sciences of the United States of America 90(7):2764-2768, National Academy of Sciences, United States (Apr. 1993).

(56) References Cited

OTHER PUBLICATIONS

Li, L., et al., "Functional Domains in Fok I Restriction Endonuclease," Proceedings of the National Academy of Sciences of the United States of America 89(10):4275-4279, National Academy of Sciences, United States (May 1992).

Lowery, F.J., et al., "Molecular Signatures of Antitumor Neoantigen-reactive T Cells from Metastatic Human Cancers," Science 375(6583):877-884, American Association for the Advancement of Science, United States (Feb. 2022).

Lucas, P., et al., "Rapid Evolution of the DNA-binding Site in LAGLIDADG Homing Endonucleases," Nucleic Acids Research 29(4):960-969, Oxford University Press, United Kingdom (Feb. 2001).

Lynn, R.C., et al., "c-Jun Overexpression in CAR T Cells Induces Exhaustion Resistance," Nature 576(7786):293-300, Nature Publishing Group, United Kingdom (Dec. 2019).

Maeda, M., et al., "IL-2/IL-2 Receptor Pathway Plays a Crucial Role in the Growth and Malignant Transformation of HTLV-1-Infected T Cells to Develop Adult T-Cell Leukemia," Frontiers in Microbiology 11:356, 17 pages, Frontiers Research Foundation, Switzerland (2020).

Majzner, R., and Mackall, C.L., "Tumor Antigen Escape from CAR T-cell Therapy," Cancer Discovery 8(10):1219-1226, American Association for Cancer Research, United States (Oct. 2018).

Mali, P., et al., "RNA-Guided Human Genome Engineering via Cas9," Science 339(6121):823-826, American Association for the Advancement of Science, United States (Feb. 2013).

Mao, Y., et al., "ROR1 Associates Unfavorable Prognosis and Promotes Lymphoma Growth in DLBCL by Affecting PI3K/Akt/mTOR Signaling Pathway," Biofactors 45(3):416-426, Ios Press, Netherlands (May 2019).

Martin, P., "New Access to 2'-O-alkylated Ribonucleosides and Properties of 2'-O-alkylated Oligoribonucleotides," Helvetica Chimica Acta 78(2):486-504, Wiley, United States (Jan. 1995).

Martinez, M., and Moon, E.K., "CAR T Cells for Solid Tumors: New Strategies for Finding, Infiltrating, and Surviving in the Tumor Microenvironment," Frontiers in Immunology 10:128, Frontiers Research Foundation, Switzerland (Feb. 2019).

Mclane, L.M., et al., "CD8 T Cell Exhaustion During Chronic Viral Infection and Cancer," Annual Review of Immunology 37:457-495, Annual Reviews Inc, United States (Apr. 2019).

Mestermann, K., et al., "The Tyrosine Kinase Inhibitor Dasatinib Acts as a Pharmacologic on/off Switch for CAR T Cells," Science Translational Medicine, 11(499):eaau5907, 11 pages, American Association for the Advancement of Science, United States (Jul. 2019).

Miller, J.C., et al., "A Tale Nuclease Architecture for Efficient Genome Editing," Nature Biotechnology 29(2):143-148, Nature America Publishing, United States (Feb. 2011).

Miller, J., et al., "Repetitive Zinc-Binding Domains in the Protein Transcription Factor IIIA from Xenopus Oocytes," The EMBO journal 4(6):1609-1614, Wiley Blackwell, England (Jun. 1985).

Mognol, G.P., et al., Exhaustion-associated Regulatory Regions in CD8 Tumor-infiltrating T Cells. Proceedings of the National Academy of Sciences of the United States of America 114(13):E2776-E2785, National Academy of Sciences, United States (Mar. 2017).

Morbitzer, R., et al., "Regulation of Selected Genome loci using de Novo-engineered Transcription Activator-like Effector (TALE)-type Transcription Factors," Proceedings of the National Academy of Sciences of the United States of America 107(50):21617-20622, National Academy of Sciences, United States (Dec. 2010).

Morris, G.J., et al., "Differences in Breast Carcinoma Characteristics in Newly Diagnosed African-American and Caucasian Patients: A Single-institution Compilation Compared with the National Cancer Institute's Surveillance, Epidemiology, and End Results database," Cancer 110(4):876-884, Wiley, United States (Aug. 2007).

Moure, C.M., et al., "Crystal Structure of the Intein Homing Endonuclease PI-Scel Bound to its Recognition Sequence," Nature Structural Biology 9(10):764-770, Nature Pub. Co, United States (Oct. 2002).

Mullican, S.E., et al., "Abrogation of Nuclear Receptors Nr4a3 and Nr4a1 Leads to Development of Acute Myeloid Leukemia," Nature Medicine 13(6):730-735, Nature Publishing Company, United States (Jun. 2007).

Nahmad, A.D., et al., "Frequent Aneuploidy in Primary Human T Cells After CRISPR-Cas9 Cleavage," Nature Biotechnology 40(12):1807-1813, Nature America Publishing, United States (Dec. 2022).

Nair, A.B., et al., "A Simple Practice Guide for Dose Conversion Between Animals and Human," Journal of Basic and Clinical Pharmacy 7(2):27-31, Medknow Publications, India (Mar. 2016).

Neelapu, S.S., et al., "Axicabtagene Ciloleucel CAR T-Cell Therapy in Refractory Large B-Cell Lymphoma," The New England Journal of Medicine 377(26):2531-2544, Massachusetts Medical Society, United States (2017).

Newick, K., et al., "CAR T Cell Therapy for Solid Tumors," Annual Review of Medicine 68:139-152, Annual Reviews, United States (Jan. 2017).

Newick, K., et al., "Chimeric Antigen Receptor T-cell Therapy for Solid Tumors," Molecular Therapy Oncolytics 3:16006, Cell Press, United States (Apr. 2016).

Newrzela, S., et al., "Resistance of Mature T Cells to Oncogene Transformation," Blood 112(6):2278-2286, Elsevier, United States (Sep. 2008).

Nissim, L., et al., "Multiplexed and Programmable Regulation of Gene Networks with an Integrated RNA and CRISPR/Cas Toolkit in Human Cells," Molecular Cell 54(4):698-710, Cell Press, United States (May 2014).

Norman, B.C., et al., "Fluticasone, Azithromycin and Montelukast Therapy in Reducing Corticosteroid Exposure in Bronchiolitis Obliterans Syndrome After Allogeneic Hematopoietic Sct: a Case Series of Eight Patients," Bone Marrow Transplantation 46(10):1369-1373, Nature Publishing Group, United Kingdom (Oct. 2011).

Nowyhed, H.N., et al., "Cutting Edge: The Orphan Nuclear Receptor Nr4a1 Regulates CD8+ T Cell Expansion and Effector Function Through Direct Repression of Irf4," The Journal of Immunology 195(8):3515-3519, American Association of Immunologists, United States (2015).

Ochman, H., et al., "Genetic Applications of an Inverse Polymerase Chain Reaction," Genetics 120(3):621-623, Genetics Society Of America, United States (1988).

Odagiu, L., et al., "Early Programming of CD8+ T Cell Response by the Orphan Nuclear Receptor NR4A3," Proceedings of the National Academy of Sciences of the United States of America 117(39):24392-24402, National Academy of Sciences, United States (Sep. 2020).

Odagiu, L., et al., "Role of the Orphan Nuclear Receptor NR4A Family in T-Cell Biology," Frontiers in Endocrinology 11:624122, Frontiers Research, Switzerland (Feb. 2021).

Oliveira, G., et al., "Phenotype, Specificity and Avidity of Antitumour CD8+ T Cells in Melanoma," Nature 596(7870):119-125, Nature Publishing Group, United Kingdom (Aug. 2021).

Oluwole, O.O., et al., "Long-term Outcomes of Patients with Large B-cell Lymphoma Treated with Axicabtagene Ciloleucel and Prophylactic Corticosteroids," Bone Marrow Transplantation 59(3):366-372, Nature Publishing Group, United Kingdom (Mar. 2024).

O'sullivan, D., et al., "Memory CD8(+) T Cells use Cell-intrinsic Lipolysis to Support the Metabolic Programming Necessary for Development," Immunity 41(1):75-88, Cell Press, United States (Jul. 2014).

Overman, M.J., et al., "Nivolumab in Patients with Metastatic DNA Mismatch Repair-Deficient or Microsatellite Instability-High Colorectal Cancer (CheckMate 142): An Open-Label, Multicentre, Phase 2 Study," The Lancet Oncology 18(9):1182-1191, Lancet Publishing Group, United Kingdom (Sep. 2017).

Pabo, C.O., et al., "Design And Selection Of Novel Cys2His2 Zinc Finger Proteins," Annual Review of Biochemistry 70:313-340, Annual Reviews, United States (2001).

Pandelakis, M., et al., "CRISPR-Based Synthetic Transcription Factors in Vivo: the Future of Therapeutic Cellular Programming," Cell Systems 10(1):1-14, Cell Press, United States (Jan. 2020).

(56)        References Cited

OTHER PUBLICATIONS

Papatheodorou, I., et al., "Expression Atlas: Gene and Protein Expression Across Multiple Studies and Organisms," Nucleic Acids Research 46(D1):D246-D251, Oxford University Press, United Kingdom (Jan. 2018).

Pardoll, D.M., "The Blockade of Immune Checkpoints in Cancer Immunotherapy," Nature Reviews Cancer 12(4):252-264, Nature Publishing Group, United Kingdom (Mar. 2012).

Paszkiewicz, P.J., et al., "Targeted Antibody-mediated Depletion of Murine CD19 CAR T Cells Permanently Reverses B Cell Aplasia" The Journal of Clinical Investigation 126(11):4262-4272, American Society for Clinical Investigation, United States (Nov. 2016).

Pena, S.V., et al., "Processing, Subcellular Localization, and Function of 519 (Granulysin), a Human Late T Cell Activation Molecule With Homology to Small, Lytic, Granule Proteins," Journal of Immunology 158(6):2680-2688, American Association of Immunologists, United States (Mar. 1997).

Porciello, N., et al., "A Non-conserved Amino Acid Variant Regulates Differential Signalling Between Human and Mouse CD28," Nature Communications 9(1):1080, Nature Publishing Group, United Kingdom (Mar. 2018).

Rapoport, A.P., et al., "NY-ESO-1-specific TCR-engineered T Cells Mediate Sustained Antigen-specific Antitumor Effects in Myeloma," Nature Medicine 21(8):914-921, Nature Publishing Company, United States (Aug. 2015).

Rhodes, D., and Klug, A., "Zinc Fingers," Scientific American 268(2):56-65, Scientific American, United States (Feb. 1993).

Riera-Sans, L., and Behrens, A., "Regulation of Alphabeta/gammadelta T Cell Development by the Activator Protein 1 Transcription Factor c-Jun," Journal of Immunology 178(9):5690-5700, American Association of Immunologists, United States (May 2007).

Rittmeyer, A., et al., "Atezolizumab Versus Docetaxel in Patients with Previously Treated non-small-cell Lung Cancer (OAK): A Phase 3, open-label, Multicentre Randomised Controlled Trial," Lancet 389(10066):255-265, Elsevier, United Kingdom (Jan. 2017).

Roberts, R.J., et al., "A Nomenclature for Restriction Enzymes, DNA Methyltransferases, Homing Endonucleases and Their Genes," Nucleic Acids Research 31(7):1805-1812, Oxford University Press, England (Apr. 2003).

Roberts, R.J., et al., "REBASE: Restriction Enzymes and Methyltransferases," Nucleic Acids Research 31(1):418-420, Oxford University Press, England (Jan. 2003).

Rosen, L.E., et al., "Homing Endonuclease I-CreI Derivatives With Novel DNA Target Specificities," Nucleic Acids Research 34(17):4791-4800, Oxford University Press, England (2006).

Rosenberg, S.A., et al., "Durable Complete Responses in Heavily Pretreated Patients With Metastatic Melanoma Using T-cell Transfer Immunotherapy," Clinical Cancer Research 17(13):4550-4557, The Association, United States (2011).

Ryan, D.E., et al., "Improving CRISPR-Cas Specificity With Chemical Modifications in Single-guide RNAs," Nucleic Acids Research 46(2):792-803, Oxford University Press, United Kingdom (Jan. 2018).

Sade-Feldman, M., et al., "Defining T Cell States Associated with Response to Checkpoint Immunotherapy in Melanoma," Cell 175(4):998-1013.e20, Cell Press, United States (Nov. 2018).

Sadelain, M., et al., "Safe Harbours for the Integration of New DNA in the Human Genome," Nature Reviews. Cancer 12(1):51-58, Nature Publishing Group, United Kingdom (Dec. 2011).

Safe, S., et al., "The Paradoxical Roles of Orphan Nuclear Receptor 4A (NR4A) in Cancer," Molecular Cancer Research 19(2):180-191, American Association for Cancer Research, United States (Feb. 2021).

Schaffner, W., "Direct Transfer of Cloned Genes From Bacteria to Mammalian Cells," Proceedings of the National Academy of Sciences of the United States of America 77(4):2163-2167, National Academy of Sciences, United States (Apr. 1980).

Schlitzer, A., et al., "Recent Advances in Understanding Dendritic Cell Development, Classification, and Phenotype," F1000Research 7:F1000, 9 pages, F1000 Research Ltd, United Kingdom (Sep. 2018).

Scholze, H., and Boch, J., "TAL Effector-DNA Specificity," Virulence 1(5):428-432, Taylor & Francis, United States (Sep. 2010).

Schutte, J., et al., "Deregulated Expression of Human C-jun Transforms Primary Rat Embryo Cells in Cooperation With an Activated C-Ha-ras Gene and Transforms Rat-1a Cells as a Single Gene," Proceedings of the National Academy of Sciences of the United States of America 86(7):2257-2261, National Academy of Sciences, United States (Apr. 1989).

Segal, D.J., and Barbas, 3rd, C.F., "Custom DNA-Binding Proteins Come of Age: Polydactyl Zinc-Finger Proteins," Current Opinion in Biotechnology 12(6):632-637, Elsevier, England (Dec. 2001).

Seligman, L.M., et al., "Mutations Altering the Cleavage Specificity of a Homing Endonuclease," Nucleic Acids Research 30(17):3870-3879, Oxford University Press, United Kingdom (Sep. 2002).

Seo, H., et al., "BATF and IRF4 Cooperate to Counter Exhaustion in Tumor-infiltrating CAR T Cells," Nature Immunology 22:983-995, Nature America Inc, United States (Aug. 2021).

Shabaneh, T.B., et al., "Safety Switch Optimization Enhances Antibody-mediated Elimination of CAR T Cells," Frontiers in Molecular Medicine 2:1026474, Frontiers Media S.A, Switzerland (Oct. 2022).

Shen, M.W., et al., "Predictable and Precise Template-free CRISPR Editing of Pathogenic Variants," Nature 563(7733):646-651, Nature Publishing Group, United Kingdom (Nov. 2018).

Sheng-Fowler, L., et al., "Issues Associated With Residual Cell-substrate DNA in Viral Vaccines," Biologicals 37(3):190-195, Academic Press, United Kingdom (Jun. 2009).

Smith, J., et al., "A Combinatorial Approach to Create Artificial Homing Endonucleases Cleaving Chosen Sequences," Nucleic Acids Research 34(22):e149, Oxford University Press, United Kingdom (2006).

Srivastava, S., and Riddell, S.R., "Chimeric Antigen Receptor T Cell Therapy: Challenges to Bench-to-Bedside Efficacy," Journal of Immunology 200(2):459-468, American Association of Immunologists, United States (Jan. 2018).

Srivastava, S., et al., "Logic-Gated ROR1 Chimeric Antigen Receptor Expression Rescues T Cell-Mediated Toxicity to Normal Tissues and Enables Selective Tumor Targeting," Cancer Cell 35(3):489-503.e8, Cell Press, United States (Mar. 2019).

Stoddard, B.L., "Homing Endonuclease Structure and Function," Quarterly Reviews of Biophysics 38(1):49-95, Cambridge Univ Press, England (Feb. 2005).

Sturm, G., et al., "Comprehensive Evaluation of Transcriptome-based Cell-type Quantification Methods for Immuno-oncology," Bioinformatics 35(14):i436-i445, Oxford University Press, England (Jul. 2019).

Sukumar, M., et al., "Inhibiting Glycolytic Metabolism Enhances CD8 T Cell Memory and Antitumor Function," Journal of Clinical Investigation 1123(10):4479-4488, American Society for Clinical Investigation, United States (Oct. 2013).

Sussman, D., et al., "Isolation and Characterization of New Homing Endonuclease Specificities at Individual Target Site Positions," Journal of Molecular Biology 342(1):31-41, Elsevier, England (Sep. 2004).

Tabares, P., et al., "Human Regulatory T Cells Are Selectively Activated by Low-dose Application of the CD28 Superagonist TGN1412/TAB08," European Journal of Immunology 44(4):1225-1236, Wiley-VCH, Germany (Apr. 2014).

Taniuchi, I., "CD4 Helper and CD8 Cytotoxic T Cell Differentiation," Annual Review of Analytical Chemistry 36:579-601, Annual Reviews Inc, United States (Apr. 2018).

Tirosh, I., et al., "Dissecting the Multicellular Ecosystem of Metastatic Melanoma by Single-cell RNA-seq," Science 352(6282):189-196, American Association for the Advancement of Science, United States (Apr. 2016).

Torre, L.A., et al., "Ovarian Cancer Statistics, 2018," CA: A Cancer Journal for Clinicians 68(4):284-296, Wiley, United States (Jul. 2018).

(56)        References Cited

OTHER PUBLICATIONS

Tsai, S.Q., et al., "CIRCLE-seq: a Highly Sensitive in Vitro Screen for Genome-wide CRISPR-Cas9 Nuclease Off-targets," Nature Methods 14(6):607-614, Nature Publishing Group, United States (Jun. 2017).

Tsuchida, C., et al., "Mitigation of Chromosome Loss in Clinical CRISPR-Cas9-engineered T Cells," Cell 186(21):4567-4582.e20, Cell Press, United States (Oct. 2023).

Turtle, C.J., et al. "CD19 CAR-T cells of defined CD4+:CD8+ composition in adult B cell All patients," The Journal of Clinical Investigation 126(6):2123-2138, American Society for Clinical Investigation, United States (Jun. 2016).

Turtle, C.J., et al., "Immunotherapy of non-Hodgkin's lymphoma with a defined ratio of CD8+ and CD4+ CD19-specific chimeric antigen receptor-modified T cells," Science Translational Medicine 8(355):355ral16, American Association for the Advancement of Science, United States (Sep. 2016).

Vakulskas, C.A., et al., "A High-fidelity Cas9 Mutant Delivered as a Ribonucleoprotein Complex Enables Efficient Gene Editing in Human Hematopoietic Stem and Progenitor Cells," Nature Medicine 24(8):1216-1224, Nature Publishing Company, United States (Aug. 2018).

Verdun, N., et al., "Secondary Cancers after Chimeric Antigen Receptor T-Cell Therapy," The New England Journal of Medicine 390(7):584-586, Massachusetts Medical Society, United States (Feb. 2024).

Vodnala, S.K., et al., "T Cell Stemness and Dysfunction in Tumors Are Triggered by a Common Mechanism," Science 363(6434):eaau0135, 1-14, American Association for the Advancement of Science, United States (Mar. 2019).

Vogelstein, B., et al., "Cancer Genome Landscapes," Science 339(6127):1546-1558, American Association for the Advancement of Science, United States (Mar. 2013).

Walker, A.J., et al., "Tumor Antigen and Receptor Densities Regulate Efficacy of a Chimeric Antigen Receptor Targeting Anaplastic Lymphoma Kinase," Molecular Therapy 25(9):2189-2201, Cell Press, United States (Sep. 2017).

Wallen, H., et al., "Fludarabine Modulates Immune Response and Extends in Vivo Survival of Adoptively Transferred CD8 T Cells in Patients With Metastatic Melanoma," PLoS one 4(3):e4749, Public Library of Science, United States (2009).

Wang, M., et al., "Role of Tumor Microenvironment in Tumorigenesis," Journal of Cancer 8(5):761-773, Ivyspring International Publisher, Australia (Feb. 2017).

Wang, M., et al., "VLS-101, a ROR1-Targeting Antibody-Drug Conjugate, Demonstrates a Predictable Safety Profile and Clinical Efficacy in Patients with Heavily Pretreated Mantle Cell Lymphoma and Diffuse Large B-Cell Lymphoma," Blood, 136(1):13-14, 5 pages, American Society of Hematology, United States (Nov. 2020).

Wang, M., et al., "Zilovertamab Vedotin Targeting of ROR1 as Therapy for Lymphoid Cancers," NEJM Evidence 1(1):EVIDoa2100001, NEJM Group, United States (Jan. 2022).

Wen, H., et al., "Determination of the Biodistribution of Chimeric Antigen Receptor-modified T Cells Against CD19 in NSG Mice," Methods in Cell Biology 167:15-37, Academic Press, United States (2022).

Wherry, E.J., et al., "Molecular and cellular insights into T cell exhaustion," Nature Reviews Immunology 15(8):486-499, Nature Pub. Group, United Kingdom (Aug. 2015).

Wherry, E.J., and Ahmed, R., "Memory CD8 T-cell Differentiation During Viral Infection," Journal of Virology 78(11):5535-5545, American Society For Microbiology, United States (2004).

Williams, K.M., et al., "Fluticasone, Azithromycin, and Montelukast Treatment for New-Onset Bronchiolitis Obliterans Syndrome after Hematopoietic Cell Transplantation," Biology of Blood and Marrow Transplantation, 22(4):710-716, Carden Jennings Publishing, United States (Apr. 2016).

Wu, T.D., et al., "Peripheral T Cell Expansion Predicts Tumour Infiltration and Clinical Response," Nature 579(7798):274-278, Nature Publishing Group, United Kingdom (Mar. 2020).

Xu, W., et al., "CD127 Expression in Naive and Memory T Cells in HIV Patients Who Have Undergone Long-Term HAART," Laboratory Medicine 48(1):57-64, Oxford University Press, United Kingdom (Feb. 2017).

Yang, Z., et al., "Contextual Reprogramming of CAR-T Cells for Treatment of HER2 + Cancers," Journal of Translational Medicine 19(1):459, BioMed Central, England (Nov. 2021).

Yang, J., et al., "Therapeutic Potential and Challenges of Targeting Receptor Tyrosine Kinase ROR1 with Monoclonal Antibodies in B-cell Malignancies," PLoS One 6(6):e21018, Public Library of Science, United States (2011).

Yost, K.E., et al., "Clonal Replacement of Tumor-specific T Cells Following PD-1 Blockade," Nature Medicine 25(8):1251-1259, Nature Publishing Company, United States (Aug. 2019).

Yuvan, Z., et al., "Opposing roles for ATF2 and c-Fos in c-Jun-mediated neuronal apoptosis," Molecular and Cellular Biology 29(9):2431-2442, Taylor & Francis, United Kingdom (May 2009).

Zhang, D.K., et al., "Enhancing CAR-T Cell Functionality in a Patient-specific Manner," Nature Communications 14(1):506, Nature Publishing Group, United Kingdom (Jan. 2023).

Zhang, D.K.Y., et al., "Activation and Expansion of Human T Cells Using Artificial Antigen- presenting Cell Scaffolds," Nature Protocols 15(3):773-798, 29 pages, (Jan. 2020).

Zhang, H., et al., "Aging-associated HELIOS Deficiency in Naive CD4+ T Cells Alters Chromatin Remodeling and Promotes Effector Cell Responses," Nature Immunology 24(1):96-109, Nature America Inc., United States (Jan. 2023).

Zhang, L., et al., "Lineage Tracking Reveals Dynamic Relationships of T Cells in Colorectal Cancer," Nature 564(7735):268-272, Nature Publishing Group, United Kingdom (Dec. 2018).

Zhang, S., et al., "ROR1 Is Expressed in Human Breast Cancer and Associated With Enhanced Tumor-cell Growth," PLoS One 7(3):e31127, Public Library of Science, United States (2012).

Zhang, S., et al., "The Onco-Embryonic Antigen ROR1 is Expressed by a Variety of Human Cancers," American Journal of Pathology 181(6):1903-1910, Elsevier, United States (Dec. 2012).

Zhang, Z., et al., "T Cell Dysfunction and Exhaustion in Cancer," Frontiers in Cell and Developmental Biology 8:17, Frontiers Media S.A., Switzerland (Feb. 2020).

Zhao, X., et al., TCF1 in T Cell Immunity: A Broadened Frontier, Nature Reviews Immunology 22(3):147-157, Nature Pub. Group, United Kingdom (Mar. 2021).

Zheng, Y., et al., "ROR1 is a Novel Prognostic Biomarker in Patients With Lung Adenocarcinoma," Scientific Reports 10:6:36447, Nature Publishing Group, United Kingdom (Nov. 2016).

* cited by examiner

FIG. 1
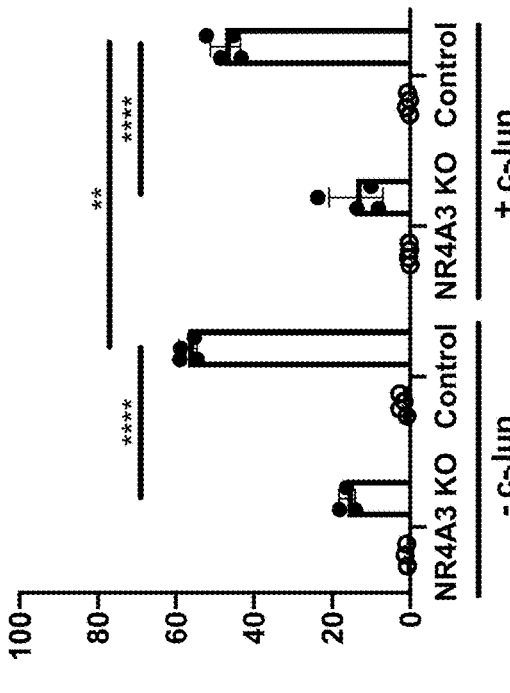
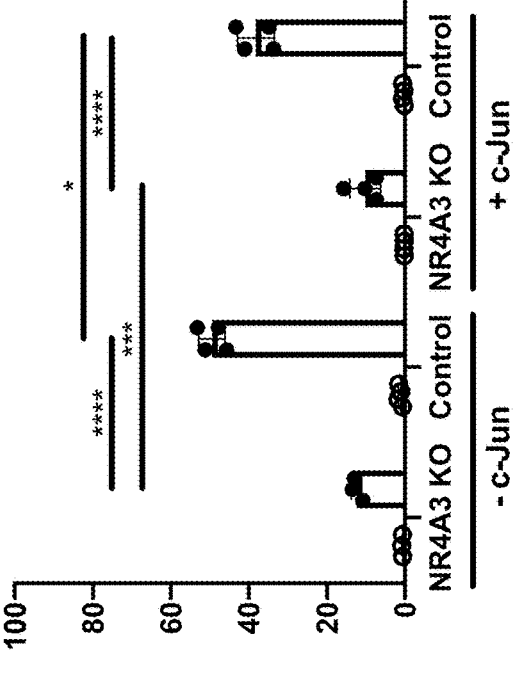

FIG. 2
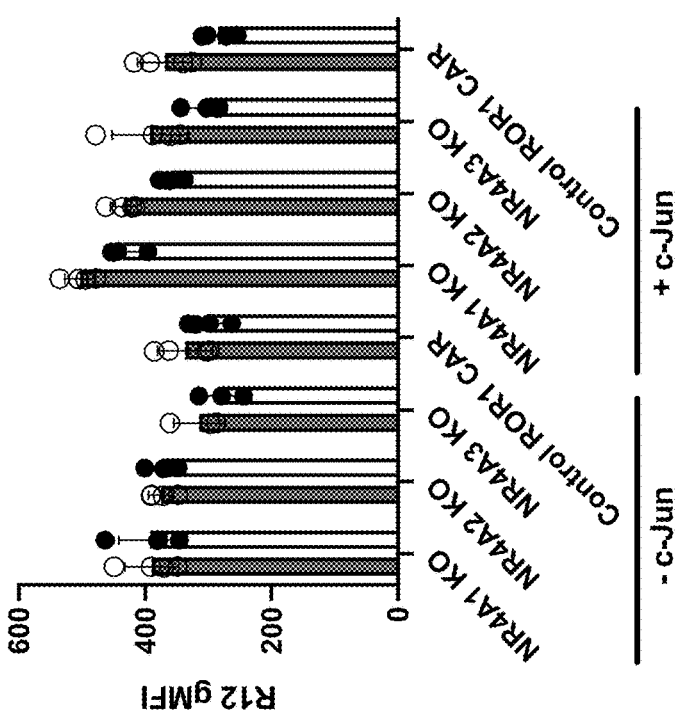
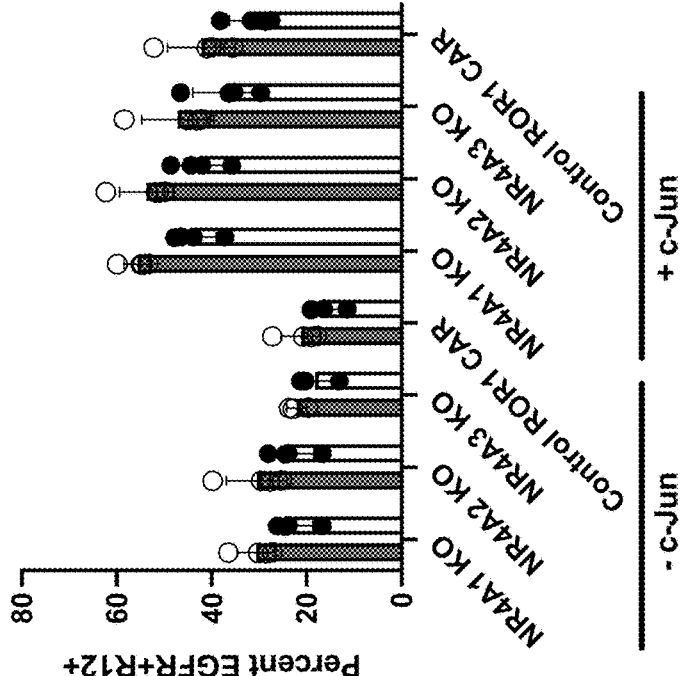

Figure 5A:
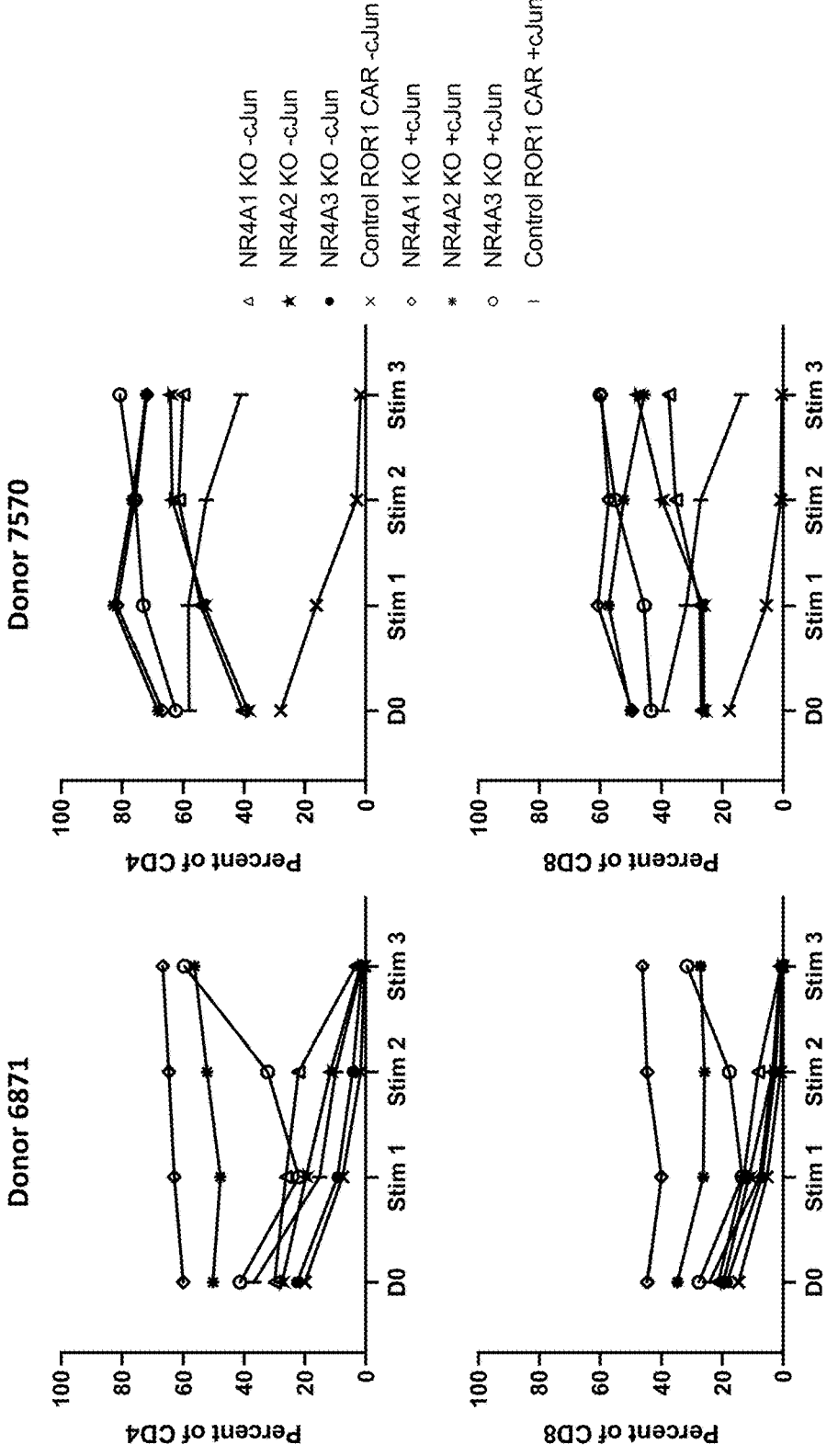

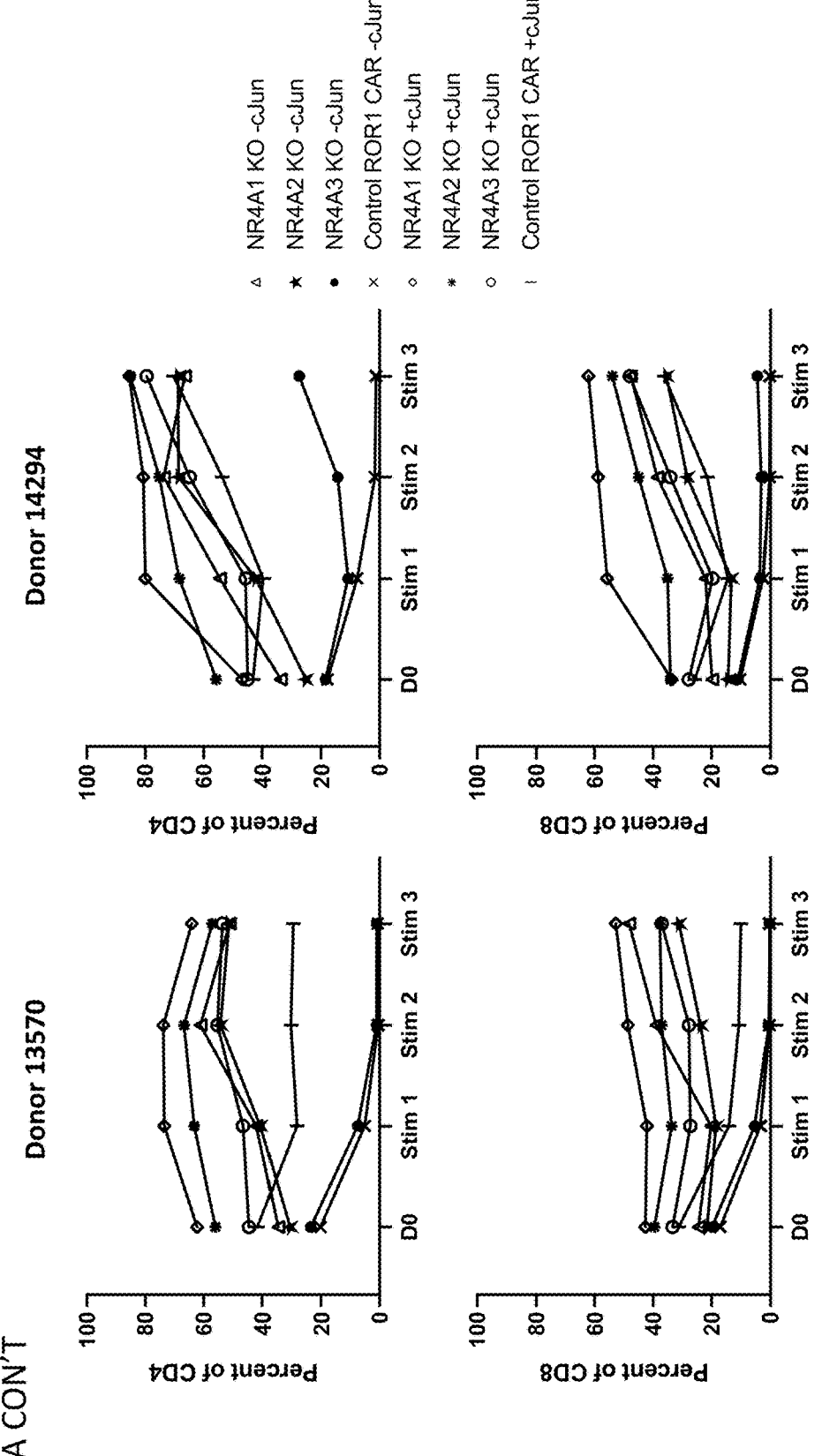
FIG. 5A CON'T

Figure 6:
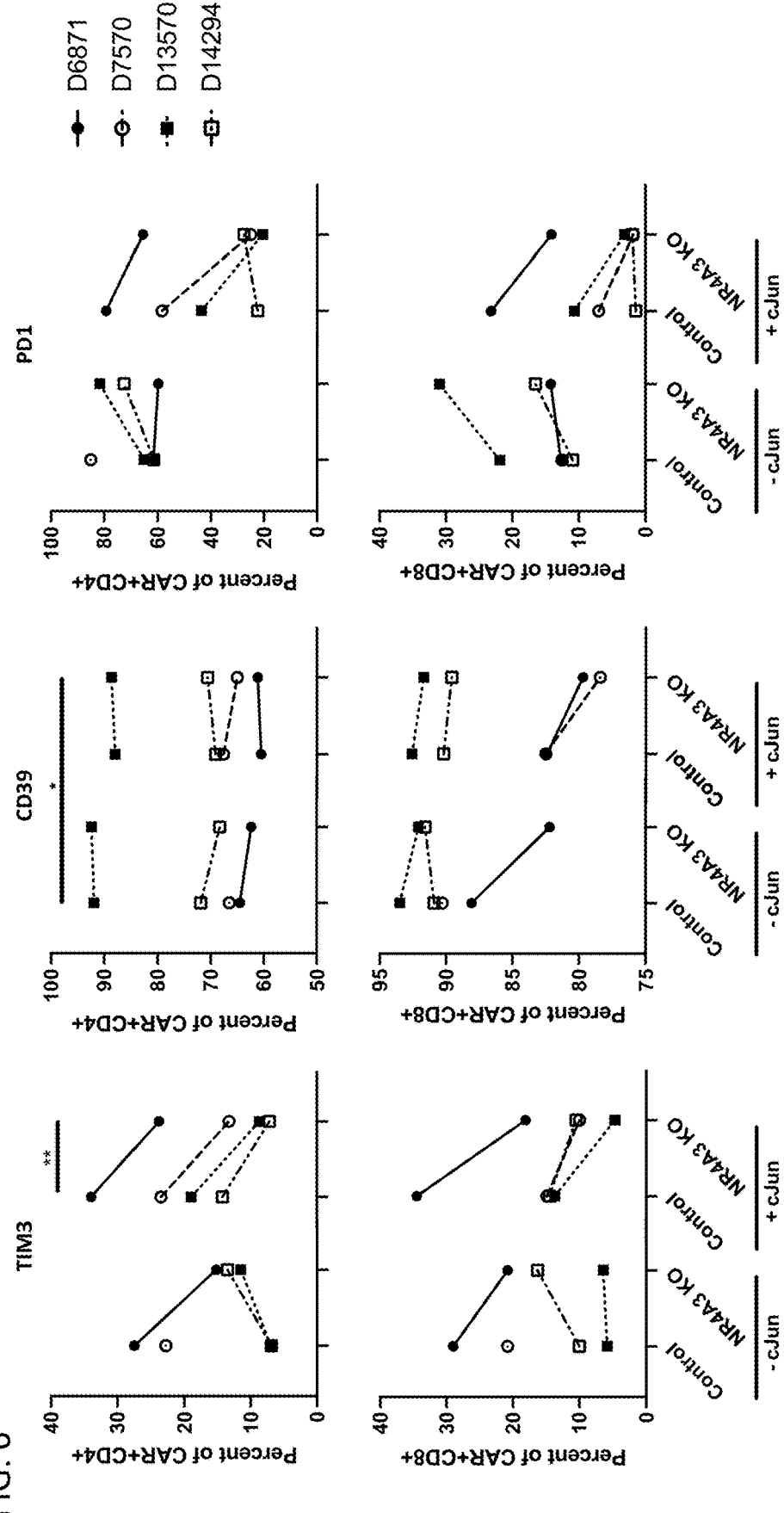

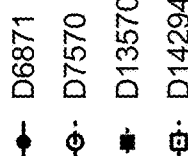
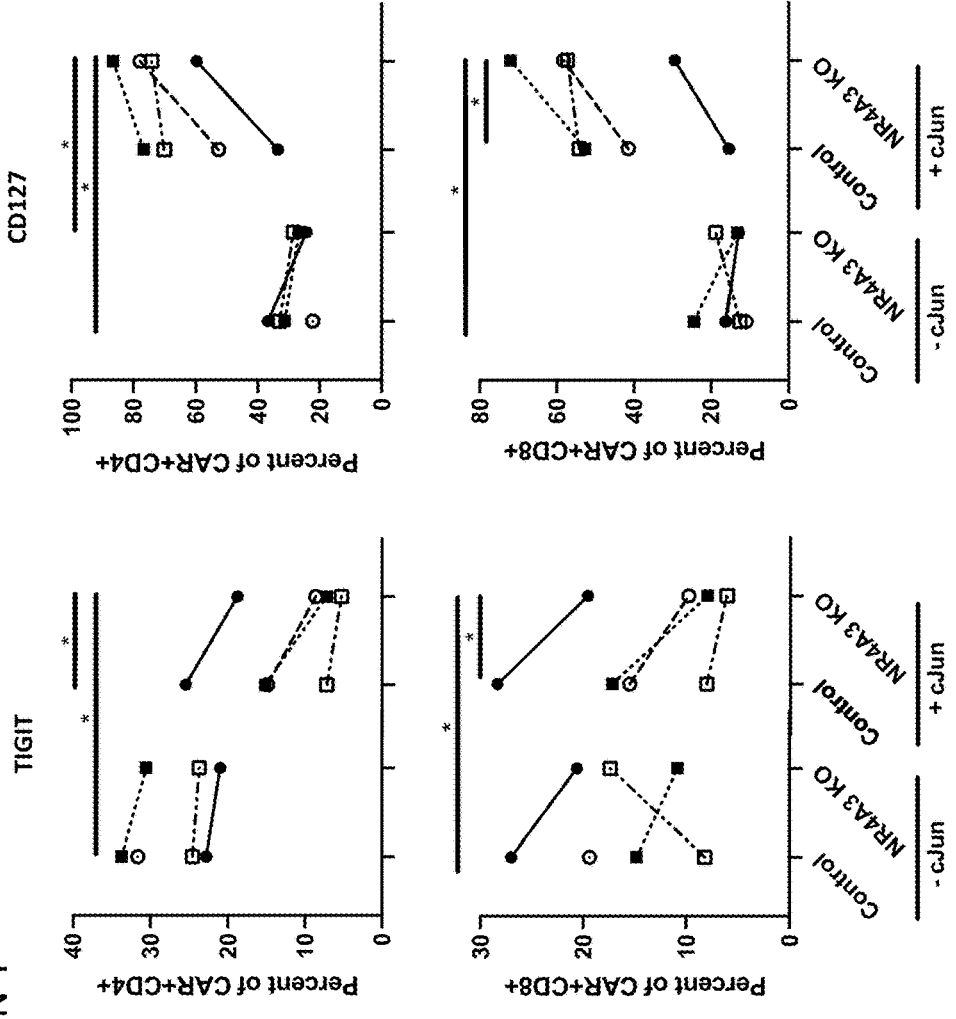
FIG. 6 CON'T

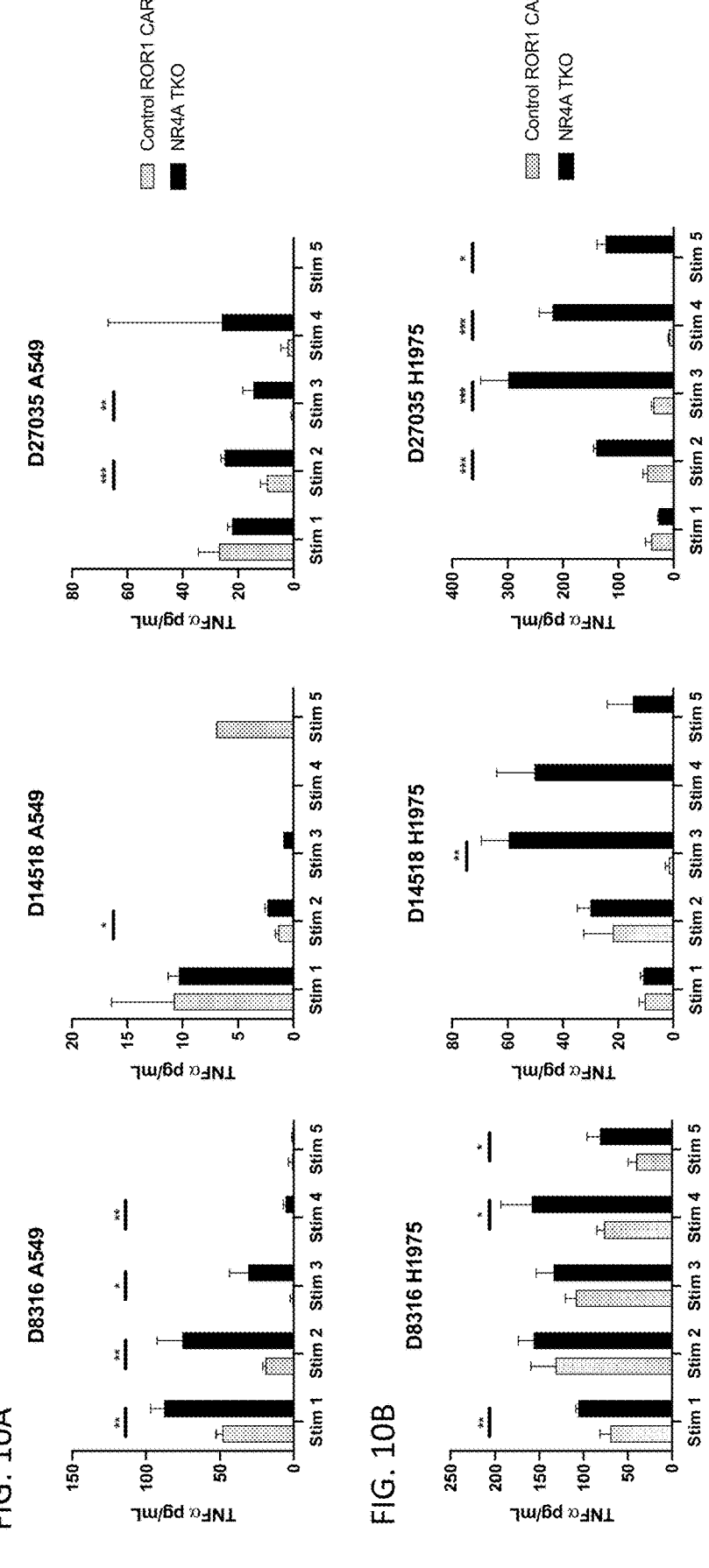

NR4A-DEFICIENT CELLS EXPRESSING C-JUN AND USES THEREOF

CROSS-REFERENCE TO RELATED APPLICATIONS

This application claims the priority benefit of U.S. Provisional Application Nos. 63/195,956, filed Jun. 2, 2021; and 63/365,023, filed May 19, 2022, each of which is herein incorporated by reference in its entirety.

REFERENCE TO SEQUENCE LISTING SUBMITTED ELECTRONICALLY VIA EFS-WEB

The content of the electronically submitted sequence listing (Name: 4385_0870003_Seglisting_ST25.txt, Size: 97,218 bytes; and Date of Creation: Jun. 1, 2022) submitted in this application is incorporated herein by reference in its entirety.

FIELD OF THE DISCLOSURE

The present disclosure is related to cell-based (e.g., T-cell) cancer immunotherapy involving the administration of immune cells modified to have reduced expression levels of a NR4A gene and/or protein and overexpression of c-Jun.

BACKGROUND OF THE DISCLOSURE

Cancer immunotherapy relies on getting T cells—the immune system's primary killers of infected and diseased cells—to attack and kill tumor cells. However, there is an important stumbling block for immunotherapy: T cells' ability to kill can fade, a phenomenon often referred to as exhaustion. Immune checkpoint blockade, chimeric antigen receptor (CAR) T cell therapy, and T cell receptor-engineered (TCR) T cell therapy are treatments that make use of functionally active T cells isolated from patients and require highly functional T cells in order to be effective. These T cells are engineered and expanded ex vivo to recognize specific antigens on target cancer cells.

When the immune system is forced to be active for extended periods, such as with persistent viral infections or the progressive development of cancer, effector T cells can become exhausted. One hallmark of exhausted T cells is the increased expression of immune checkpoint proteins like PD-1 and CTLA-4, which can cause those T cells to stand down (i.e., become non-functional). Immune checkpoint inhibitors block these checkpoint proteins and, in so doing, can increase the immune response against tumors. Some studies have suggested that blocking the activity of checkpoint proteins in exhausted T cells fails to achieve that end. This is important, because so-called hot tumors, those that include high levels of immune cells and thus should be ideal candidates to respond to immunotherapy, often harbor populations composed mostly of exhausted T cells. Moreover, tumor microenvironments can induce senescence and exhausted cellular phenotype. Therefore, devising strategies to reverse and/or prevent these exhausted states are crucial to improving immunotherapeutic efficacy.

BRIEF SUMMARY OF THE DISCLOSURE

In some aspects, the present disclosure provides a cell composition comprising a population of modified immune cells that express a reduced expression level of (i) a Nuclear Receptor Subfamily 4 Group A gene and/or protein selected from the group consisting of a NR4A Member 1 (NR4A1) gene and/or protein, a NR4A Member 2 (NR4A2) gene and/or protein, and a NR4A Member 3 (NR4A3) gene and/or protein and (ii) an increased expression level of a c-Jun protein. In some aspects, the NR4A gene and/or NR4A protein comprises a NR4A1 gene and/or NR4A1 protein. In some aspects, the NR4A gene and/or NR4A protein comprises a NR4A2 gene and/or NR4A2 protein. In some aspects, the NR4A gene and/or NR4A protein comprises a NR4A3 gene and/or NR4A3 protein. In some aspects, the NR4A gene and/or NR4A protein comprises both a NR4A1 gene and/or NR4A1 protein and a NR4A2 gene and/or NR4A2 protein. In some aspects, the NR4A gene and/or NR4A protein comprises both a NR4A1 gene and/or NR4A1 protein and a NR4A3 gene and/or NR4A3 protein. In some aspects, the NR4A gene and/or NR4A protein comprises both a NR4A2 gene and/or NR4A2 protein and a NR4A3 gene and/or NR4A3 protein. In some aspects, the NR4A gene and/or NR4A protein comprises a NR4A1 gene and/or NR4A1 protein, a NR4A2 gene and/or NR4A2 protein and a NR4A3 gene and/or NR4A3 protein.

In some aspects, the expression level of the NR4A gene and/or NR4A protein in the population of modified immune cells is reduced by at least about 5%, at least about 10%, at least about 20%, at least about 30%, at least about 40%, at least about 50%, at least about 60%, at least about 70%, at least about 80%, at least about 90%, or at least about 100% compared to a reference cell composition (e.g., corresponding cell composition wherein the cells have not been modified to express lower levels of the NR4A gene and/or NR4A protein).

In some aspects, the modified immune cells comprise lymphocytes, neutrophils, monocytes, macrophages, dendritic cells, and any combination thereof. In some aspects, the lymphocytes comprise T cells, tumor-infiltrating lymphocytes (TIL), lymphokine-activated killer cells, natural killer (NK) cells, and any combination thereof. In some aspects, the lymphocytes are T cells. In some aspects, the T cells comprise a chimeric antigen receptor (CAR) and/or a T cell receptor (TCR), e.g., engineered TCR. In some aspects, the modified immune cells comprise a CAR and/or a TCR that specifically binds to a tumor antigen. In some aspects, the CAR and/or the TCR specifically binds to CD19, TRAC, TCRβ, BCMA, CLL-1, CS1, CD38, CD19, TSHR, CD123, CD22, CD30, CD70, CD171, CD33, EGFRvIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, Mesothelin, IL-1 1Ra, PSCA, PRSS21, VEGFR2, LewisY, CD24, PDGFR-beta, SSEA-4, CD20, Folate receptor alpha, ERBB2 (Her2/neu), MUC1, MUC16, EGFR, NCAM, Prostase, PAP, ELF2M, Ephrin B2, IGF-I receptor, CAIX, LMP2, gplOO, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-la, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MARTI, Ras mutant (e.g., including KRAS, HRAS, NRAS mutant proteins), hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, or any combinations thereof.

In some aspects, the CAR and/or the TCR specifically binds to ROR1. In some aspects, the CAR comprises an antigen-binding domain derived from R12, R11, 2A2, or any combination thereof. In some aspects, the CAR comprises a heavy chain variable domain comprising SEQ ID NO: 17 and a light chain variable domain comprising SEQ ID NO: 21.

In some aspects, the population of modified immune cells has less than about 50%, less than about 40%, less than about 30%, less than about 20%, less than about 10%, or less than about 5% of effector T cells. In some aspects, the population of modified immune cells comprises at least about 50%, at least about 60%, at least about 70%, at least about 80%, at least about 90%, at least about 95%, or about 100% of naïve T (TN) cells, central memory T cells (TCM cells), stem memory T (TSCM) cells, or any combination thereof.

In some aspects, the modified immune cells have been modified with a gene editing tool to reduce the expression of a NR4A gene and/or NR4A protein. In some aspects, the gene editing tool is capable of reducing the level of (i) the NR4A1 gene and/or protein, (ii) the NR4A2 gene and/or protein, (iii) the NR4A3 gene and/or protein, or (iv) any combination thereof. In some aspects, the gene editing tool comprises a shRNA, siRNA, miRNA, antisense oligonucleotides, CRISPR, zinc finger nuclease, TALEN, meganuclease, restriction endonuclease, or any combination thereof. In some aspects, the gene editing tool is CRISPR. In some aspects, the gene editing tool comprises a guide RNA comprising, consisting of, or consisting essentially of the sequence set forth in any one of SEQ ID NO: 25, SEQ ID NO: 26, SEQ ID NO: 27, SEQ ID NO: 28, SEQ ID NO: 29, SEQ ID NO: 30, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 61, SEQ ID NO: 65, SEQ ID NO: 67, SEQ ID NO: 68, SEQ ID NO: 70, SEQ ID NO: 71, SEQ ID NO: 75, SEQ ID NO: 76, SEQ ID NO: 82, SEQ ID NO: 83, SEQ ID NO: 86, SEQ ID NO: 94, and SEQ ID NO: 96.

In some aspects, the c-Jun protein comprises an amino acid sequence having at least about 70%, at least about 80%, at least about 85%, at least about 90%, at least about 95%, at least about 96%, at least about 97%, at least about 98%, at least about 99%, or about 100% sequence identity to the amino acid sequence as set forth in SEQ ID NO: 6. In some aspects, the c-Jun protein comprises the amino acid sequence as set forth in SEQ ID NO: 6.

In some aspects, the modified immune cells described herein have been modified with a nucleotide sequence encoding the c-Jun protein, such that the modified immune cells overexpress the c-Jun protein. In some aspects, the nucleotide sequence encoding the c-Jun protein comprises: (a) a nucleic acid sequence having at least 89%, at least 90%, at least about 95%, at least about 96%, at least about 97%, at least about 98%, at least about 99%, or about 100% sequence identity to the nucleic acid sequence as set forth in SEQ ID NO: 7; (b) a nucleic acid sequence having at least 90%, at least about 95%, at least about 96%, at least about 97%, at least about 98%, at least about 99%, or about 100% sequence identity to the nucleic acid sequence as set forth in SEQ ID NO: 8; (c) a nucleic acid sequence having at least about 30%, at least about 40%, at least about 50%, at least about 60%, at least about 70%, at least about 80%, at least about 90%, at least about 95%, at least about 96%, at least about 97%, at least about 98%, at least about 99%, or about 100% sequence identity to the nucleic acid sequence as set forth in SEQ ID NO: 10; (d) a nucleic acid sequence having at least 79%, at least 80%, at least 81%, at least 82%, at least 83%, at least 84%, at least 85%, at least 86%, at least 87%, at least 88%, at least 89%, at least 90%, at least about 95%, at least about 96%, at least about 97%, at least about 98%, at least about 99%, or about 100% sequence identity to the nucleic acid sequence as set forth in SEQ ID NO: 11; (e) a nucleic acid sequence having at least 88%, at least 89%, at least 90%, at least about 95%, at least about 96%, at least about 97%, at least about 98%, at least about 99%, or about 100% sequence identity to the nucleic acid sequence as set forth in SEQ ID NO: 12; (f) a nucleic acid sequence having at least 82%, at least 83%, at least 84%, at least 85%, at least 90%, at least about 95%, at least about 96%, at least about 97%, at least about 98%, at least about 99%, or about 100% sequence identity to the nucleic acid sequence as set forth in SEQ ID NO: 13; (g) a nucleic acid sequence having at least 90%, at least about 95%, at least about 96%, at least about 97%, at least about 98%, at least about 99%, or about 100% sequence identity to the nucleic acid sequence as set forth in SEQ ID NO:14; (h) a nucleic acid sequence having at least 55%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or about 100% sequence identity to the nucleic acid sequence as set forth in SEQ ID NO: 15; or (i) a nucleic acid sequence having at least 85%, at least 86%, at least 87%, at least 88%, at least 89%, at least about 90%, at least about 95%, at least about 96%, at least about 97%, at least about 98%, at least about 99%, or about 100% sequence identity to the nucleic acid sequence as set forth in SEQ ID NO: 16.

In some aspects, a nucleotide sequence encoding the c-Jun protein comprises a nucleic acid sequence having at least 89%, at least 90%, at least about 95%, at least about 96%, at least about 97%, at least about 98%, or at least about 99% sequence identity to the nucleic acid sequence as set forth in SEQ ID NO: 7. In some aspects, a nucleotide sequence encoding the c-Jun protein comprises a nucleic acid sequence having at least 90%, at least about 95%, at least about 96%, at least about 97%, at least about 98%, or at least about 99% sequence identity to the nucleic acid sequence as set forth in SEQ ID NO: 8. In some aspects, a nucleotide sequence encoding the c-Jun protein comprises a nucleic acid sequence having at least about 30%, at least about 40%, at least about 50%, at least about 60%, at least about 70%, at least about 80%, at least about 90%, at least about 95%, at least about 96%, at least about 97%, at least about 98%, or at least about 99% sequence identity to the nucleic acid sequence as set forth in SEQ ID NO: 10. In some aspects, a nucleotide sequence encoding the c-Jun protein comprises a nucleic acid sequence having at least 79%, at least 80%, at least 81%, at least 82%, at least 83%, at least 84%, at least 85%, at least 86%, at least 87%, at least 88%, at least 89%, at least 90%, at least 95%, at least about 96%, at least about 97%, at least about 98%, or at least about 99% sequence identity to the nucleic acid sequence as set forth in SEQ ID NO: 11. In some aspects, a nucleotide sequence encoding the c-Jun protein comprises a nucleic acid sequence having at least 88%, at least 89%, at least 90%, at least about 95%, at least about 96%, at least about 97%, at least about 98%, or at least about 99% sequence identity to the nucleic acid sequence as set forth in SEQ ID NO: 12. In some aspects, a nucleotide sequence encoding the c-Jun protein comprises a nucleic acid sequence having at least 82%, at least 83%, at least 84%, at least 85%, at least 90%, at least about 95%, at least about 96%, at least about 97%, at least about 98%, or at least about 99% sequence identity to the nucleic acid sequence as set forth in SEQ ID NO: 13. In some aspects, a nucleotide sequence encoding the c-Jun protein comprises a nucleic acid sequence having at least 90%, at least about 95%, at least about 96%, at least about 97%, at least about 98%, or at least about 99% sequence identity to the nucleic acid sequence as set forth in SEQ ID NO: 14. In some aspects, a nucleotide sequence encoding the c-Jun protein comprises a nucleic acid sequence having at least 55%, at least about 55%, at least about 60%, at least about 65%, at least about 70%, at least about 75%, at least about 80%, at least about 85%, at least 90%, at least about 95%, at least about 96%, at least about 97%, at least about 98%, or at least about 99% sequence identity to the nucleic acid sequence as set forth in SEQ ID NO: 15. In some aspects, a nucleotide sequence encoding the c-Jun protein comprises a nucleic acid sequence having at least 85%, at least 86%, at least 87%, at least 88%, at least 89%, at least 90%, at least about 95%, at least about 96%, at least about 97%, at least about 98%, or at least about 99% sequence identity to the nucleic acid sequence as set forth in SEQ ID NO: 16. In some aspects, the modified immune cells have been modified with a transcriptional activator that is capable of increasing the endogenous expression of c-Jun.

In some aspects, the population of modified immune cells exhibits one or more enhanced properties in the subject compared to reference immune cells (e.g., corresponding cell that was not modified to have increased c-Jun expression and/or reduced expression of NR4A gene(s) and/or NR4A protein(s)). In some aspects, the one or more enhanced properties of the modified immune cell comprises (i) enhanced proliferation, (ii) enhanced cytotoxicity, (iii) enhanced cytokine expression, (iv) enhanced persistence, or (v) any combination thereof.

In some aspects, wherein the modified immune cells exhibit enhanced cytokine expression. In some aspects, the cytokines are Interleukin-2 (IL-2), Interferon-γ (IFN-γ), Tumor necrosis factor-α (TNF-α), or any combination thereof. In some aspects, the expression level of IL-2 is increased at least about 2 fold to at least about 10 fold compared to the expression level of IL-2 in a population of reference immune cells. In some aspects, the expression level of IFN-γ is increased at least about 2 fold to at least about 10 fold compared to the expression level of IFN-γ in a population of reference immune cells. In some aspects, the expression level of TNF-α is increased at least about 2 fold to at least about 10 fold compared to the expression level of TNF-α in a population of reference immune cells.

In some aspects, the modified immune cells exhibit reduced exhaustion or dysfunction compared to reference immune cells (e.g., corresponding cell that was not modified to have increased c-Jun expression and/or reduced expression of NR4A gene(s) and/or NR4A protein(s)). In some aspects, the modified immune cells exhibit reduced or no apoptosis (apoptosis resistant). In some aspects, the modified immune cells express reduced immune checkpoint markers (are immune checkpoint resistant). In some aspects, the modified immune cells maintain an anti-tumor function in tumor microenvironment (TME). In some aspects, the modified immune cells exhibit (i) enhanced activity in low oxygen environment, (ii) enhanced activity in low nutrition environment (i.e., glucose), (iii) enhanced activity in presence of suppressive metabolite/cytokine (e.g., Adenosine, TGF-β, ROS etc), (iv) enhanced activity when exposed to suppressive cells (e.g., MDSC, Treg, etc.), or (v) any combination thereof.

In some aspects, the present disclosure provides a pharmaceutical composition comprising the population of modified immune cells described herein and a pharmaceutically acceptable carrier.

In some aspects, the present disclosure provides a method of treating a tumor in a subject in need thereof, comprising administering to the subject the cell compositions or pharmaceutical compositions described herein. In some aspects, the administering reduces a tumor volume in the subject, compared to a reference tumor volume (e.g., tumor volume in the subject prior to the administration and/or tumor volume in a subject that did not receive the administration). In some aspects, the tumor volume is reduced by at least about 5%, at least about 10%, at least about 20%, at least about 30%, at least about 40%, at least about 50%, at least about 60%, at least about 70%, at least about 80%, at least about 90%, or at least about 100% after the administration compared to the reference tumor volume (e.g., the tumor volume in the subject prior to the administration and/or tumor volume in a subject that did not receive the administration). In some aspects, the administering reduces a tumor weight in the subject, compared to a reference tumor weight (e.g., tumor weight in the subject prior to the administration and/or tumor weight in a subject that did not receive the administration). In some aspects, the tumor weight is reduced by at least about 5%, at least about 10%, at least about 20%, at least about 30%, at least about 40%, at least about 50%, at least about 60%, at least about 70%, at least about 80%, at least about 90%, or at least about 100% after the administration compared to the reference tumor weight (e.g., tumor weight in the subject prior to the administration and/or tumor weight in a subject that did not receive the administration).

In some aspects, the administering enhances one or more properties of the immune cells in the subject. In some aspects, the enhanced properties of the immune cells comprise (i) enhanced proliferation, (ii) enhanced cytotoxicity, (iii) enhanced cytokine expression, (iv) enhanced persistence, or (v) any combination thereof. In some aspects, the administering enhances cytokine expression. In some aspects, the cytokine comprises IL-2, IFN-γ, TNF-α, or any combination thereof. In some aspects, the administering reduces or prevents exhaustion or dysfunction of the immune cells. In some aspects, the immune cells exhibit reduced or no apoptosis (apoptosis resistant). In some aspects, the immune cells exhibit reduced or no immune checkpoint markers (are immune checkpoint resistant). In some aspects, the immune cells maintain an anti-tumor function in tumor microenvironment (TME). In some aspects, the immune cells exhibit (i) enhanced activity in low oxygen environment, (ii) enhanced activity in low nutrition environment (i.e., glucose), (iii) enhanced activity in presence of suppressive metabolite/cytokine resistant (Adenosine, TGF-β, ROS etc), (iv) enhanced activity when exposed to suppressive cells (MDSC, Treg, etc.), or any combination thereof.

In some aspects, the tumor is derived from a cancer comprising a breast cancer, head and neck cancer, uterine cancer, brain cancer, skin cancer, renal cancer, lung cancer, colorectal cancer, prostate cancer, liver cancer, bladder cancer, kidney cancer, pancreatic cancer, thyroid cancer, esophageal cancer, eye cancer, stomach (gastric) cancer, gastrointestinal cancer, ovarian cancer, cervical cancer, carcinoma, sarcoma, leukemia, lymphoma, myeloma, or a combination thereof.

In some aspects, the method comprises administering an additional therapeutic agent to the subject. In some aspects, the additional therapeutic agent comprises a chemotherapeutic drug, targeted anti-cancer therapy, oncolytic drug, cytotoxic agent, immune-based therapy, cytokine, surgical procedure, radiation procedure, activator of a costimulatory molecule, immune checkpoint inhibitor, a vaccine, a cellular immunotherapy, or any combination thereof. In some aspects, the additional therapeutic agent is an immune checkpoint inhibitor. In some aspects, the immune checkpoint inhibitor comprises an anti-PD-1 antibody, an anti-PD-L1 antibody, an anti-LAG-3 antibody, an anti-CTLA-4 antibody, an anti-GITR antibody, an anti-TIM3 antibody, and any combination thereof.

In some aspects, the additional therapeutic agent and the cell composition are administered concurrently. In some aspects, wherein the additional therapeutic agent and the cell composition are administered sequentially. In some aspects, the cell composition are administered parenterally, intramuscularly, subcutaneously, ophthalmic, intravenously, intraperitoneally, intradermally, intraorbitally, intracerebrally, intracranially, intraspinally, intraventricular, intrathecally, intracisternally, intracapsularly, intratumorally, or any combination thereof.

In some aspects, the present disclosure provides a method of preparing the immune cell (or cell composition) described herein, comprising modifying the cells with a gene editing tool, wherein the gene editing tool reduces the expression of any one of the NR4A genes and/or NR4A proteins and modifying the immune cells to overexpress c-Jun. In some aspects, modifying the immune cells to overexpress c-Jun comprises contacting the immune cells with a nucleotide sequence encoding a c-Jun protein. In some aspects, modifying the immune cells to overexpress c-Jun comprises contacting the immune cells with a transcriptional activator that is capable of increasing the expression of the endogenous c-Jun protein. In some aspects, the transcriptional activator is attached to a Cas protein, which has been modified to lack endonuclease activity.

Also provided herein is a method of producing a cell that overexpresses a c-Jun protein and has reduced level of a NR4A gene and/or NR4A protein, comprising modifying the cell with (i) a nucleotide sequence encoding a c-Jun protein and (ii) a gene editing tool, wherein the gene editing tool comprises a guide RNA (gRNA) and is capable of reducing the expression the NR4A gene and/or NR4A protein, and wherein the gRNA comprises, consists essentially of, or consists of the sequence set forth in any one of SEQ ID NO: 25, SEQ ID NO: 26, SEQ ID NO: 27, SEQ ID NO: 28, SEQ ID NO: 29, SEQ ID NO: 30, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 61, SEQ ID NO: 65, SEQ ID NO: 67, SEQ ID NO: 68, SEQ ID NO: 70, SEQ ID NO: 71, SEQ ID NO: 75, SEQ ID NO: 76, SEQ ID NO: 82, SEQ ID NO: 83, SEQ ID NO: 86, SEQ ID NO: 94, and SEQ ID NO: 96.

In some aspects, the present disclosure provides a method of reducing or inhibiting exhaustion of cells expressing a chimeric antigen receptor (CAR) or a T cell receptor (TCR), comprising modifying the cells to reduce the expression level of a NR4A gene and/or protein and modifying the cells to overexpress a c-Jun protein. In some aspects, the NR4A gene and/or NR4A protein comprises NR4A1 gene and/or NR4A1 protein. In some aspects, the NR4A gene and/or NR4A protein comprises NR4A2 gene and/or NR4A2 protein. In some aspects, the NR4A gene and/or NR4A protein comprises NR4A3 gene and/or NR4A3 protein. In some aspects, the reduced expression of the NR4A gene and/or protein reduces or inhibits exhaustion of the cells.

In some aspects, the cells are immune cells. In some aspects, the expression level of the NR4A gene and/or protein in the cells is reduced by at least about 5%, at least about 10%, at least about 20%, at least about 30%, at least about 40%, at least about 50%, at least about 60%, at least about 70%, at least about 80%, at least about 90%, or at least about 100% compared to a reference cell composition (e.g., corresponding cell composition wherein the cells have not been modified to express lower levels of the NR4A gene and/or NR4A protein).

In some aspects, modifying the cells comprises contacting the cell with a gene editing tool that is capable of reducing the expression levels of the NR4A gene and/or protein in the cell. In some aspects, modifying the cells to overexpress a c-Jun protein comprises contacting the immune cells with a nucleotide sequence encoding a c-Jun protein. In some aspects, modifying the immune cells to overexpress c-Jun comprises contacting the immune cells with a transcriptional activator that is capable of increasing the expression of the endogenous c-Jun protein. In some aspects, the transcriptional activator is attached to a Cas protein, which has been modified to lack endonuclease activity.

In some aspects, the present disclosure further provides a method of increasing the production of a cytokine by a cell expressing a chimeric antigen receptor (CAR) or a T cell receptor (TCR) in response to an antigen stimulation, comprising modifying the cells with (i) a nucleotide sequence encoding a c-Jun protein, such that the cell overexpresses the c-Jun protein after the modification, and (ii) a gene editing tool, wherein the gene editing tool comprises a guide RNA (gRNA) and is capable of reducing the expression the NR4A gene and/or NR4A protein, and wherein the gRNA comprises, consists essentially of, or consists of the sequence set forth in any one of SEQ ID NO: 25, SEQ ID NO: 26, SEQ ID NO: 27, SEQ ID NO: 28, SEQ ID NO: 29, SEQ ID NO: 30, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 61, SEQ ID NO: 65, SEQ ID NO: 67, SEQ ID NO: 68, SEQ ID NO: 70, SEQ ID NO: 71, SEQ ID NO: 75, SEQ ID NO: 76, SEQ ID NO: 82, SEQ ID NO: 83, SEQ ID NO: 86, SEQ ID NO: 94, and SEQ ID NO: 96.

In some aspects, the cytokine comprises IFN-γ, IL-2, TNF-α, or a combination thereof. In some aspects, after the modification, the production of the cytokine in response to the antigen stimulation is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, or at least about 50-fold, compared to a reference cell (e.g., corresponding cell which was not modified with the c-Jun nucleotide sequence and/or gene editing tool).

Present disclosure also provides a method of increasing an effector function of a cell expressing a chimeric antigen receptor (CAR) or a T cell receptor (TCR) in response to persistent antigen stimulation, comprising modifying the cells with (i) a nucleotide sequence encoding a c-Jun protein, such that the cell overexpresses the c-Jun protein after the modification, and (ii) a gene editing tool, wherein the gene editing tool comprises a guide RNA (gRNA) and is capable of reducing the expression the NR4A gene and/or NR4A protein, and wherein the gRNA comprises, consists essentially of, or consists of the sequence set forth in any one of SEQ ID NO: 25, SEQ ID NO: 26, SEQ ID NO: 27, SEQ ID NO: 28, SEQ ID NO: 29, SEQ ID NO: 30, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 61, SEQ ID NO: 65, SEQ ID NO: 67, SEQ ID NO: 68, SEQ ID NO: 70, SEQ ID NO: 71, SEQ ID NO: 75, SEQ ID NO: 76, SEQ ID NO: 82, SEQ ID NO: 83, SEQ ID NO: 86, SEQ ID NO: 94, and SEQ ID NO: 96.

In some aspects, after the modification, the cell retains the effector function for at least one, at least two, or at least three additional rounds of an antigen stimulation assay, as compared to a reference cell (e.g., corresponding cell which was not modified with the c-Jun nucleotide sequence and/or gene editing tool). In some aspects, the effector function comprises the ability: (i) to kill target cells (e.g., tumor cells) (ii) to produce a cytokine upon further antigen stimulation, or (iii) both (i) and (ii).

In some aspects, the present disclosure provides a cell composition prepared by the methods described herein. In some aspects, provided herein is a cell composition comprising a cell which (a) expresses a ligand binding protein (e.g., CAR or TCR), (b) has an increased level of a c-Jun protein, and (b) expresses a reduced level of a (i) NR4A1 gene and/or NR4A1 protein, (ii) NR4A2 gene and/or NR4A2 protein, (iii) NR4A3 gene and/or NR4A3 protein, or (iv) any combination of (i) to (iii), wherein the cell has been modified with a gRNA comprising, consisting of, or consisting essentially of the sequence set forth in any one of set forth in any one of SEQ ID NO: 25, SEQ ID NO: 26, SEQ ID NO: 27, SEQ ID NO: 28, SEQ ID NO: 29, SEQ ID NO: 30, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 61, SEQ ID NO: 65, SEQ ID NO: 67, SEQ ID NO: 68, SEQ ID NO: 70, SEQ ID NO: 71, SEQ ID NO: 75, SEQ ID NO: 76, SEQ ID NO: 82, SEQ ID NO: 83, SEQ ID NO: 86, SEQ ID NO: 94, and SEQ ID NO: 96. In some aspects, the cell composition is an in vivo cell. In some aspects, the cell is an ex vivo cell or an in vitro cell. In some aspects, a pharmaceutical composition comprises the cells.

In some aspects, the present disclosure provides a kit comprising (i) a gene editing tool to reduce the expression of a NR4A gene and/or protein, (ii) a vector comprising a chimeric antigen receptor (CAR) or a T cell receptor (TCR), (iii) a nucleotide sequence encoding a c-Jun protein, and instructions for treating tumor according to the methods described herein. In some aspects, a kit comprising (i) a gene editing tool to reduce the expression of a NR4A gene and/or protein, (ii) a vector comprising a chimeric antigen receptor (CAR) or a T cell receptor (TCR), (iii) a nucleotide sequence encoding a c-Jun protein and instructions for preparing a cell composition according to the methods described herein.

In some aspects, the present disclosure provides use of the cell compositions or pharmaceutical compositions described herein for the manufacture of a medicament in treating a tumor in a subject in need hereof, comprising administering to the subject.

In some aspects, the present disclosure provides a cell composition of pharmaceutical composition described herein for treating a tumor in a subject in need thereof, comprising administering to the subject.

BRIEF DESCRIPTION OF THE DRAWINGS/FIGURES

FIG. 1 shows the percentage of NR4A3 expression in NR4A3-edited ("NR4A3 KO") and control non edited CD4$^+$ (left) and CD8$^+$ (right) ROR1 CAR T cells with ("+ c-Jun") or without c-Jun ("− c-Jun") overexpression on day 7 of CAR T cell production following a 2-hour CD3/CD28 Dynabead stimulation in four independent donors (Stim, filled circles). Unstim cells (opened circles, without Dynabeads) were used as a negative control. Unpaired t-test of stimulated conditions was used for statistical analysis. *$p<0.05$, $p<0.005$, *$p<0.001$, ****$p<0.0001$.

FIG. 2 shows the percentage of EGFR$^+$R12$^+$ ROR1 CAR expression (left) and geometric mean fluorescence of ROR1 CAR on EGFR$^+$R12$^+$ T cells (right) in NR4A1- ("NR4A1 KO"), NR4A2- ("NR4A2 KO"), NR4A3-edited ("NR4A3 KO"), and control non-edited CD4+(open circle) and CD8$^+$ (closed circle) ROR1 CAR T cells with or without c-Jun overexpression from four donors on day 7 of CAR T cell production. Unpaired t-test of stimulated conditions were used for statistical analysis and was not significant.

Figure 4A:
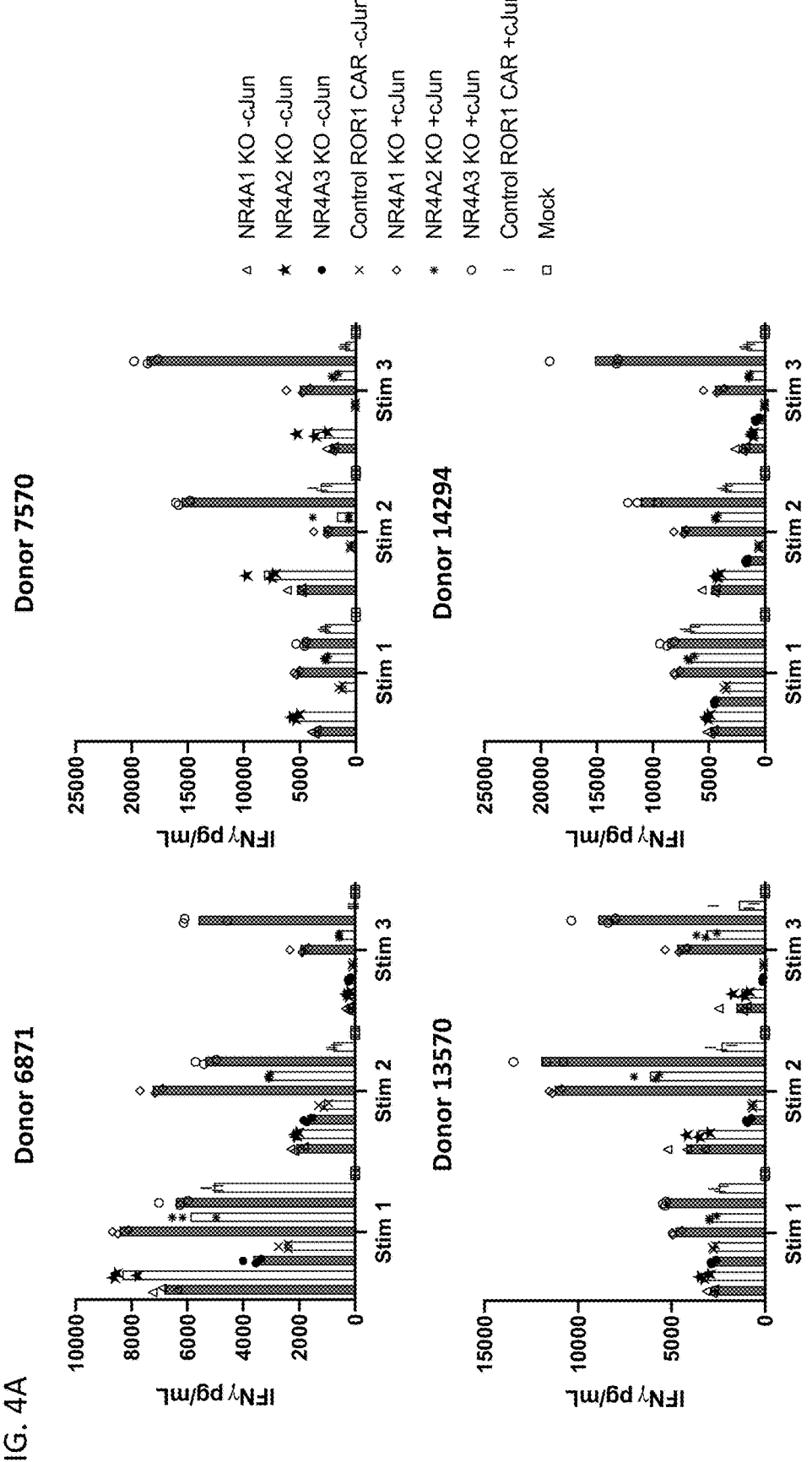
Figure 4B:
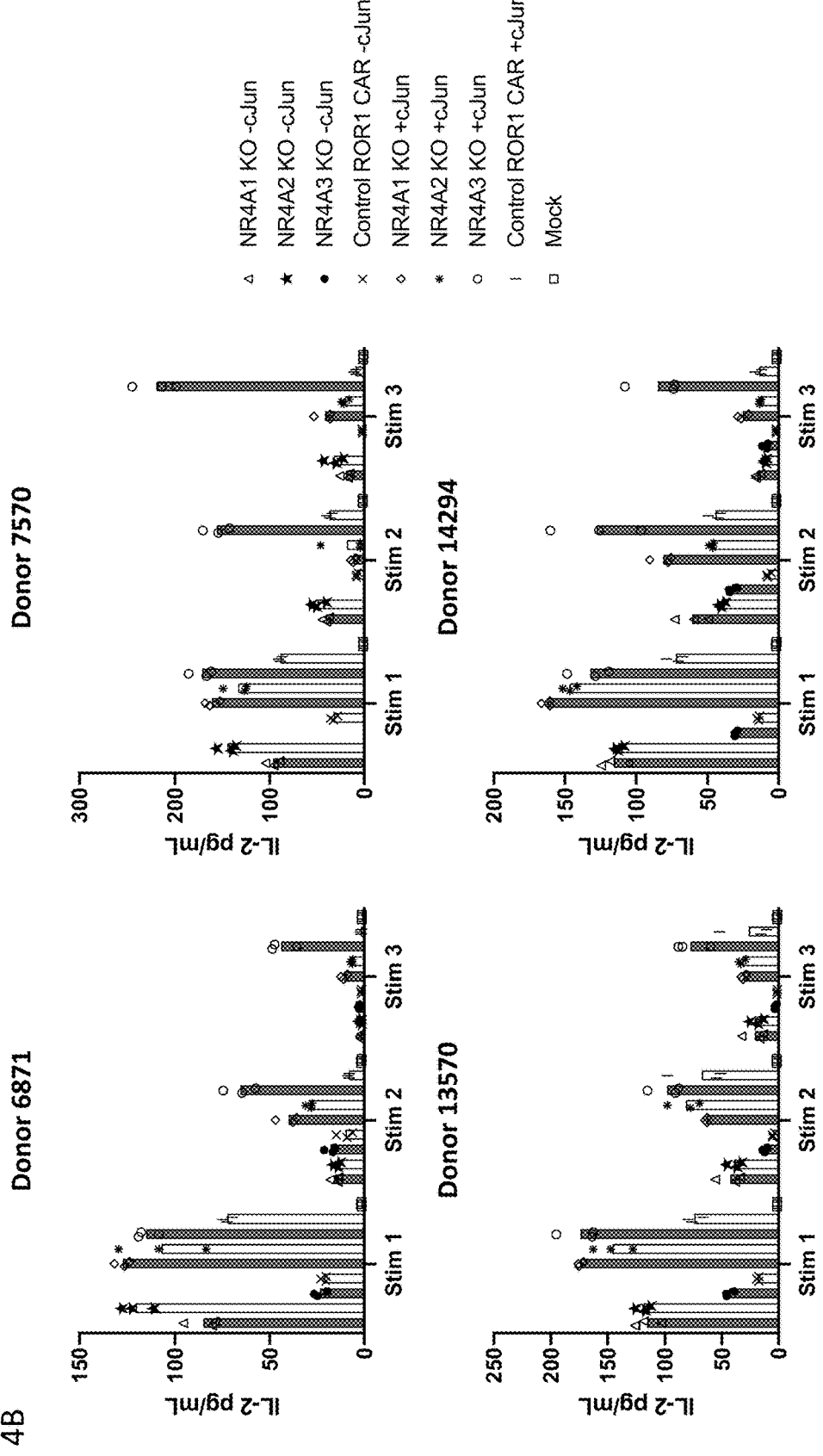
Figure 4C:
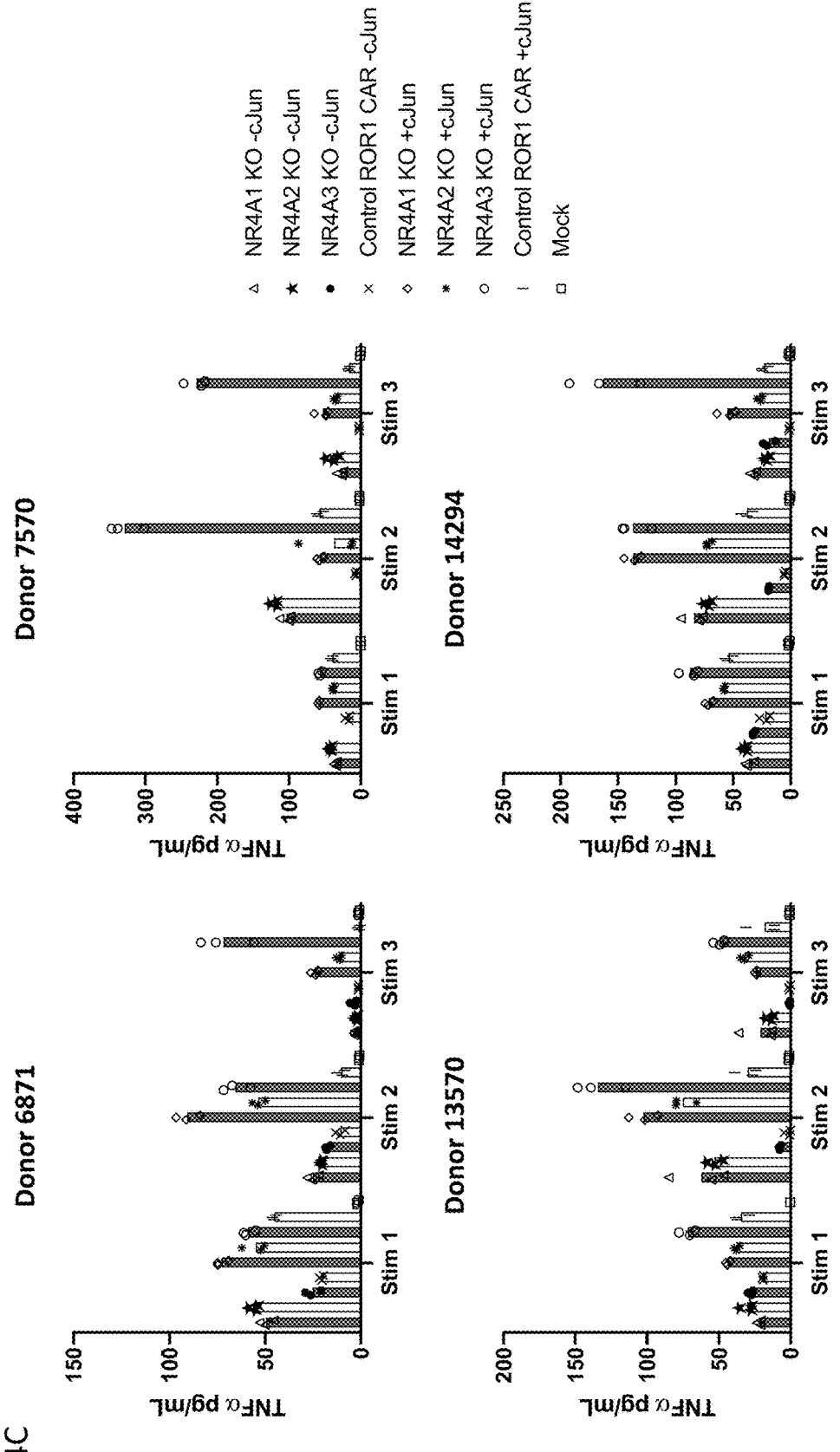

FIG. 3 shows successive anti-ROR1 lysis of H1975-NLR NSCLC cells by NR4A-edited, control non-edited ROR1 CAR T cells with or without c-Jun overexpression, and mock untransduced T cells in four independent donors in the sequential stimulation assay. The different groups shown include: (a) NR4A1 knockout without c-Jun overexpression (triangle), (b) NR4A2 knockout without c-Jun overexpression (star), (c) NR4A3 knockout without c-Jun overexpression (black circle), (d) control non-edited ROR1 CAR T cell without c-Jun overexpression (x symbol), (e) NR4A1 knockout with c-Jun overexpression (diamond), (f) NR4A2 knockout with c-Jun overexpression (asterisk), (g) NR4A3 knockout with c-Jun overexpression (open circle), (h) control non-edited ROR1 CAR T cell with c-Jun overexpression (vertical line), and (i) nontransduced mock T cells (square). Lysis of H1975-NLR target cells were quantified by measuring total NLR intensity. NLR intensity was normalized relative to the starting intensity after replating for each round of stimulation. NLR—NucLight Red. Each graph shows data from four independent donors FIGS. 4A-4C show secreted interferon-gamma (IFN-γ) (FIG. 4A), interleukin-2 (IL-2) (FIG. 4B), and tumor-necrosis factor-alpha (TNF-α) (FIG. 4C) produced from NR4A-edited, control non-edited ROR1 CAR T cells with or without c-Jun overexpression, and mock untransduced T cells during the H1975 sequential stimulation assay corresponding to FIG. 3. The different groups shown are the same as in FIG. 3. Supernatants were collected 24 hours after each replating and cytokines were quantified by MSD. Graphs show data from 4 independent donors. Error bars represent mean+/−SD of triplicate wells.

FIG. 5A shows the percentage of ROR1 CAR expression of ROR1 CAR on EGFR$^+$R12$^+$ CD4$^+$ (upper) and CD8$^+$ (lower) T cells from NR4A-edited and control non-edited ROR1 CAR T cells with or without c-Jun overexpression after each replating during the H1975 sequential stimulation assay corresponding to FIG. 3. The different groups shown include: (a) NR4A1 knockout without c-Jun overexpression (triangle), (b) NR4A2 knockout without c-Jun overexpression (star), (c) NR4A3 knockout without c-Jun overexpression (black circle), (d) control non-edited ROR1 CAR T cell without c-Jun overexpression (x symbol), (e) NR4A1 knockout with c-Jun overexpression (diamond), (f) NR4A2 knockout with c-Jun overexpression (asterisk), (g) NR4A3 knockout with c-Jun overexpression (open circle), and (h) control non-edited ROR1 CAR T cell with c-Jun overexpression (vertical line).

Figure 5B:
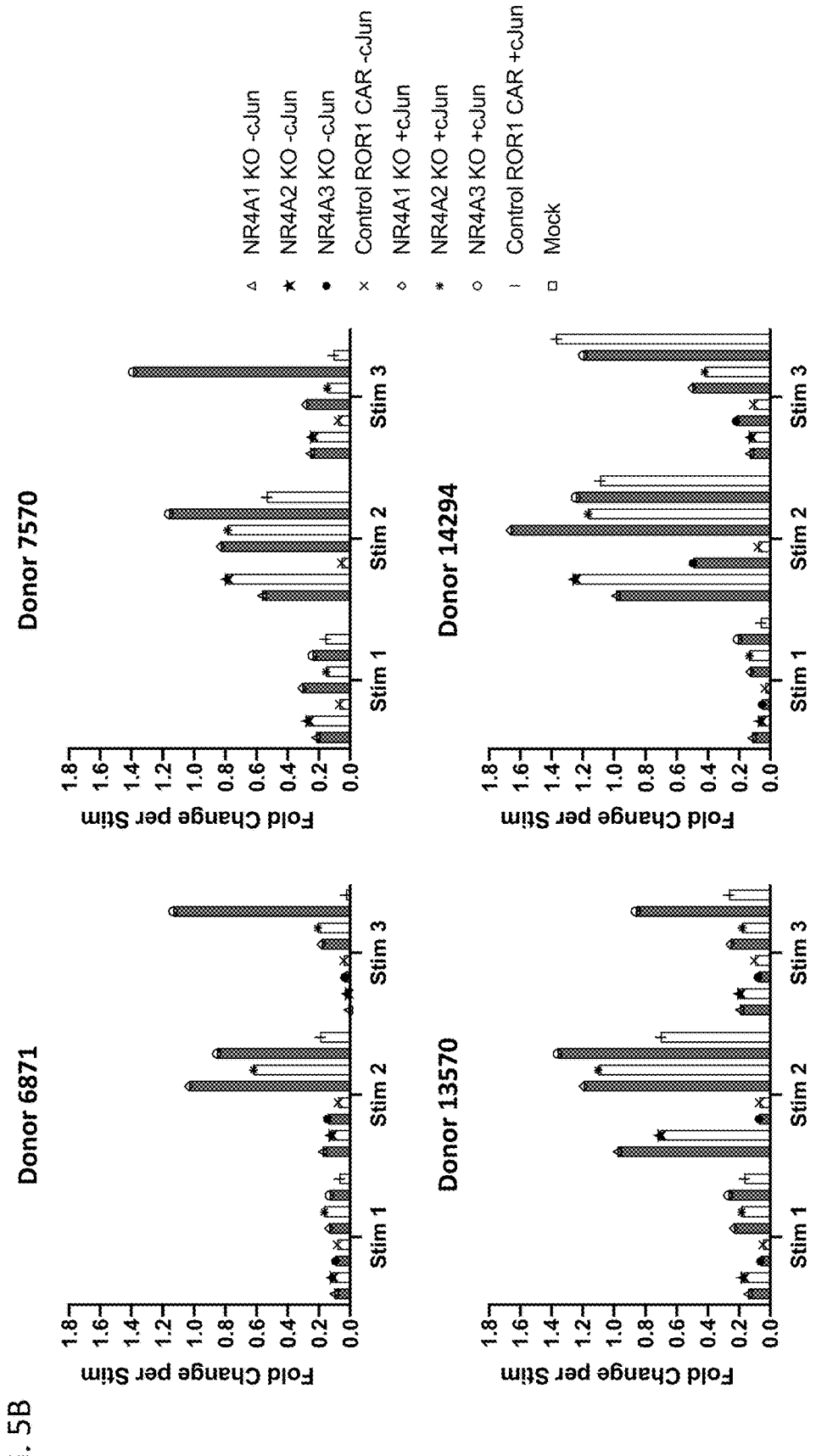

FIG. 5B shows fold change in projected CD3$^+$ROR1 CAR$^+$ T cell numbers from NR4A-edited and control non-edited ROR1 CAR T cells with or without c-Jun overexpression during the H1975 sequential stimulation assay corresponding to FIG. 3. Projected cell numbers were calculated to include the 25% transfer of the cells to the next stimulation. Fold change was calculated as (projected cell numbers from stimulation/projected cell numbers from previous stimulation). Graphs show data from four independent donors. The groups shown are the same as in FIG. 3.

FIG. 6 shows expression of inhibitory receptors (TIM3, CD39, and PD1) on ROR1 CAR$^+$ CD4$^+$ (upper) and CD8$^+$ (lower) T cells from NR4A3-edited ("NR4A3 KO") and control non-edited ROR1 CAR T cells with ("+ cJun") or without ("– cJun") c-Jun overexpression from the H1975 sequential stimulation assay corresponding to the second stimulation in FIG. 3. Paired t-test was used for statistical analysis. *p<0.05, ** p<0.005. n=4 independent donors.

Figures 7A, 7B:
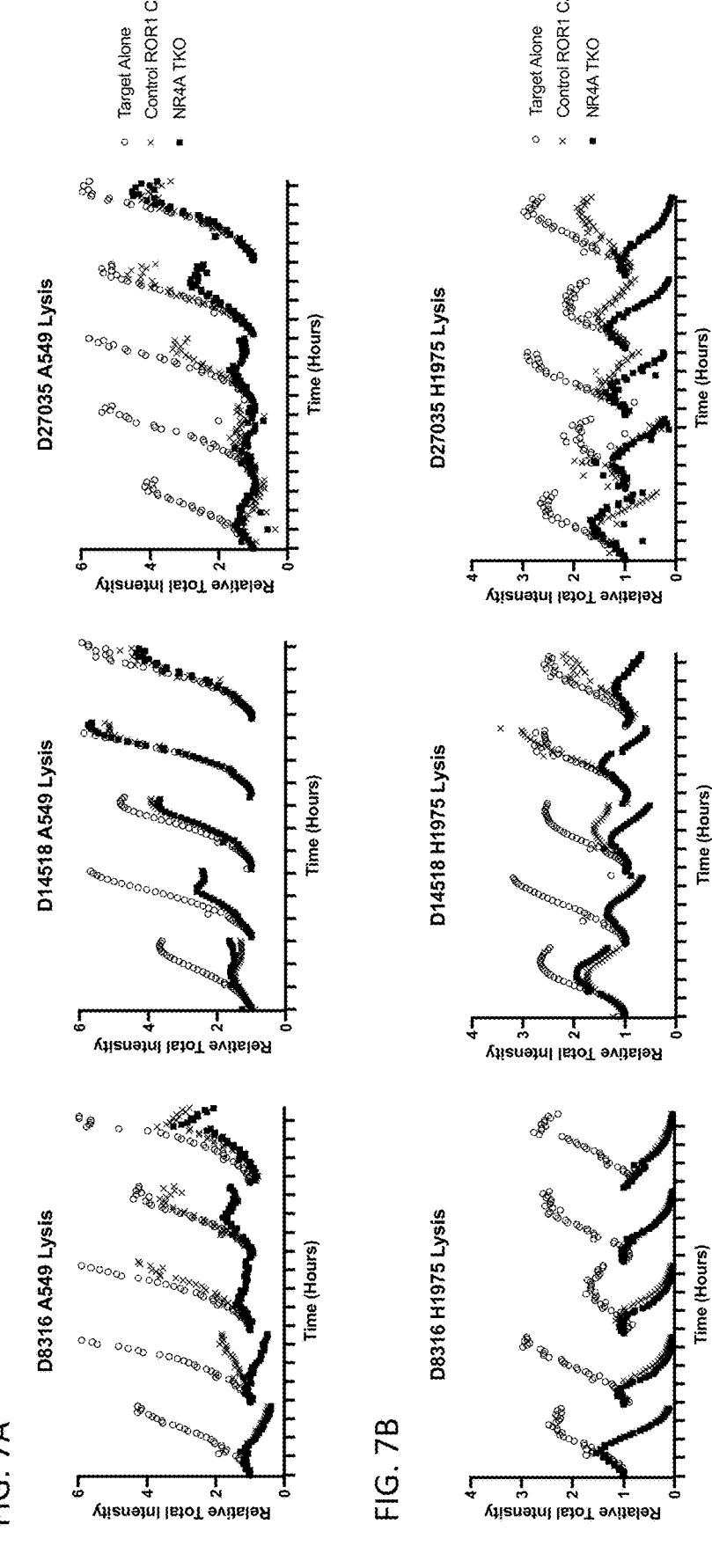

FIGS. 7A and 7B show successive lysis of A549-NLR and H1975-NLR cells, respectively, by anti-ROR1 CAR T cells overexpressing c-Jun and modified to have reduced levels of NR4A1, NR4A2, and NR4A3 (triple KO, NR4A TKO). Anti-ROR1 CAR T cells overexpressing c-Jun without editing ("Control ROR1 CAR", containing endogenous levels of NR4A1, NR4A2, and NR4A3) and untreated target cells ("Target Alone") are shown as controls. Lysis of target cells were quantified by measuring total NLR intensity. NLR intensity was normalized relative to the starting intensity after replating for each round of stimulation. NLR—NucLight Red.

Figures 8A, 8B:
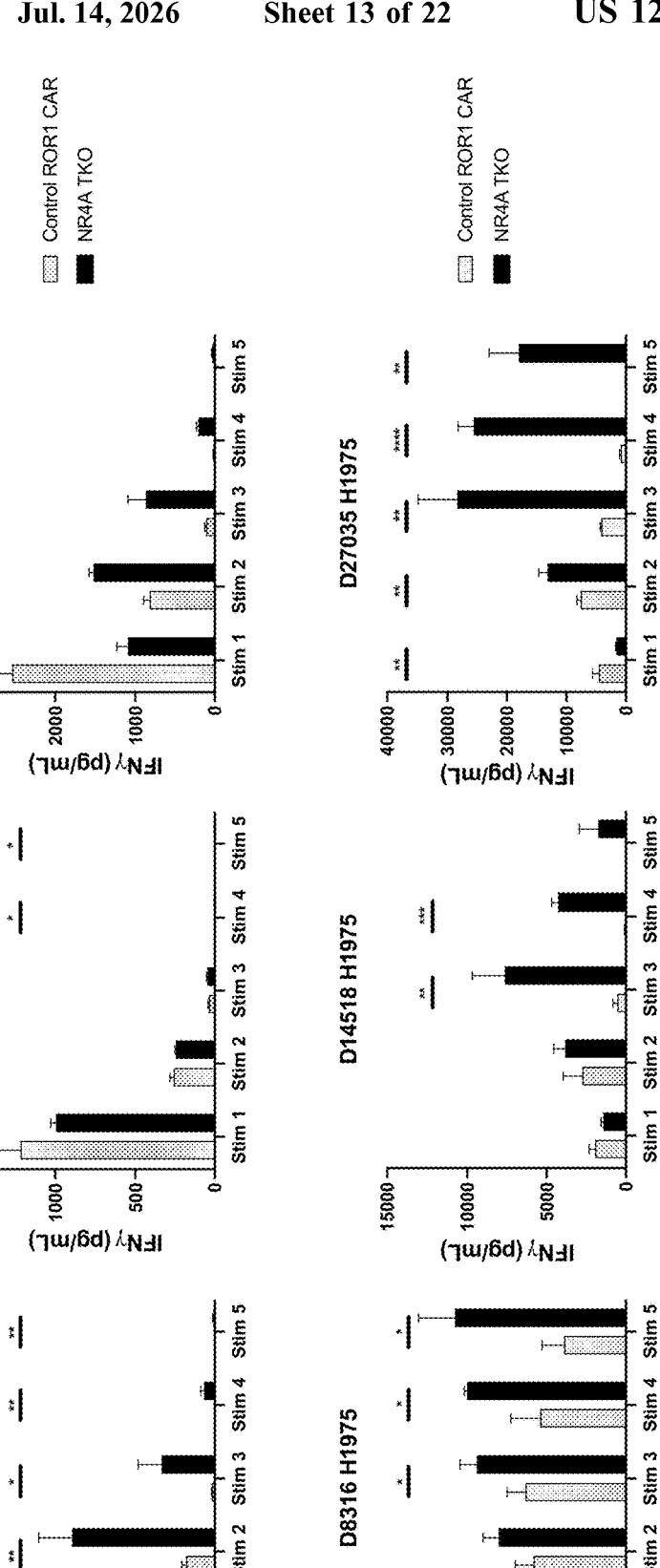

FIGS. 8A and 8B show IFN-γ level produced by anti-ROR1 CAR T cells overexpressing c-Jun and modified with reduced levels of NR4A1, NR4A2, and NR4A3 (triple knockout (NR4A TKO; black bars) during a sequential stimulation assay (see FIGS. 7A and 7B) using A549 and H1975 target cells, respectively. Supernatants were collected 24 hours after each replating (i.e., stim 1, stim 2, stim 3, stim 4, and stim 5) and cytokines were quantified by MSD. Anti-ROR1 CAR T cells overexpressing c-Jun without editing ("Control ROR1 CAR", containing endogenous levels of NR4A1, NR4A2, and NR4A3). are shown as control (gray bars). In each of FIGS. 8A and 8B, the results from three separate donors are provided. Unpaired t-test was used for statistical analysis. *p<0.05,  p<0.005, * p<0.001, **** p<0.0001.

Figures 9A, 9B:
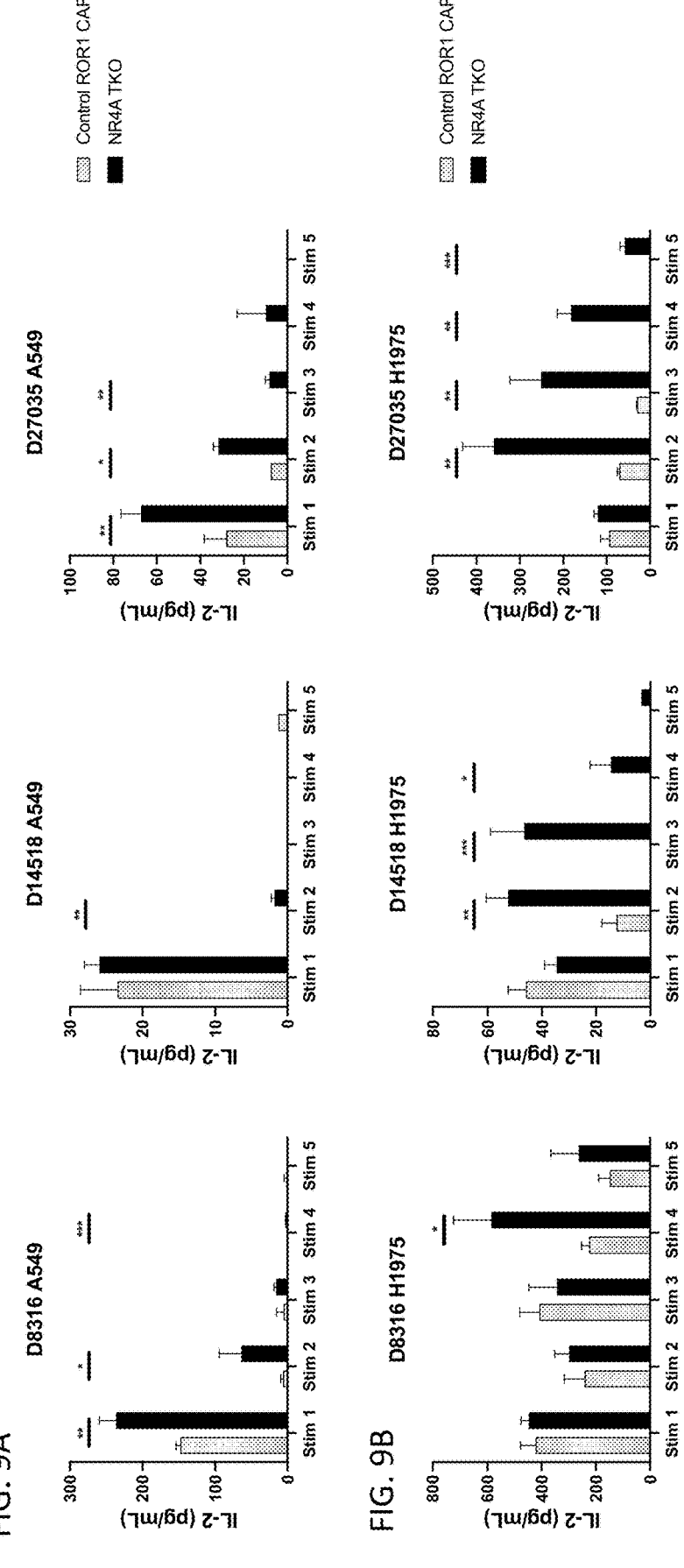

FIGS. 9A and 9B show IL-2 level produced by anti-ROR1 CAR T cells overexpressing c-Jun and modified with reduced levels of NR4A1, NR4A2, and NR4A3 (triple knockout (NR4A TKO); black bars) during a sequential stimulation assay (see, e.g., FIGS. 7A and 7B) using A549 and H1975 target cells, respectively. Supernatants were collected 24 hours after each replating (i.e., stim 1, stim 2, stim 3, stim 4, and stim 5) and cytokines were quantified by MSD. Anti-ROR1 CAR T cells overexpressing c-Jun without editing ("Control ROR1 CAR", containing endogenous levels of NR4A1, NR4A2, and NR4A3). are shown as control (gray bars). In each of FIGS. 9A and 9B, the results from three separate donors are provided. Unpaired t-test was used for statistical analysis. *p<0.05,  p<0.005, * p<0.001, **** p<0.0001.

FIGS. 10A and 10B show TNF-α level produced by anti-ROR1 CAR T cells overexpressing c-Jun and modified with reduced levels of NR4A1, NR4A2, and NR4A3 (triple knockout (NR4A TKO; black bars)) during a sequential stimulation assay (see, e.g., FIGS. 7A and 7B) using A549 and H1975 target cells, respectively. Supernatants were collected 24 hours after each replating (i.e., stim 1, stim 2, stim 3, stim 4, and stim 5) and cytokines were quantified by MSD. Anti-ROR1 CAR T cells overexpressing c-Jun without editing ("Control ROR1 CAR", containing endogenous levels of NR4A1, NR4A2, and NR4A3) are shown as control (gray bars). In each of FIGS. 10A and 10B, the results from three separate donors are provided. Unpaired t-test was used for statistical analysis. *p<0.05,  p<0.005, * p<0.001, ****p<0.0001.

Figure 11:
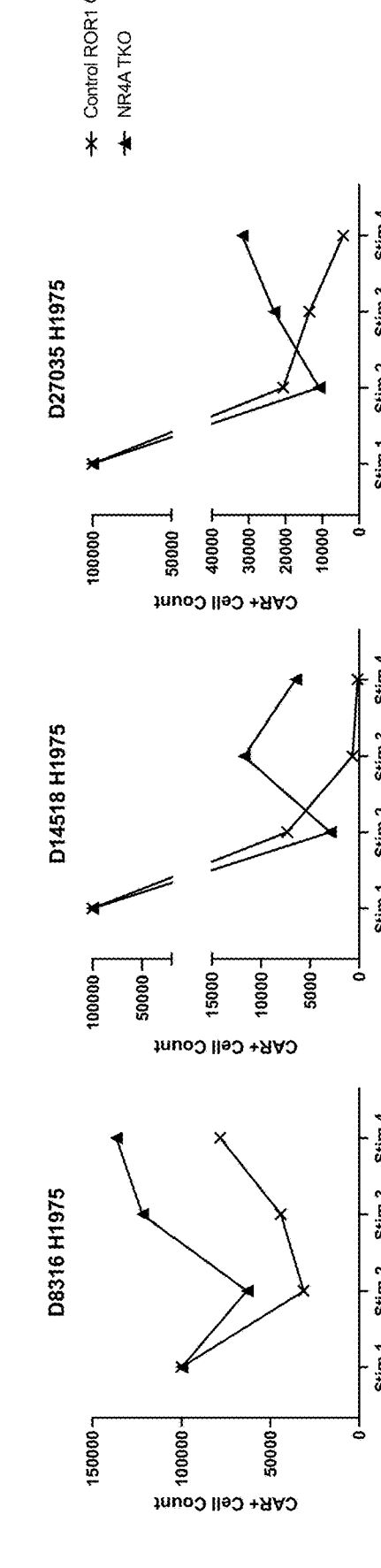

FIG. 11 shows persistence of anti-ROR1 CAR T cells overexpressing c-Jun and modified with reduced levels of NR4A1, NR4A2, and NR4A3 (triple knockout (NR4A TKO); triangle) during a sequential stimulation assay (see, e.g., FIGS. 7A and 7B) using H1975 target cells. The NR4A-edited anti-ROR1 CAR T cells and control groups are the same as that described in FIGS. 7A and 7B. Persistence was measured by quantifying the number of cParp(–) CD3+EGFR+ ROR1 CAR T cells after each sequential stimulation by flow cytometry (i.e., stim-1, stim-2, stim-3, stim-4).

Figure 12:
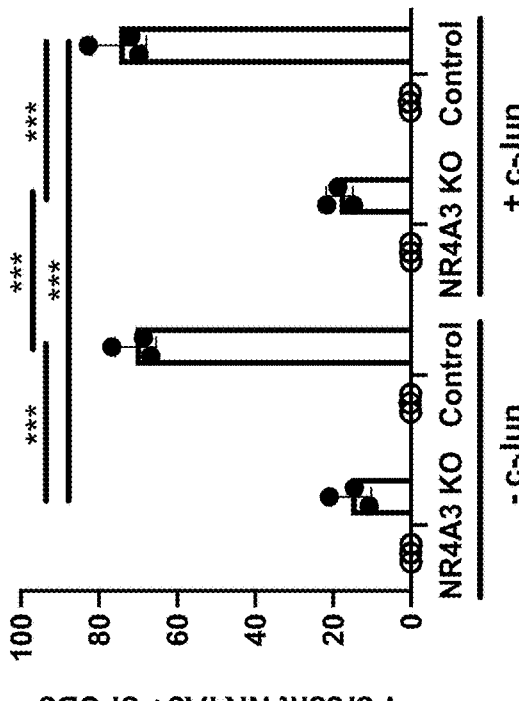

FIG. 12 shows the percentage of NR4A3 expression in NR4A3-edited (KO) and control non-edited CD4+ (left graph) and CD8+ (right graph) NY-ESO-1 TCR T cells with or without c-Jun overexpression on day 7 of TCR T cell production following a 2-hour PMA+ionomycin stimulation in three independent donors (Stim, filled circles). Unstim cells (opened circles, without PMA+ionomycin stimulation) were used as a negative control. Unpaired t-test of stimulated conditions was used for statistical analysis. *p<0.05,  p<0.005, * p<0.001, **** p<0.0001.

Figure 13:
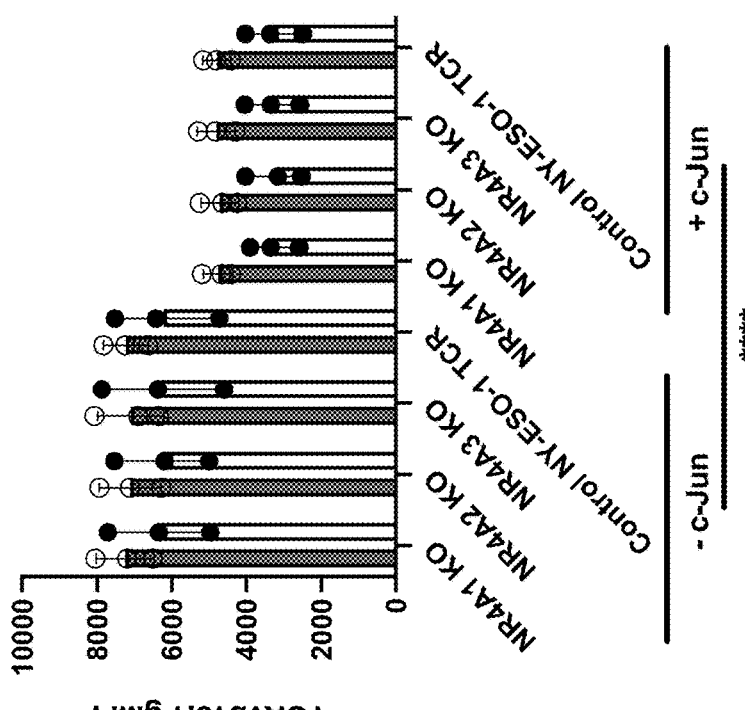

FIG. 13 shows the percentage of TCRv 13.1+ NY-ESO-1 TCR expression (left graph) and geometric mean fluorescence of NY-ESO-1 TCR on TCRv 13.1+ T cells (right graph) in NR4A1-, NR4A2-, NR4A3-edited (KO), and control non-edited CD4+ (opened circles) and CD8+ (closed circles) NY-ESO-1 TCR T cells with or without c-Jun overexpression from three donors on day 7 of TCR T cell production. Unpaired t-test was used for statistical analysis. **** p<0.0001.

Figure 14:
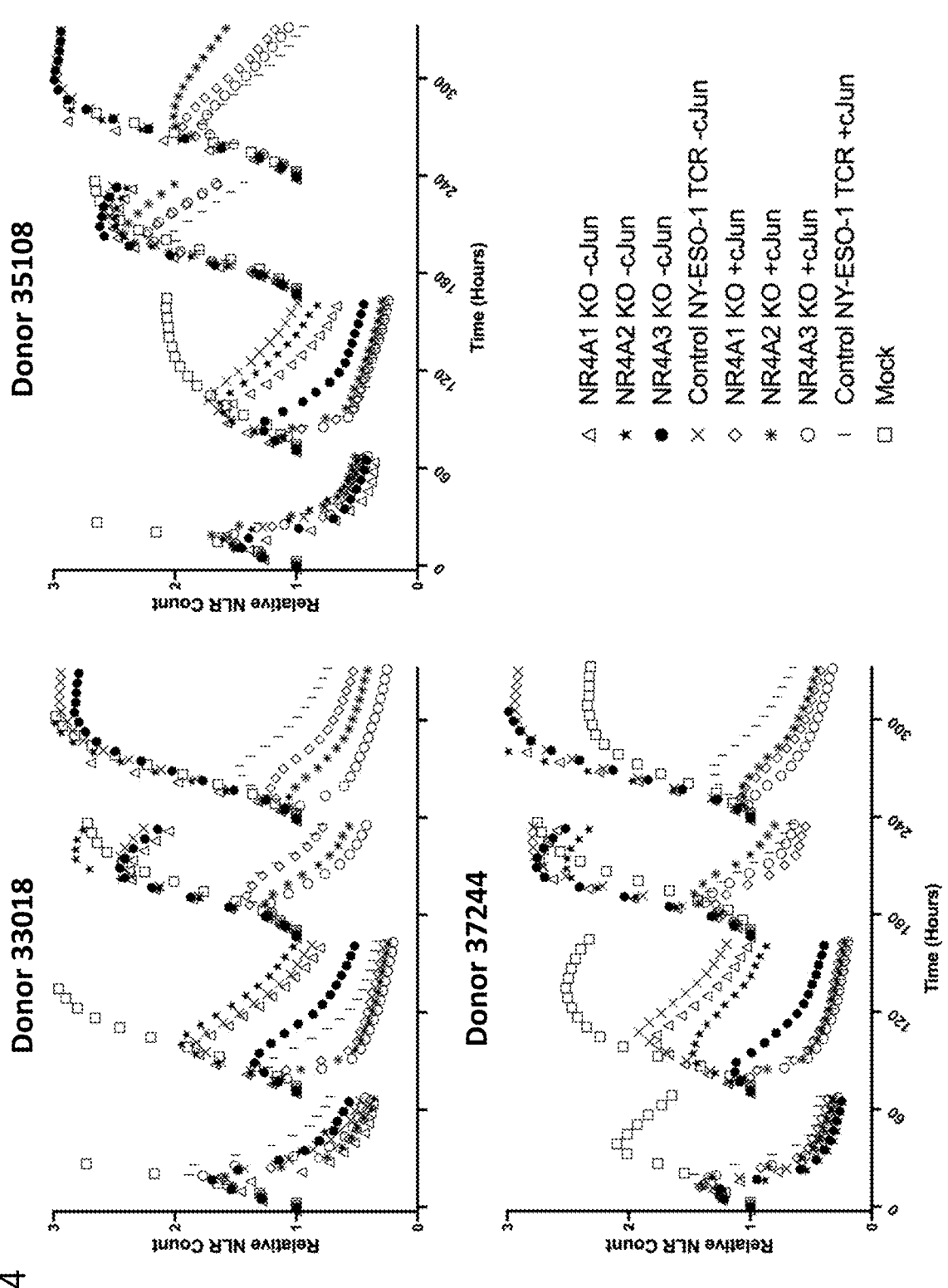

FIG. 14 shows successive lysis of NY-ESO-1+ A375-NLR melanoma cells by NR4A-edited (KO), control non-edited NY-ESO-1 TCR T cells with or without c-Jun overexpression, and mock untransduced T cells from three independent donors in the sequential stimulation assay. Specifically, the different NY-ESO-1 TCR T cells shown include: (a) NR4A1 knockout without c-Jun overexpression (triangle), (b) NR4A2 knockout without c-Jun overexpression (star), (c) NR4A3 knockout without c-Jun overexpression (black circle), (d) control non-edited ROR1 CAR T cell without c-Jun overexpression (x symbol), (e) NR4A1 knockout with c-Jun overexpression (diamond), (f) NR4A2 knockout with c-Jun overexpression (asterisk), (g) NR4A3 knockout with c-Jun overexpression (open circle), (h) control non-edited ROR1 CAR T cell with c-Jun overexpression (vertical line), and (i) nontransduced mock T cells (square). Lysis of A375-NLR target cells were quantified by measuring total NLR count. NLR count was normalized relative to the starting count after replating for each round of stimulation. NLR—NucLight Red. Each graph represents data from an independent donor.

Figure 15A:
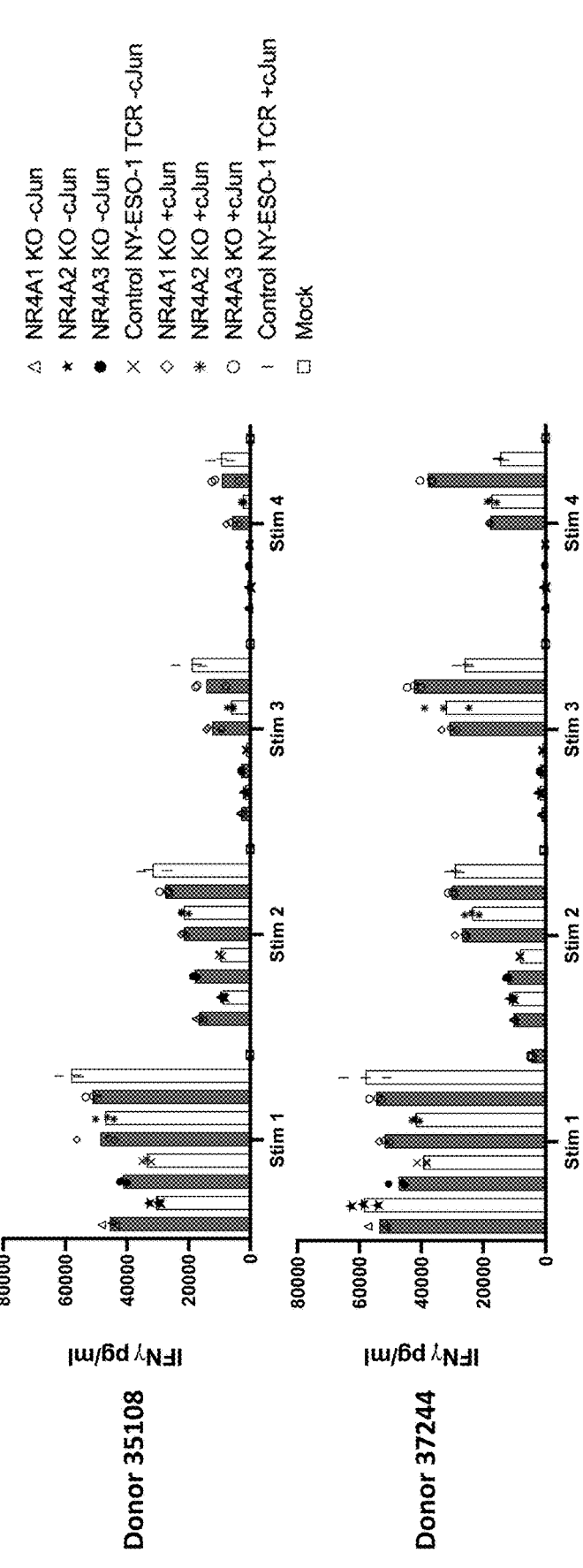
Figure 15B:
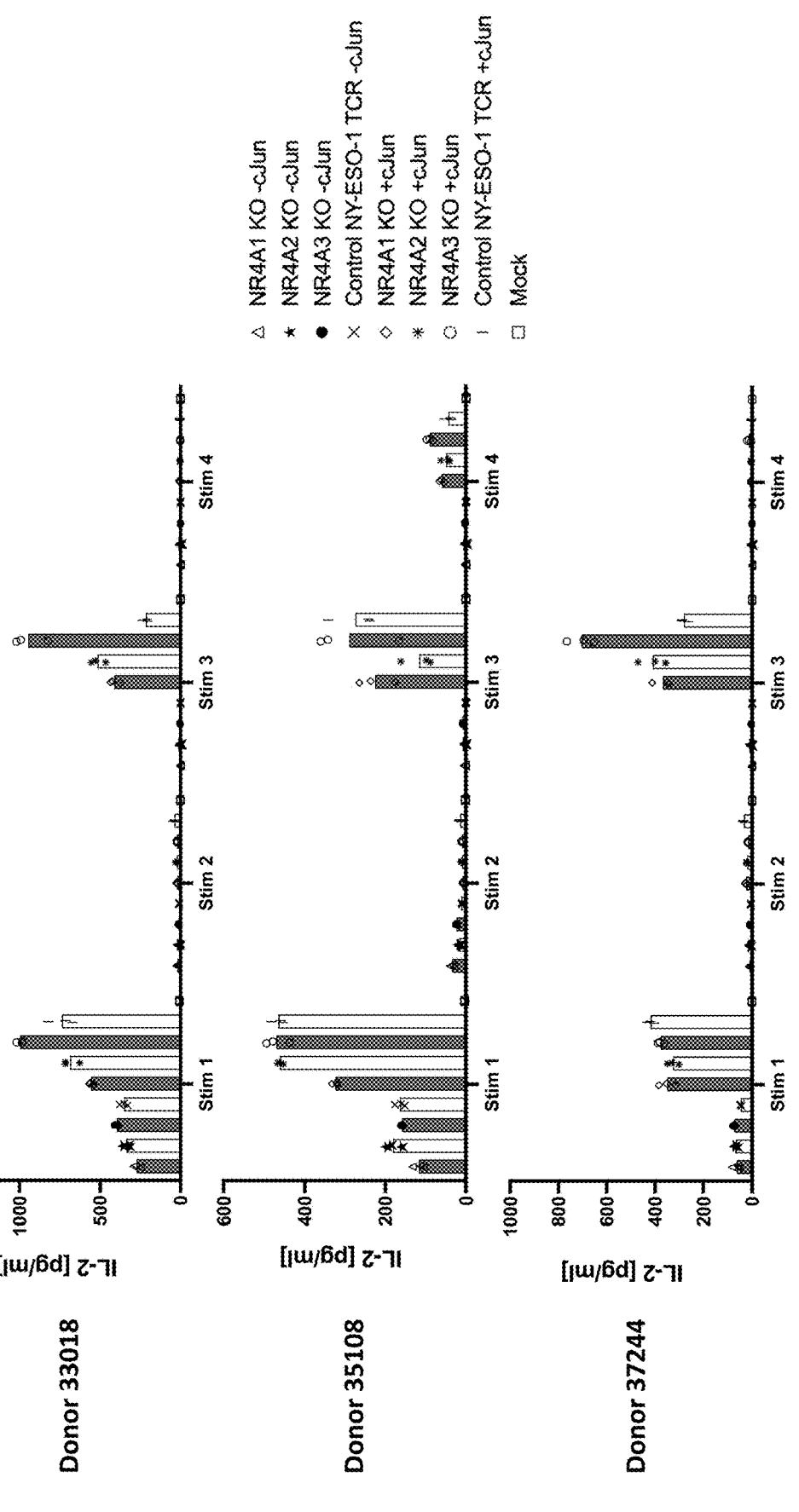
Figure 15C:
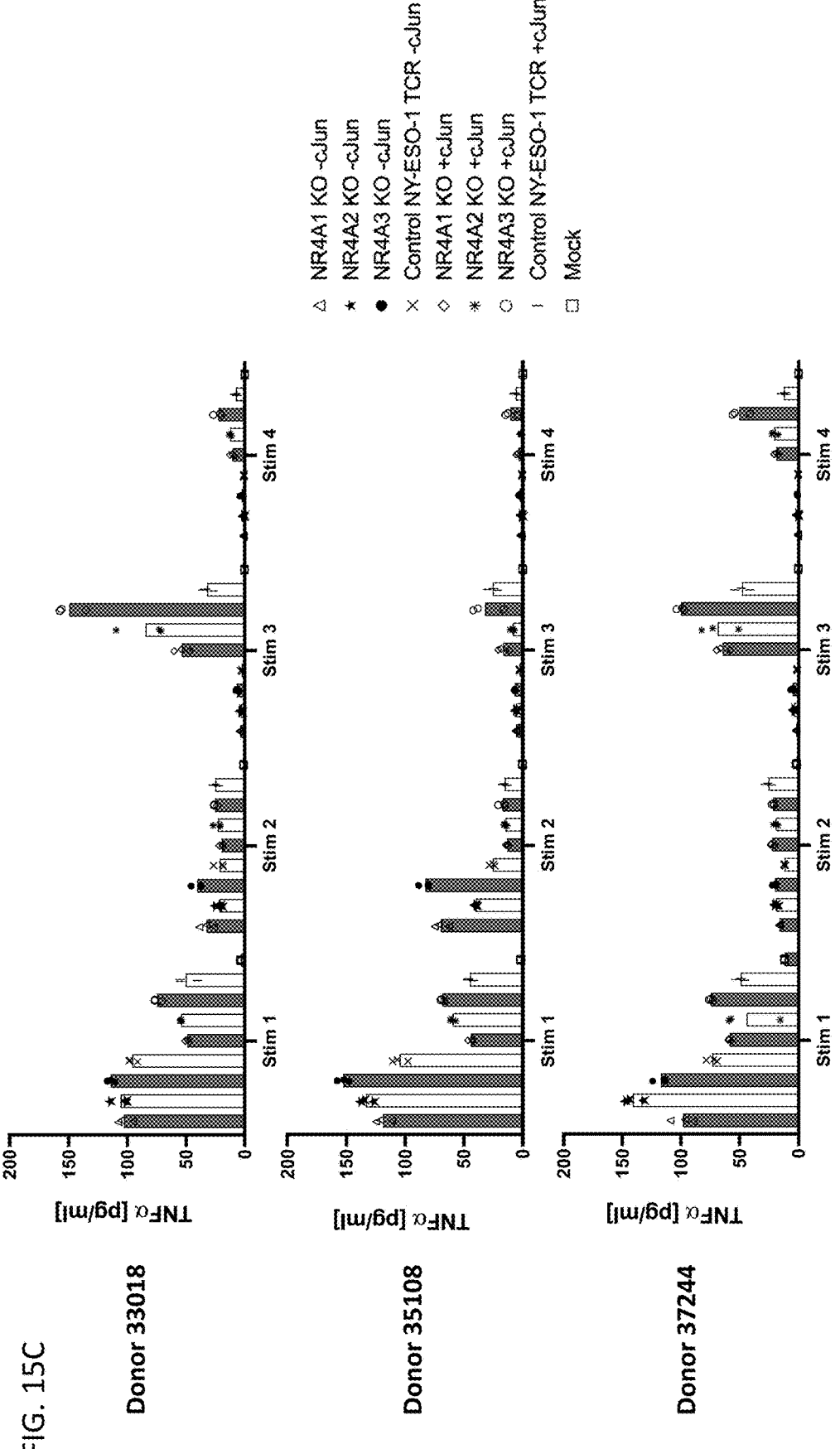

FIGS. 15A-15C show secreted interferon-gamma (IFN-γ) (FIG. 15A), interleukin-2 (IL-2) (FIG. 15B), and tumor-necrosis factor-alpha (TNF-α) (FIG. 15C) produced from NR4A-edited, control non-edited NY-ESO-1 TCR T cells with or without c-Jun overexpression, and mock untransduced T cells during the A375 sequential stimulation assay corresponding to FIG. 14. Supernatants were collected 24 hours after each replating and cytokines were quantified by MSD. The different groups are the same as that described in FIG. 14. Graphs show data from 3 independent donors.

DETAILED DESCRIPTION OF THE DISCLOSURE

The present disclosure is directed to compositions comprising a population of modified immune cells that (i) express reduced levels of a Nuclear Receptor Subfamily 4 Group A (NR4A) Member 1 (NR4A1), Member 2 (NR4A2) or Member 3 (NR4A3) gene and/or NR4A1, NR4A2, or NR4A3 protein and (ii) an increased expression level of transcription factor c-Jun. As further described herein, in some aspects, immune cells useful for the present disclosure have been modified to express a reduced level of a single member of the NR4A family ("single knockout"). For example, in some aspects, modified immune cells described herein have: (i) an increased level of a c-Jun and (ii) a reduced level of a NR4A1 gene and/or NR4A1 protein. In some aspects, modified immune cells described herein have: (i) an increased level of a c-Jun and (ii) a reduced level of a NR4A2 gene and/or NR4A2 protein. In some aspects, modified immune cells described herein have: (i) an increased level of a c-Jun and (ii) a reduced level of a NR4A3 gene and/or NR4A3 protein. In some aspects, immune cells useful for the present disclosure have been modified to express a reduced level of two members of the NR4A family ("double knockout"). For example, in some aspects, modified immune cells described herein have: (i) an increased level of a c-Jun and (ii) a reduced level of both a NR4A1 gene and/or NR4A1 protein and a NR4A2 gene and/or NR4A2 protein. In some aspects, modified immune cells described herein have: (i) an increased level of a c-Jun and (ii) a reduced level of both a NR4A1 gene and/or NR4A1 protein and a NR4A3 gene and/or NR4A3 protein. In some aspects, modified immune cells described herein have: (i) an increased level of a c-Jun and (ii) a reduced level of both a NR4A2 gene and/or NR4A2 protein and a NR4A3 gene and/or NR4A3 protein. In some aspects, immune cells useful for the present disclosure have been modified to express a reduced level of all the members of the NR4A family ("triple knockout"). Accordingly, in some aspects, modified immune cells described herein have: (i) an increased level of a c-Jun and (ii) a reduced level of each of the following: a NR4A1 gene and/or NR4A1 protein, a NR4A2 gene and/or NR4A2 protein, and a NR4A3 gene and/or NR4A3 protein. The reduction in levels of NR4A genes can be accomplished by using gene editing techniques, e.g., gene editing techniques such as CRISPR. As is apparent from the present disclosure, unless indicated otherwise, the term "NR4A gene and/or NR4A protein" comprises any of the NR4A single knockout, double knockout, and triple knockout described herein.

Both reduction in levels of a NR4A gene and/or NR4A protein expression and increased expression levels of transcription factor c-Jun can lead to one or more persistent effector functions, e.g., in immune cells, such as those described herein. One aspect of the persistent effector functions is enhanced T cell activation (e.g., enhanced expansion, enhanced cytotoxicity, enhanced cytokine expression). Reducing the levels of a NR4A1, NR4A2, or NR4A3 gene and/or protein (or combinations thereof) and increasing expression levels of transcription factor c-Jun can lead to exhaustion/dysfunction resistant cells. Furthermore, reducing levels of NR4A3 gene and/or NR4A3 protein and increasing expression levels of transcription factor c-Jun can result in the maintenance of anti-tumor function in TME environments.

The disclosure also provides, e.g., methods of treating a tumor in a subject in need thereof comprising administering to the subject the cell compositions described herein (e.g., composition comprising an immune cell that has been modified to have (i) a reduced level of one or more members of the NR4A family and (ii) an increased level of the c-Jun protein).

The disclosure also provides, e.g., methods to generate modified immune cells that express (i) reduced levels of one of the Nuclear Receptor Subfamily 4 Group A Members (NR4A1, NR4A2 or NR4A3) genes and/or proteins and endogenous levels of the other two NR4A members (e.g., NR4A1 and NR4A2 genes and proteins; NR4A1 and NR4A3 genes and proteins; or NR4A2 and NR4A3 genes and proteins), and (ii) increased expression levels of transcription factor c-Jun, methods to use the modified immune cells, pharmaceutical compositions comprising the modified immune cells, or kits comprising the modified immune cells. As further described herein, in some aspects, present disclosure also provides methods of generating modified immune cells that have increased level of a c-Jun protein and reduced level of two or all three members of the NR4A family.

Before the present disclosure is described in greater detail, it is to be understood that this disclosure is not limited to the particular compositions or process steps described, as such can, of course, vary. As will be apparent to those of skill in the art upon reading this disclosure, each of the individual aspects described and illustrated herein has discrete components and features which can be readily separated from or combined with the features of any of the other several aspects without departing from the scope or spirit of the present disclosure. Any recited method can be carried out in the order of events recited or in any other order which is logically possible.

The headings provided herein are not limitations of the various aspects of the disclosure, which can be defined by reference to the specification as a whole. It is also to be understood that the terminology used herein is for the purpose of describing particular aspects only, and is not intended to be limiting, since the scope of the present disclosure will be limited only by the appended claims.

I. Terms

In order that the present disclosure can be more readily understood, certain terms are first defined. As used in this application, except as otherwise expressly provided herein, each of the following terms shall have the meaning set forth below. Additional definitions are set forth throughout the application.

Throughout this disclosure, the term "a" or "an" entity refers to one or more of that entity; for example, "an immune cell," is understood to represent one or more immune cells. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary of Biochemistry and Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

Abbreviations used herein are defined throughout the present disclosure. Various aspects of the disclosure are described in further detail in the following subsections.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As used herein, the term "approximately," as applied to one or more values of interest, refers to a value that is similar to a stated reference value. In some aspects, the term "approximately" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As described herein, any concentration range, percentage range, ratio range or integer range is to be understood to include the value of any integer within the recited range and, when appropriate, fractions thereof (such as one tenth and one hundredth of an integer), unless otherwise indicated.

As used herein, "administering" refers to the physical introduction of a therapeutic agent or a composition comprising a therapeutic agent to a subject, using any of the various methods and delivery systems known to those skilled in the art. The different routes of administration for a therapeutic agent described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, intratracheal, pulmonary, subcutaneous, subcuticular, intraarticular, subcapsular, subarachnoid, intraventricle, intravitreal, epidural, and intrasternal injection and infusion, as well as in vivo electroporation. Alternatively, a therapeutic agent described herein can be administered via a non-parenteral route, such as a topical, epidermal, or mucosal route of administration, for example, intranasally, orally, vaginally, rectally, sublingually, or topically. Administering can also be performed, for example, once, a plurality of times, and/or over one or more extended periods.

As used herein, the term "antigen" refers to any natural or synthetic immunogenic substance, such as a protein, peptide, or hapten. As used herein, the term "cognate antigen" refers to an antigen which an immune cell (e.g., T cell) recognizes and thereby, induces the activation of the immune cell (e.g., triggering intracellular signals that induce effector functions, such as cytokine production, and/or for proliferation of the cell).

Nucleotides are referred to by their commonly accepted single-letter codes. Unless otherwise indicated, nucleic acids are written left to right in 5' to 3' orientation. Nucleotides are referred to herein by their commonly known one-letter symbols recommended by the IUPAC-IUB Biochemical Nomenclature Commission. Accordingly, A represents adenine, C represents cytosine, G represents guanine, T represents thymine, U represents uracil.

It is to be understood that in the disclosed sequences T and U are interchangeable depending on whether the sequence is a DNA or an RNA. For example, gRNA spacer sequences are presented as DNAs (A/T/C/G) in the present disclosure, whereas the gRNA chimeric frames are presented as RNAs (A/U/C/G).

Amino acids are referred to herein by either their commonly known three letter symbols or by the one-letter symbols recommended by the IUPAC-IUB Biochemical Nomenclature Commission. Unless otherwise indicated, amino acid sequences are written left to right in amino to carboxy orientation.

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" can comprise one or more polypeptides. Unless otherwise specified, the terms "protein" and "polypeptide" can be used interchangeably.

The term "nucleic acid molecule," as used herein, is intended to include DNA molecules and RNA molecules. A nucleic acid molecule can be single-stranded or double-stranded, and can be cDNA.

The term "polynucleotide" as used herein refer to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, doubleand single-stranded ribonucleic acid ("RNA"). It also includes modified, for example by alkylation, and/or by capping, and unmodified forms of the polynucleotide. More particularly, the term "polynucleotide" includes polydeoxyribonucleotides (containing 2-deoxy-D-ribose), polyribonucleotides (containing D-ribose), including mRNAs and gRNAs, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA.

The term "vector," as used herein, is intended to refer to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" can be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

A "cancer" refers a broad group of various diseases characterized by the uncontrolled growth of abnormal cells in the body. Unregulated cell division and growth results in the formation of malignant tumors that invade neighboring tissues and can also metastasize to distant parts of the body through the lymphatic system or bloodstream. "Cancer" as used herein refers to primary, metastatic and recurrent cancers.

As used herein, the term "immune response" refers to a biological response within a vertebrate against foreign agents, which response protects the organism against these agents and diseases caused by them. An immune response is mediated by the action of a cell of the immune system (e.g., a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell or a Th cell, such as a CD4$^+$ or CD8$^+$ T cell, or the inhibition of a T$_{reg}$ cell. As used herein, the term "T cell" and "T lymphocytes" are interchangeable and refer to any lymphocytes produced or processed by the thymus gland. In some aspects, a T cell is a CD4$^+$ T cell. In some aspects, a T cell is a CD8$^+$ T cell. In some aspects, a T cell is a NKT cell.

As used herein, the term "anti-tumor immune response" refers to an immune response against a tumor antigen. An increased ability to stimulate an immune response or the immune system, can result from an enhanced agonist activity of T cell costimulatory receptors and/or an enhanced antagonist activity of inhibitory receptors. An increased ability to stimulate an immune response or the immune system can be reflected by a fold increase of the EC$_{50}$ or maximal level of activity in an assay that measures an immune response, e.g., an assay that measures changes in cytokine or chemokine release, cytolytic activity (determined directly on target cells or indirectly via detecting CD107a or granzymes) and proliferation. In some aspects, the ability to stimulate an immune response or the immune system activity can be enhanced, e.g., by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%. In some aspects, the ability to stimulate an immune response or the immune system activity can be enhanced, e.g., at least about 1.2 fold, at least about 1.4 fold, at least about 1.6 fold, at least about 1.8 fold, at least about 2 fold, at least about 3 fold, at least about 4 fold, at least about 5 fold, at least about 6 fold, at least about 7 fold, at least about 8 fold, at least about 9 fold, at least about 10 fold, or more.

A "subject" includes any human or nonhuman animal. The term "nonhuman animal" includes, but is not limited to, vertebrates such as nonhuman primates, sheep, dogs, and rodents such as mice, rats and guinea pigs. In some aspects, the subject is a human. The terms "subject" and "patient" are used interchangeably herein.

The term "therapeutically effective amount" or "therapeutically effective dosage" refers to an amount of an agent (e.g., a modified immune cells disclosed herein) that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to solid tumors, an effective amount comprises an amount sufficient to cause a tumor to shrink and/or to decrease the growth rate of the tumor (such as to suppress tumor growth) or to prevent or delay other unwanted cell proliferation. In some aspects, an effective amount is an amount sufficient to delay tumor development. In some aspects, an effective amount is an amount sufficient to prevent or delay tumor recurrence. An effective amount can be administered in one or more administrations. The effective amount of the composition can, for example, (i) reduce the number of cancer cells; (ii) reduce tumor size; (iii) inhibit, retard, slow to some extent and can stop cancer cell infiltration into peripheral organs; (iv) inhibit (i.e., slow to some extent and can stop tumor metastasis; (v) inhibit tumor growth; (vi) prevent or delay occurrence and/or recurrence of tumor; and/or (vii) relieve to some extent one or more of the symptoms associated with the cancer.

In some aspects, a "therapeutically effective amount" is the amount of the modified cell herein clinically proven to affect a significant decrease in cancer or slowing of progression (regression) of cancer, such as an advanced solid tumor.

The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

As used herein, the term "standard of care" refers to a treatment that is accepted by medical experts as a proper treatment for a certain type of disease and that is widely used by healthcare professionals. The term can be used interchangeable with any of the following terms: "best practice," "standard medical care," and "standard therapy."

By way of example, an "anti-cancer agent" promotes cancer regression in a subject or prevents further tumor growth. In some aspects, a therapeutically effective amount of the drug promotes cancer regression to the point of eliminating the cancer.

"Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, or a prevention of impairment or disability due to the disease affliction.

The terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

As used herein, the term "immune checkpoint inhibitor" refers to molecules that totally or partially reduce, inhibit, interfere with or modulate one or more checkpoint proteins. Checkpoint proteins regulate T-cell activation or function. Numerous checkpoint proteins are known, such as CTLA-4 and its ligands CD80 and CD86; and PD-1 with its ligands PD-L1 and PD-L2. Pardoll, D. M., *Nat Rev Cancer* 12(4): 252-64 (2012). These proteins are responsible for co-stimulatory or inhibitory interactions of T-cell responses. Immune checkpoint proteins regulate and maintain self-tolerance and the duration and amplitude of physiological immune responses. Immune checkpoint inhibitors include antibodies or are derived from antibodies.

As used herein, the term "oxidative stress" refers to the condition characterized by an excess of oxidants and/or a decrease in antioxidant levels. Cellular oxidants can include, but are not limited to, radicals of oxygen (superoxide anion, hydroxyl radical, and/or peroxy radicals); reactive non-radical oxygen species such as, for example, hydrogen peroxide and singlet oxygen; carbon radicals; nitrogen radicals; sulfur radicals; and combinations thereof. In some aspects, the condition of oxidative stress can result in, for example, cellular damage, impaired performance of cells, and/or cell death.

As used herein, the term "modified cell" refers to a cell, e.g., a T cell, that has undergone non naturally-occurring engineering so that a phenotype of the cell (i.e., expression level of a NR4A gene and/or NR4A protein and expression level of a c-Jun protein) is different from the unmodified cell (i.e., reference cell). As will be apparent from the disclosure, modified cells disclosed herein overexpress a c-Jun protein and express reduced levels of a NR4A gene and/or NR4A protein compared to reference cells (e.g., corresponding cells that have not been modified). For example, in some aspects, modified cells described herein overexpress a c-Jun protein and express a reduced level of a NR4A1 gene and/or NR4A1 protein. In some aspects, modified cells described herein overexpress a c-Jun protein and express a reduced level of a NR4A2 gene and/or NR4A2 protein. In some aspects, modified cells described herein overexpress a c-Jun protein and express a reduced level of a NR4A3 gene and/or NR4A3 protein. In some aspects, modified cells described herein overexpress a c-Jun protein and express a reduced level of (i) a NR4A1 gene and/or NR4A1 protein and (ii) a NR4A2 gene and/or NR4A2 protein. In some aspects, modified cells described herein overexpress a c-Jun protein and express a reduced level of (i) a NR4A1 gene and/or NR4A1 protein and (ii) a NR4A3 gene and/or NR4A3 protein. In some aspects, modified cells described herein overexpress a c-Jun protein and express a reduced level of (i) a NR4A2 gene and/or NR4A2 protein and (ii) a NR4A3 gene and/or NR4A3 protein. In some aspects, modified cells described herein overexpress a c-Jun protein and express a reduced level of (i) a NR4A1 gene and/or NR4A1 protein, (ii) a NR4A2 gene and/or NR4A2 protein, and (iii) a NR4A3 gene and/or NR4A3 protein. As used herein, the term "corresponding cell" refers to a cell that belongs to the same immune cell classification as the modified cell. For example, if the modified cell is a T cell, the corresponding cell would also be a T cell.

As used herein, the term "endogenous expression" or "endogenous expression levels" or "endogenous levels" (or grammatical variants thereof) refers to gene and/or protein expression (e.g., amount, kinetics, etc.) that is naturally occurring (e.g., the gene and/or protein is not directly manipulated by non-naturally-occurring engineering). For example, in some aspects, a modified cell disclosed herein (e.g., CAR or TCR T cell with a NR4A3 knocked down and overexpressing a c-Jun protein) does not express endogenous levels of a NR4A3 gene and/or protein, but because the two NR4A1 and NR4A2 genes have not been knocked down (e.g., by CRISPR, e.g., a non-naturally occurring engineering) the modified cells endogenously express NR4A1 and NR4A2 gene and/or NR4A1 and NR4A2 protein.

In some aspects, a modified cell is produced by introducing a foreign or exogenous nucleic acid into a cell. In some aspects, the foreign or exogenous nucleic acid can encode a gene editing tool disclosed herein. A nucleic acid can be introduced into a cell by methods known in the art, such as, for example, electroporation (see, e.g., Heiser W. C. *Transcription Factor Protocols: Methods in Molecular Biology*™ 2000; 130: 117-134), chemical (e.g., calcium phosphate or lipid) transfection (see, e.g., Lewis W. H., et al., *Somatic Cell Genet.* 1980 May; 6(3): 333-47; Chen C., et al., *Mol Cell Biol.* 1987 August; 7(8): 2745-2752), fusion with bacterial protoplasts containing recombinant plasmids (see, e.g., Schaffner W. *Proc Natl Acad Sci USA.* 1980 April; 77(4): 2163-7), or microinjection of purified DNA directly into the nucleus of the cell (see, e.g., Capecchi M. R. Cell. 1980 November; 22(2 Pt 2): 479-88).

It is to be understood that disclosures referring to a "modified cell" or to a "cell" are equally applicable to a population of those cells, i.e., to a plurality of those cells.

As used herein, the terms "elevated concentrations" or "elevated levels" and grammatical variants thereof refer to above-normal levels of a substance (e.g., a reactive oxygen species; ROS) compared to appropriate controls (e.g., healthy tissue or cells).

As used herein, the terms "reactive oxygen species" and "ROS" refer to highly reactive chemicals, containing oxygen, that react easily with other molecules, resulting in potentially damaging modifications. Reactive oxygen species include, for example, oxygen ions, free radicals and peroxides both inorganic and organic such as hydrogen peroxide, superoxide, hydroxyl radical, lipid hydroperoxidase and singlet oxygen. They are generally very small molecules and are highly reactive due to the presence of unpaired valence shell electrons. Nearly all cancers are associated with elevated concentrations of reactive oxygen species. Liou, G., et al., *Free Radic Res* 44(5): 1-31 (2010).

The terms "chimeric antigen receptor" and "CAR," as used herein, refer to a recombinant fusion protein that has an antigen-specific extracellular domain coupled to an intracellular domain that directs the cell to perform a specialized function upon binding of an antigen to the extracellular domain. The terms "artificial T cell receptor," "chimeric T-cell receptor," and "chimeric immunoreceptor" can each be used interchangeably herein with the term "chimeric antigen receptor." Chimeric antigen receptors are distinguished from other antigen binding agents by their ability to both bind MHC-independent antigen and transduce activation signals via their intracellular domain.

The antigen-specific extracellular domain of a chimeric antigen receptor recognizes and specifically binds an antigen, typically a surface-expressed antigen of a malignancy. An antigen-specific extracellular domain specifically binds an antigen when, for example, it binds the antigen with an affinity constant or affinity of interaction ($K_D$) between about 0.1 pM to about 10 µM, for example, about 0.1 pM to about 1 µM or about 0.1 pM to about 100 nM. Methods for determining the affinity of interaction are known in the art. An antigen-specific extracellular domain suitable for use in a CAR of the present disclosure can be any antigen-binding polypeptide, a wide variety of which are known in the art. In some aspects, the antigen-binding domain is a single chain Fv (scFv). Other antibody-based recognition domains (cAb VHH (camelid antibody variable domains) and humanized versions thereof, lgNAR VH (shark antibody variable domains) and humanized versions thereof, sdAb VH (single domain antibody variable domains) and "camelized" antibody variable domains are suitable for use. In some aspects, T cell receptor (TCR) based recognition domains, such as single chain TCR (scTv, single chain two-domain TCR containing V.alpha.V.beta.) are also suitable for use.

A chimeric antigen receptor disclosed herein can also include an intracellular domain that provides an intracellular signal to the cell (expressing the CAR) upon antigen binding to the antigen-specific extracellular domain. In some aspects, the intracellular signaling domain of a CAR is responsible for activation of at least one of the effector functions of the T cell in which the chimeric receptor is expressed.

The term "intracellular domain" refers to the portion of a CAR that transduces the effector function signal upon binding of an antigen to the extracellular domain and directs the T cell to perform a specialized function. Non-limiting examples of suitable intracellular domains include the zeta chain of the T-cell receptor or any of its homologs (e.g., eta, delta, gamma, or epsilon), MB 1 chain, 829, Fc RIII, Fc RI, and combinations of signaling molecules, such as CD3.zeta. and CD28, CD27, 4-1BB, DAP-10, OX40, and combinations thereof, as well as other similar molecules and fragments. Intracellular signaling portions of other members of the families of activating proteins can be used, such as FcγRIII and FcεRI. While usually the entire intracellular domain will be employed, in many cases it will not be necessary to use the entire intracellular polypeptide. To the extent that a truncated portion of the intracellular signaling domain can find use, such truncated portion can be used in place of the intact chain as long as it still transduces the effector function signal. The term intracellular domain is thus meant to include any truncated portion of the intracellular domain sufficient to transduce the effector function signal. Typically, the antigen-specific extracellular domain is linked to the intracellular domain of the chimeric antigen receptor by a transmembrane domain. A transmembrane domain traverses the cell membrane, anchors the CAR to the T cell surface, and connects the extracellular domain to the intracellular signaling domain, thus impacting expression of the CAR on the T cell surface. Chimeric antigen receptors can also further comprise one or more costimulatory domain and/or one or more spacer. A costimulatory domain is derived from the intracellular signaling domains of costimulatory proteins that enhance cytokine production, proliferation, cytotoxicity, and/or persistence in vivo.

A "peptide hinge" or "spacer" connects the antigen-specific extracellular domain to the transmembrane domain. The transmembrane domain is fused to the costimulatory domain, optionally a costimulatory domain is fused to a second costimulatory domain, and the costimulatory domain is fused to a signaling domain, not limited to CD3ζ. For example, inclusion of a spacer domain between the antigen-specific extracellular domain and the transmembrane domain, and between multiple scFvs in the case of tandem CAR, can affect flexibility of the antigen-binding domain(s) and thereby CAR function. Suitable transmembrane domains, costimulatory domains, and spacers are known in the art.

As used herein, the terms "ug" and "uM" are used interchangeably with "µg" and "µM," respectively.

As used herein, the term "gene-editing" refers to the process of changing the genetic information present in the genome of a cell. This gene-editing can be performed by manipulating genomic DNA, resulting in a modification of the genetic information. In some aspects, such gene-editing can influence expression of the DNA that has been edited. In some aspects, such gene-editing does not affect the expression of the DNA that has been edited. In some aspects, gene-editing of a modified cell disclosed herein can be done using a gene editing tool described herein. Non-limiting examples of gene editing tools include RNA interference molecules (e.g., shRNA, siRNA, miRNA), antisense oligonucleotides, CRISPR, zinc finger nuclease (ZFN), transcription activator-like effector nuclease (TALEN), meganucleases, restriction endonuclease, or any combination thereof.

As used herein, the term "nuclease" refers to an enzyme which possesses catalytic activity for DNA cleavage. Any nuclease agent that induces a nick or double-strand break into a desired recognition site can be used in the methods and compositions disclosed herein. A naturally-occurring or native nuclease agent can be employed so long as the nuclease agent induces a nick or double-strand break in a desired recognition site. Alternatively, a modified or engineered nuclease agent can be employed. An "engineered nuclease agent" comprises a nuclease that is engineered (modified or derived) from its native form to specifically recognize and induce a nick or double-strand break in the desired recognition site. Thus, an engineered nuclease agent can be derived from a native, naturally-occurring nuclease agent or it can be artificially created or synthesized. The modification of the nuclease agent can be as little as one amino acid in a protein cleavage agent or one nucleotide in a nucleic acid cleavage agent. In some aspects, the engineered nuclease induces a nick or double-strand break in a recognition site, wherein the recognition site was not a sequence that would have been recognized by a native (non-engineered or non-modified) nuclease agent. Producing a nick or double-strand break in a recognition site or other DNA can be referred to herein as "cutting" or "cleaving" the recognition site or other DNA.

"Coding sequence" or "encoding nucleic acid" as used herein means the nucleic acids (RNA or DNA molecule) that comprise a nucleotide sequence which encodes a protein, e.g., a Cas9 protein, a CAR, or a TCR, or a polynucleotide, e.g., a gRNA. The coding sequence can further include initiation and termination signals operably linked to regulatory elements including a promoter and polyadenylation signal capable of directing expression in the cells of an individual or mammal to which the nucleic acid is administered. The coding sequence can be codon optimized.

"Complement" or "complementary" as used herein refers to Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

Various aspects described herein are described in further detail in the following subsections.

II. Modified Immune Cells

Success of cellular immunotherapy for solid tumors has been limited due to exhaustion of tumor-infiltrating lymphocyte (TIL) in the tumor microenvironment. Persistent exposure to tumor antigens leads to T cell exhaustion, which is characterized by progressive loss of cytotoxicity and cytokine production, and increased expressions of inhibitory markers such as PD-1 (Wherry et al., *Nat. Rev. Immunol.* 15, 486-499 (2015)). Additionally, exhausted TILs upregulate and alternatively use transcription factors, particularly the NR4A family (Chen et al., *Nature* 567, 530-534 (2019)).

The present disclosure provides modified immune cells, i.e., cells modified, e.g., by gene editing, which express reduced levels of a NR4A gene and/or NR4A protein, and which overexpress a c-Jun protein, and as a result, display an enhanced function, e.g., persistent effector function and/or reduced exhaustion (e.g., T cells which overexpress a c-Jun protein and express reduced levels of a NR4A gene and/or protein, e.g., CAR or TCR T cells which overexpress a c-Jun protein and express reduced levels of a NR4A gene and/or protein).

In some aspects, the present disclosure provides a population of modified immune cells that express a reduced expression level of (i) a Nuclear Receptor Subfamily 4 Group A gene and/or protein selected from the group consisting of a NR4A Member 1 (NR4A1) gene and/or protein, a NR4A Member 2 (NR4A2) gene and/or protein, and a NR4A Member 3 (NR4A3) gene and/or protein and (ii) an increased expression level of a c-Jun protein. In some aspects, the NR4A gene and/or protein comprises a NR4A1 gene and/or NR4A1 protein. In some aspects, the NR4A gene and/or protein comprises a NR4A2 gene and/or NR4A2 protein. In some aspects, the NR4A gene and/or protein comprises a NR4A3 gene and/or NR4A3 protein. In some aspects, the NR4A gene and/or protein comprises any combinations of a NR4A1 gene and/or protein, NR4A2 gene and/or protein, and NR4A3 gene and/or protein.

II.A. NR4A3

Nuclear Receptor Subfamily 4 Group A Member 3, generally abbreviated "NR4A3," and also known as MINOR, CSMF, NOR1, CHN, Mitogen-Induced Nuclear Orphan Receptor, Neuron-Derived Orphan Receptor, Nuclear Hormone Receptor NOR-1, "Chondrosarcoma, Extraskeletal Myxoid, Fused to EWS," and TEC, is a protein which in humans is encoded by the NR4A3 gene. The NR4A family of orphan nuclear receptors includes NR4A1 (Nur77), NR4A2 (Nurr1), and NR4A3 (Nor-1). They work as transcription factors in a ligand-independent manner. Their functions are mostly controlled by the rapid and transient induction of their expression by a variety of extracellular signals, and thus are considered as immediate-early genes. The NR4As are involved in various cellular functions including apoptosis, survival, proliferation, angiogenesis, inflammation, DNA repair, and fatty acid metabolism.

The NR4A3 gene is located on chromosome 9 (bases 99,821,885 to 99,866,893; 45,039 bases; plus strand orientation; NCBI Reference Sequence: NC_000009.12). NR4A3 is a transcriptional activator that binds to regulatory elements in promoter regions in a cell- and response element (target)-specific manner. NR4A3 induces gene expression by binding as monomers to the NR4A1 response element (NBRE) 5'-AAAAGGTCA-3' (SEQ ID NO: 100) site and as homodimers to the Nur response element (NurRE) site in the promoter of their regulated target genes (by similarity) and plays a role in the regulation of proliferation, survival, and differentiation of many different cell types.

The NR4A3 proteins have three isoforms produced by alternative splicing. The sequences are shown in the Table 1 below.

TABLE 1

| NR4A3 protein isoforms. |
| --- |

| | |
| --- | --- |
| NR4A3 Isoform Alpha (identifier: Q92570-1) (SEQ ID NO: 1) | MPCVQAQYSPSPPGSSYAAQTYSSEYTTEIMNPDYTKLTMDLGSTEITATATTSLPSISTFVEGY SSNYELKPSCVYQMQRPLIKVEEGRAPSYHHHHHHHHHHHHHHQQQHQQPSIPPASSPEDEVLPS TSMYFKQSPPSTPTTPAFPPQAGALWDEALPSAPGCIAPGPLLDPPMKAVPTVAGARFPLFHFKP SPPHPPAPSPAGGHHLGYDPTAAAALSLPLGAAAAAGSQAAALESHPYGLPLAKRAAPLAFPPLG LTPSPTASSLLGESPSLPSPPSRSSSSGEGTCAVCGDNAACQHYGVRTCEGCKGFFKRTVQKNAK YVCLANKNCPVDKRRRNRCQYCRFQKCLSVGMVKEVVRTDSLKGRRGRLPSKPKSPLQQEPSQPS PPSPPICMMNALVRALTDSTPRDLDYSRYCPTDQAAAGTDAEHVQQFYNLLTASIDVSRSWAEKI PGFTDLPKEDQTLLIESAFLELFVLRLSIRSNTAEDKFVFCNGLVLHRLQCLRGFGEWLDSIKDF SLNLQSLNLDIQALACLSALSMITERHGLKEPKRVEELCNKITSSLKDHQSKGQALEPTESKVLG ALVELRKICTLGLQRIFYLKLEDLVSPPSIIDKLFLDTLPF |
| NR4A3 Isoform Beta (identifier: Q92570-2) (SEQ ID NO: | MPCVQAQYSPSPPGSSYAAQTYSSEYTTEIMNPDYTKLTMDLGSTEITATATTSLPSISTFVEGY SSNYELKPSCVYQMQRPLIKVEEGRAPSYHHHHHHHHHHHHHHQQQHQQPSIPPASSPEDEVLPS TSMYFKQSPPSTPTTPAFPPQAGALWDEALPSAPGCIAPGPLLDPPMKAVPTVAGARFPLFHFKP SPPHPPAPSPAGGHHLGYDPTAAAALSLPLGAAAAAGSQAAALESHPYGLPLAKRAAPLAFPPLG LTPSPTASSLLGESPSLPSPPSRSSSSGEGTCAVCGDNAACQHYGVRTCEGCKGFFKRTVQKNAK |

TABLE 1-continued

NR4A3 protein isoforms.

| 2) | YVCLANKNCPVDKRRRNRCQYCRFQKCLSVGMVKEVVRTDSLKGRRGRLPSKPKSPLQQEPSQPS<br>PPSPPICMMNALVRALTDSTPRDLDYSRVSFMISCFQMNDQGLYLWLLVIRVD |
|---|---|
| NR4A3<br>Isoform3<br>(identifier:<br>Q92570-3)<br>(SEQ ID NO:<br>3) | MHDSIRFGNVDMPCVQAQYSPSPPGSSYAAQTYSSEYTTEIMNPDYTKLTMDLGSTEITATATTS<br>LPSISTFVEGYSSNYELKPSCVYQMQRPLIKVEEGRAPSYHHHHHHHHHHHHHQQQHQQPSIPP<br>ASSPEDEVLPSTSMYFKQSPPSTPTTPAFPPQAGALWDEALPSAPGCIAPGPLLDPPMKAVPTVA<br>GARFPLFHFKPSPPHPPAPSPAGGHHLGYDPTAAAALSLPLGAAAAAGSQAAALESHPYGLPLAK<br>RAAPLAFPPLGLTPSPTASSLLGESPSLPSPPSRSSSSGEGTCAVCGDNAACQHYGVRTCEGCKG<br>FFKRTVQKNAKYVCLANKNCPVDKRRRNRCQYCRFQKCLSVGMVKEVVRTDSLKGRRGRLPSKPK<br>SPLQQEPSQPSPPSPPICMMNALVRALTDSTPRDLDYSRYCPTDQAAAGTDAEHVQQFYNLLTAS<br>IDVSRSWAEKIPGFTDLPKEDQTLLIESAFLELFVLRLSIRSNTAEDKFVFCNGLVLHRLQCLRG<br>FGEWLDSIKDFSLNLQSLNLDIQALACLSALSMITERHGLKEPKRVEELCNKITSSLKDHQSKGQ<br>ALEPTESKVLGALVELRKICTLGLQRIFYLKLEDLVSPPSIIDKLFLDTLPF |

In some aspects, the cell composition useful for the present disclosure comprises a population of modified immune cells that (i) overexpress c-Jun, e.g., recombinantly produced c-Jun protein, (ii) has reduced level of NR4A3 gene and/or NR4A3 protein, and (iii) express a ligand binding protein (e.g., CAR or TCR) (e.g., specifically binds to ROR1), and that additionally have endogenous expression of NR4A1 and NR4A2 genes and NR4A1 and NR4A2 proteins. In some aspects, such modified immune cells (e.g., overexpressing c-Jun and reduced level of NR4A3 gene and/or NR4A3 protein) also has reduced level of one of the following: (i) NR4A1 gene and/or NR4A1 protein; (ii) NR4A2 gene and/or NR4A2 protein; or (iii) both (i) and (ii). Therefore, unless indicated otherwise, modified immune cells having reduced level of NR4A3 gene and/or NR4A3 protein can have endogenous or reduced expression of the other members of the NR4A family. As used herein, the term "NR4A3 gene" refers to any transcript, genomic DNA, pre-mRNA, or mRNA. As used herein, the term "NR4A3 protein" refers to isoform alpha, isoform beta, or isoform 3 disclosed above, as well as variants and mutants thereof. As used herein, the term NR4A3 protein also encompasses any fragment or variant of any of the isoforms disclosed herein that has at least one function of the wild type NR4A3 protein.

As used herein the term "reduced levels," "lower levels," "reduced expression levels," or "lower levels" (or variants thereof) refers both to reduction in physical levels (e.g., less gene sequence due to edition from the genome, or less protein due a decrease in protein expression) and to reduction in function. For example, a reduction in level of NR4A3 gene can refer to a decrease in gene function, e.g., due to the introduction of a mutation introducing a stop codon or a frame shift, to an epigenetic modification that would alter transcription, or to a mutation or other change on a promoter gene or another gene that regulates NR4A3 expression. In some aspects, a reduction in level of NR4A3 gene in a modified cell refers to a decrease in the amount (e.g., concentration) of genomic DNA, pre-mRNA, and/or mRNA that is capable of encoding a functional NR4A3 protein, e.g., wild type NR4A3 protein, compared to a reference cell. Similarly, a reduction in NR4A3 protein can refer to changes resulting in the expression of a functional NR4A3 protein, e.g., wild type NR4A3 protein, including but not limited to changes (e.g., mutations or post-translational modifications) that cause a loss of function (partial or complete), or to the activity of molecules that bind to functional sites of NR4A3 altering, e.g., its interaction with other cell signaling partners.

NR4A3 gene levels (e.g., presence/absence of the entire gene or a portion thereof, or gene function) can be measured by various methods known in the art. NR4A3 protein levels (e.g., presence/absence of the NR4A3 protein or fragments thereof, or quantification or protein function) can be measured by various methods known in the art.

In some aspects, the expression levels of NR4A3 gene and/or expression levels of NR4A3 protein in the population of immune cells (e.g., CAR or TCR-expressing cells) are reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to a population of reference immune cells, e.g., corresponding cells that have not been modified to express lower levels of NR4A3 gene and/or NR4A3 protein. In some aspects, the expression of NR4A3 gene and/or NR4A3 protein in protein in the population of immune cells (e.g., T cells, a population of CAR-expressing cells or a TCR-expressing cells) is completely inhibited after the modification.

In some aspects, the expression level of NR4A3 gene in the population of immune cells is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to a population of reference immune cells, e.g., corresponding cells that have not been modified to express lower levels of NR4A3 gene.

In some aspects, the expression level of NR4A3 protein in the population of immune cells is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to a population of reference immune cells, e.g., corresponding cells that have not been modified to express lower levels of NR4A3 protein.

In some aspects, the expression levels of NR4A3 gene and NR4A3 protein in the population of immune cells are reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to a population of reference immune cells, e.g., corresponding cells that have not been modified to express lower levels of NR4A3 gene and NR4A3 protein.

In some aspects, modified immune cells disclosed herein (i.e., cells that expresses reduced levels of NR4A3 gene and/or NR4A3 protein) comprise lymphocytes, neutrophils, monocytes, macrophages, dendritic cells, or combinations thereof. In some aspects, modified immune cells disclosed herein (i.e., a population of cells that expresses reduced levels of NR4A3 gene and/or NR4A3 protein) comprise lymphocytes. In some aspects, the lymphocytes are T cells, e.g., CD8+ T cells and/or CD4+ T cells. As used herein, "modified immune cells" include progeny cells of the originally modified immune cells, wherein the progeny cells also express reduced levels of NR4A3 gene and/or NR4A3 protein.

II.B. NR4A2

Nuclear receptor subfamily 4 group A member 2, generally abbreviated NR4A2, also known as NOT, RNR1, HZF-3, NURR1, TINUR, is a protein which in humans is encoded by the NR4A2 gene. The NR4A2 gene is located on chromosome 2 (bases 156,324,432 to 156,332,724, NCBI Reference Sequence: NC_000002.12).

The NR4A2 proteins have two isoforms produced by alternative splicing. The sequences are shown in Table 2 below.

protein can have endogenous or reduced expression of the other members of the NR4A family. As used herein, the term "NR4A2 gene" refers to any transcript, genomic DNA, pre-mRNA, or mRNA. As used herein, the term "NR4A2 protein" refers to isoform 1 or 2 disclosed above, as well as variants and mutants thereof. As used herein, the term NR4A2 protein also encompasses any fragment or variant of any of the isoforms disclosed herein that has at least one function of the wild type NR4A2 protein.

As used herein the term "reduced levels," "lower levels," "reduced expression levels," or "lower levels" (or variants thereof) refers both to reduction in physical levels (e.g., less gene sequence due to edition from the genome, or less protein due a decrease in protein expression) and to reduction in function. For example, a reduction in level of NR4A2 gene can refer to a decrease in gene function, e.g., due to the introduction of a mutation introducing a stop codon or a frame shift, to an epigenetic modification that would alter transcription, or to a mutation or other change on a promoter gene or another gene that regulates NR4A2 expression. In some aspects, a reduction in level of NR4A2 gene in a modified cell refers to a decrease in the amount (e.g., concentration) of genomic DNA, pre-mRNA, and/or mRNA that is capable of encoding a functional NR4A2 protein, e.g., wild type NR4A2 protein, compared to a reference cell. Similarly, a reduction in NR4A2 protein can refer to changes resulting in the expression of a functional NR4A2 protein, e.g., wild type NR4A2 protein, including but not limited to changes (e.g., mutations or post-translational modifications) that cause a loss of function (partial or complete), or to the

TABLE 2

| NR4A2 protein isoforms. | |
|---|---|
| NR4A2 Isoform 1 (identifier: P43354-1) (SEQ ID NO: 43) | MPCVQAQYGSSPQGASPASQSYSYHSSGEYSSDFLTPEFVKFSMDLTNTEITATTSLPSFSTFMD NYSTGYDVKPPCLYQMPLSGQQSSIKVEDIQMHNYQQHSHLPPQSEEMMPHSGSVYYKPSSPPTP TTPGFQVQHSPMWDDPGSLHNFHQNYVATTHMIEQRKTPVSRLSLFSFKQSPPGTPVSSCQMRFD GPLHVPMNPEPAGSHHVVDGQTFAVPNPIRKPASMGFPGLQIGHASQLLDTQVPSPPSRGSPSNE GLCAVCGDNAACQHYGVRTCEGCKGFFKRTVQKNAKYVCLANKNCPVDKRRRNRCQYCRFQKCLA VGMVKEVVRTDSLKGRRGRLPSKPKSPQEPSPPSPPVSLISALVRAHVDSNPAMTSLDYSRFQAN PDYQMSGDDTQHIQQFYDLLTGSMEIIRGWAEKIPGFADLPKADQDLLFESAFLELFVLRLAYRS NPVEGKLIFCNGVVLHRLQCVRGFGEWIDSIVEFSSNLQNMNIDISAFSCIAALAMVTERHGLKE PKRVEELQNKIVNCLKDHVTFNNGGLNRPNYLSKLLGKLPELRTLCTQGLQRIFYLKLEDLVPPP AIIDKLFLDTLPF |
| NR4A2 Isoform 2 (identifier: P43354-2) (SEQ ID NO: 44) | MDNYSTGYDVKPPCLYQMPLSGQQSSIKVEDIQMHNYQQHSHLPPQSEEMMPHSGSVYYKPSSPP TPTTPGFQVQHSPMWDDPGSLHNFHQNYVATTHMIEQRKTPVSRLSLFSFKQSPPGTPVSSCQMR FDGPLHVPMNPEPAGSHHVVDGQTFAVPNPIRKPASMGFPGLQIGHASQLLDTQVPSPPSRGSPS NEGLCAVCGDNAACQHYGVRTCEGCKGFFKRTVQKNAKYVCLANKNCPVDKRRRNRCQYCRFQKC LAVGMVKEVVRTDSLKGRRGRLPSKPKSPQEPSPPSPPVSLISALVRAHVDSNPAMTSLDYSRFQ ANPDYQMSGDDTQHIQQFYDLLTGSMEIIRGWAEKIPGFADLPKADQDLLFESAFLELFVLRLAY RSNPVEGKLIFCNGVVLHRLQCVRGFGEWIDSIVEFSSNLQNMNIDISAFSCIAALAMVTERHGL KEPKRVEELQNKIVNCLKDHVTFNNGGLNRPNYLSKLLGKLPELRTLCTQGLQRIFYLKLEDLVP PPAIIDKLFLDTLPF |

In some aspects, the cell composition useful for the present disclosure comprises a population of modified immune cells that (i) overexpress c-Jun, e.g., recombinantly produced c-Jun protein, (ii) has reduced level of NR4A2 gene and/or NR4A2 protein, and (iii) express a ligand binding protein (e.g., CAR or TCR) (e.g., specifically binds to ROR1), and that additionally have endogenous expression of NR4A1 and NR4A3 genes and NR4A1 and NR4A3 proteins. In some aspects, such modified immune cells (e.g., overexpressing c-Jun and reduced level of NR4A2 gene and/or NR4A2 protein) also has reduced level of one of the following: (i) NR4A1 gene and/or NR4A1 protein; (ii) NR4A3 gene and/or NR4A3 protein; or (iii) both (i) and (ii). Therefore, unless indicated otherwise, modified immune cells having reduced level of NR4A2 gene and/or NR4A2 activity of molecules that bind to functional sites of NR4A2 altering, e.g., its interaction with other cell signaling partners.

NR4A2 gene levels (e.g., presence/absence of the entire gene or a portion thereof, or gene function) can be measured by various methods known in the art. NR4A2 protein levels (e.g., presence/absence of the NR4A2 protein or fragments thereof, or quantification or protein function) can be measured by various methods known in the art.

In some aspects, the expression levels of NR4A2 gene and/or expression levels of NR4A2 protein in the population of immune cells (e.g., CAR or TCR-expressing cells) are reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to a population of reference immune cells, e.g., corresponding cells that have not been modified to express lower levels of NR4A2 gene and/or NR4A2 protein. In some aspects, the expression of NR4A2 gene and/or NR4A2 protein in the population of immune cells (e.g., a population of CAR-expressing cells or a TCR-expressing cells) is completely inhibited after the modification.

In some aspects, the expression level of NR4A2 gene in the population of immune cells is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to a population of reference immune cells, e.g., corresponding cells that have not been modified to express lower levels of NR4A2 gene.

In some aspects, the expression level of NR4A2 protein in the population of immune cells is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to a population of reference immune cells, e.g., corresponding cells that have not been modified to express lower levels of NR4A2 protein.

about 45%, at least about 50%, at least about 55%, at least about 60%, at least about 65%, at least about 70%, at least about 75%, at least about 80%, at least about 85%, at least about 90%, at least about 95%, or about 100% compared to a population of reference immune cells, e.g., corresponding cells that have not been modified to express lower levels of NR4A2 gene and NR4A2 protein.

In some aspects, modified immune cells disclosed herein (i.e., cells that express reduced levels of NR4A2 gene and/or NR4A2 protein) comprise lymphocytes, neutrophils, monocytes, macrophages, dendritic cells, or combinations thereof. In some aspects, modified immune cells disclosed herein (i.e., a population of cells that expresses reduced levels of NR4A2 gene and/or NR4A2 protein) comprise lymphocytes. In some aspects, the lymphocytes are T cells, e.g., CD8+ T cells and/or CD4+ T cells. As used herein, "modified immune cells" include progeny cells of the originally modified immune cells, wherein the progeny cells also express reduced levels of NR4A2 gene and/or NR4A2 protein.

II.C. NR4A1

Nuclear Receptor Subfamily 4 Group A Member 1, generally abbreviated NR4A1, and also known as AMR, N10, TR3, NP10, GFRP1, NAK-1, NGFIB, and NUR77, is a protein which in humans is encoded by the NR4A1 gene. The NR4A1 gene is located on chromosome 12 (bases 52022832 to 52059507; NCBI Reference Sequence NC_000012.12).

The NR4A1 proteins have three isoforms produced by alternative splicing. The sequences are shown in Table 3 below.

TABLE 3

| NR4A1 protein isoforms. | |
|---|---|
| NR4A1 Isoform 1 (identifier: P22736-1) (SEQ ID NO: 45) | MPCIQAQYGTPAPSPGPRDHLASDPLTPEFIKPTMDLASPEAAPAAPTALPSFSTFMDGYTGEFD TFLYQLPGTVQPCSSASSSASSTSSSSATSPASASFKFEDFQVYGCYPGPLSGPVDEALSSSGSD YYGSPCSAPSPSTPSFQPPQLSPWDGSFGHFSPSQTYEGLRAWTEQLPKASGPPQPPAFFSFSPP TGPSPSLAQSPLKLFPSQATHQLGEGESYSMPTAFPGLAPTSPHLEGSGILDTPVTSTKARSGAP GGSEGRCAVCGDNASCQHYGVRTCEGCKGFFKRTVQKNAKYICLANKDCPVDKRRRNRCQFCRFQ KCLAVGMVKEVVRTDSLKGRRGRLPSKPKQPPDASPANLLTSLVRAHLDSGPSTAKLDYSKFQEL VLPHFGKEDAGDVQQFYDLLSGSLEVIRKWAEKIPGFAELSPADQDLLLESAFLELFILRLAYRS KPGEGKLIFCSGLVLHRLQCARGFGDWIDSILAFSRSLHSLLVDVPAFACLSALVLITDRHGLQE PRRVEELQNRIASCLKEHVAAVAGEPQPASCLSRLLGKLPELRTLCTQGLQRIFYLKLEDLVPPP PIIDKIFMDTLPF |
| NR4A1 Isoform 2 (identifier: P22736-2) (SEQ ID NO: 46) | MWLAKACWSIQSEMPCIQAQYGTPAPSPGPRDHLASDPLTPEFIKPTMDLASPEAAPAAPTALPS FSTFMDGYTGEFDTFLYQLPGTVQPCSSASSSASSTSSSSATSPASASFKFEDFQVYGCYPGPLS GPVDEALSSSGSDYYGSPCSAPSPSTPSFQPPQLSPWDGSFGHFSPSQTYEGLRAWTEQLPKASG PPQPPAFFSFSPPTGPSPSLAQSPLKLFPSQATHQLGEGESYSMPTAFPGLAPTSPHLEGSGILD TPVTSTKARSGAPGGSEGRCAVCGDNASCQHYGVRTCEGCKGFFKRTVQKNAKYICLANKDCPVD KRRRNRCQFCRFQKCLAVGMVKEVVRTDSLKGRRGRLPSKPKQPPDASPANLLTSLVRAHLDSGP STAKLDYSKFQELVLPHFGKEDAGDVQQFYDLLSGSLEVIRKWAEKIPGFAELSPADQDLLLESA FLELFILRLAYRSKPGEGKLIFCSGLVLHRLQCARGFGDWIDSILAFSRSLHSLLVDVPAFACLS ALVLITDRHGLQEPRRVEELQNRIASCLKEHVAAVAGEPQPASCLSRLLGKLPELRTLCTQGLQR IFYLKLEDLVPPPPIIDKIFMDTLPF |
| NR4A1 Isoform 3 (identifier: P22736-3) (SEQ ID NO: 47) | MPCIQAQYGTPAPSPGPRDHLASDPLTPEFIKPTMDLASPEAAPAAPTALPSFSTFMDGYTGEFD TFLYQLPGTVQPCSSASSSASSTSSSSATSPASASFKFEDFQVYGCYPGPLSGPVDEALSSSGSD YYGSPCSAPSPSTPSFQPPQLSPWDGSFGHFSPSQTYEGLRAWTEQLPKASGPPQPPAFFSFSPP TGPSPSLAQSPLKLFPSQATHQLGEGESYSMPTAFPGLAPTSPHLEGSGILDTPVTSTKARSGAP GGSEGRCAVCGDNASCQHYGVRTCEGCKGFFKVPRSPRWGLLLEMERGWPHPIGTCGLPLGSPPS |

In some aspects, the expression levels of NR4A2 gene and NR4A2 protein in the population of immune cells are reduced by at least about 5%, at least about 10%, at least about 15%, at least about 20%, at least about 25%, at least about 30%, at least about 35%, at least about 40%, at least In some aspects, the cell composition useful for the present disclosure comprises a population of modified immune cells that (i) overexpress c-Jun, e.g., recombinantly produced c-Jun protein, (ii) has reduced level of NR4A1 gene and/or NR4A1 protein, and (iii) expresses a ligand binding protein (e.g., CAR or TCR) (e.g., specifically binds to ROR1), and that additionally have endogenous expression of NR4A2 and NR4A3 genes and NR4A2 and NR4A3 proteins. In some aspects, such modified immune cells (e.g., overexpressing c-Jun and reduced level of NR4A1 gene and/or NR4A1 protein) also have reduced level of one of the following: (i) NR4A2 gene and/or NR4A2 protein; (ii) NR4A3 gene and/or NR4A3 protein; or (iii) both (i) and (ii). Therefore, unless indicated otherwise, modified immune cells having reduced level of NR4A1 gene and/or NR4A1 protein can have endogenous or reduced expression of the other members of the NR4A family. As used herein, the term "NR4A1 gene" refers to any transcript, genomic DNA, pre-mRNA, or mRNA. As used herein, the term "NR4A1 protein" refers to isoform 1, isoform 2, or isoform 3 disclosed above, as well as variants and mutants thereof. As used herein, the term NR4A1 protein also encompasses any fragment or variant of any of the isoforms disclosed herein that has at least one function of the wild type NR4A1 protein.

As used herein the term "reduced levels," "lower levels," "reduced expression levels," or "lower levels" (or variants thereof) refers both to reduction in physical levels (e.g., less gene sequence due to editing from the genome, or less protein due a decrease in protein expression) and to reduction in function. For example, a reduction in level of NR4A1 gene can refer to a decrease in gene function, e.g., due to the introduction of a mutation introducing a stop codon or a frame shift, to an epigenetic modification that would alter transcription, or to a mutation or other change on a promoter gene or another gene that regulates NR4A1 expression. In some aspects, a reduction in level of NR4A1 gene in a modified cell refers to a decrease in the amount (e.g., concentration) of genomic DNA, pre-mRNA, and/or mRNA that is capable of encoding a functional NR4A1 protein, e.g., wild type NR4A1 protein, compared to a reference cell. Similarly, a reduction in NR4A1 protein can refer to changes resulting in the expression of a functional NR4A1 protein, e.g., wild type NR4A1 protein, including but not limited to changes (e.g., mutations or post-translational modifications) that cause a loss of function (partial or complete), or to the activity of molecules that bind to functional sites of NR4A1 altering, e.g., its interaction with other cell signaling partners.

NR4A1 gene levels (e.g., presence/absence of the entire gene or a portion thereof, or gene function) can be measured by various methods known in the art. NR4A1 protein levels (e.g., presence/absence of the NR4A1 protein or fragments thereof, or quantification or protein function) can be measured by various methods known in the art.

In some aspects, the expression levels of NR4A1 gene and/or expression levels of NR4A1 protein in the population of immune cells (e.g., CAR or TCR-expressing cells) are reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to a population of reference immune cells, e.g., corresponding cells that have not been modified to express lower levels of NR4A1 gene and/or NR4A1 protein. In some aspects, the expression of NR4A1 gene and/or NR4A1 protein in protein in the population of immune cells (e.g., a population of CAR-expressing cells or a TCR-expressing cells) is completely inhibited after the modification.

In some aspects, the expression level of NR4A1 gene in the population of immune cells is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to a population of reference immune cells, e.g., corresponding cells that have not been modified to express lower levels of NR4A1 gene.

In some aspects, the expression level of NR4A1 protein in the population of immune cells is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to a population of reference immune cells, e.g., corresponding cells that have not been modified to express lower levels of NR4A1 protein.

In some aspects, the expression levels of NR4A1 gene and NR4A1 protein in the population of immune cells are reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to a population of reference immune cells, e.g., corresponding cells that have not been modified to express lower levels of NR4A1 gene and NR4A1 protein.

In some aspects, modified immune cells disclosed herein (i.e., cells that expresses reduced levels of NR4A1 gene and/or NR4A1 protein) comprise lymphocytes, neutrophils, monocytes, macrophages, dendritic cells, or combinations thereof. In some aspects, modified immune cells disclosed herein (i.e., a population of cells that expresses reduced levels of NR4A1 gene and/or NR4A1 protein) comprise lymphocytes. In some aspects, the lymphocytes are T cells, e.g., CD8+ T cells and/or CD4+ T cells. As used herein, "modified immune cells" include progeny cells of the originally modified immune cells, wherein the progeny cells also express reduced levels of NR4A1 gene and/or NR4A1 protein.

II.D. c-Jun Protein

In addition to the reduced levels of a NR4A gene and/or protein as described above, modified immune cells of the present disclosure (e.g., CAR or TCR expressing immune cells) are also modified to have an increased level of a c-Jun protein. As demonstrated herein, in some aspects, immune cells are modified to comprise an exogenous nucleotide sequence encoding a c-Jun protein to increase the level of a c-Jun protein compared to a reference immune cell (e.g., corresponding immune cell that was not modified to comprise the exogenous nucleotide sequence encoding a c-Jun protein). In some aspects, the c-Jun protein can be encoded by a polycistronic polynucleotide, wherein the polynucleotide encodes multiple proteins including c-Jun and a ligand binding protein (e.g., CAR or TCR) and, in some aspects, one or more additional proteins (e.g., a safety switch protein such as EGFRt). In some aspects, modified immune cells with a reduced level of NR4A gene and/or NR4A protein comprises a polynucleotide encoding a chimeric polypeptide, which comprise a c-Jun polypeptide and a ligand binding protein (e.g., CAR or TCR). In some aspects, such a chimeric polypeptide can include cleavable linkers such that the c-Jun polypeptide and the ligand binding protein (e.g., CAR or TCR) are cleaved into separate functioning proteins after translation. In some aspects, a modified immune cell provided herein (i.e., having reduced level of a gene and/or protein of one or more members of the NR4A family) is capable of naturally expressing a c-Jun protein (e.g., without modifying the cell with an exogenous nucleotide sequence encoding a c-Jun protein). In some aspects, such immune cells have been modified with a transcriptional activator (e.g., CRISPR/Cas-system-based transcription activator, e.g., CRISPRa), such that the expression of the endogenous c-Jun protein is increased compared to a reference cell (e.g., corresponding cell that has not been modified with the transcriptional activator).

As used herein, the term "transcriptional activator" refers to a protein that increases the transcription of a gene or set of genes (e.g., by binding to enhancers or promoter-proximal elements of a nucleic acid sequence and thereby, inducing its transcription). Non-limiting examples of such transcriptional activators that can be used with the present disclosure include: Transcription Activator-like Effector (TALE)-based transcriptional activator, zinc finger protein (ZFP)-based transcriptional activator, Clustered Regularly Interspaced Short Palindromic Repeats (CRISPR)/CRISPR-associated protein (Cas) system-based transcriptional activator, or a combination thereof. See, e.g., Kabadi et al., *Methods* 69(2): 188-197 (September 2014), which is incorporated herein by reference in its entirety.

In some aspects, a cell described herein has been modified with a CRISPR/Cas-system-based transcriptional activator, such as CRISPR activation (CRISPRa). See, e.g., Nissim et al., *Molecular Cell* 54: 1-13 (May 2014), which is incorporated herein by reference in its entirety. CRISPRa is a type of CRISPR tool that comprises the use of modified Cas proteins that lacks endonuclease activity but retains the ability to bind to its guide RNA and the target DNA nucleic acid sequence. Non-limiting examples of such modified Cas proteins which can be used with the present disclosure are known in the art. See, e.g., Pandelakis et al., *Cell Systems* 10(1): 1-14 (January 2020), which is incorporated herein by reference in its entirety. In some aspects, the modified Cas protein comprises a modified Cas9 protein (also referred to in the art as "dCas9"). In some aspects, the modified Cas protein comprises a modified Cas12a protein. In some aspects, a modified Cas protein that is useful for the present disclosure is bound to a guide polynucleotide (e.g., small guide RNA) ("modified Cas-guide complex"), wherein the guide polynucleotide comprises a recognition sequence that is complementary to a region of a nucleic acid sequence encoding a protein of interest (e.g., c-Jun). In some aspects, the guide polynucleotide comprises a recognition sequence that is complementary to the promoter region of an endogenous nucleic acid sequence encoding a protein of interest. In some aspects, one or more transcriptional activators are attached to the modified Cas-guide complex (e.g., the N- and/or C-terminus of the modified Cas protein), such that when the modified Cas-guide complex is introduced into a cell, the one or more transcription activators can bind to a regulatory element (e.g., promoter region) of a nucleic acid sequence, and thereby induce and/or increase the expression of the encoded protein (e.g., c-Jun). In some aspects, the one or more transcription activators can bind to a regulatory element (e.g., promoter region) of an endogenous gene, and thereby induce and/or increase the expression of the encoded protein (e.g., c-Jun). Non-limiting Illustrative examples of common general activators that can be used include the omega subunit of RNAP, VP16, VP64 and p65. See, e.g., Kabadi and Gersbach, *Methods* 69: 188-197 (2014), which is incorporated herein by reference in its entirety.

In some aspects, one or more transcriptional repressors (e.g., Kruppel-associated box domain (KRAB)) can be attached to the modified Cas-guide complex (e.g., the N- and/or C-terminus of the modified Cas protein), such that when introduced into a cell, the one or more transcriptional repressors can repress or reduce the transcription of a gene, e.g., such as those that can interfere with the expression of c-Jun (e.g., Bach2). See, e.g., US20200030379A1 and Yang et al., *J Transl Med* 19:459 (2021), each of which is incorporated herein by reference in its entirety. In some aspects, a modified Cas protein useful for the present disclosure can be attached to both one or more transcriptional activators and one or more transcriptional repressors.

As will be apparent to those skilled in the art, in some aspects, a cell described herein has been modified using a combination of multiple approaches. For instance, in some aspects, a cell has been modified to have a reduced level of a NR4A gene and/or NR4A protein (e.g., NR4A1, NR4A2, NR4A3, or a combination thereof) and to comprise (i) an exogenous nucleotide sequence encoding one or more proteins (e.g., a ligand-binding protein, e.g., CAR or TCR) and (ii) an exogenous transcriptional activator (e.g., CRISPRa) that increases expression of an endogenous protein (e.g., c-Jun). In some aspects, a cell has been modified to have a reduced level of a NR4A gene and/or NR4A protein (e.g., NR4A1, NR4A2, NR4A3, or a combination thereof) and to comprise (i) an exogenous nucleotide sequence encoding a first protein (e.g., a ligand-binding protein) and (ii) an exogenous nucleotide sequence encoding a second protein (e.g., a c-Jun protein). As described herein, in some aspects, the exogenous nucleotide sequences encoding the first and second proteins can be part of a single polycistronic vector.

In some aspects, due to the above-described modification (e.g., introduction of the exogenously introduced c-Jun nucleotide sequence and/or transcriptional activator), the modified cells overexpress, i.e., express a higher level (e.g., at least about 10, at least about 20, at least about 30, at least about 40, at least about 50, at least about 60, at least about 70, at least about 80, at least about 90, or at least about 100% more, or at least about 1.5-, at least about 2-, at least about 3-, at least about 4-, at least about 5-, or at least about 10-fold more) of, a c-Jun protein than corresponding cells without such a modification ("reference cell"). The terms "express increased levels [or amounts] of," "overexpress," or have "increased expression of" (and similar forms of the phrase used herein), are used interchangeably.

c-Jun is an oncogenic transcription factor belonging to the activator protein-1 (AP-1) family. It interacts with various proteins (e.g., c-Fos) to form dimeric complexes that modulate a diverse range of cellular signaling pathways, including cell proliferation and tumor progression. Accordingly, increased c-Jun expression has been observed in certain cancers, and there has been much interest in developing c-Jun antagonists to treat such cancer. See, e.g., Brennan, A., et al., *J Exp Clin Cancer Res* 39(1): 184 (September 2020).

In humans, the c-Jun protein is encoded by the JUN gene, which is located on chromosome 1 (nucleotides 58,780,791 to 58,784,047 of Genflank Accession No. NC_000001.11, minus strand orientation). Synonyms of the JUN gene, and the encoded protein thereof, are known and include "Jun proto-oncogene, AP-1 transcription factor subunit," "v-Jun avian sarcoma virus 17 oncogene homolog," "transcription factor AP-1," "Jun oncogene," "AP-1," "Jun activation domain binding protein," "p39", and "enhancer-binding protein AP1." The wild-type human c-Jun protein sequence is 331 amino acids in length. The amino acid and nucleic acid sequences of the wild-type human c-Jun are provided in Tables 4 and 5, respectively.

TABLE 4 c-Jun Protein Sequence

| | |
|---|---|
| Wild-type human c-Jun (UniProt: P05412-1) (SEQ ID ID NO: 4) | MTAKMETTFYDDALNASFLPSESGPYGYSNPKILKQSMTLNLADPVGSLKPHLRAKNSDL LTSPDVGLLKLASPELERLIIQSSNGHITTTPTPTQFLCPKNVTDEQEGFAEGFVRALAE LHSQNTLPSVTSAAQPVNGAGMVAPAVASVAGGSGSGGFSASLHSEPPVYANLSNFNPGA LSSGGGAPSYGAAGLAFPAQPQQQQQPPHHLPQQMPVQHPRLQALKEEPQTVPEMPGETP PLSPIDMESQERIKAERKRMRNRIAASKCRKRKLERIARLEEKVKTLKAQNSELASTANM LREQVAQLKQKVMNHVNSGCQLMLTQQLQTF |

TABLE 5 c-Jun Nucleic Acid Sequence

| | |
|---|---|
| Wild-type JUN (GenBank Accession No. NM_002228.4) (SEQ ID NO: 5) * coding region is boldedand capitalized (SEQ ID NO: 6) | gctcagagttgcactgagtgtggctgaagcagcgaggcgggagtggaggtgcgcggagt caggcagacagacagacacagccagccagccaggtcggcagtatagtccgaactgcaaa tcttattttcttttcaccttctctctaactgcccagagctagcgcctgtggctcccggg ctggtgtttcgggagtgtccagagagcctggtctccagccgcccccgggaggagagccc tgctgcccaggcgctgttgacagcggcggaaagcagcggtacccacgcgcccgccgggg gaagtcggcgagcggctgcagcagcaaagaacttttcccggctgggaggaccggagacaa gtggcagagtcccggagccaacttttgcaagcctttcctgcgtcttaggcttctccacg gcggtaaagaccagaaggcggcggagagccacgcaagagaagaaggacgtgcgctcagc ttcgctcgcaccggttgttgaacttgggcgagcgcgagccgcggctgccgggcgccccc tcccctagcagcggaggaggggacaagtcgtcggagtccgggcggccaagacccgccg ccggccggccactgcagggtccgcactgatccgctccgcgggagagccgcgctgctctgg gaagtgagttcgcctgcggactccgaggaaccgctgcgcacgaagagcgctcagtgagt gaccgcgacttttcaaagccgggtagcgcgcgcgagtcgacaagtaagagtgcgggagg catcttaattaaccctgcgctccctggagcgagctggtgaggagggcgcagcggggacg acagccagcgggtgcgtgcgctcttagagaaactttccctgtcaaaggctccggggggc gcgggtgtcccccgcttgccacagccctgttgcggccccgaaacttgtgcgcgcagccc aaactaacctcacgtgaagtgacggactgttctATGACTGCAAAGATGGAAACGACCTT CTATGACGATGCCCTCAACGCCTCGTTCCTCCCGTCCGAGAGCGGACCTTATGGCTACA GTAACCCCAAGATCCTGAAACAGAGCATGACCCTGAACCTGGCCGACCCAGTGGGGAGC CTGAAGCCGCACCTCCGCGCCAAGAACTCGGACCTCCTCACCTCGCCCGACGTGGGGCT GCTCAAGCTGGCGTCGCCCGAGCTGGAGCGCCTGATAATCCAGTCCAGCAACGGGCACA TCACCACCACGCCGACCCCCACCCAGTTCCTGTGCCCCAAGAACGTGACAGATGAGCAG GAGGGCTTCGCCGAGGGCTTCGTGCGCGCCCTGGCCGAACTGCACAGCCAGAACACGCT GCCCAGCGTCACGTCGGCGGCGCAGCCGGTCAACGGGGCAGGCATGGTGGCTCCCGCGG TAGCCTCGGTGGCAGGGGGCAGCGGCAGCGGCGGCTTCAGCGCCAGCCTGCACAGCGAG CCGCCGGTCTACGCAAACCTCAGCAACTTCAACCCAGGCGCGCTGAGCAGCGGCGGCGG GGCGCCCTCCTACGGCGCGGCCGGCCTGGCCTTTCCCGCGCAACCCCAGCAGCAGCAGC AGCCGCCGCACCACCTGCCCCAGCAGATGCCCGTGCAGCACCCGCGGCTGCAGGCCCTG AAGGAGGAGCCTCAGACAGTGCCCGAGATGCCCGGCGAGACACCGCCCCTGTCCCCCAT CGACATGGAGTCCCAGGAGCGGATCAAGGCGGAGAGGAAGCGCATGAGGAACCGCATCG CTGCCTCCAAGTGCCGAAAAAGGAAGCTGGAGAGAATCGCCCGGCTGGAGGAAAAAGTG AAAACCTTGAAAGCTCAGAACTCGGAGCTGGCGTCCACGGCCAACATGCTCAGGGAACA GGTGGCACAGCTTAAACAGAAAGTCATGAACCACGTTAACAGTGGGTGCCAACTCATGC TAACGCAGCAGTTGCAAACATTTtgaagagagaccgtcgggggctgaggggcaacgag aaaaaaaataacacagagagacagacttgagaacttgacaagttgcgacggagagaaaa aagaagtgtccgagaactaaagccaagggtatccaagttggactgggttgcgtcctgac ggcgccccagtgtgcacgagtgggaaggacttggcgcgccctcccttggcgtggagcc agggagcggccgcctgcgggctgccccgctttgcggacgggctgtccccgcgcgaacgg aacgttggacttttcgttaacattgaccaagaactgcatggacctaacattcgatctca ttcagtattaaaggggggaggggagggggttacaaactgcaatagagactgtagattg cttctgtagtactccttaagaacacaaagcggggggagggttggggaggggcggcagga gggaggtttgtgagagcgaggctgagcctacagatgaactcttttctggcctgccttcgt taactgtgtatgtacatatatatattttttaatttgatgaaagctgattactgtcaata aacagcttcatgcctttgtaagttatttcttgtttgtttgtttgggtatcctgcccagt gttgtttgtaaataagagatttggagcactctgagtttaccatttgtaataaagtatat aattttttttatgtttttgtttctgaaaattccagaaaggatatttaagaaaatacaataa actattggaaagtactcccctaacctcttttctgcatcatctgtagatactagctatct aggtggagttgaaagagttaagaatgtcgattaaaatcactctcagtgcttcttactat taagcagtaaaaactgttctctattagacttagaaataaatgtacctgatgtacctga tgctatggtcaggttatactcctcctcccccagctatctatatggaattgcttaccaaa ggatagtgcgatgtttcaggaggctggaggaaggggggttgcagtggagagggacagcc cactgagaagtcaaacatttcaaagtttggattgtatcaagtggcatgtgctgtgacca tttataatgttagtagaaattttacaataggtgcttattctcaaagcaggaattggtgg cagattttacaaaagatgtatccttccaatttggaatcttctctttgacaattcctaga taaaaagatggcctttgcttatgaatatttataacagcattcttgtcacaatatgta ttcaaataccaa |

II.D.1. Codon Optimization

As described herein, modified immune cells with a reduced level of NR4A gene and/or NR4A protein comprises a polynucleotide which comprises a nucleotide sequence encoding a c-Jun protein, wherein the nucleotide sequence has been codon-optimized. Accordingly, in some aspects, the nucleotide sequence encoding a c-Jun protein (also referred to herein as "c-Jun nucleotide sequence") described herein differs from that of the wild-type c-Jun nucleotide sequence (e.g., SEQ ID NO: 6).

In some aspects, a nucleotide sequence encoding a c-Jun protein has at least about 500%, at least about 5500, at least about 600%, at least about 650%, at least about 700%, at least about 7500 at least about 800%, at least about 850%, at least about 900%, at least about 9500 at least about 960%, at least about 9700 at least about 980%, or at least about 9900 sequence identity to any one of the nucleic acid sequences set forth in SEQ TD NOs: 7 to 16. In some aspects, a nucleotide sequence encoding a c-Jun protein comprises the nucleic acid sequence set forth in any one of SEQ ID NOs: 7 to 16.

In some aspects, a nucleotide sequence encoding a c-Jun protein has at least about 800%, at least about 850%, at least about 9000, at least about 9500 at least about 9600, at least about 9700, at least about 9800, or at least about 9900 sequence identity to the nucleic acid sequence set forth in SEQ ID NO: 7. In some aspects, a nucleotide sequence encoding a c-Jun protein has at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 7. In some aspects, the nucleotide sequence comprises the nucleic acid sequence set forth in SEQ ID NO: 7.

In some aspects, a nucleotide sequence encoding a c-Jun protein has at least about 80%, at least about 85%, at least about 90%, at least about 95%, at least about 96%, at least about 97%, at least about 98%, or at least about 99% sequence identity to the nucleic acid sequence set forth in SEQ ID NO: 8. In some aspects, a nucleotide sequence encoding a c-Jun protein has at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 8. In some aspects, the nucleotide sequence comprises the nucleic acid sequence set forth in SEQ ID NO: 8.

In some aspects, a nucleotide sequence encoding a c-Jun protein has at least about 80%, at least about 85%, at least about 90%, at least about 95%, at least about 96%, at least about 97%, at least about 98%, or at least about 99% sequence identity to the nucleic acid sequence set forth in SEQ ID NO: 9. In some aspects, a nucleotide sequence encoding a c-Jun protein described herein has at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 9. In some aspects, the nucleotide sequence comprises the nucleic acid sequence set forth in SEQ ID NO: 9.

In some aspects, a nucleotide sequence encoding a c-Jun protein has at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the nucleic acid sequence set forth in SEQ ID NO: 10. In some aspects, a nucleotide sequence has at least 96%, at least 97%, at least 98%, or at least 99% to the nucleic acid sequence set forth in SEQ ID NO: 10. In some aspects, the nucleotide sequence comprises the nucleic acid sequence set forth in SEQ ID NO: 10.

In some aspects, a nucleotide sequence encoding a c-Jun protein has at least about 70%, at least about 75%, at least about 80%, at least about 85%, at least about 90%, at least about 95%, at least about 96%, at least about 97%, at least about 98%, or at least about 99% sequence identity to the nucleic acid sequence set forth in SEQ ID NO: 11. In some aspects, a nucleotide sequence encoding a c-Jun protein has at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 11. In some aspects, the nucleotide sequence comprises the nucleic acid sequence set forth in SEQ ID NO: 11.

In some aspects, a nucleotide sequence encoding a c-Jun protein has at least about 80%, at least 85%, at least 90%, at least about 95%, at least about 96%, at least about 97%, at least about 98%, or at least about 99% sequence identity to the nucleic acid sequence set forth in SEQ ID NO: 12. In some aspects, a nucleotide sequence encoding a c-Jun protein has at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 12. In some aspects, the nucleotide sequence comprises the nucleic acid sequence set forth in SEQ ID NO: 12.

In some aspects, a nucleotide sequence encoding a c-Jun protein has at least about 80%, at least about 85%, at least about 90%, at least about 95%, at least about 96%, at least about 97%, at least about 98%, or at least about 99% sequence identity to the nucleic acid sequence set forth in SEQ ID NO: 13. In some aspects, a nucleotide sequence encoding a c-Jun protein has at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 13. In some aspects, the nucleotide sequence comprises the nucleotide sequence set forth in SEQ ID NO: 13.

In some aspects, a nucleotide sequence encoding a c-Jun protein has at least about 80%, at least about 85%, at least about 90%, at least about 95%, at least about 96%, at least about 97%, at least about 98%, or at least about 99% sequence identity to the nucleic acid sequence set forth in SEQ ID NO: 14. In some aspects, a nucleotide sequence encoding a c-Jun protein has at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 14. In some aspects, the nucleotide sequence comprises the nucleotide sequence set forth in SEQ ID NO: 14.

In some aspects, a nucleotide sequence encoding a c-Jun protein has at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to the nucleic acid sequence set forth in SEQ ID NO: 15. In some aspects, a nucleotide sequence encoding a c-Jun protein has at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 15. In some aspects, the nucleotide sequence comprises the nucleotide sequence set forth in SEQ ID NO: 15.

In some aspects, a nucleotide sequence encoding a c-Jun protein has at least about 85%, at least about 90%, at least about 95%, at least about 96%, at least about 97%, at least about 98%, or at least about 99% sequence identity to the nucleic acid sequence set forth in SEQ ID NO: 16. In some aspects, a nucleotide sequence encoding a c-Jun protein has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 16. In some aspects, the nucleotide sequence comprises the nucleotide sequence set forth in SEQ ID NO: 16.

In some aspects, a nucleotide sequence encoding a c-Jun protein has at least about 85%, at least about 90%, at least about 95%, at least about 96%, at least about 97%, at least about 98%, or at least about 99% sequence identity to the nucleic acid sequence set forth in SEQ ID NO: 16. In some aspects, a nucleotide sequence encoding a c-Jun protein has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 16. In some aspects, the nucleotide sequence comprises the nucleotide sequence set forth in SEQ ID NO: 16.

TABLE 6

| Codon-Optimized c-Jun Nucleotide Sequences | |
| --- | --- |
| Codon-optimized c-Jun nucleotide sequence #1 (SEQ ID NO: 7) | atgacagccaagatggaaaccacattctacgacgacgccctgaacgcctcattcctgc cttctgagagcggaccttacggctacagcaatcctaagatcctgaaacagagcatgac ccttaacctggctgatcctgttggaagcctgaaacctcacctgagagccaaaaacagc gacctgctcaccagccctgatgtgggcctgctgaagctggcctctccagagctggaac ggctgatcatccagagcagcaacggccacatcacaaccacccctacccctacacaatt cctgtgccctaagaacgtgaccgacgagcaggagggcttcgccgaaggctttgtgcgg gccctggcagaactgcactctcagaacaccctgcctagcgtgacctccgccgcccagc ctgtcaacggcgccggaatggtggcccctgccgtggcttctgtggccggcggcagcgg cagcggcggattcagcgcctctctgcactctgagcctcctgtctacgccaatctgtct aatttcaaccccggagccctgtccagcggcggcggagctcctagctacggcgctgctg gactggccttccccgcccagccccagcaacagcagcagcctccacaccacctgcccca gcagatgcccgtgcagcaccctagactgcaggccctgaaggaagaaccccaaacagtg cctgagatgcctggcgagacacctccactgagccccatcgacatggaaagccaggagc ggatcaaggccgagagaaagagaatgcggaaacagaatcgccgctagcaagtgcagaaa gcggaagctggaaagaatcgccagactggaagagaaggtgaagaccctgaaagcccaa aatagcgagctggccagcaccgccaacatgctgcggggaacaggtggcccagctgaagc agaaggtgatgaaccacgtgaactctggttgtcagctgatgctgacccagcagctcca gaccttc |
| Codon-optimized c-Jun nucleotide sequence #2 (SEQ ID NO: 8) | atgacagccaagatggaaaccaccttctacgacgacgccctcaacgcctccttcctgc cttctgagagcggtccttacggctacagcaaccccaagatcctgaagcaaagcatgac cctgaacctggccgacccccgttggctccctgaaacctcacctgagagccaaaaacagc gacctgctgaccagccctgatgtgggcctgctgaagctggcctctccagagctggaaa gactgattatccagagcagcaacggccacatcaccacaacacctacccctacacagtt cctgtgccctaagaacgtgactgatgagcaggaggggctttgccgagggcttcgtgaga gccctggctgagctgcattctcagaacaccctgcctagcgtgacctctgccgcccagc ctgttaatggcgccggcatggtggcccctgccgtggcctctgtgtggccggaggcagcgg cagcggcggattcagcgcctctctgcacagcgagcccccgtctacgccaacctgagc aatttcaaccctggcgccctgtccagcggcggcggcgcccttcatatggcgctgccg gcctggccttccccgctcagccccagcagcagcaacagcctccacaccacctgcccca gcagatgcccgtgcagcaccccagactgcaggccctgaaggaagaacctcagaccgtg cccgagatgcctggcgagacccctcctctgagccctatcgacatggaaagccaggaga gaatcaaggccgagaggaagcggatgcggaacagaatcgccgccagcaagtgcagaaa aagaaagctggaacggatcgccagactggaggagaaggtgaagacactgaaagcccaa aattctgaactggcctctaccgccaatatgctgcgcgcgagcaggtggctcaactgaagc agaaggtgatgaaccacgtgaacagcggatgtcagctgatgctgacacagcagctgca gacttt |
| Codon-optimized c-Jun nucleotide sequence #3 (SEQ ID NO: 9) | atgaccgccaagatggaaaccacctcctacgacgacgccctgaacgccagctttctgc cttctgagtctggccccctacggctacagcaaccccaagatcctgaagcagagcatgac cctgaacctggccgatcctgtgggcagcctgaaacctcacctgagagccaagaacagc gacctgctgacaagccctgatgtgggcctgctgaaactggcctctcctgagctggaac ggctgatcatccagagcagcaacggccacatcaccaccacacctacccaacacagtt tctgtgccccaagaacgtgaccgacgagcaagagggattcgccgagggctttgttaga gccctggccgaactgcacagccagaataccctgcctagcgtgacatctgccgctcagc ctgttaatggcgccggaatggttgtcctgccgtggctttctgttgctggcggatctgg atctggcggctttagcgcctctctgcactctgagcctccagtgtacgccaacctgagc aacttcaacccctggcgctcttagctctggtggcggagcaccttcttatggcgctgccg gattggcctttcctgctcagcctcagcagcagcaacagcctcctcatcatctgcccca gcagatgcctgtgcagcaccctagactgcaggccctgaaagaggaaccccagacagtc cctgagatgcccggcgaaacacctcctctgagccccatcgacatggaaagccaagagc ggatcaaggccgagcggaagcggatgagaaatagaatcgccgcctccaagtgccggaa gaggaagctggaaagaatcgcccggctggaagagaaagtgaaaaccctgaaggcccag aactccgagctggcctctaccgccaacatgctgagagaacaggtggcccagctgaaac agaaagtcatgaaccacgtgaacagcggctgccagctgatgctgacacagcagctgca gaccttc |
| Codon-optimized c-Jun nucleotide sequence #4 (SEQ ID NO: 10) | atgactgccaaaatggagactacattctatgacgacgccctcaatgccagttttttgc cgagtgaatccggcccctacggctattcaaaccctaagatcctcaagcaatcaatgac cctcaatcttgctgacccagttggctccctgaaaccccatctcagagctaaaaatagt gacctccttacttcccctgatgttggactcctcaaacttgcttctcccgaactcgaac gcttgatcattcaatcttccaacggccacatcacaacaacacccacacccacccagtt tctttgcccaaaaaatgtcaccgatgaacaggaaggtttcgcggaaggattcgtccgc gcgctggccgaactgcactcccagaatacacttccttcagttacgtcagccgcccagc cagtgaatggtgcgggaatggttgctcctgcggtcgcttctgtcgcaggggggctccgg ttctggcggatttagcgcctctctgcattccgagccacctgtatatgctaatctttct |

TABLE 6-continued

Codon-Optimized c-Jun Nucleotide Sequences

```
                      aattttaaccccggagccttgtctagcggcggtggtgcccccagctacggtgctgcag
                      gactcgccttcccagctcaacctcagcagcagcaacaaccccccatcaccttcccca
                      acagatgccagtacaacatccaaggctccaggccctcaaagaggaaccacagacggtg
                      cccgaaatgcctggcgaaactccaccactttcccctattgatatggaatcccaagagc
                      gcatcaaggccgaaagaaagcgaatgcggaatagaatagcagcttcaaaatgtagaaa
                      acggaaattggaacgaatcgcacggttggaagaaaaggtgaagaccttgaaagcccag
                      aacagtgagctcgcctctaccgctaacatgctgcgcgagcaagtcgcacaacttaagc
                      agaaggtgatgaaccatgtgaatagcggatgtcaacttatgctgactcaacagttgca
                      aacctttt Codon-optimized       atgaccgcgaaaatggagacaacattttacgatgatgcactgaacgcctcttttctgc
c-Jun nucleotide      caagtgaatccggcccctacggatactcaaaccctaagattctgaaacagtctatgac
sequence #5 (SEQ      tctcaacctggccgacccagttggcagtctgaagcctcatttgcgagccaagaatagt
ID NO: 11)            gatctgctgacctccccagacgtgggactgctgaaactcgcctcacctgaacttgagc
                      gcttgattatacagtcatccaatgggcacatcacaacaacacctactcctacccagtt
                      tctgtgccccaaaaacgtcaccgatgagcaggaggggattcgcggaaggctttgtgcgc
                      gccctggctgaattgcatagtcagaacactcttcccagcgtaaccagcgccgcccaac
                      cagtgaatggagccggtatggtggctcccgcggtggctagtgttgcggggggggtcagg
                      ctctggtggggttcagtgcttctcttcactctgaaccccctgtgtatgccaatctgtct
                      aactttaaccctggggccctctcctctggtggggggtgcccccagctacggagcggccg
                      gcctggcctttcctgcccagcctcagcagcagcagcaaccccctcatcatcttccgca
                      gcagatgccagtacagcatccacgcctgcaggctcttaaggaggagccccagacggtg
                      cccgaaatgcccgggggaaactccaccccttgtcccccattgacatggagtcccaggagc
                      ggatcaaggctgaaagaaagaggatgcggaatcgcatcgcagcctctaaatgccgcaa
                      gcggaaacttgagaggatcgcgcggttggaggaaaaagtaaaaaccttgaaggcacag
                      aactctgagctggcgagtactgccaacatgctcagagaacaagtcgcacagctgaagc
                      agaaagtgatgaaccatgtgaacagcggttgtcagctgatgctgactcagcagctgca
                      gaccttc Codon-optimized       atgaccgccaagatggagaccacattctacgatgacgctctgaacgcttcctttctgc
c-Jun nucleotide      cttccgagtccggcccctacggctactccaatcccaagattctgaagcagagcatgac
sequence #6 (SEQ      actgaatctggctgatcccgtgggatctctgaagcctcatctgagagccaagaattcc
ID NO: 12)            gatctgctgacaagccccgacgtgggactgctcaaactggccagccccgaactggaga
                      ggcteattatccagagctccaacggccacatcaccacaacacctaccccctacccagtt
                      tctctgtcccaagaacgtgacagacgagcaagagggattgccgaaggcttcgtgaga
                      gccctcgccgaactgcatagccagaacacactgccttccgtgaccagcgctgctcaac
                      ccgtgaacgcgcgctggcatggtcgctcccgccgtcgccagcgtggctggaggaagcgg
                      atccggaggcttcagcgcttccctccacagcgaacctcccgtgtacgctaatctgagc
                      aacttcaaccccggcgctctgagcagcggaggaggagctcctagctatggagctgccg
                      gactggcttttcccgcccagccccagcagcagcagcagcccccccatcatctgcctca
                      gcagatgcccgtgcagcatcccagactccaagctctgaaggaggagcctcagaccgtc
                      cccgagatgcccggcgaaacccccccctctgtcccccatcgacatggaaagccaagaga
                      ggatcaaggccgagaggaagaggatgaggaatagaatcgccgccagcaagtgtagaaa
                      gaggaagctgagaggatcgccgactggaggagaaggtgaagaccctcaaggctcag
                      aattccgagctggccagcacagccaacatgctgagagagcaagtggcccagctcaagc
                      agaaggtgatgaaccacgtcaacagcggatgccagctgatgctcacccagcagctgca
                      gaccttc Codon-optimized       atgaccgctaaaatggaaaccactttctatgacgatgccctgaacgcctccttcttc
c-Jun nucleotide      cgtccgagtccggacccctacggatactcaaatcctaagatcctcaaacagtcgatgac
sequence #7 (SEQ      cctcaacctggccgacccgtgggatccctgaagccgcacttgcgcgccaagaactcc
ID NO: 13)            gacctcctgacgagcccagacgtgggcgctgctgaagctcgcatcacccgaacttgagc
                      ggttgatcattcagtcctccaacggacatatcaccaccactcccacccccaactcagtt
                      tctgtgtccgaagaacgtgaccgatgagcaagagggattcgccgagggattcgtgcgg
                      gccctggccgagctgcatagccagaacaccttccatccgtgacctcggcggctcagc
                      ctgtgaacggcgcgggaatggtcgcgcccgccgtggcctcggtggccgggggcagcgg
                      cagcgggggattttccgcgtcgctgcactccgagccgccggtgtacgccaacctgtca
                      aacttcaaccctggggccctgagctccggcggtggagcaccttcgtacggcgcgctg
                      gcctggcgttccccgcgcaaccacagcagcaacagcagcccccctcaccacctcccca
                      acaaatgcctgtgcagcaccccgaggctgcaggccctcaaggaagaaccccagactgtg
                      ccggaaatgccgggggagactccgcgcgctgtcccctatcgacatggaatcacaggaac
                      gcattaaggcagagcggaagcgcatgcggaaccggattgccgcctccaagtgccgcaa
                      gagaaagctcgaaagaatcgccagattggaagaaaaggtcaagactctgaaggcccag
                      aactctgagctggcatccaccgctaatatgctgagggaacaagtggcccagctgaaac
                      agaaggtcatgaaccacgtcaacagcggttgccagctgatgctgacccagcaactcca
                      gacattc Codon-optimized       atgaccgccaagatggagaccaccttctacgacgacgccctgaacgccagcttcctgc
c-Jun nucleotide      ccagcgagagcggaccctacggctact ctaaccccaagatcctgaaacagagcatgac
sequence #8 (SEQ      actgaatctggccgacccctgggcagcctgaagcctcaccttagagccaagaacagc
ID NO: 14)            gacctgctgaccagccccgacgtgggcctgctgaagctcgcctctccagagttagaga
                      gactgatcatccagtccagcaacggccacatcacaaccaccccaacccctacccagtt
                      cctgtgccccaagaacgtgaccgacgagcaggagggcttcgccgagggctttgtgaga
                      gccctggccgagttgcactctcagaacaccctgccctccgtgaccagcgccgctcaac
                      ctgtgaacggcgcaggaatggttgctcctgccgtggccagcgttgcaggcggatctgg
                      aagtgaggcttctccgcctcccttcacagcgagcctcccgtgtacgccaacctgagc
                      aacttcaaccccggcgccctgagcagtggaggaggcgctcccagctatggagcagctg
                      gattagccttccccgcccagccacagcagcagcaacagcctcccccaccacctgcctca
```

TABLE 6-continued

Codon-Optimized c-Jun Nucleotide Sequences

|  |  |
|---|---|
|  | gcaaatgcctgtgcagcaccctcggctgcaggcccttaaggaggagccccagaccgtt cctgagatgcctggcgagacccctcccctgagccctatcgacatggagtcccaggagc ggatcaaggccgagcggaagcggatgcggaaccggatcgctgcttccaagtgccggaa gagaaagctggagagaatcgcccggctggaggagaaggtgaagaccctgaaggcccag aactccgagctggcctccaccgccaacatgctgcgggagcaggttgcacagctgaagc agaaggtcatgaaccacgtgaacagcggctgccagctgatgctgacccagcagctgca gaccttc |
| Codon-optimized c-Jun nucleotide sequence #9 (SEQ ID NO: 15) | atgacagcgaagatggagacaaccttctatgacgatgctcttaacgcctccttcctgc cttccgaaagcgggccctacgggtactctaatcctaagatacttaagcaatcgatgac tctcaacctcgctgacccggttggctcactgaaaccacacctgagagctaagaatagt gacctgctcactagtcccgatgtcgggcttctgaagctggcctctcccgagctggaga ggcttatcatccaatcatcaaatggccacatcaccactaccccaacaccaactcaatt cctttgccctaaaaacgtgaccgacgaacaggaaggcttcgccgagggtttgtccgg gccttggccgagctgcattctcaaaatacactgccaagcgtcacttctgcggcgcagc cggttaacggagcagggatggtggctcccgccgttgctagcgtggccggcggttccgg ctccggcggtttctctgcctccttgcattctgagccaccagtctacgcgaacctgtcc aactttaatccggggcgctgagtagcggaggcggcgcccctagctatggggcagctg gactggccttcccggcacaacccaacaacaacagcaaccgccacaccatcttcctca acaaatgccagtgcaacatccacgcttacaagccctcaaggaggaaccccagaccgtg cctgagatgcccggcgaaacccccgccattgagccctattgacatggaaagtcaagaga gaattaaggcagagcgcaagagaatgaggaaccggatcgcagcatctaagtgccgcaa acggaaattggagcggatcgctcgcttggaggagaaggtcaagactctcaaggcccag aactccgagcttgcgagcacagctaatatgctgcgcgagcaggtggcccagttaaaac aaaaggtcatgaaccatgtgaacagcggctgtcagctgatgcttacgcaacagctgca aacctttggctccggtgcaacgaacttcagcctgctgaagcaggccggagatgttgag gaaaatccaggtccc |
| Codon-optimized c-Jun nucleotide sequence #10 (SEQ ID NO: 16) | atgacggccaaaatggagactacgttctacgatgacgcactcaacgcgtccttcctgc cctctgagagtggaccctatggctactccaatccaaagatcctgaagcagtctatgac cctcaacctggcggacccggtgggctcccttaagccgcacttgcgcgccaagaactcc gacctgctgacctcccctgatgtgggcctcctcaagctcgctagccctgaattggaga ggctgatcatccagagctcaaatggccacatcaccaccacacctaccccaacccagtt cctgtgcccaaaaaacgtgaccgacgagcaggagggcttcgcggagggcttcgtcaga gctctggccgagctgcactcacagaacacgctcccttccgtgacctccgctgcccagc cggtcaatggcgctggaatggtggctccggctgtggcctctgttgccggcggctccgg ctccggaggcttttcagcttctctgcattctgagccccagtgtacgctaacctgagc aacttcaaccccggggcgctcagctccggtggcggtgccccgagctacggcgcggctg ggctggcgttccccgctcagcctcagcagcaacagcaacctccccaccacctgccaca gcagatgcctgtgcagcaccacgcctgcaggccttgaaggaggaacctcagactgtg ccagagatgcccggcgagacccccaccctgtccccgattgacatggagagccaggagc gcatcaaggcagagcgcaagcgtatgcgcaaccgcatcgcggcctccaagtgccgaaa gcgcaagctggagcggattgctcgcctggaggagaaggtgaagaccctgaaggcccag aattccgagctggcctcgaccgccaacatgctacgagaacaggtcgcgcagctgaaac agaaggtcatgaaccatgtcaacagcgggtgccagctgatgttgacccagcagcttca gaccttc |

The c-Jun nucleotide sequence disclosed herein can be codon-optimized using any methods known in the art. For instance, in some aspects, the codons of a c-Jun nucleotide sequence disclosed herein has been optimized to modify (e.g., increase or decrease) one or more of the following parameters compared to the wild-type nucleotide sequence (e.g., SEQ ID NO: 6): (i) codon adaptation index (i.e., codon usage bias); (ii) guanine-cytosine (GC) nucleotide content; (iii) mRNA secondary structure and unstable motifs; (iv) repeat sequences (e.g., direct repeats, inverted repeats, dyad repeats); (v) restriction enzyme recognition sites; or (vi) combinations thereof.

Not to be bound by any one theory, in some aspects, such codon optimization can increase the expression of the protein encoded by the nucleotide sequence. Accordingly, in some aspects, a codon-optimized c-Jun nucleotide sequence of the present disclosure is capable of increasing the expression of the encoded c-Jun transcription factor when transfected, transduced or otherwise introduced into a human cell, e.g., a human T cell, compared to a corresponding expression in a cell transfected with the wild-type nucleotide sequence (e.g., SEQ ID NO: 6). In some aspects, the expression of the c-Jun transcription factor is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more, compared to the corresponding expression in the cell transfected, transduced, or otherwise genetically modified to express with the wild-type nucleotide sequence (e.g., SEQ ID NO: 6).

In some aspects, the increased expression of the c-Jun transcription factor in the modified immune cells with a reduced level of NR4A gene and/or NR4A protein (e.g., NR4A1, NR4A2, NR4A3, or a combination thereof) can improve and/or enhance one or more properties of the transfected cells (e.g., immune cells, e.g., T cells, such as CD4+ and/or CD8+ T cells). Non-limiting examples of such properties include: resistance to exhaustion (e.g., as indicated by reduced expression of exhaustion markers, such as PD-1, CD39, TIM-3, and/or LAG-3; increased survival; and/or increased cytokine production), increased persistence/survival, increased expansion/proliferation, improved effector function (e.g., cytokine production upon antigen stimulation, lysis of cells expressing the target antigen, or both), or combinations thereof.

Assays useful for measuring exhaustion, cell phenotype, persistence, cytotoxicity and/or killing, proliferation, cytokine production/release, and gene expression profiles are known in the art and include, for example flow cytometry, intracellular cytokine staining (ICS), INCUCYTE® immune cell killing analysis, Meso Scale Discovery (MSD) or similar assay, persistent antigen stimulation assays, bulk and single cell RNAseq (see e.g., Fron Genet. 2020; 11:220; 2019 Bioinformatics 35:i436-445; 2019 Annual Review of Biomed. Data Sci. 2:139-173), cytotoxicity/killing assays, ELISA, western blot and other standard molecular and cell biology methods such as described herein or as described, for example, in Current Protocols in Molecular Biology or Current Protocols in Immunology (John Wiley & Sons, Inc., 1999-2021) or elsewhere.

In some aspects, the increased expression of the c-Jun transcription factor in the modified immune cells with a reduced level of NR4A gene and/or NR4A protein increases the resistance of the cell to exhaustion. In some aspects, the modified immune cells (i.e., overexpressing c-Jun) have reduced levels of NR4A1 gene and/or protein. In some aspects, the modified immune cells (i.e., overexpressing c-Jun) have reduced levels of NR4A2 gene and/or protein. In some aspects, the modified immune cells (i.e., overexpressing c-Jun) have reduced levels of NR4A3 gene and/or protein. In some aspects, the modified immune cells (i.e., overexpressing c-Jun) have reduced levels of both a NR4A1 gene and/or NR4A1 protein and a NR4A2 gene and/or NR4A2 protein. In some aspects, the modified immune cells (i.e., overexpressing c-Jun) have reduced levels of both a NR4A1 gene and/or NR4A1 protein and a NR4A3 gene and/or NR4A3 protein. In some aspects, the modified immune cells (i.e., overexpressing c-Jun) have reduced levels of both a NR4A2 gene and/or NR4A2 protein and a NR4A3 gene and/or NR4A3 protein. In some aspects, the modified immune cells (i.e., overexpressing c-Jun) have reduced levels of each of the following: a NR4A1 gene and/or NR4A1 protein, a NR4A2 gene and/or NR4A2 protein, and a NR4A3 gene and/or NR4A3 protein. In some aspects, the resistance to exhaustion is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more, compared to a reference cell (e.g., corresponding cell that was not modified to have increased c-Jun expression and/or reduced expression of NR4A gene(s) and/or NR4A protein (s)).

In some aspects, the over-expression of the c-Jun transcription factor in the modified immune cells with a reduced level of NR4A gene and/or NR4A protein (e.g., NR4A1, NR4A2, NR4A3, or a combination thereof) can decrease exhaustion in an exhausted cell. In some aspects, the modified immune cells (i.e., overexpressing c-Jun) have reduced levels of NR4A1 gene and/or protein. In some aspects, the modified immune cells (i.e., overexpressing c-Jun) have reduced levels of NR4A2 gene and/or protein. In some aspects, the modified immune cells (i.e., overexpressing c-Jun) have reduced levels of NR4A3 gene and/or protein. In some aspects, the modified immune cells (i.e., overexpressing c-Jun) have reduced levels of both a NR4A1 gene and/or NR4A1 protein and a NR4A2 gene and/or NR4A2 protein. In some aspects, the modified immune cells (i.e., overexpressing c-Jun) have reduced levels of both a NR4A1 gene and/or NR4A1 protein and a NR4A3 gene and/or NR4A3 protein. In some aspects, the modified immune cells (i.e., overexpressing c-Jun) have reduced levels of both a NR4A2 gene and/or NR4A2 protein and a NR4A3 gene and/or NR4A3 protein. In some aspects, the modified immune cells (i.e., overexpressing c-Jun) have reduced levels of each of the following: a NR4A1 gene and/or NR4A1 protein, a NR4A2 gene and/or NR4A2 protein, and a NR4A3 gene and/or NR4A3 protein. In some aspects, exhaustion is decreased in modified immune cells by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold, compared to a reference cell (e.g., corresponding exhausted cell that was not modified to have increased c-Jun expression and/or reduced expression of a NR4A gene(s) and/or NR4A protein (s)).

In some aspects, the increased expression of the c-Jun transcription factor in the modified immune cells with a reduced level of NR4A gene and/or NR4A protein (e.g., NR4A1, NR4A2, NR4A3, or a combination thereof) can increase the persistence/survival of the cell, e.g., when administered to a subject in vivo. In some aspects, the modified immune cells (i.e., overexpressing c-Jun) have reduced levels of NR4A1 gene and/or protein. In some aspects, the modified immune cells (i.e., overexpressing c-Jun) have reduced levels of NR4A2 gene and/or protein. In some aspects, the modified immune cells (i.e., overexpressing c-Jun) have reduced levels of NR4A3 gene and/or protein. In some aspects, the modified immune cells (i.e., overexpressing c-Jun) have reduced levels of both a NR4A1 gene and/or NR4A1 protein and a NR4A2 gene and/or NR4A2 protein. In some aspects, the modified immune cells (i.e., overexpressing c-Jun) have reduced levels of both a NR4A1 gene and/or NR4A1 protein and a NR4A3 gene and/or NR4A3 protein. In some aspects, the modified immune cells (i.e., overexpressing c-Jun) have reduced levels of both a NR4A2 gene and/or NR4A2 protein and a NR4A3 gene and/or NR4A3 protein. In some aspects, the modified immune cells (i.e., overexpressing c-Jun) have reduced levels of each of the following: a NR4A1 gene and/or NR4A1 protein, a NR4A2 gene and/or NR4A2 protein, and a NR4A3 gene and/or NR4A3 protein. In some aspects, the persistence/survival of the cell is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more, compared to a reference cell (e.g., corresponding cell that was not modified to have increased c-Jun expression and/or reduced expression of a NR4A gene(s) and/or NR4A protein (s)).

In some aspects, the increased expression of the c-Jun transcription factor in the modified immune cells with a reduced level of NR4A gene and/or NR4A protein (e.g., NR4A1, NR4A2, NR4A3, or a combination thereof) can increase the expansion/proliferation of the cell, e.g., upon antigen stimulation. In some aspects, the modified immune cells (i.e., overexpressing c-Jun) have reduced levels of NR4A1 gene and/or protein. In some aspects, the modified immune cells (i.e., overexpressing c-Jun) have reduced levels of NR4A2 gene and/or protein. In some aspects, the modified immune cells (i.e., overexpressing c-Jun) have reduced levels of NR4A3 gene and/or protein. In some aspects, the modified immune cells (i.e., overexpressing c-Jun) have reduced levels of both a NR4A1 gene and/or NR4A1 protein and a NR4A2 gene and/or NR4A2 protein. In some aspects, the modified immune cells (i.e., overexpressing c-Jun) have reduced levels of both a NR4A1 gene and/or NR4A1 protein and a NR4A3 gene and/or NR4A3 protein. In some aspects, the modified immune cells (i.e., overexpressing c-Jun) have reduced levels of both a NR4A2 gene and/or NR4A2 protein and a NR4A3 gene and/or NR4A3 protein. In some aspects, the modified immune cells (i.e., overexpressing c-Jun) have reduced levels of each of the following: a NR4A1 gene and/or NR4A1 protein, a NR4A2 gene and/or NR4A2 protein, and a NR4A3 gene and/or NR4A3 protein. In some aspects, the expansion/ proliferation of the cell is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more, compared to a reference cell (e.g., corresponding cell that was not modified to have increased c-Jun expression and/or reduced expression of a NR4A gene(s) and/or NR4A protein(s)).

In some aspects, the increased expression of the c-Jun transcription factor in the modified immune cells with a reduced level of NR4A gene and/or NR4A protein (e.g., NR4A1, NR4A2, NR4A3, or a combination thereof) can increase the effector function of the cell, e.g., increased cytokine production, granzyme release, and/or cytotoxicity in response to persistent antigen stimulation. In some aspects, the modified immune cells (i.e., overexpressing c-Jun) have reduced levels of NR4A1 gene and/or protein. In some aspects, the modified immune cells (i.e., overexpressing c-Jun) have reduced levels of NR4A2 gene and/or protein. In some aspects, the modified immune cells (i.e., overexpressing c-Jun) have reduced levels of NR4A3 gene and/or protein. In some aspects, the modified immune cells (i.e., overexpressing c-Jun) have reduced levels of both a NR4A1 gene and/or NR4A1 protein and a NR4A2 gene and/or NR4A2 protein. In some aspects, the modified immune cells (i.e., overexpressing c-Jun) have reduced levels of both a NR4A1 gene and/or NR4A1 protein and a NR4A3 gene and/or NR4A3 protein. In some aspects, the modified immune cells (i.e., overexpressing c-Jun) have reduced levels of both a NR4A2 gene and/or NR4A2 protein and a NR4A3 gene and/or NR4A3 protein. In some aspects, the modified immune cells (i.e., overexpressing c-Jun) have reduced levels of each of the following: a NR4A1 gene and/or NR4A1 protein, a NR4A2 gene and/or NR4A2 protein, and a NR4A3 gene and/or NR4A3 protein. In some aspects, the effector function of the cell (e.g., in response to persistent antigen stimulation) is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more, compared to a reference cell (e.g., corresponding cell that was not modified to have increased c-Jun expression and/or reduced expression of a NR4A gene(s) and/or NR4A protein(s)).

Not to be bound by any one theory, overexpression of c-Jun in T cells modified to express a reduced level of NR4A gene and/or NR4A protein (e.g., NR4A1, NR4A2, NR4A3, or a combination thereof) helps sustain the active state of the cells by, e.g., alleviating or preventing T cell dysfunction (e.g., T cell exhaustion). The c-Jun nucleotide sequences provided herein (e.g., codon optimized c-Jun described herein) can be used to engineer immune cells that have been modified to have a reduced level of NR4A gene and/or NR4A protein (e.g., NR4A1, NR4A2, NR4A3, or a combination thereof), such as T cells, which then exhibit sustained, potent cytotoxicity against desired target cells (e.g., the target of the endogenous TCR or the target of a chimeric binding protein as described herein). As compared to T cells that do not overexpress c-Jun, engineered T cells overexpressing the codon optimized c-Jun disclosed herein display fewer signs of T cell exhaustion. In some aspects, the modified T cells provide herein (i.e., overexpressing c-Jun) have reduced levels of NR4A1 gene and/or protein. In some aspects, the modified T cells provided herein (i.e., overexpressing c-Jun) have reduced levels of NR4A2 gene and/or protein. In some aspects, the modified T cells provided herein (i.e., overexpressing c-Jun) have reduced levels of NR4A3 gene and/or protein. In some aspects, the modified T cells (i.e., overexpressing c-Jun) have reduced levels of both a NR4A1 gene and/or NR4A1 protein and a NR4A2 gene and/or NR4A2 protein. In some aspects, the modified T cells (i.e., overexpressing c-Jun) have reduced levels of both a NR4A1 gene and/or NR4A1 protein and a NR4A3 gene and/or NR4A3 protein. In some aspects, the modified T cells (i.e., overexpressing c-Jun) have reduced levels of both a NR4A2 gene and/or NR4A2 protein and a NR4A3 gene and/or NR4A3 protein. In some aspects, the modified T cells (i.e., overexpressing c-Jun) have reduced levels of each of the following: a NR4A1 gene and/or NR4A1 protein, a NR4A2 gene and/or NR4A2 protein, and a NR4A3 gene and/or NR4A3 protein.

As described herein, in some aspects, the present disclosure comprises a modified immune cell overexpressing c-Jun and express reduced levels of NR4A3 gene and/or NR4A3 protein while having endogenous levels of NR4A1 and NR4A2 genes and NR4A1 and NR4A2 proteins, and a ligand binding protein (e.g., CAR or TCR) (e.g., specifically binds to ROR1). In some aspects, the present disclosure comprises a modified immune cell overexpressing a c-Jun protein and expressing reduced levels of NR4A2 gene and/or NR4A2 protein while having endogenous levels of NR4A1 and NR4A3 genes and NR4A1 and NR4A3 proteins, and a ligand binding protein (e.g., CAR or TCR) (e.g., specifically binds to ROR1). In some aspects, the present disclosure comprises a modified immune cell overexpressing c-Jun and expressing reduced levels of NR4A1 gene and/or NR4A1 protein while having endogenous levels of NR4A2 and NR4A3 genes and NR4A2 and NR4A3 proteins, and a ligand binding protein (e.g., CAR or TCR) (e.g., specifically binds to ROR1). As described herein, in some aspects, modified immune cells described herein have reduced level of two members of the NR4A family. For example, in some aspects, an immune cell described herein has been modified to (i) express a ligand binding protein (e.g., CAR or TCR) (e.g., specifically binds to ROR1), (ii) overexpress a c-Jun protein, and (ii) have reduced level of both a NR4A1 gene and/or NR4A1 protein and a NR4A2 gene and/or NR4A2 protein. In some aspects, an immune cell has been modified to (i) express a ligand binding protein (e.g., CAR or TCR) (e.g., specifically binds to ROR1), (ii) overexpress a c-Jun protein, and (ii) have reduced level of both a NR4A1 gene and/or NR4A1 protein and a NR4A3 gene and/or NR4A3 protein. In some aspects, an immune cell has been modified to (i) express a ligand binding protein (e.g., CAR or TCR) (e.g., specifically binds to ROR1), (ii) overexpress a c-Jun protein, and (ii) have reduced level of both a NR4A2 gene and/or NR4A2 protein and a NR4A3 gene and/or NR4A3 protein. As described herein, in some aspects, modified immune cells described herein have reduced level of all members of the NR4A family. Accordingly, in some aspects, an immune cell provided herein has been modified to (i) express a ligand binding protein (e.g., CAR or TCR) (e.g., specifically binds to ROR1), (ii) overexpress a c-Jun protein, and (iii) a NR4A1 gene and/or NR4A1 protein, a NR4A2 gene and/or NR4A2 protein, and a NR4A3 gene and/or NR4A3 protein.

Alternatively, a c-Jun protein useful for the present disclosure can be a mutant human c-Jun protein, so long as the mutant c-Jun protein does not impact the mutant's ability to rescue dysfunctional (exhausted) T cells. In some aspects, a mutant c-Jun protein comprises at least about 70% (e.g., at least about 75%, at least about 80%, at least about 85%, at least about 90%, at least about 95%, at least about 96%, at least about 97%, at least about 98%, or at least about 99%) sequence identity with the C-terminal amino acid residues (e.g., C-terminal 50, 75, 100, 150, 200, or 250 or more residues), the C-terminal portion (e.g., quarter, third, or half) or C-terminal domains (e.g., epsilon, bZIP, and amino acids C-terminal thereof) of a wildtype c-Jun protein. In some aspects, the N-terminal amino acid residues (e.g., N-terminal 50, 75, 100, or 150 or more), the N-terminal portion (e.g., quarter, third, or half) or N-terminal domains (e.g., delta, transactivation domain, and amino acids N-terminal thereof) of a wildtype c-Jun protein are deleted, mutated, or otherwise inactivated.

In some aspects, the c-Jun protein comprises an inactivating mutation (e.g., substitutions, deletions, or insertions) in its transactivation domain and/or its delta domain. In some aspects, the c-Jun protein comprises one or both of S63A and S73A mutations. In some aspects, the c-Jun protein has a deletion between residues 2 and 102 or between residues 30 and 50 as compared to wildtype human c-Jun.

In some aspects, the c-Jun polypeptide useful for the present modified immune cells comprises a truncated c-Jun polypeptide, as disclosed in WO2019/118902, which is expressly incorporated herein by reference in its entirety.

In some aspects, the overexpressed c-Jun polypeptide, along with a reduced expression of a NR4A gene and/or protein, is capable of preventing and/or reducing exhaustion of a cell (e.g., immune cell expressing a CAR or TCR (e.g., anti-ROR1 CAR T cell) with reduced NR4A3 gene and/or NR4A3 protein expression and having endogenous expression of NR4A1 and NR4A2 gene and/or protein, immune cell expressing a CAR or TCR (e.g., anti-ROR1 CAR T cell) with reduced NR4A2 gene and/or NR4A2 protein expression and having endogenous expression of NR4A1 and NR4A3 gene and/or protein, or immune cell expressing a CAR or TCR (e.g., anti-ROR1 CAR T cell) with reduced NR4A1 gene and/or NR4A1 protein expression and having endogenous expression of NR4A2 and NR4A3 gene and/or protein) when overexpressed in the cell. Without wishing to be bound by any one theory, in some aspects, cells overexpressing a c-Jun protein, with a reduced expression of a NR4A gene and/or protein, are exhaustion-resistant, thereby addressing a major barrier to progress for adoptive cellular therapy (e.g., CAR T cell therapies). In some aspects, the resistance to exhaustion is increased by at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more, compared to a reference cell (e.g., corresponding cell that does not overexpress the c-Jun protein and has endogenous expression of NR4A1, NR4A2, and NR4A3 gene and/or protein).

Overexpression of a c-Jun protein in immune cells, such as T cells, along with reduced expression of NR4A gene (e.g., NR4A1, NR4A2, or NR4A3) and/or protein, in some aspects, helps sustain the active state of the cells by, e.g., alleviating or preventing T cell dysfunction (e.g., T cell exhaustion). The present engineered immune cells, such as T cells, exhibit sustained, potent cytotoxicity against antigen-bearing cells (e.g., ROR1-bearing tumor cells). As compared to T cells that do not overexpress the c-Jun protein and do not have reduced expression of a NR4A (e.g., NR4A1, NR4A2, and/or NR4A3) gene and/or protein, the present engineered T cells display fewer signs of T cell exhaustion and increased signs of effector cells that can persist and function longer.

In some aspects, the immune cells provided herein (e.g., expressing a CAR or TCR, e.g., anti-ROR1 CAR engineered cells described herein, and overexpressing a c-Jun protein and having reduced NR4A1, NR4A2, and/or NR4A3 gene and/or protein expression) have reduced expression of one or more exhaustion markers, including but not limited to, TIGIT, PD-1 and CD39. Expression of exhaustion markers can be measured in bulk populations by flow cytometry, using bulk RNASeq transcriptome analysis or in some aspects, individual cell transcriptome analysis can be carried out using single cell RNASeq. In some aspects, the expression of one or more exhaustion markers in an immune cell described herein (e.g., expressing a CAR or TCR, e.g., anti-ROR1 CAR engineered T cells, and overexpressing a c-Jun protein and having reduced NR4A (e.g., NR4A1, NR4A2, and/or NR4A3) gene and/or protein expression) is reduced by at least about 1.5-fold, at least about 2-fold, at least about 2.5-fold, at least about 3.0-fold, at least about 3.5-fold, at least about 4-fold, at least 4.5-fold, at least about 5-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, or at least about 100-fold or more compared to a reference cell (e.g., corresponding cell that has not been engineered to overexpress the c-Jun protein and expresses endogenous levels of NR4A1, NR4A2, and NR4A3 genes and/or proteins). In some aspects, expression of TIGIT in an immune cell described herein (e.g., expressing a CAR or TCR, e.g., anti-ROR1 CAR engineered T cells, and overexpressing a c-Jun protein and having reduced expression of NR4A1, NR4A2, and/or NR4A3 gene and/or protein) is reduced by at least about 1.5-fold, at least about 2-fold, at least about 2.5-fold, at least about 3.0-fold, at least about 3.5-fold, at least about 4-fold, at least about 4.5-fold, at least about 5-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, or at least about 100-fold or more compared to a reference cell (e.g., corresponding cell that has not been engineered to overexpress the c-Jun protein or has endogenous expression of NR4A1, NR4A2, and NR4A3 proteins). In some aspects, expression of PD-1 in an immune cell described herein (e.g., expressing a CAR or TCR, e.g., anti-ROR1 CAR engineered T cells, and overexpressing a c-Jun protein and having reduced expression of NR4A1, NR4A2, and/or NR4A3 gene and/or protein) is reduced by at least about 1.5-fold, at least about 2-fold, at least about 2.5-fold, at least about 3.0-fold, at least about 3.5-fold, at least about 4-fold, at least about 4.5-fold, at least about 5-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, or at least about 100-fold or more compared to a reference cell (e.g., corresponding cell that has not been engineered to overexpress the c-Jun protein and has endogenous NR4A1, NR4A2, and NR4A3 genes and/or protein expression). In some aspects, expression of CD39 in in an immune cell described herein (e.g., expressing a CAR or TCR, e.g., anti-ROR1 CAR engineered T cells) and overexpressing a c-Jun protein and having reduced expression of NR4A1, NR4A2, and/or NR4A3 gene and/or protein) is reduced by at least about 1.5-fold, at least about 2-fold, at least about 2.5-fold, at least about 3.0-fold, at least about 3.5-fold, at least about 4-fold, at least about 4.5-fold, at least about 5-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, or at least about 100-fold or more compared to a reference cell (e.g., corresponding cell that has not been engineered to overexpress the c-Jun protein and has endogenous expression of NR4A1, NR4A2, and NR4A3 genes and/or proteins).

In some aspects, after antigen stimulation, a population of immune cells described herein (e.g., expressing a CAR or TCR, e.g., engineered anti-ROR1 CAR T cells, and overexpressing a c-Jun protein and having reduced expression of NR4A1, NR4A2, and/or NR4A3 gene and/or protein) secretes at least about 5-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, at least about 100-fold, at least about 125-fold, or at least about 150-fold more of IL-2, IFN-γ, and/or TNF-α as compared to a control population of corresponding cells that do not overexpress the c-Jun protein and do not have reduced level of NR4A1, NR4A2, and NR4A3 genes and/or proteins. In some aspects, a population of immune cells described herein (e.g., expressing a CAR or TCR, e.g., engineered anti-ROR1 CAR T cells, and overexpressing a c-Jun protein and having reduced level of NR4A1, NR4A2, and/or NR4A3 gene and/or protein) express at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 8-fold, at least about 10-fold, at least about 15-fold, at least about 20-fold, at least about 30-fold, at least about 40-fold, at least about 50-fold, or at least about 100-fold or more IL-2, IFN-γ, and/or TNF-α at day 0 and/or day 14 of persistent antigen stimulation at 1:1, 1:5, 1:10 and/or 1:20 E:T ratio as compared to a control population of corresponding cells that do not overexpress the c-Jun protein and do not have reduced level of NR4A1, NR4A2, and NR4A3 gene and/or proteins. Cytokine secretion can be measured using methods known in the art such as by ELISA or MSD analysis.

In some aspects, a population of immune cells described herein (e.g., expressing a CAR or TCR, e.g., engineered anti-ROR1 CAR T cells) and overexpressing a c-Jun protein and having reduced level of NR4A1, NR4A2, and/or NR4A3 gene and/or protein) demonstrate at least about 2-fold, at least about 4-fold, at least about 6-fold, at least about 8-fold, at least about 10-fold, at least about 15-fold, at least about 20-fold, at least about 25-fold, at least about 30-fold, at least about 40-fold, at least about 50-fold, at least about 75-fold, at least about 100-fold, at least about 150-fold, at least about 200-fold, or at least about 250-fold or higher enhanced killing efficiency as compared to a control population of corresponding cells that do not overexpress the c-Jun protein and do not have reduced level of NR4A1, NR4A2, and NR4A3 genes and/or proteins, for example, as quantified by area under curve (AUC).

In some aspects, a population of immune cells described herein (e.g., expressing a CAR or TCR, e.g., engineered anti-ROR1 CAR T cells) and overexpressing a c-Jun protein and having reduced level of NR4A1, NR4A2, and/or NR4A3 gene and/or protein) demonstrate at least equal or at least about 1.5-fold, at least about 2-fold, at least about 2.5-fold, at least about 3-fold, at least about 3.5-fold, at least about 4-fold, at least about 5-fold, at least about 8-fold, at least about 10-fold, at least about 15-fold, at least about 20-fold, at least about 25-fold, at least about 30-fold, at least about 50-fold, at least about 75-fold, at least about 100-fold, at least about 125-fold, at least about 150-fold, at least about 200-fold, at least about 225-fold, at least about 250-fold, at least about 300-fold, at least about 400-fold, or at least about 500-fold or more enhanced proliferation in response to antigen as compared to a control population of corresponding cells that do not overexpress the c-Jun protein and do not have reduced level of NR4A1, NR4A2, and NR4A3 genes and/or proteins. Antigen induced proliferation can be tested using proliferation assays known in the art, such as those described herein.

Assays useful for measuring one or more properties of a cell described herein (e.g., anti-ROR1 CAR T cell), such as exhaustion, cell phenotype, persistence, cytotoxicity and/or killing, proliferation, cytokine release, and gene expression profiles, are known in the art and include, for example, flow cytometry, intracellular cytokine staining (ICS), IncuCyte immune cell killing analysis, Meso Scale Discovery (MSD) or similar assay, persistent antigen stimulation assay, sequential antigen stimulation assay (similar to persistent antigen stimulation assay but without resetting E:T cell ratio with each round of restimulation), bulk and single cell RNAseq (see e.g., Fron Genet. 2020; 11:220; 2019 Bioinformatics 35:i436-445; 2019 Annual Review of Biomed. Data Sci. 2:139-173), cytotoxicity/killing assays, ELISA, western blot and other standard molecular and cell biology methods such as described herein or as described, for example, in Current Protocols in Molecular Biology or Current Protocols in Immunology (John Wiley & Sons, Inc., 1999-2021) or elsewhere.

In some aspects, the population of immune cells is a pure population. In some aspects, the pure population comprises at least about 70%, at least about 75%, at least about 80%, at least about 85%, at least about 90%, at least about 95%, or at least 99% of cells belonging to the same immune cell type (e.g., 99% of the immune cells are lymphocytes). In some aspects, the population of immune cells comprises, one, two, three, four, or five different cell types, e.g., a population of immune cells comprising two cell types could comprise lymphocytes and dendritic cells.

In some aspects, a population of modified immune cells disclosed herein comprises, consists, or consists essentially of lymphocytes. In some aspects, a population of modified immune cells disclosed herein comprises lymphocytes, wherein the lymphocytes are selected from the group consisting of T cells, tumor-infiltrating lymphocytes (TIL), lymphokine-activated killer cells, natural killer (NK) T cells, and any combination thereof. In some specific aspects, the lymphocytes are T cells. In some specific aspects, the lymphocytes are NK cells.

In some aspects, a modified immune cell disclosed herein is a T cell. In some aspects, the T cell comprises a CAR. In some aspects, the modified T cell that can be prepared to express a CAR (a CAR T cell) is, e.g., a $CD8^+$ T cell or $CD4^+$ T cell. In some aspects, a CAR-expressing cell disclosed herein is a CAR T cell, e.g., a mono CAR T cell, a genome-edited CAR T cell, a dual CAR T cell, or a tandem CAR T cell. In some aspects, a modified cell disclosed herein is an NK cell. In some aspects, the NK cell comprises a CAR. In some aspects, the CAR NK cell is a mono CAR NK cell, a dual CAR NK cell, or a tandem CAR NKT cell. In some aspects, a modified cell of the presence disclosure comprises both T cells and NK cells. In some aspects, the T cells and NK cells both comprise CARs. Examples of such CAR T cells and CAR NK cells are provided in International Application No. PCT/US2019/044195. In some aspects, the T cell, NK cell, or both comprise any of the other ligand binding proteins described herein. For example, in some aspects, the T cell comprises a TCR, e.g., engineered TCR. In some aspects, the NK cell comprises a TCR, e.g., engineered TCR.

In some aspects, the modified immune cell can be any immune cell type. In some aspects, the cells are modified immune cells for any adoptive cell transfer (ACT) therapy (also known as adoptive cell therapy). ACT therapy can be an autologous therapy or allogenic therapy. In some aspects, the ACT therapy includes, but are not limited to a CAR T therapy, a tumor-infiltrating lymphocyte (TIL) therapy, an NK cell therapy, or any combination thereof.

In some aspects, the modified immune cells are TILs for a TIL therapy. The use of TILs as an adoptive cell transfer therapy to treat cancer have been studied for more than two decades using TIL adoptive cell therapy for melanoma. Rosenberg S A et al., (July 2011). *Clinical Cancer Research* 17 (13): 4550-7 (July 2011). In adoptive T cell transfer therapy, TILs are expanded ex vivo from surgically resected tumors that have been cut into small fragments or from single cell suspensions isolated from the tumor fragments. Multiple individual cultures are established, grown separately and assayed for specific tumor recognition. TILs are expanded over the course of a few weeks. Selected TIL lines that presented best tumor reactivity are then further expanded in a "rapid expansion protocol" (REP), which uses anti-CD3 activation for a typical period of two weeks. The TILs grown in the culture can be modified any time during the ex vivo process so that the expression of NR4A1, NR4A2, or NR4A3 gene and/or NR4A1, NR4A2, or NR4A3 protein, including combinations thereof, is reduced and that the expression of a c-Jun protein is increased. The final post-REP TIL is infused back into the patient. The process can also involve a preliminary chemotherapy regimen to deplete endogenous lymphocytes in order to provide the adoptively transferred TILs with enough access to surround the tumor sites.

As described herein, immune cells of the present disclosure (e.g., overexpressing a c-Jun protein and having reduced level of NR4A1, NR4A2, and/or NR4A3 gene and/or protein) can comprise a ligand binding protein (also referred to herein as a "chimeric binding protein"). Non-limiting examples of ligand binding proteins (e.g., chimeric binding proteins) useful for the present disclosure comprises a chimeric antigen receptor (CAR), T cell receptor (TCR) (e.g., engineered TCR), chimeric antibody-T cell receptor (caTCR), chimeric signaling receptor (CSR), T cell receptor mimic (TCR mimic), and combinations thereof.

In some aspects, an immune cell disclosed herein, e.g., a T cell, can comprise a chimeric antigen receptor (CAR) that specifically binds to an antigen (e.g., tumor antigen). Non-limiting examples of CARs that can be used with the present disclosure are known in the art. See, e.g., US 2020/0172879 A1 and US 2019/0183932 A1, each of which is incorporated herein by reference in its entirety.

In some aspects, an immune cell disclosed herein, e.g., a T cell, comprises a T cell receptor (TCR), e.g., an engineered T cell receptor (also known as "transgenic TCRs"). T cell receptor is a heterodimer composed of 2 different transmembrane polypeptide chains: an a chain and a p chain, each consisting of a constant region, which anchors the chain inside the T cell surface membrane, and a variable region, which recognizes and binds to the antigen presented by MHCs. The TCR complex is associated with 6 polypeptides forming 2 heterodimers, CD3γε and CD3δε, and 1 homodimer CD3 ζ, which together forms the CD3 complex. T cell receptor-engineered T cell therapy utilizes the modification of T cells that retain these complexes to specifically target the antigens expressed by particular tumor cells. As used herein, the term "engineered TCR" or "engineered T cell receptor" refers to a T cell receptor (TCR) engineered to specifically bind with a desired affinity to a major histocompatibility complex (MHC)/peptide target antigen that is selected, cloned, and/or subsequently introduced into a population of T cells.

In some aspects, an immune cell disclosed herein, e.g., a T cell, comprises a chimeric antibody-T cell receptor (caTCR). As used herein, a "chimeric antibody-T cell receptor" or "caTCR" comprises (i) an antibody moiety that specifically binds to an antigen of interest and (ii) a T cell receptor module capable of recruiting at least one TCR-associated signaling molecule. In some aspects, the antibody moiety and the T cell receptor module are fused together. In some aspects, the chimeric binding protein comprises a chimeric signaling receptor (CSR). "Chimeric signaling receptor" or "CSR" comprises a ligand-binding domain that specifically binds to a target ligand and a co-stimulatory signaling domain capable of providing a stimulatory signal to an immune cell that expresses the CSR. Non-limiting examples of caTCR and CSR are further described in U.S. Pat. No. 10,822,413 B2, which is incorporated herein by reference in its entirety.

In some aspects, an immune cell disclosed herein, e.g., a T cell, comprises a T cell receptor mimic (TCR mimic). As used herein, the term "T cell receptor mimic" or "TCR mimic" refers to an antibody (or a fragment thereof) that has been engineered to recognize tumor antigens, where the tumor antigens are displayed in the context of HLA molecules. As will be apparent to those skilled in the art, these antibodies can mimic the specificity of TCR. Non-limiting examples of TCR mimics are provided, e.g., in US 2009/0226474 A1 and US 2019/0092876 A1, each of which is incorporated herein by reference in its entirety.

In some aspects, a ligand binding protein (e.g., CARs or TCRs) that can be expressed on a modified cell disclosed herein specifically bind (i.e., target) one or more antigens expressed on a tumor cell, such as a malignant B cell, a malignant T cell, or a malignant plasma cell.

In some aspects, the ligand binding protein (e.g., CAR or TCR) specifically binds to (i.e., targets) an antigen selected from the group consisting of CD19, TRAC, TCRβ, BCMA, CLL-1, CS1, CD38, CD19, TSHR, CD123, CD22, CD30, CD70, CD171, CD33, EGFRvIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, mesothelin, IL-11Ra, PSCA, PRSS21, VEGFR2, LewisY, CD24, PDGFR-beta, SSEA-4, CD20, folate receptor alpha, ERBB2 (Her2/neu), MUC1, MUC16, EGFR, NCAM, prostase, PAP, ELF2M, Ephrin B2, IGF-I receptor, CAIX, LMP2, gplOO, ber-abl, tyrosinase, EphA2, fucosyl GM1, sLe, GM3, TGS5, HMWMAA, o-acetyl-GD2, folate receptor beta, TEM1/ CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-la, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, surviving, telomerase, PCTA-1/Galectin 8, MelanA/MARTI, Ras mutant (e.g., including KRAS, HRAS, NRAS mutant proteins), hTERT, sarcoma translocation breakpoints, ML-IAP, ERG (TMPRSS2 ETS fusion gene), NA17, PAX3, androgen receptor, cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD3ε, CD4, CD5, CD7, the extracellular portion of the APRIL protein, and any combinations thereof.

In some aspects, the immune cells described herein (e.g., modified CAR or TCR engineered cells) can target main types of antigens (e.g., tumor antigens): shared tumor-associated antigens (shared TAAs) and unique tumor-associated antigens (unique TAAs), or tumor-specific antigens. The former can include, without any limitation, cancer-testis (CT) antigens, overexpressed antigens, and differentiation antigens, while the latter can include, without any limitation, neoantigens and oncoviral antigens. Human papillomavirus (HPV) E6 protein and HPV E7 protein belong to the category of oncoviral antigens.

In some aspects, the immune cells described herein (e.g., modified CAR or TCR engineered cells) can target a CT antigen, e.g., melanoma-associated antigen (MAGE) including, but not limited to, MAGE-A1, MAGE-A2, MAGE-A3, MAGE-A4, MAGE-A6, MAGE-A8, MAGE-A9.23, MAGE-A10, and MAGE-A12. In some aspects, the immune cells described herein (e.g., modified CAR or TCR engineered cells) can target glycoprotein (gp100), melanoma antigen recognized by T cells (MART-1), and/or tyrosinase, which are mainly found in melanomas and normal melanocytes. In some aspects, the immune cells described herein (e.g., modified CAR or TCR engineered cells) can target Wilms tumor 1 (WT1), i.e., one kind of overexpressed antigen that is highly expressed in most acute myeloid leukemia (AML), acute lymphoid leukemia, almost every type of solid tumor and several critical tissues, such as heart tissues. In some aspects, the immune cells described herein (e.g., modified CAR or TCR engineered cells) can target mesothelin, another kind of overexpressed antigen that is highly expressed in mesothelioma but is also present on mesothelial cells of several tissues, including trachea.

In some aspects, a modified immune cell of the present disclosure, e.g., a CAR T or NK cell or a TCR-engineered T cell, can target any one of the tumor antigens disclosed above or a combination thereof. As described herein, in some aspects, the immune cells provided herein can specifically target a ROR1 antigen. Receptor tyrosine kinase-like orphan receptor 1 (ROR1) is overexpressed in approximately 57% of patients with triple negative breast cancer (TNBC) and 42% of patients with non-small cell lung carcinoma (NSCLC) adenocarcinomas (Balakrishnan 2017) and represents a highly attractive target for chimeric antigen receptor (CAR) T cells. Receptor tyrosine kinase-like orphan receptor 1-positive (ROR1+) solid tumors can be safely targeted with anti-ROR1 CAR T cells (Specht 2020); however, efficacy has been limited, in part, because the CAR T cells exhibit exhaustion or dysfunction following infusion in patients with solid-tumor malignancies. In addition, solid tumors have immune-suppressive barriers that limit antitumor activity of immunotherapies, such as CAR T cells (Newick 2016, Srivastava 2018, Martinez 2019).

Without wishing to be bound by any one theory, cells expressing the anti-ROR1 chimeric binding proteins described herein (e.g., anti-ROR1 CAR or anti-ROR1 TCR) have been modified to overexpress a c-Jun protein and at the same time to express reduced level of NR4A1, NR4A2, and/or NR4A3 gene and/or NR4A1, NR4A2, and/or NR4A3 protein. As described herein, in some aspects, cells expressing the anti-ROR1 chimeric binding proteins (e.g., anti-ROR1 CAR or anti-ROR1 TCR) have been modified to overexpress a c-Jun protein and at the same to have reduced level of multiple members of the NR4A family. These modified cells are more resistant to exhaustion and exhibit improved effector functions compared to other anti-ROR1 cells available in the art (e.g., expresses the ligand binding protein but has not been modified to overexpress a c-Jun protein and/or have reduced level of multiple members of the NR4A family).

In some aspects, the modified immune cells described herein (e.g., overexpressing a c-Jun protein and having reduced level of a NR4A1, NR4A2, and/or NR4A3 gene and/or NR4A1, NR4A2, and/or NR4A3 protein) comprise a ROR1 binding chimeric antigen receptor ("anti-ROR1 CAR"). An exemplary anti-ROR1 CAR is described in Hudecek, et al., Clin. Cancer Res. 19.12(2013):3153-64, which is incorporated herein by reference in its entirety. In some aspects, a CAR T cell of the present disclosure comprising an anti-ROR1 CAR is generated as described in Hudecek et al. (for example, as described in Hudecek et al. at page 3155, first full paragraph, incorporated herein by reference in its entirety). In some aspect, an anti-ROR1 CAR of the present disclosure includes an antibody or fragment thereof comprising the VH and/or VL sequences of the 2A2, R11, and R12 anti-ROR1 monoclonal antibodies described in Hudecek et al. at paragraph bridging pages 3154-55; Baskar et al. MAbs 4(2012):349-61; and Yang et al. PLoS ONE 6(2011):e21018, which are incorporated herein by reference in their entirety.

In some aspects, an anti-ROR1 chimeric binding protein useful for the present disclosure (e.g., anti-ROR1 CAR or anti-ROR1 TCR) is capable of cross-competing with an anti-ROR1 antibody, e.g., R12, antibody. The R12 antibody sequences are shown in Table 7. In some aspects, an anti-ROR1 chimeric binding protein useful for the present disclosure (e.g., anti-ROR1 CAR or anti-ROR1 TCR) binds to the same epitope of the R12 antibody. As will be apparent to those skilled in the arts, any anti-ROR1 antibody known in the art can be used with the present disclosure. Non-limiting examples of such antibodies include the 2A2 and R11 antibodies described in Hudecek, et al. Clin. Cancer Res. 19.12(2013):3153-64; Baskar et al. MAbs 4(2012):349-61; and Yang et al. PLoS ONE 6(2011):e21018; U.S. Pat. No. 9,316,646 B2; and U.S. Pat. No. 9,758,586 B2; each of which is incorporated herein by reference in its entirety.

58

TABLE 7

| R12 antibody CDRs and heavy chain variable region/light chain variable region | |
|---|---|
| R12 VH (SEQ ID NO: 17) | QEQLVESGGRLVTPGGSLTLSCKASGFDFSAYY MSWVRQAPGKGLEWIATIYPSSGKTYYATWVNG RFTISSDNAQNTVDLQMNSLTAADRATYFCARD SYADDGALFNIWGPGTLVTISS |
| R12 VH CDR1 (SEQ ID NO: 18) | AYYMS |
| R12 VH CDR2 (SEQ ID NO: 19) | TIYPSSGKTYYATWVNG |
| R12 VH CDR3 (SEQ ID NO: 20) | DSYADDGALFNI |
| R12 VL (SEQ ID NO: 21) | ELVLTQSPSVSAALGSPAKITCTLSSAHKTDTI DWYQQLQGEAPRYLMQVQSDGSYTKRPGVPDRF SGSSSGADRYLIIPSVQADDEADYYCGADYIGG YVFGGGTQLTVTG |
| R12 VL CDR1 (SEQ ID NO: 22) | TLSSAHKTDTID |
| R12 VL CDR2 (SEQ ID NO: 23) | GSYTKRP |
| R12 VL CDR3 (SEQ ID NO: 24) | GADYIGGYV |

In some aspects, the antigen-binding domain of an anti-ROR1 chimeric binding protein described herein (e.g., anti-ROR1 CAR) which can be expressed on the modified immune cells disclosed herein comprises the VH CDR3 of the R12 antibody. In some aspects, the antigen-binding domain of an anti-ROR1 chimeric binding protein of the present disclosure (e.g., anti-ROR1 CAR) comprises the VH CDR1, VH CDR2, and VH CDR3 of the R12 antibody. In some aspects, the antigen-binding domain of an anti-ROR1 chimeric binding protein of the present disclosure (e.g., anti-ROR1 CAR) comprises the VH CDR1, VH CDR2, VH CDR3, VL CDR1, VL CDR2, and VL CDR3 of the R12 antibody. In some aspects, the antigen-binding domain of an anti-ROR1 chimeric binding protein of the present disclosure, e.g., R12 scFv, comprises the VH and the VL of the R12 antibody.

In some aspects, the intracellular domain of a chimeric binding protein (e.g., any of the CARs or TCR provided herein, e.g., anti-ROR1 CAR) which can be expressed on the modified immune cells disclosed herein comprises a signaling domain, such as that derived from CD3zeta, FcR gamma, FcR beta, CD3 gamma, CD3 delta, CD3 epsilon, CD5, CD22, CD79a, CD79b, or CD66d. In some aspect, the chimeric binding protein (e.g., CAR or TCR) further comprises a co-stimulatory domain, such as that derived from 2B4, HVEM, ICOS, LAG3, DAP10, DAP12, CD27, CD28, 4-1BB (CD137), OX40 (CD134), CD30, CD40, ICOS (CD278), glucocorticoid-induced tumor necrosis factor receptor (GITR), lymphocyte function-associated antigen-1 (LFA-1), CD2, CD7, LIGHT, NKG2C, or B7-H3. In some aspects, the chimeric binding protein (e.g., CAR or TCR) comprises a 4-1BB costimulatory domain.

In some aspects, a transmembrane domain of a chimeric binding protein (e.g., CAR or TCR provided herein) which can be expressed on the modified immune cells disclosed herein can include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R α, ITGA1, VLA1, CD49a, ITGA4, IA4, CD49D, ITGA6, VLA-6, CD49f, ITGAD, CD1 Id, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMFI, CD150, IPO-3), BLAME (SLAMF8), SELPLG (CD162), LTBR, PAG/Cbp, NKG2D, NKG2C, or CD19.

In some aspects, the chimeric binding protein (e.g., CAR or TCR) which can be expressed on the modified immune cells disclosed herein further comprises a sequence encoding a costimulatory domain, e.g., a costimulatory domain described herein. In some aspects, the costimulatory domain comprises a costimulatory domain of interleukin-2 receptor (IL-2R), interleukin-12 receptor (IL-12R), IL-7, IL-21, IL-23, IL-15, CD2, CD3, CD4, CD7, CD8, CD27, CD28, CD30, CD40, 4-1BB/CD137, ICOS, lymphocyte function-associated antigen-1 (LFA-1), LIGHT, NKG2C, OX40, DAP10, B7-H3, CD28 deleted for Lck binding (ICA), BTLA, GITR, HVEM, LFA-1, LIGHT, NKG2C, PD-1, TILR2, TILR4, TILR7, TILR9, Fc receptor gamma chain, Fc receptor F chain, a ligand that specifically binds with CD83, or any combination thereof.

As further described herein, in some aspects, the immune cells described herein are modified, e.g., by a gene editing tool, to reduce the expression of the NR4A1, NR4A2, or NR4A3 gene and/or protein (including combinations thereof). The reduced expression of the NR4A1, NR4A2, and/or NR4A3 gene can be done, e.g., by editing the entire NR4A1, NR4A2, and/or NR4A3 gene, by editing a portion of the NR4A1, NR4A2, and/or NR4A3 gene, by editing a regulatory regions controlling the expression of the NR4A1, NR4A2, and/or NR4A3 gene. Accordingly, to reduce the expression of NR4A1, NR4A2, and/or NR4A3 gene and/or protein (including combinations thereof) in an immune cell expressing a ligand binding protein (e.g., a CAR-expressing cell or a TCR-expressing cell provided herein), any methods known in the art for reducing the expression of a gene and/or protein in a cell can be used. For instance, in some aspects, the expression of NR4A1, NR4A2, and/or NR4A3 gene and/or protein encoded thereof, of an immune cell provided herein (e.g., a CAR-expressing cell or a TCR-expressing cell) can be reduced by contacting the cell with a gene editing tool that is capable of reducing the expression levels of the NR4A1, NR4A2, and/or NR4A3 gene, and the protein encoded thereof. Non-limiting examples of the gene editing tool are shown below. In some specific aspects, the gene editing tool comprises, e.g., a shRNA, siRNA, miRNA, antisense oligonucleotides, CRISPR, zinc finger nuclease, TALEN, meganuclease, restriction endonuclease, or any combination thereof. In some aspects, the gene editing tool is CRISPR. In some aspects, the gene editing tool comprises a guide RNA (gRNA) that specifically targets a member of the NR4A family. Non-limiting examples of such gRNAs are provided in Tables A, C, and D.

In some aspects, the population of immune cells provided herein (e.g., CAR or TCR-expressing cells produced by the methods disclosed herein, i.e., expressing reduced levels of NR4A1, NR4A2, and/or NR4A3 gene and/or protein and increased level of a c-Jun protein) exhibits one or more enhanced or improved properties as compared to reference immune cells (i.e., corresponding immune cells that have not been modified to have reduced level of NR4A1, NR4A2, and NR4A3 genes and/or protein and to express the c-Jun protein). In some aspects, improving one or more properties of immune cells disclosed herein can help treat a tumor (e.g., reduce tumor volume and/or tumor weight). The one or more properties that can be improved with the present disclosure include any properties of an immune cell disclosed herein that can be useful in treating cancers. For example, in some aspects, the population of immune cells (e.g., CAR or TCR-expressing cells produced by the methods disclosed herein, i.e., expressing reduced levels of NR4A1, NR4A2, and/or NR4A3 gene and/or protein and increased levels of a c-Jun protein) can exhibit greater effector activity compared to a reference cell (e.g., CAR or TCR-expressing cell that has not been modified to express lower levels of NR4A1, NR4A2, and NR4A3 gene and protein to express the c-Jun protein).

In some aspects, the enhanced properties of the modified immune cells comprise
  (i) increased expansion and/or proliferation of the immune cells,
  (ii) increased cytotoxicity of the immune cells,
  (iii) increased cytokine expression of the immune cells, or
  (iv) any combination thereof,
with respect to reference cells.

In some aspects, the modified immune cells disclosed herein (e.g., CAR or TCR-expressing cells described herein that overexpress c-Jun and have reduced level of one or more of the following: a NR4A1 gene and/or NR4A1 protein, a NR4A2 gene and/or NR4A2 protein, and a NR4A3 gene and/or NR4A3 protein) are exhaustion-resistant and/or dysfunction-resistant compared to reference immune cells (i.e., corresponding immune cells that have not been modified to have reduced NR4A1, NR4A2, and NR4A3 gene and/or protein expression and to overexpress the c-Jun protein).

In some aspects, the modified immune cells disclosed herein (e.g., CAR or TCR-expressing cells described herein that overexpress c-Jun and have reduced level of one or more of the following: a NR4A1 gene and/or NR4A1 protein, a NR4A2 gene and/or NR4A2 protein, and a NR4A3 gene and/or NR4A3 protein) are apoptosis-resistant, i.e., they exhibit reduced or no apoptosis compared to reference immune cells (i.e., corresponding immune cells that have not been modified to have reduced NR4A1, NR4A2, and NR4A3 gene and/or protein expression and to overexpress the c-Jun protein).

In some aspects, the modified immune cells disclosed herein (e.g., CAR or TCR-expressing cells described herein that overexpress c-Jun and have reduced level of one or more of the following: a NR4A1 gene and/or NR4A1 protein, a NR4A2 gene and/or NR4A2 protein, and a NR4A3 gene and/or NR4A3 protein) are immune check-point-resistant, i.e., they exhibit reduced or no immune checkpoint activity compared to reference immune cells (i.e., corresponding immune cells that have not been modified to have reduced NR4A1, NR4A2, and NR4A3 gene and/or protein expression and to overexpress the c-Jun protein).

In some aspects, the modified immune cells disclosed herein (e.g., CAR or TCR-expressing cells described herein that overexpress c-Jun and have reduced level of one or more of the following: a NR4A1 gene and/or NR4A1 protein, a NR4A2 gene and/or NR4A2 protein, and a NR4A3 gene and/or NR4A3 protein) exhibit enhanced T cell activation compared to reference immune cells (i.e., corresponding immune cells that have not been modified to have reduced NR4A1, NR4A2, and NR4A3 gene and/or protein expression and to overexpress the c-Jun protein). In some aspects, such enhanced T cell activation can be evidenced, e.g., by the modified immune cells exhibiting enhanced expansion, enhanced cytotoxicity, enhanced cytokine expression, or any combination thereof compared to reference immune cells (i.e., corresponding immune cells that have not been modified to have reduced NR4A1, NR4A2, and NR4A3 gene and/or protein expression and to overexpress the c-Jun protein).

In some aspects, the modified immune cells disclosed herein (e.g., CAR or TCR-expressing cells described herein that overexpress c-Jun and have reduced level of one or more of the following: a NR4A1 gene and/or NR4A1 protein, a NR4A2 gene and/or NR4A2 protein, and a NR4A3 gene and/or NR4A3 protein) maintain an anti-tumor function in a tumor microenvironment (TME) compared to reference immune cells (i.e., corresponding immune cells that have not been modified to have reduced NR4A1, NR4A2, and NR4A3 gene and/or protein expression and to overexpress the c-Jun protein).

The present disclosure also provides pharmaceutical compositions comprising the modified immune cell populations disclosed herein and a pharmaceutical acceptable carrier. Such pharmaceutical compositions are further described elsewhere in the present disclosure.

III. Methods of Treatment

Provided herein are methods for treating a tumor (or a cancer) in a subject in need thereof, comprising administering to the subject a cell composition of the disclosure, e.g., a cell overexpressing a c-Jun protein and expressing reduced levels of NR4A (e.g., NR4A1, NR4A2, and/or NR4A3) gene and/or the protein encoded thereof, i.e., NR4A protein. As used herein, the term "cell composition" refers to the immune cells alone or in combination with one or more additional agents (e.g., excipients). In some aspects, the cell comprises a ligand binding protein (e.g., CAR or TCR) that specifically binds to a tumor antigen described herein. In some aspects, a tumor antigen comprises ROR1. Accordingly, in some aspects, a method of treating a tumor provided herein comprises administering to the subject a cell composition described herein, wherein the cell (i) overexpresses a c-Jun protein, (ii) has reduced level of a NR4A gene and/or protein (e.g., NR4A1, NR4A2, NR4A3, or combinations thereof), and (iii) expresses a CAR that specifically targets a tumor antigen. In some aspects, a method of treating a tumor provided herein comprises administering to the subject a cell composition described herein, wherein the cell (i) overexpresses a c-Jun protein, (ii) has reduced level of a NR4A gene and/or protein (e.g., NR4A1, NR4A2, NR4A3, or combinations thereof), and (iii) expresses a TCR (e.g., engineered TCR) that specifically targets a tumor antigen.

In some aspects, the expression level of the NR4A (NR4A1, NR4A2, and/or NR4A3) gene is reduced by at least about 5%, at least about 10%, at least about 15%, at least about 30%, at least about 40%, at least about 50%, at least about 60%, at least about 70%, at least about 80%, at least about 90%, or at least about 100%, compared to a reference cell (e.g., corresponding cell that has not been modified to express lower levels of the NR4A (NR4A1, NR4A2, or NR4A3) gene). In some aspects, the expression level of the NR4A (NR4A1, NR4A2, and/or NR4A3) protein is reduced by at least about 5%, at least about 10%, at least about 15%, at least about 30%, at least about 40%, at least about 50%, at least about 60%, at least about 70%, at least about 80%, at least about 90%, or at least about 100%, compared to a reference cell (e.g., corresponding cell that has not been modified to express lower levels of NR4A (NR4A1, NR4A2, or NR4A3) protein). In some aspects, the expression levels of both the NR4A (NR4A1, NR4A2, and/or NR4A3) gene and protein are reduced by at least about 5%, at least about 10%, at least about 15%, at least about 30%, at least about 40%, at least about 50%, at least about 60%, at least about 70%, at least about 80%, at least about 90%, or at least about 100%, compared to a reference cell (e.g., corresponding cell that has not been modified to express lower levels of the NR4A (NR4A1, NR4A2, or NR4A3) gene and/or protein). Methods of reducing the expression level of the NR4A (NR4A1, NR4A2, and/or NR4A3) gene and/or protein are provided elsewhere in the present disclosure.

In some aspects, administering the cell composition of the disclosure reduces a tumor volume in the subject compared to a reference tumor volume. In some aspects, the reference tumor volume is the tumor volume in the subject prior to the administration of the modified cell. In some aspects, the reference tumor volume is the tumor volume in a corresponding subject that did not receive the administration. Unless indicated otherwise, a "corresponding subject that did not receive the administration" (or variants thereof) comprises any of the following: (1) a corresponding subject (e.g., suffering from the same tumor) who received an administration of the corresponding cells that express endogenous level of c-Jun and all members of the NR4A family; (2) a corresponding subject who received an administration of the corresponding cells that overexpress c-Jun but has endogenous level of all members of the NR4A family; (3) a corresponding subject who received an administration of the corresponding cells that has reduced level of one or more members of the NR4A family but does not overexpress c-Jun; and (4) any combination of (1) to (3). In some aspects, the tumor volume in the subject is reduced by at least about 5%, at least about 10%, at least about 15%, at least about 30%, at least about 40%, at least about 50%, at least about 60%, at least about 70%, at least about 80%, at least about 90%, or at least about 100% after the administration compared to the reference tumor volume.

In some aspects, treating a tumor comprises reducing a tumor weight in the subject. In some aspects, a modified cell disclosed herein can reduce the tumor weight in a subject when administered to the subject. In some aspects, the tumor weight is reduced by at least about 5%, at least about 10%, at least about 15%, at least about 30%, at least about 40%, at least about 50%, at least about 60%, at least about 70%, at least about 80%, at least about 90%, or at least about 100% after the administration compared to a reference tumor weight. In some aspects, the reference tumor weight is the tumor weight in the subject prior to the administration of the modified cell. In some aspects, the reference tumor weight is the tumor weight in a corresponding subject that did not receive the administration.

In some aspects, administering the cell composition of the disclosure to a subject, e.g., suffering from a tumor, can increase the number and/or percentage of TILs (e.g., CD4$^+$ or CD8$^+$) in a tumor and/or TME of the subject. In some aspects, the number and/or percentage of TILs in a tumor and/or TME is increased by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, or at least about 300% or more compared to a reference (e.g., corresponding value in a subject that did not receive the modified cell or the same subject prior to the administration of the modified cell). In some aspects, administering the cell composition of the disclosure to a subject, e.g., suffering from a tumor, can increase the number and/or percentage of TILs (e.g., CD4$^+$ or CD8$^+$) in a tumor and/or TME of the subject by at least about 2-fold, at least about 2.5-fold, at least about 3-fold, at least about 3.5-fold, at least about 4-fold, at least about 5-fold, at least about 8-fold, at least about 10-fold, at least about 15-fold, at least about 20-fold, at least about 25-fold, at least about 30-fold, at least about 50-fold, at least about 75-fold, or at least about 100-fold as compared to a reference (e.g., corresponding value in a subject that did not receive the modified cell or the same subject prior to the administration of the modified cell).

In some aspects, administering the cell composition of the disclosure can reduce the number and/or percentage of regulatory T cells in a tumor and/or TME of a subject. In some aspects, the number and/or percentage of regulatory T cells in a tumor and/or TME is decreased by at least about 5%, at least about 10%, at least about 15%, at least about 30%, at least about 40%, at least about 50%, at least about 60%, at least about 70%, at least about 80%, at least about 90%, or about 100% compared to a reference (e.g., the corresponding number and/or percentage in a subject that did not receive an administration of the modified cell).

In some aspects, administering the cell composition of the disclosure can decrease the number and/or percentage of myeloid-derived suppressor cells (MDSCs) in the tumor and/or TME of a subject. In some aspects, the MDSCs are monocytic MDSCs (M-MDSCs). In some aspects, the MDSCs are polymorphonuclear MDSCs (PMN-MDSCs). In some aspects, the MDSCs comprise both M-MDSCs and PMN-MDSCs. In some aspects, the number and/or percentage of MDSCs in the tumor and/or TME is decreased by at least about 5%, at least about 10%, at least about 15%, at least about 30%, at least about 40%, at least about 50%, at least about 60%, at least about 70%, at least about 80%, at least about 90%, or about 100% compared to a reference (e.g., value in a corresponding subject that did not receive an administration of the modified cell).

In addition to the above, administering the cell composition of the disclosure can have other effects which are conducive for the treatment of a tumor. Such effects are described further below.

As described herein, the cell composition of the disclosure (i.e., overexpresses a c-Jun protein and expresses reduced levels of a NR4A1, NR4A2, and/or NR4A3 gene and/or protein and a binding molecule that specifically binds to a tumor antigen, e.g., ROR1) can be used to treat a variety of cancer types, e.g., a tumor derived from a cancer comprising a breast cancer, head and neck cancer, uterine cancer, brain cancer, skin cancer, renal cancer, lung cancer, colorectal cancer, prostate cancer, liver cancer, bladder cancer, kidney cancer, pancreatic cancer, thyroid cancer, esophageal cancer, eye cancer, stomach (gastric) cancer, gastrointestinal cancer, ovarian cancer, cervical cancer, carcinoma, sarcoma, leukemia, lymphoma, myeloma, or a combination thereof. A comprehensive and non limiting list of cancer indications is provided in the Indication section of this application.

In some aspects, the cell composition of the disclosure can be used in combination with other therapeutic agents (e.g., anti-cancer agents and/or immunomodulating agents). Accordingly, in some aspects, a method of treating a tumor disclosed herein comprises administering the cell composition of the disclosure in combination with one or more additional therapeutic agents. In some aspects, the cell composition of the disclosure can be used in combination with one or more anti-cancer agents, such that multiple elements of the immune pathway can be targeted. In some aspects, an anti-cancer agent comprises an immune checkpoint inhibitor (i.e., blocks signaling through the particular immune checkpoint pathway). Non-limiting examples of immune checkpoint inhibitors that can be used in the present methods comprise a CTLA-4 antagonist (e.g., anti-CTLA-4 antibody), PD-1 antagonist (e.g., anti-PD-1 antibody, anti-PD-L1 antibody), TIM-3 antagonist (e.g., anti-TIM-3 antibody), or combinations thereof. A comprehensive and non-limiting list of combination treatment is disclosed in detail in the Combination Treatments section of this application.

In some aspects, the cell composition of the disclosure is administered to the subject prior to or after the administration of the additional therapeutic agent. In some aspects, the cell composition of the disclosure is administered to the subject concurrently with the additional therapeutic agent. In some aspects, the cell composition of the disclosure and the additional therapeutic agent can be administered concurrently as a single composition in a pharmaceutically acceptable carrier. In some aspects, the cell composition of the disclosure and the additional therapeutic agent are administered concurrently as separate compositions.

In some aspects, a subject that can be treated with the present disclosure is a nonhuman animal such as a rat or a mouse. In some aspects, the subject that can be treated is a human.

In some aspects, treating a tumor, e.g., in a method disclosed herein, comprises enhancing the activation of a T cell (e.g., tumor-specific T cell). As used herein, the term "enhancing the activation of a T cell" refers to altering the cell signaling during activation to promote the retention of T cell memory.

Accordingly, in some aspects, the present disclosure relates to methods of enhancing the activation of a T cell by overexpressing a c-Jun protein and reducing the expression levels of a NR4A (NR4A1, NR4A2, or NR4A3) gene and/or protein in the cell. The activation status of a cell can be determined by any method known in the art, e.g., by analyzing one or more functional properties (e.g., proliferation, cytotoxicity, cytokine production) of the cell or by analyzing the phenotypic expression of the cell. In some aspects, enhancing the activation of a T cell (e.g., tumor-specific T cell) can result in one or more of the following improved properties in the cell: (i) enhanced expansion, (ii) enhanced cytotoxicity, (iii) enhanced cytokine expression, or (iv) any combination thereof.

In some aspects, enhancing the activation of a T cell (e.g., tumor-specific T cell) results in enhanced expansion of the cell. In some aspects, the expansion of the T cell is enhanced (i.e., increased) by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least 220%, at least about 230%, at least about 240%, at least about 250%, at least about 260%, at least about 270%, at least about 280%, at least about 290%, or at least about 300% or more as compared to that of a reference cell (e.g., a corresponding cell that has not been modified to express lower levels of the NR4A (NR4A1, NR4A2, and/or NR4A3) gene and/or protein and to overexpress the c-Jun protein). In some aspects, the enhanced expansion can result in an increase in the number of the modified T cell (i.e., overexpressing a c-Jun protein and expressing reduced levels of NR4A1, NR4A2, and/or NR4A3 gene and/or protein), e.g., in a subject. In some aspects, the number of the modified T cell is increased by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least 220%, at least about 230%, at least about 240%, at least about 250%, at least about 260%, at least about 270%, at least about 280%, at least about 290%, or at least about 300% or more as compared to that of a reference cell (e.g., corresponding cell that has not been modified to express lower levels of the NR4A gene and/or protein and to overexpress the c-Jun protein).

In some aspects, enhancing the activation of a T cell (e.g., tumor-specific T cell) results in enhanced cytotoxicity of the cell. As used herein, the term "cytotoxicity" refers to the ability of a cell composition of the disclosure (e.g., tumor-specific T cell) to attack and induce damage in a tumor cell. The cell composition of the disclosure (e.g., tumor-specific T cell) can attack and induce damage in a tumor cell by any method known in the art, such as by inducing apoptosis in a tumor cell through the release of cytotoxic molecules (e.g., perforin, granzymes, and granulysin) or through Fas-Fas ligand interaction. In some aspects, the cytotoxicity of the T cell is enhanced (i.e., increased) by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least 220%, at least about 230%, at least about 240%, at least about 250%, at least about 260%, at least about 270%, at least about 280%, at least about 290%, or at least about 300% or more as compared to that of a reference cell (e.g., corresponding cell that has not been modified to express lower levels of the NR4A (NR4A1, NR4A2, and/or NR4A3) gene and protein and to overexpress the c-Jun protein).

In some aspects, enhancing the activation of a T cell (e.g., tumor-specific T cell) results in enhanced cytokine expression in the cell. In some aspects, the cytokine expression is enhanced (i.e., increased) by at least about at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold or more as compared to that of a reference cell (e.g., corresponding cell that has not been modified to overexpress the c-Jun protein and to express lower levels of the NR4A (NR4A1, NR4A2, and/or NR4A3) gene and/or protein). As used herein, the term "cytokine" refers to any cytokine that can be useful in the treatment of a cancer. Non-limiting examples of such cytokines include IFN-γ, TNF-α, IL-2, and any combination thereof.

In some aspects, the expansion and/or proliferation of the immune cells, cytotoxicity of the immune cells, or cytokine expression of the immune cells, is increased by about 2 fold to about 100, to about 150, to about 200, to about 250, to about 300, to about 350, to about 400, to about 450, to about 500 fold or more. In some aspects, the expansion and/or proliferation of the immune cells, cytotoxicity of the immune cells, or cytokine expression of the immune cells, is increased by about 10 fold to about 500 fold, from about 20 fold to about 400 fold, from about 25 fold to about 250 fold, from about 10 fold to about 50 fold. In some aspects, the expansion and/or proliferation of the immune cells, cytotoxicity of the immune cells, or cytokine expression of the immune cells, is increased by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold or more as compared to that of reference cells (e.g., corresponding immune cells that have not been modified to overexpress the c-Jun protein and express lower levels of the NR4A (NR4A1, NR4A2, and/or NR4A3) gene and/or protein).

In some aspects, the modified immune cells according to the present disclosure exhibits increased cytokine expression with respect to reference cells. In some aspects, the cytokines are interleukin-2 (IL-2), interferon-7 (IFN-γ), tumor necrosis factor-α (TNF-α), or any combination thereof.

In some aspects, the expression level of IL-2 in the modified immune cells is increased at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold, at least about 15 fold, at least about 20 fold, at least about 25 fold, at least about 30 fold, at least about 40 fold, at least about 50 fold, or at least about 100 fold or more compared to the expression level of IL-2 in reference immune cells.

In some aspects, the expression level of IFN-γ in the modified immune cells is increased at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold, at least about 15 fold, at least about 20 fold, at least about 25 fold, at least about 30 fold, at least about 40 fold, at least about 50 fold, or at least about 100 fold or more compared to the expression level of IFN-γ in reference immune cells.

In some aspects, the expression level of TNF-α in the modified immune cells is increased at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold, at least about 15 fold, at least about 20 fold, at least about 25 fold, at least about 30 fold, at least about 40 fold, at least about 50 fold, or at least about 100 fold or more compared to the expression level of TNF-α in reference immune cells.

In some aspects, an immune cell expressing a ligand binding protein (e.g., a CAR or TCR-expressing cell) disclosed herein (i.e., overexpressing a c-Jun protein and expressing reduced levels of a NR4A (NR4A1, NR4A2, and/or NR4A3) gene and/or NR4A protein) produces increased amounts of IL-2 when stimulated with an antigen, such as a cognate antigen (e.g., tumor antigen), e.g., sequential stimulation and/or chronic stimulation. In some aspects, the amount of IL-2 produced by the immune cells (e.g., CAR or TCR-expressing cell) is increased by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold, at least about 15 fold, at least about 20 fold, at least about 25 fold, at least about 30 fold, at least about 40 fold, at least about 50 fold, or at least about 100 fold or more as compared to that of a reference cell (e.g., corresponding cell that has not been modified to overexpress the c-Jun protein and to express lower levels of the NR4A (NR4A1, NR4A2, and/or NR4A3) gene and/or protein).

In some aspects, an immune cell expressing a ligand binding protein (e.g., a CAR or TCR-expressing cell) disclosed herein (i.e., overexpressing a c-Jun protein and expressing reduced levels of a NR4A (NR4A1, NR4A2, and/or NR4A3) gene and/or protein) produces increased amounts of IFN-γ when stimulated with an antigen, such as a cognate antigen (e.g., tumor antigen), e.g., sequential stimulation and/or chronic stimulation. In some aspects, the amount of IFN-γ produced by the immune cells (e.g., CAR or TCR-expressing cell) is increased by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold, at least about 15 fold, at least about 20 fold, at least about 25 fold, at least about 30 fold, at least about 40 fold, at least about 50 fold, or at least about 100 fold or more as compared to a reference cell (e.g., corresponding cell that has not been modified to overexpress the c-Jun protein and express lower levels of a NR4A (NR4A1, NR4A2, and/or NR4A3) gene and/or protein).

In some aspects, an immune cell expressing a ligand binding protein (e.g., a CAR or TCR-expressing cell) disclosed herein (i.e., overexpressing a c-Jun protein and expressing reduced levels of a NR4A (NR4A1, NR4A2, and/or NR4A3) gene and/or protein) produces increased amounts of TNF-α when stimulated with an antigen, such as a cognate antigen (e.g., tumor antigen), e.g., sequential stimulation and/or chronic stimulation. In some aspects, the amount of TNF-α produced by the immune cells (e.g., CAR or TCR-expressing cell) is increased by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold, at least about 15 fold, at least about 20 fold, at least about 25 fold, at least about 30 fold, at least about 40 fold, at least about 50 fold, or at least about 100 fold or more as compared to that of a reference cell (e.g., corresponding cell that has not been modified to overexpress the c-Jun protein and express lower levels of a NR4A (NR4A1, NR4A2, and/or NR4A3) gene and/or protein).

In some aspects, the modified immune cells disclosed herein (e.g., CAR or TCR-expressing cells described herein) exhibit increased cell expansion and/or cell proliferation compared to reference immune cells (i.e., corresponding immune cells that have not been modified to overexpress the c-Jun protein and to have a reduced level of a NR4A (NR4A1, NR4A2, and/or NR4A3) gene and/or protein). In some aspects, the cell expansion and/or cell proliferation in the modified immune cells is increased by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold, at least about 15 fold, at least about 20 fold, at least about 25 fold, at least about 30 fold, at least about 40 fold, at least about 50 fold, or at least about 100 fold or more as compared to that of the reference immune cells.

In some aspects, the modified immune cells disclosed herein (e.g., CAR or TCR-expressing cells described herein) exhibit increased persistence and/or survival compared to reference immune cells (i.e., corresponding immune cells that have not been modified to overexpress the c-Jun protein and to have a reduced level of a NR4A (NR4A1, NR4A2, and/or NR4A3) gene and/or protein). In some aspects, the persistence and/or survival in the modified immune cells is increased by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold, at least about 15 fold, at least about 20 fold, at least about 25 fold, at least about 30 fold, at least about 40 fold, at least about 50 fold, or at least about 100 fold or more as compared to that of the reference immune cells.

In some aspects, the modified immune cells disclosed herein (e.g., CAR or TCR-expressing cells described herein) exhibit increased anti-tumor activity compared to reference immune cells (i.e., corresponding immune cells that have not been modified to overexpress the c-Jun protein and to have a reduced level of a NR4A (NR4A1, NR4A2, and/or NR4A3) gene and/or protein). In some aspects, the anti-tumor activity in the modified immune cells is increased by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold, at least about 15 fold, at least about 20 fold, at least about 25 fold, at least about 30 fold, at least about 40 fold, at least about 50 fold, or at least about 100 fold or more as compared to that of the reference immune cells.

In some aspects, the modified immune cells disclosed herein (e.g., CAR or TCR-expressing cells described herein) exhibit reduced exhaustion or dysfunction compared to reference immune cells (i.e., corresponding immune cells that have not been modified to overexpress the c-Jun protein and to have a reduced level of a NR4A (NR4A1, NR4A2, and/or NR4A3) gene and/or protein). In some aspects, the exhaustion or dysfunction in the modified immune cells is decreased by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold compared to the reference immune cells.

In some aspects, the modified cells disclosed herein can be used in combination with other therapeutic agents (e.g., anti-cancer agents and/or immunomodulating agents). Accordingly, in some aspects, a method of treating a tumor disclosed herein comprises administering the modified cells of the present disclosure in combination with one or more additional therapeutic agents to a subject. Such agents can include, for example, chemotherapeutic drug, targeted anti-cancer therapy, oncolytic drug, cytotoxic agent, immune-based therapy, cytokine, surgical procedure, radiation procedure, activator of a costimulatory molecule, immune checkpoint inhibitor, a vaccine, a cellular immunotherapy, or any combination thereof. In some aspects, the modified cells disclosed herein (i.e., overexpressing a c-Jun protein and expressing reduced levels of NR4A1, NR4A2, and/or NR4A3 gene and/or protein) can be used in combination with a standard of care treatment (e.g., surgery, radiation, and chemotherapy). Methods described herein can also be used as a maintenance therapy, e.g., a therapy that is intended to prevent the occurrence or recurrence of tumors.

In some aspects, the modified cells of the present disclosure can be used in combination with one or more anti-cancer agents, such that multiple elements of the immune pathway can be targeted. Non-limiting of such combinations include: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/PD-L1/PD-L2 pathway and/or depleting or blocking Tregs or other immune suppressing cells (e.g., myeloid-derived suppressor cells); a therapy that stimulates positive immune regulation, e.g., with agonists that stimulate the CD-137, OX-40, and/or CD40 or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); a therapy that inhibits a metabolic enzyme such as indoleamine dioxigenase (IDO), dioxigenase, arginase, or nitric oxide synthetase; a therapy that reverses/prevents T cell anergy or exhaustion; a therapy that triggers an innate immune activation and/or inflammation at a tumor site; administration of immune stimulatory cytokines; blocking of immuno repressive cytokines; or any combination thereof.

In some aspects, an anti-cancer agent comprises an immune checkpoint inhibitor (i.e., blocks signaling through the particular immune checkpoint pathway). Non-limiting examples of immune checkpoint inhibitors that can be used in the present methods comprise a CTLA-4 antagonist (e.g., anti-CTLA-4 antibody), PD-1 antagonist (e.g., anti-PD-1 antibody, anti-PD-L1 antibody), TIM-3 antagonist (e.g., anti-TIM-3 antibody), or combinations thereof. Non-limiting examples of such immune checkpoint inhibitors include the following: anti-PD1 antibody (e.g., nivolumab (OP-DIVO®), pembrolizumab (KEYTRUDA®; MK-3475), pidilizumab (CT-011), PDR001, MEDI0680 (AMP-514), TSR-042, REGN2810, JS001, AMP-224 (GSK-2661380), PF-06801591, BGB-A317, BI 754091, SHR-1210, and combinations thereof); anti-PD-L1 antibody (e.g., atezolizumab (TECENTRIQ®; RG7446; MPDL3280A; RO5541267), durvalumab (MEDI4736, IMFINZI®), BMS-936559, avelumab (BAVENCIO®), LY3300054, CX-072 (Proclaim-CX-072), FAZ053, KN035, MDX-1105, and combinations thereof); and anti-CTLA-4 antibody (e.g., ipilimumab (YERVOY®), tremelimumab (ticilimumab; CP-675,206), AGEN-1884, ATOR-1015, and combinations thereof).

In some aspects, an anti-cancer agent comprises an immune checkpoint activator (i.e., promotes signaling through the particular immune checkpoint pathway). In some aspects, immune checkpoint activator comprises OX40 agonist (e.g., anti-OX40 antibody), LAG-3 agonist (e.g. anti-LAG-3 antibody), 4-1BB (CD137) agonist (e.g., anti-CD137 antibody), GITR agonist (e.g., anti-GITR antibody), TIM3 agonist (e.g., anti-TIM3 antibody), or combinations thereof.

In some aspects, a modified cell disclosed herein is administered to the subject prior to or after the administration of the additional therapeutic agent. In some aspects, the modified cell is administered to the subject concurrently with the additional therapeutic agent. In some aspects, the modified cell and the additional therapeutic agent can be administered concurrently as a single composition in a pharmaceutically acceptable carrier. In some aspects, the modified cell and the additional therapeutic agent are administered concurrently as separate compositions. In some aspects, the additional therapeutic agent and the modified immune cells are administered sequentially.

IV. Methods of Making Modified Immune Cells

The present disclosure provides methods of generating or preparing cells overexpressing a c-Jun protein and having a reduced level of a NR4A (NR4A1, NR4A2, and/or NR4A3) gene and/or protein, comprising, e.g., (i) modifying the cells with a gene editing tool, wherein the gene editing tool reduces the expression of the NR4A gene and/or protein and (ii) modifying the cells to overexpress a c-Jun protein. In some aspects, the cells can be modified by transducing the cells with a polynucleotide comprising a nucleotide sequence expressing a c-Jun protein. As described herein, in some aspects, the cells can be modified with a transcriptional activator that is capable of increasing the expression of endogenous c-Jun protein. In some aspects, the NR4A gene and/or protein comprises NR4A1 and/or NR4A1 protein. In some aspects, the NR4A gene and/or protein comprises NR4A2 and/or NR4A2 protein. In some aspects, the NR4A gene and/or protein comprises NR4A3 and/or NR4A3 protein. In some aspects, the NR4A gene and/or protein comprises both the NR4A1 gene and/or protein and the NR4A2 gene and/or protein. In some aspects, the NR4A gene and/or protein comprises both the NR4A1 gene and/or protein and the NR4A3 gene and/or protein. In some aspects, the NR4A gene and/or protein comprises both the NR4A2 gene and/or protein and the NR4A3 gene and/or protein. In some aspects, the NR4A gene and/or protein comprises the NR4A1 gene and/or protein, the NR4A2 gene and/or protein, and the NR4A3 gene and/or protein. In some aspects, the increased expression of a c-Jun protein in combination with reduced expression of the NR4A (NR4A1, NR4A2, and/or NR4A3) gene and/or protein synergistically reduces or inhibits exhaustion of the cells.

Accordingly, the present disclosure also provides methods of reducing or inhibiting exhaustion of cells expressing a ligand binding protein (e.g., chimeric antigen receptor (CAR) or a T cell receptor (TCR)), comprising modifying the cells to reduce the expression level of a NR4A (NR4A1, NR4A2, and/or NR4A3) gene and/or protein and overexpress a c-Jun protein. In some aspects, the cells are immune cells. Also, the present disclosure provides methods of promoting a persistent effector function in immune cells, comprising modifying the cells to express reduced levels of a NR4A (NR4A1, NR4A2, and/or NR4A3) gene and/or protein and overexpress a c-Jun protein. In some aspects, the NR4A gene and/or protein comprises NR4A1 and/or NR4A1 protein. In some aspects, the NR4A gene and/or protein comprises NR4A2 and/or NR4A2 protein. In some aspects, the NR4A gene and/or protein comprises NR4A3 and/or NR4A3 protein. In some aspects, the NR4A gene and/or protein comprises both the NR4A1 gene and/or protein and the NR4A2 gene and/or protein. In some aspects, the NR4A gene and/or protein comprises both the NR4A1 gene and/or protein and the NR4A3 gene and/or protein. In some aspects, the NR4A gene and/or protein comprises both the NR4A2 gene and/or protein and the NR4A3 gene and/or protein. In some aspects, the NR4A gene and/or protein comprises the NR4A1 gene and/or protein, the NR4A2 gene and/or protein, and the NR4A3 gene and/or protein.

Gene editing, e.g., base editing, can be conducted using any editing tool known in the art. For example, in some aspects a modified cell (e.g., an immune cell) can be modified using techniques such as CRISPR/Cas, TALEN, Zinc finger nucleases (ZFN), meganucleases, restriction endonucleases, interference RNAs (RNAi), or antisense oligonucleotides. In some aspects, a NR4A (NR4A1, NR4A2, and/or NR4A3) gene and/or expression can also be modified using shRNA, siRNA, or miRNA. All these techniques are discussed more in detail below. In some aspects, the method used for reducing the expression of a NR4A (NR4A1, NR4A2, and/or NR4A3) gene and/or protein comprises using one or more gene editing tools (e.g., two, three, or more tools). In some aspects, the method used for reducing the expression of a NR4A (NR4A1, NR4A2, and/or NR4A3) gene and/or protein comprises at least one method acting on NR4A DNA (e.g., CRISPR) or RNA (e.g., antisense oligonucleotides) and at least one method acting on NR4A protein (e.g., inhibition of binding to cell signaling partner or post-translational modifications).

In some aspects, cells (e.g., immune cells) modified as disclosed herein, e.g., by using a gene editing tool to reduce or abolish NR4A (NR4A1, NR4A2, and/or NR4A3) gene levels, can be further modified to express a ligand binding protein (e.g., CAR or a TCR). Accordingly, in some aspects, a method of preparing an immune cell described herein comprises modifying an immune cell with (i) a gene editing tool (e.g., capable of specifically targeting one or more members of the NR4A family), (ii) a nucleotide sequence encoding a c-Jun protein, and (iii) a nucleotide sequence encoding a ligand binding protein (e.g., CAR or TCR). In some aspects, a method of preparing an immune cell described herein comprises modifying an immune cell with (i) a gene editing tool (e.g., capable of specifically targeting one or more members of the NR4A family), (ii) a transcriptional activator that is capable of increasing the endogenous expression of c-Jun, and (iii) a nucleotide sequence encoding a ligand binding protein (e.g., CAR or TCR). As described herein, in some aspects, the gene editing tool comprises a guide RNA which comprises, consists essentially of, or consists of the sequence set forth in any one of SEQ ID NO: 25, SEQ ID NO: 26, SEQ ID NO: 27, SEQ ID NO: 28, SEQ ID NO: 29, SEQ ID NO: 30, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 61, SEQ ID NO: 65, SEQ ID NO: 67, SEQ ID NO: 68, SEQ ID NO: 70, SEQ ID NO: 71, SEQ ID NO: 75, SEQ ID NO: 76, SEQ ID NO: 82, SEQ ID NO: 83, SEQ ID NO: 86, SEQ ID NO: 94, and SEQ ID NO: 96. (See, e.g., Tables A, C, and D). Non-limiting examples of other gene editing tools that can be used are further described elsewhere in the present disclosure.

In some aspects, the nucleotide sequence encoding a c-Jun protein that can be used with the above method comprises any of the c-Jun nucleotide sequences provided herein. For example, in some aspects, the nucleotide sequence encoding a c-Jun protein comprises: (a) a nucleic acid sequence having at least 89%, at least 90%, at least about 95%, at least about 96%, at least about 97%, at least about 98%, at least about 99%, or about 100% sequence identity to the nucleic acid sequence as set forth in SEQ ID NO: 7; (b) a nucleic acid sequence having at least 90%, at least about 95%, at least about 96%, at least about 97%, at least about 98%, at least about 99%, or about 100% sequence identity to the nucleic acid sequence as set forth in SEQ ID NO: 8; (c) a nucleic acid sequence having at least about 30%, at least about 40%, at least about 50%, at least about 60%, at least about 70%, at least about 80%, at least about 90%, at least about 95%, at least about 96%, at least about 97%, at least about 98%, at least about 99%, or about 100% sequence identity to the nucleic acid sequence as set forth in SEQ ID NO: 10; (d) a nucleic acid sequence having at least 79%, at least 80%, at least 81%, at least 82%, at least 83%, at least 84%, at least 85%, at least 86%, at least 87%, at least 88%, at least 89%, at least 90%, at least about 95%, at least about 96%, at least about 97%, at least about 98%, at least about 99%, or about 100% sequence identity to the nucleic acid sequence as set forth in SEQ ID NO: 11; (e) a nucleic acid sequence having at least 88%, at least 89%, at least 90%, at least about 95%, at least about 96%, at least about 97%, at least about 98%, at least about 99%, or about 100% sequence identity to the nucleic acid sequence as set forth in SEQ ID NO: 12; (f) a nucleic acid sequence having at least 82%, at least 83%, at least 84%, at least 85%, at least 90%, at least about 95%, at least about 96%, at least about 97%, at least about 98%, at least about 99%, or about 100% sequence identity to the nucleic acid sequence as set forth in SEQ ID NO: 13; (g) a nucleic acid sequence having at least 90%, at least about 95%, at least about 96%, at least about 97%, at least about 98%, at least about 99%, or about 100% sequence identity to the nucleic acid sequence as set forth in SEQ ID NO:14; (h) a nucleic acid sequence having at least 55%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or about 100% sequence identity to the nucleic acid sequence as set forth in SEQ ID NO: 15; or (i) a nucleic acid sequence having at least 85%, at least 86%, at least 87%, at least 88%, at least 89%, at least about 90%, at least about 95%, at least about 96%, at least about 97%, at least about 98%, at least about 99%, or about 100% sequence identity to the nucleic acid sequence as set forth in SEQ ID NO: 16.

In some aspects, immune cells modified according to the gene editing methods disclosed herein and expressing a CAR or a TCR can have improved anticancer properties. Non-limiting examples of such anticancer properties are described elsewhere in the present disclosure.

While the methods for reducing the expression of a NR4A (NR4A1, NR4A2, and/or NR4A3) gene and/or protein, e.g., gene editing, are provided in the context of CAR- or TCR-expressing cells, those skilled in the art will recognize that the methods disclosed herein can be used for any cells, where reducing the expression of a NR4A (NR4A1, NR4A2, and/or NR4A3) gene and/or protein is desired. For example, in some aspects, the methods for reducing the expression of a NR4A (NR4A1, NR4A2, and/or NR4A3) gene and/or protein disclosed herein can be applied to immune cells. In some aspects, the immune cell comprises a lymphocyte, neutrophil, monocyte, macrophage, dendritic cell, or combinations thereof. In some aspects, a lymphocyte comprises a T cell, tumor-infiltrating lymphocyte (TIL), lymphokine-activated killer cell, natural (NK) cell, or combinations thereof. In some aspects, a lymphocyte is a T cell, e.g., CD4$^+$ T cell or a CD8$^+$ T cell. In some aspects, a lymphocyte is a tumor infiltrating lymphocyte (TIL). In some aspects, a TIL is a CD8$^+$ TIL. In some aspects, a TIL is a CD4$^+$ TTL. Thus, the present disclosure provides cell compositions comprising modified cells (e.g., modified immune cells, wherein the parent cell is, for example, any cell disclosed above) prepared according to the methods for reducing the expression of a NR4A (NR4A1, NR4A2, and/or NR4A3) gene and/or protein and overexpression of a c-Jun protein disclosed herein, wherein the modified cells exhibit reduced expression of a NR4A (NR4A1, NR4A2, and/or NR4A3) gene and/or protein and increased expression of a c-Jun protein with respect to a reference cell (e.g., corresponding cell that has not been modified to express lower levels of the NR4A (NR4A1, NR4A2, and/or NR4A3) gene and/or protein and overexpress the c-Jun protein). In some aspects, these modified cells can be used to prepare a pharmaceutical composition.

In some aspects, modifying the cells described herein comprises (i) contacting the cells with a gene editing tool that is capable of reducing the expression levels of a NR4A (NR4A1, NR4A2, and/or NR4A3) gene and/or protein in the cell and (ii) contacting the cells with a polynucleotide comprising a nucleotide sequence encoding a c-Jun protein.

In some aspects, modifying the cells described herein comprises (i) contacting the cells with a gene editing tool that is capable of reducing the expression levels of a NR4A (NR4A1, NR4A2, and/or NR4A3) gene and/or protein in the cell and (ii) contacting the cells with a transcriptional activator that is capable of increasing the endogenous expression of c-Jun. In some aspects, the contacting of the gene editing tool (or any other tool capable of reducing expression of a NR4A (NR4A1, NR4A2, and/or NR4A3) gene and/or protein) with a cell to be modified can occur in vivo, in vitro, ex vivo, or combinations thereof. In some aspects, the contacting occurs in vivo (e.g., gene therapy). In some aspects, the contacting occurs in vitro. In some aspects, the contacting occurs ex vivo. In some aspects, the cell is an autologous cell. In some aspects, the cell is a heterologous cell. In some aspects, the contacting of the gene editing tool (or any other tool capable of reducing expression of the NR4A (NR4A1, NR4A2, and/or NR4A3) gene and/or protein) reduces the expression level of the NR4A gene and/or protein in the cells by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold, 20 fold, 30 fold, 40 fold, or at least about 50 fold compared to the level of the NR4A gene and/or protein in a reference cell (e.g., corresponding cell that has not been modified to express lower levels of the NR4A gene and/or NR4A protein).

In some aspects, contacting a cell with a gene editing tool comprises different routes of delivery. Generally, for the gene editing tools disclosed herein to reduce the expression of a NR4A (NR4A1, NR4A2, and/or NR4A3) gene and/or protein in a cell, the gene editing tool must be able to enter the cell and bind to the gene of interest. In some aspects, any delivery vehicle known in the art for delivering molecules of interest to a cell can be used. See, e.g., U.S. Pat. No. 10,047,355 B2, which is herein incorporated by reference in its entirety. Additional disclosure relating to vectors that can be used are provided elsewhere in the present disclosure.

In some aspects, a gene editing tool can mutate the gene encoding an NR4A (NR4A1, NR4A2, and/or NR4A3) protein in such a way as to abrogate expression of the functional protein. In some aspects, a gene editing tool can remove the entire gene encoding a NR4A1, NR4A2 and/or NR4A3 protein, thereby abrogating expression of the protein. In some aspects, a gene editing tool removes a portion (e.g., one or more exons) of the gene encoding a NR4A (NR4A1, NR4A2, and/or NR4A3) protein. In some aspects, a gene editing tool, e.g., a base editor, modifies a specific nucleotide base without generating an indel. As used herein, the term "indel" refers to the insertion or deletion of a nucleotide base within a nucleic acid that can lead to frame shift mutations within a coding region of a gene. Non-limiting examples of base editors are disclosed in U.S. Publication No. 2017/0121693, published May 4, 2017, which is incorporated herein by reference in its entirety.

In some aspects, a method of preparing a modified immune cell described herein further comprises modifying the cell to express a ligand binding protein (e.g., CAR or a TCR). In some aspects, the cells are further modified to express a CAR. In some aspects, the cells are further modified to express a TCR (e.g., engineered TCR). In some aspects, modifying the cell to express a ligand binding protein (e.g., CAR or TCR) comprises contacting the cell with a nucleic acid sequence encoding the ligand binding protein (e.g., CAR or TCR). In some aspects, the nucleic acid sequence encoding the ligand binding protein (e.g., CAR or TCR) is expressed from a vector (e.g., expression vector). In some aspects, the vector can further comprise a nucleotide sequence encoding an additional protein of interest (e.g., a c-Jun protein).

In some aspects, a gene editing tool disclosed herein is expressed from a vector comprising a nucleic acid sequence encoding the gene editing tool. In some aspects, the nucleic acid sequence encoding the gene editing tool, the nucleic acid sequence encoding a c-Jun protein, and the nucleic acid sequence encoding the ligand binding protein (e.g., CAR or TCR) are on separate vectors. In some aspects, the nucleic acid sequence encoding the gene editing tool and the nucleic acid sequence encoding the ligand binding protein (e.g., CAR or TCR) are on the same vector. In some aspects, the nucleic acid sequence encoding the gene editing tool and the nucleic acid sequence encoding the c-Jun protein are on the same vector. In some aspects, the nucleic acid sequence encoding the c-Jun protein and the nucleic acid sequence encoding the ligand binding protein (e.g., CAR or TCR) are on the same vector. In some aspects, the nucleic acid sequence encoding the gene editing tool, the nucleic acid sequence encoding the c-Jun protein, and the nucleic acid sequence encoding the ligand binding protein are all on the same vector.

IV.A. Gene Editing Tools

One or more gene editing tools can be used to modify the cells of the present disclosure. Non-limiting examples of the gene editing tools are disclosed below:

IV.A.1. CRISPR/Cas System

In some aspects, the gene editing tool that can be used in the present disclosure comprises a CRISPR/Cas system. Such systems can employ, for example, a nucleic acid molecule encoding a Cas9 nuclease, which in some instances, is codon-optimized for the desired cell type in which it is to be expressed (e.g., T cells, e.g., CAR-expressing or engineered TCR-expressing T cells). As further described herein, in some aspects, such a system can comprise a Cas9 nuclease protein.

CRISPR/Cas systems use Cas nucleases, e.g., Cas9 nucleases, that are targeted to a genomic site by complexing with a guide RNA (e.g., synthetic guide RNA) (gRNA) that hybridizes to a target DNA sequence immediately preceding an NGG motif recognized by the Cas nuclease, e.g., Cas9. This results in a double-strand break three nucleotides upstream of the NGG motif. A unique capability of the CRISPR/Cas9 system is the ability to simultaneously target multiple distinct genomic loci by co-expressing a single Cas9 protein with two or more gRNAs (e.g., at least one, two, three, four, five, six, seven, eight, nine or ten gRNAs). Such systems can also employ a guide RNA that comprises two separate molecules. In some aspects, the two-molecule gRNA comprises a crRNA-like ("CRISPR RNA" or "tar-geter-RNA" or "crRNA" or "crRNA repeat") molecule and a corresponding tracrRNA-like ("trans-acting CRISPR RNA" or "activator-RNA" or "tracrRNA" or "scaffold") molecule.

A crRNA comprises both the DNA-targeting segment (single stranded) of the gRNA and a stretch of nucleotides that forms one half of a double stranded RNA (dsRNA) duplex of the protein-binding segment of the gRNA. A corresponding tracrRNA (activator-RNA) comprises a stretch of nucleotides that forms the other half of the dsRNA duplex of the protein-binding segment of the gRNA. Thus, a stretch of nucleotides of a crRNA is complementary to and hybridizes with a stretch of nucleotides of a tracrRNA to form the dsRNA duplex of the protein-binding domain of the gRNA. As such, each crRNA can be said to have a corresponding tracrRNA. The crRNA additionally provides the single stranded DNA-targeting segment. Accordingly, a gRNA comprises a sequence that hybridizes to a target sequence (e.g., NR4A1, NR4A2, and/or NR4A3 mRNA), and a tracrRNA. Thus, a crRNA and a tracrRNA (as a corresponding pair) hybridize to form a gRNA. If used for modification within a cell, the exact sequence and/or length of a given crRNA or tracrRNA molecule can be designed to be specific to the species in which the RNA molecules will be used (e.g., humans).

Naturally-occurring genes encoding the three elements (Cas9, tracrRNA and crRNA) are typically organized in operon(s). Naturally-occurring CRISPR RNAs differ depending on the Cas9 system and organism but often contain a targeting segment of between 21 to 72 nucleotides length, flanked by two direct repeats (DR) of a length of between 21 to 46 nucleotides (see, e.g., WO2014/131833). In the case of S. pyogenes, the DRs are 36 nucleotides long and the targeting segment is 30 nucleotides long. The 3' located DR is complementary to and hybridizes with the corresponding tracrRNA, which in turn binds to the Cas9 protein.

Alternatively, a CRISPR system used herein can further employ a fused crRNA-tracrRNA construct (i.e., a single transcript) that functions with the codon-optimized Cas9. This single RNA is often referred to as a guide RNA or gRNA. Within a gRNA, the crRNA portion is identified as the "target sequence" for the given recognition site and the tracrRNA is often referred to as the "scaffold." Briefly, a short DNA fragment containing the target sequence is inserted into a guide RNA expression plasmid. The gRNA expression plasmid comprises the target sequence (in some aspects around 20 nucleotides), a form of the tracrRNA sequence (the scaffold) as well as a suitable promoter that is active in the cell and necessary elements for proper processing in eukaryotic cells. Many of the systems rely on custom, complementary oligos that are annealed to form a double stranded DNA and then cloned into the gRNA expression plasmid.

The gRNA expression cassette and the Cas9 expression cassette are then introduced into the cell. See, for example, Mali P et al., (2013) Science 2013 Feb. 15; 339(6121):823-6; Jinek M et al., Science 2012 Aug. 17; 337(6096):816-21; Hwang W Y et al., Nat Biotechnol 2013 March; 31(3):227-9; Jiang W et al., Nat Biotechnol 2013 March; 31(3):233-9; and Cong L et al., Science 2013 Feb. 15; 339(6121):819-23, each of which is herein incorporated by reference in its entirety. See also, for example, WO/2013/176772 A1, WO/2014/065596 A1, WO/2014/089290 A1, WO/2014/093622 A2, WO/2014/099750 A2, and WO/2013142578 A1, each of which is herein incorporated by reference in its entirety.

In some aspects, the Cas9 nuclease can be provided in the form of a protein. For instance, in some aspects, a cell useful for the present disclosure (e.g., CAR or TCR expressing immune cell) can be modified (e.g., to have reduced level of a NR4A gene and/or NR4A protein) by introducing a Cas9 nuclease protein and a nucleic acid molecule comprising a gRNA. In some aspects, the Cas9 nuclease protein and the nucleic acid molecule comprising a gRNA can be introduced into the cell sequentially. In some aspects, the Cas9 nuclease protein and the nucleic acid molecule comprising a gRNA can be introduced into the cell concurrently. For instance, in some aspects, the concurrent administration comprises introducing the Cas9 nuclease protein and the nucleic acid molecule comprising a gRNA at the same time but as separate compositions. In some aspects, the Cas9 protein can be provided in the form of a complex with the nucleic acid molecule comprising a gRNA (i.e., as a single composition).

In some aspects, the Cas9 nuclease can be provided in the form of a nucleic acid encoding the protein. Accordingly, in some aspects, a cell useful for the present disclosure (e.g., CAR or TCR expressing immune cell) can be modified (e.g., to have reduced level of a NR4A gene and/or NR4A protein) by introducing a first nucleic acid molecule encoding a Cas9 nuclease protein and a second nucleic acid molecule comprising a gRNA. In some aspects, the first and second nucleic acid molecules can be introduced the cell sequentially. In some aspects, the first and second nucleic acid molecules can be introduced into the cell concurrently. For instance, in some aspects, the first and second nucleic acid molecules can be introduced into the cell at the same time but as separate compositions. In some aspects, the first and second nucleic acid molecules can be part of a single polynucleotide, and the cell is modified to comprise the single polynucleotide.

The nucleic acid encoding the Cas9 nuclease can be RNA (e.g., messenger RNA (mRNA)) or DNA. In some aspects, the gRNA can be provided in the form of RNA. In some aspects, the gRNA can be provided in the form of DNA encoding the RNA. In some aspects, the gRNA can be provided in the form of separate crRNA and tracrRNA molecules, or separate DNA molecules encoding the crRNA and tracrRNA, respectively.

In some aspects, the gRNA comprises a third nucleic acid sequence encoding a Clustered Regularly Interspaced Short Palindromic Repeats (CRISPR) RNA (crRNA) and a trans-activating CRISPR RNA (tracrRNA). In some aspects, the Cas protein is a type I Cas protein. In some aspects, the Cas protein is a type II Cas protein. In some aspects, the type II Cas protein is Cas9. In some aspects, the type II Cas, e.g., Cas9, is a human codon-optimized Cas.

In some aspects, the Cas protein is a "nickase" that can create single strand breaks (i.e., "nicks") within the target nucleic acid sequence without cutting both strands of double stranded DNA (dsDNA). Cas9, for example, comprises two nuclease domains—a RuvC-like nuclease domain and an HNH-like nuclease domain—which are responsible for cleavage of opposite DNA strands. Mutation in either of these domains can create a nickase. Examples of mutations creating nickases can be found, for example, WO/2013/176772 A1 and WO/2013/142578 A1, each of which is herein incorporated by reference.

In some aspects, two separate Cas proteins (e.g., nickases) specific for a target site on each strand of dsDNA can create overhanging sequences complementary to overhanging sequences on another nucleic acid, or a separate region on the same nucleic acid. The overhanging ends created by contacting a nucleic acid with two nickases specific for target sites on both strands of dsDNA can be either 5' or 3' overhanging ends. For example, a first nickase can create a single strand break on the first strand of dsDNA, while a second nickase can create a single strand break on the second strand of dsDNA such that overhanging sequences are created. The target sites of each nickase creating the single strand break can be selected such that the overhanging end sequences created are complementary to overhanging end sequences on a different nucleic acid molecule. The complementary overhanging ends of the two different nucleic acid molecules can be annealed by the methods disclosed herein. In some aspects, the target site of the nickase on the first strand is different from the target site of the nickase on the second strand.

In some aspects, the expression of a NR4A (NR4A1, NR4A2, and/or NR4A3) gene, and the NR4A protein encoded thereof, is reduced by contacting the cell with a CRISPR (e.g., CRISPR-Cas9 system) that is, e.g., specific to the NR4A (NR4A1, NR4A2, and/or NR4A3) gene. In some aspects, the CRISPR is specific to the NR4A1 gene. Accordingly, in some aspects, after the contacting with the CRISPR, the cell (e.g., CAR or TCR expressing immune cell) has: (i) a reduced level of the NR4A1 gene and/or protein, (ii) endogenous level of the NR4A2 gene and/or protein, and (iii) endogenous level of the NR4A3 gene and/or protein. In some aspects, the CRISPR is specific for the NR4A2 gene. Accordingly, in some aspects, after the contacting with the CRISPR, the cell (e.g., CAR or TCR expressing immune cell) has: (i) endogenous level of the NR4A1 gene and/or protein, (ii) reduced level of the NR4A2 gene and/or protein, and (iii) endogenous level of the NR4A3 gene and/or protein. In some aspects, the CRISPR is specific for the NR4A3 gene. Accordingly, in some aspects, after the contacting with the CRISPR, the cell (e.g., CAR or TCR expressing immune cell) has: (i) endogenous level of the NR4A1 gene and/or protein, (ii) endogenous level of the NR4A2 gene and/or protein, and (iii) reduced level of the NR4A3 gene and/or protein.

As described herein, in some aspects, the CRISPR targets multiple NR4A genes. For instance, in some aspects, the CRISPR is capable of targeting both the NR4A1 gene and the NR4A2 gene. Accordingly, in some aspects, after the contacting with the CRISPR, the cell (e.g., CAR or TCR expressing immune cell) has: (i) reduced level of the NR4A1 gene and/or protein, (ii) reduced level of the NR4A2 gene and/or protein, and (iii) endogenous level of the NR4A3 gene and/or protein. In some aspects, the CRISPR is capable of targeting both the NR4A1 gene and the NR4A3 gene. Accordingly, in some aspects, after the contacting with the CRISPR, the cell (e.g., CAR or TCR expressing immune cell) has: (i) reduced level of the NR4A1 gene and/or protein, (ii) endogenous level of the NR4A2 gene and/or protein, and (iii) reduced level of the NR4A3 gene and/or protein. In some aspects, the CRISPR is capable of targeting both the NR4A2 gene and/or the NR4A3 gene. In some aspects, after the contacting with the CRISPR, the cell (e.g., CAR or TCR expressing immune cell) has: (i) endogenous level of the NR4A1 gene and/or protein, (ii) reduced level of the NR4A2 gene and/or protein, and (iii) reduced level of the NR4A3 gene and/or protein. In some aspects, the CRISPR is capable of targeting the NR4A1 gene, the NR4A2 gene, and the NR4A3 gene. Accordingly, in some aspects, after the contacting with the CRISPR, the cell (e.g., CAR or TCR expressing immune cell) has: (i) reduced level of the NR4A1 gene and/or protein, (ii) reduced level of the NR4A2 gene and/or protein, and (iii) reduced level of the NR4A3 gene and/or protein.

In some aspects, gene editing using CRISPR reduces a NR4A (NR4A1, NR4A2, and/or NR4A3) gene level by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least 70%, at least about 75%, at least about 80%, at least about 85%, at least about 90%, at least about 95%, or about 100% with respect to the NR4A (NR4A1, NR4A2, and/or NR4A3) gene levels observed in a reference cell (e.g., a corresponding cell that has not been subjected to gene editing using CRISPR). In some aspects, the CRISPR completely abolishes the expression of NR4A (NR4A1, NR4A2, and/or NR4A3) in the immune cells. In some aspects, the NR4A (NR4A1, NR4A2, and/or NR4A3) gene levels can be measured using any technique known in the art, e.g., by digital droplet PCR.

In some aspects, a nucleic acid encoding a gRNA and/or a Cas9 disclosed herein is an RNA or a DNA. In some aspects, the RNA or DNA encoding a gRNA and/or a Cas9 disclosed herein is a synthetic RNA or a synthetic DNA, respectively. In some aspects, the synthetic RNA or DNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine or pseudouridine). In some aspects, the polynucleotide (e.g., a synthetic RNA or a synthetic DNA) comprises only natural nucleobases, i.e., A, C, T and U in the case of a synthetic DNA, or A, C, T, and U in the case of a synthetic RNA or synthetic DNA.

In general, the CRISPR gene editing methods disclosed herein comprise contacting a cell, e.g., an immune cell, in vivo, in vitro, or ex vivo with (i) a Cas9 or a nucleic acid encoding the Cas9; and, (ii) at least one NR4A (NR4A1, NR4A2, or NR4A3) gene guide RNA (gRNA) or a nucleic acid encoding the gRNA, wherein the gRNA targets a sequence in the NR4A gene (e.g., an intron and/or exon sequence), wherein contacting the cell with the Cas9 and the at least one gRNA results in a reduction of the expression of the NR4A (NR4A1, NR4A2, or NR4A3) gene and/or protein.

In some aspects, a gRNA that can be used to target the NR4A3 gene comprises, consists of, or consists essentially of any one or more of the sequences set forth in SEQ ID NOs: 30, 52-57, 58, 61, 65, 67, 68, 70, 71, 75, 76, 82, 83, 86, 94, and 96. In some aspects, a gRNA that can be used to target the NR4A3 gene comprises, consists of, or consists essentially of the sequence set forth in SEQ ID NO: 30. In some aspects, a gRNA that can be used to target the NR4A3 gene comprises the sequence set forth in SEQ ID NO: 30. In some aspects, a gRNA that can be used to target the NR4A3 gene consists of the sequence set forth in SEQ ID NO: 30. In some aspects, a gRNA that can be used to target the NR4A3 gene consists essentially of the sequence set forth in SEQ ID NO: 30. In some aspects, a gRNA that can be used to target the NR4A3 gene comprises, consists of, or consists essentially of the sequence set forth in SEQ ID NO: 52. In some aspects, a gRNA that can be used to target the NR4A3 gene comprises the sequence set forth in SEQ ID NO: 52. In some aspects, a gRNA that can be used to target the NR4A3 gene consists of the sequence set forth in SEQ ID NO: 52. In some aspects, a gRNA that can be used to target the NR4A3 gene consists essentially of the sequence set forth in SEQ ID NO: 52. In some aspects, a gRNA that can be used to target the NR4A3 gene comprises, consists of, or consists essentially of the sequence set forth in SEQ ID NO: 53. In some aspects, a gRNA that can be used to target the NR4A3 gene comprises the sequence set forth in SEQ ID NO: 53. In some aspects, a gRNA that can be used to target the NR4A3 gene consists of the sequence set forth in SEQ ID NO: 53. In some aspects, a gRNA that can be used to target the NR4A3 gene consists essentially of the sequence set forth in SEQ ID NO: 53. In some aspects, a gRNA that can be used to target the NR4A3 gene comprises, consists of, or consists essentially of the sequence set forth in SEQ ID NO: 54. In some aspects, a gRNA that can be used to target the NR4A3 gene comprises the sequence set forth in SEQ ID NO: 54. In some aspects, a gRNA that can be used to target the NR4A3 gene consists of the sequence set forth in SEQ ID NO: 54. In some aspects, a gRNA that can be used to target the NR4A3 gene consists essentially of the sequence set forth in SEQ ID NO: 54. In some aspects, a gRNA that can be used to target the NR4A3 gene comprises, consists of, or consists essentially of the sequence set forth in SEQ ID NO: 55. In some aspects, a gRNA that can be used to target the NR4A3 gene comprises the sequence set forth in SEQ ID NO: 55. In some aspects, a gRNA that can be used to target the NR4A3 gene consists of the sequence set forth in SEQ ID NO: 55. In some aspects, a gRNA that can be used to target the NR4A3 gene consists essentially of the sequence set forth in SEQ ID NO: 55. In some aspects, a gRNA that can be used to target the NR4A3 gene comprises, consists of, or consists essentially of the sequence set forth in SEQ ID NO: 56. In some aspects, a gRNA that can be used to target the NR4A3 gene comprises the sequence set forth in SEQ ID NO: 56. In some aspects, a gRNA that can be used to target the NR4A3 gene consists of the sequence set forth in SEQ ID NO: 56. In some aspects, a gRNA that can be used to target the NR4A3 gene consists essentially of the sequence set forth in SEQ ID NO: 56. In some aspects, a gRNA that can be used to target the NR4A3 gene comprises, consists of, or consists essentially of the sequence set forth in SEQ ID NO: 57. In some aspects, a gRNA that can be used to target the NR4A3 gene comprises the sequence set forth in SEQ ID NO: 57. In some aspects, a gRNA that can be used to target the NR4A3 gene consists of the sequence set forth in SEQ ID NO: 57. In some aspects, a gRNA that can be used to target the NR4A3 gene consists essentially of the sequence set forth in SEQ ID NO: 57. In some aspects, a gRNA that can be used to target the NR4A3 gene comprises, consists of, or consists essentially of the sequence set forth in SEQ ID NO: 58. In some aspects, a gRNA that can be used to target the NR4A3 gene comprises the sequence set forth in SEQ ID NO: 58. In some aspects, a gRNA that can be used to target the NR4A3 gene consists of the sequence set forth in SEQ ID NO: 58. In some aspects, a gRNA that can be used to target the NR4A3 gene consists essentially of the sequence set forth in SEQ ID NO: 58. In some aspects, a gRNA that can be used to target the NR4A3 gene comprises, consists of, or consists essentially of the sequence set forth in SEQ ID NO: 61. In some aspects, a gRNA that can be used to target the NR4A3 gene comprises the sequence set forth in SEQ ID NO: 61. In some aspects, a gRNA that can be used to target the NR4A3 gene consists of the sequence set forth in SEQ ID NO: 61. In some aspects, a gRNA that can be used to target the NR4A3 gene consists essentially of the sequence set forth in SEQ ID NO: 61. In some aspects, a gRNA that can be used to target the NR4A3 gene comprises, consists of, or consists essentially of the sequence set forth in SEQ ID NO: 65. In some aspects, a gRNA that can be used to target the NR4A3 gene comprises the sequence set forth in SEQ ID NO: 65. In some aspects, a gRNA that can be used to target the NR4A3 gene consists of the sequence set forth in SEQ ID NO: 65. In some aspects, a gRNA that can be used to target the NR4A3 gene consists essentially of the sequence set forth in SEQ ID NO: 65. In some aspects, a gRNA that can be used to target the NR4A3 gene comprises, consists of, or consists essentially of the sequence set forth in SEQ ID NO: 67. In some aspects, a gRNA that can be used to target the NR4A3 gene comprises the sequence set forth in SEQ ID NO: 67. In some aspects, a gRNA that can be used to target the NR4A3 gene consists of the sequence set forth in SEQ ID NO: 67. In some aspects, a gRNA that can be used to target the NR4A3 gene consists essentially of the sequence set forth in SEQ ID NO: 67. In some aspects, a gRNA that can be used to target the NR4A3 gene comprises, consists of, or consists essentially of the sequence set forth in SEQ ID NO: 68. In some aspects, a gRNA that can be used to target the NR4A3 gene comprises the sequence set forth in SEQ ID NO: 68. In some aspects, a gRNA that can be used to target the NR4A3 gene consists of the sequence set forth in SEQ ID NO: 68. In some aspects, a gRNA that can be used to target the NR4A3 gene consists essentially of the sequence set forth in SEQ ID NO: 68. In some aspects, a gRNA that can be used to target the NR4A3 gene comprises, consists of, or consists essentially of the sequence set forth in SEQ ID NO: 70. In some aspects, a gRNA that can be used to target the NR4A3 gene comprises the sequence set forth in SEQ ID NO: 70. In some aspects, a gRNA that can be used to target the NR4A3 gene consists of the sequence set forth in SEQ ID NO: 70. In some aspects, a gRNA that can be used to target the NR4A3 gene consists essentially of the sequence set forth in SEQ ID NO: 70. In some aspects, a gRNA that can be used to target the NR4A3 gene comprises, consists of, or consists essentially of the sequence set forth in SEQ ID NO: 71. In some aspects, a gRNA that can be used to target the NR4A3 gene comprises the sequence set forth in SEQ ID NO: 71. In some aspects, a gRNA that can be used to target the NR4A3 gene consists of the sequence set forth in SEQ ID NO: 71. In some aspects, a gRNA that can be used to target the NR4A3 gene consists essentially of the sequence set forth in SEQ ID NO: 71. In some aspects, a gRNA that can be used to target the NR4A3 gene comprises, consists of, or consists essentially of the sequence set forth in SEQ ID NO: 75. In some aspects, a gRNA that can be used to target the NR4A3 gene comprises the sequence set forth in SEQ ID NO: 75. In some aspects, a gRNA that can be used to target the NR4A3 gene consists of the sequence set forth in SEQ ID NO: 75. In some aspects, a gRNA that can be used to target the NR4A3 gene consists essentially of the sequence set forth in SEQ ID NO: 75. In some aspects, a gRNA that can be used to target the NR4A3 gene comprises, consists of, or consists essentially of the sequence set forth in SEQ ID NO: 76. In some aspects, a gRNA that can be used to target the NR4A3 gene comprises the sequence set forth in SEQ ID NO: 76. In some aspects, a gRNA that can be used to target the NR4A3 gene consists of the sequence set forth in SEQ ID NO: 76. In some aspects, a gRNA that can be used to target the NR4A3 gene consists essentially of the sequence set forth in SEQ ID NO: 76. In some aspects, a gRNA that can be used to target the NR4A3 gene comprises, consists of, or consists essentially of the sequence set forth in SEQ ID NO: 82. In some aspects, a gRNA that can be used to target the NR4A3 gene comprises the sequence set forth in SEQ ID NO: 82. In some aspects, a gRNA that can be used to target the NR4A3 gene consists of the sequence set forth in SEQ ID NO: 82. In some aspects, a gRNA that can be used to target the NR4A3 gene consists essentially of the sequence set forth in SEQ ID NO: 82. In some aspects, a gRNA that can be used to target the NR4A3 gene comprises, consists of, or consists essentially of the sequence set forth in SEQ ID NO: 83. In some aspects, a gRNA that can be used to target the NR4A3 gene comprises the sequence set forth in SEQ ID NO: 83. In some aspects, a gRNA that can be used to target the NR4A3 gene consists of the sequence set forth in SEQ ID NO: 83. In some aspects, a gRNA that can be used to target the NR4A3 gene consists essentially of the sequence set forth in SEQ ID NO: 83. In some aspects, a gRNA that can be used to target the NR4A3 gene comprises, consists of, or consists essentially of the sequence set forth in SEQ ID NO: 86. In some aspects, a gRNA that can be used to target the NR4A3 gene comprises the sequence set forth in SEQ ID NO: 86. In some aspects, a gRNA that can be used to target the NR4A3 gene consists of the sequence set forth in SEQ ID NO: 86. In some aspects, a gRNA that can be used to target the NR4A3 gene consists essentially of the sequence set forth in SEQ ID NO: 86. In some aspects, a gRNA that can be used to target the NR4A3 gene comprises, consists of, or consists essentially of the sequence set forth in SEQ ID NO: 94. In some aspects, a gRNA that can be used to target the NR4A3 gene comprises the sequence set forth in SEQ ID NO: 94. In some aspects, a gRNA that can be used to target the NR4A3 gene consists of the sequence set forth in SEQ ID NO: 94. In some aspects, a gRNA that can be used to target the NR4A3 gene consists essentially of the sequence set forth in SEQ ID NO: 94. In some aspects, a gRNA that can be used to target the NR4A3 gene comprises, consists of, or consists essentially of the sequence set forth in SEQ ID NO: 96. In some aspects, a gRNA that can be used to target the NR4A3 gene comprises the sequence set forth in SEQ ID NO: 96. In some aspects, a gRNA that can be used to target the NR4A3 gene consists of the sequence set forth in SEQ ID NO: 96. In some aspects, a gRNA that can be used to target the NR4A3 gene consists essentially of the sequence set forth in SEQ ID NO: 96.

As described herein, in some aspects, the gene editing methods can further comprise reducing the level of (i) NR4A1 gene and/or NR4A1 protein, (ii) NR4A2 gene and/or NR4A2 protein, or (iii) both (i) and (ii). In some aspects, a gRNA that can be used to target the NR4A1 gene comprises, consists of, or consists essentially of the sequence set forth in SEQ ID NO: 25. In some aspects, a gRNA that can be used to target the NR4A1 gene comprises the sequence set forth in SEQ ID NO: 25. In some aspects, a gRNA that can be used to target the NR4A1 gene consists of the sequence set forth in SEQ ID NO: 25. In some aspects, a gRNA that can be used to target the NR4A1 gene consists essentially of the sequence set forth in SEQ ID NO: 25. In some aspects, a gRNA that can be used to target the NR4A1 gene comprises, consists of, or consists essentially of the sequence set forth in SEQ ID NO: 26. In some aspects, a gRNA that can be used to target the NR4A1 gene comprises the sequence set forth in SEQ ID NO: 26. In some aspects, a gRNA that can be used to target the NR4A1 gene consists of the sequence set forth in SEQ ID NO: 26. In some aspects, a gRNA that can be used to target the NR4A1 gene consists essentially of the sequence set forth in SEQ ID NO: 26. In some aspects, a gRNA that can be used to target the NR4A2 gene comprises, consists of, or consists essentially of the sequence set forth in SEQ ID NO: 27. In some aspects, a gRNA that can be used to target the NR4A2 gene comprises the sequence set forth in SEQ ID NO: 27. In some aspects, a gRNA that can be used to target the NR4A2 gene consists of the sequence set forth in SEQ ID NO: 27. In some aspects, a gRNA that can be used to target the NR4A2 gene consists essentially of the sequence set forth in SEQ ID NO: 27. In some aspects, a gRNA that can be used to target the NR4A2 gene comprises, consists of, or consists essentially of the sequence set forth in SEQ ID NO: 28. In some aspects, a gRNA that can be used to target the NR4A2 gene comprises the sequence set forth in SEQ ID NO: 28. In some aspects, a gRNA that can be used to target the NR4A2 gene consists of the sequence set forth in SEQ ID NO: 28. In some aspects, a gRNA that can be used to target the NR4A2 gene consists essentially of the sequence set forth in SEQ ID NO: 28. In some aspects, a gRNA that can be used to target the NR4A2 gene comprises, consists of, or consists essentially of the sequence set forth in SEQ ID NO: 29. In some aspects, a gRNA that can be used to target the NR4A2 gene comprises the sequence set forth in SEQ ID NO: 29. In some aspects, a gRNA that can be used to target the NR4A2 gene consists of the sequence set forth in SEQ ID NO: 29. In some aspects, a gRNA that can be used to target the NR4A2 gene consists essentially of the sequence set forth in SEQ ID NO: 29.

As used herein, the term "contacting" (for example, contacting a cell, e.g., an immune cell with at least one gRNA and at least one Cas9) is intended to include incubating at least one gRNA and at least one Cas protein, e.g., Cas9, in the cell together in vitro (e.g., adding the gRNA and/or Cas protein, or nucleic acid(s) encoding the gRNA(s) and/or Cas9 protein(s) to cells in culture) or contacting a cell in vivo or ex vivo.

The step of contacting an NR4A (NR4A1, NR4A2, and/or NR4A3) gene target sequence with at least one gRNA and at least one Cas protein, e.g., Cas9, as disclosed herein (or at least one nucleic acid encoding them) can be conducted in any suitable manner. For example, the cells, e.g., immune cells, can be treated in cell culture conditions. It is understood that the cells contacted with at least one gRNA and at least one Cas protein, e.g., a Cas9 protein, disclosed herein (or at least one nucleic acid encoding them) can also be simultaneously or subsequently contacted with another agent, e.g., a vector comprising at least one nucleic acid sequence encoding a CAR or a TCR. In some aspects, after the cell has been contacted in vitro or ex vivo, the method further comprises introducing the cell into the subject, thereby treating or ameliorating the symptoms of a disease or condition, e.g., cancer.

For ex vivo methods, cells can include autologous cells, i.e., an immune cell or cells taken from a subject who is in need of altering a target polynucleotide sequence (e.g., the NR4A (NR4A1, NR4A2, and/or NR4A3) gene) in the cell or cells (i.e., the donor and recipient are the same individual). Autologous cells have the advantage of avoiding any immunologically-based rejection of the cells. Alternatively, the cells can be heterologous, e.g., taken from a donor. Typically, when the cells come from a donor, they will be from a donor who is sufficiently immunologically compatible with the recipient, i.e., will not be subject to transplant rejection, to lessen or remove the need for immunosuppression. In some aspects, the cells are taken from a xenogeneic source, i.e., a non-human mammal that has been genetically engineered to be sufficiently immunologically compatible with the recipient, or the recipient's species. Methods for determining immunological compatibility are known in the art, and include tissue typing to assess donor-recipient compatibility for HLA and ABO determinants. See, e.g., Transplantation Immunology, Bach and Auchincloss, Eds. (Wiley, John & Sons, Incorporated 1994).

In some aspects, the present disclosure provides a method of generating a modified immune cell comprising altering the NR4A (NR4A1, NR4A2, and/or NR4A3) gene sequence in a cell, e.g., an immune cell (such as a T cell), ex vivo by contacting the NR4A gene sequence in the cell with a Cas9 protein (or a nucleic acid encoding such Cas9 protein) and one gRNA which target motifs in the NR4A (NR4A1, NR4A2, and/or NR4A3) gene (for example motifs located in exons 3 and 4 of NR4A3, wherein the gRNAs direct the Cas9 protein to the target gene and hybridize to the target motifs, wherein the NR4A gene is partially or totally cleaved, and wherein the efficiency of cleavage is from about 10% to about 100%. Non-limiting examples of such gRNAs are provided herein (see, e.g., Tables A, C, and D). As described herein, in some aspects, the method of generating a modified immune cell described herein comprises altering the NR4A gene sequence by contacting the cell with a first nucleic acid molecule encoding the Cas9 protein and a second nucleic acid molecule comprising a gRNA that targets one or more members of the NR4A gene family. In some aspects, the first and nucleic acid molecules are contacted with the cell sequentially. In some aspects, the first and nucleic acid molecules are contacted with the cell concurrently. For instance, in some aspects, the cell is contacted with a single polynucleotide comprising the first nucleic acid molecule encoding the Cas9 protein and the second nucleic acid molecule comprising a gRNA.

In some aspects, the cell has been modified (e.g., transfected) with a nucleic acid (e.g., a vector) encoding a ligand binding protein (e.g., CAR or a TCR) previously, subsequently, or concurrently to the altering step described above. Additionally, as further described elsewhere in the present disclosure, in some aspects, the cell has been modified to have increased level of a c-Jun protein previously, subsequently, or concurrently to the altering step described above.

In some aspects, the efficiency of cleavage is at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

The CRISPR/Cas system of the present disclosure can use gRNA spacer sequences of varying lengths, depending on the Cas used, e.g., a Cas9. Cas9 from different species must be paired with their corresponding gRNAs to form a functional ribonucleoprotein (RNP) complex, in other words, chimeric gRNA frames engineered from different bacterial species can have different length due to differences in spacer sequence and chimeric frame sequence.

In some aspects, the gRNA spacer sequence can be least about 18 nucleotides (e.g., about 18, about 19, about 20, about 21, or about 22 nucleotides) long. For example, the length of S. pyogenes gRNA spacer sequences in gRNAs binding to S. pyogenes Cas9 is 20 nucleotides, while the length of S. aureus gRNA spacer sequences in gRNAs binding to S. aureus Cas9 is 21 nucleotides. In some aspects, the gRNA spacer sequence can comprise 10, 11, 12, 13, 14, 15, 16, 17, 18, 19, 20, 21, 22, 23, 24, 25, 26, 27, 28, 29, 30, 31, 32, 33, 34 or 35 nucleotides.

Although a perfect match between the gRNA spacer sequence and the DNA strand to which it binds on the NR4A (NR4A1, NR4A2, and/or NR4A3) gene is preferred, a mismatch between a gRNA spacer sequence and a NR4A target sequence is also permitted as along as it still results in a reduction of NR4A gene levels or a decrease in NR4A gene function. A "seed" sequence of between about 8-about 12 consecutive nucleotides on the gRNA perfectly complementary to the target NR4A sequence is preferred for proper recognition of the target sequence on the NR4A gene. The remainder of the gRNA spacer sequence can comprise one or more mismatches.

In general, gRNA activity is inversely correlated with the number of mismatches. Preferably, the gRNA spacer sequences of the present disclosure comprise less than about 7 mismatches. In some aspects, gRNA spacer sequence comprises 7 mismatches, 6 mismatches, 5 mismatches, 4 mismatches, 3 mismatches, more preferably 2 mismatches, or less, and even more preferably no mismatch, with the corresponding NR4A gene target sequence. The smaller the number of nucleotides in the gRNA the smaller the number of mismatches tolerated. The binding affinity is thought to depend on the sum of matching gRNA-DNA combinations.

The gRNA spacer sequences of the present disclosure can be selected to minimize off-target effects of the CRISPR/Cas editing system. Accordingly, in some aspects, the gRNA spacer sequence is selected such that it contains at least two mismatches when compared with all other genomic nucleotide sequences in the cell. In some aspects, the gRNA spacer sequence is selected such that it contains at least one mismatch when compared with all other genomic nucleotide sequences in the cell. Those skilled in the art will appreciate that a variety of techniques can be used to select suitable gRNA spacer sequences for minimizing off-target effects (e.g., bioinformatics analyses).

In some aspects, the gRNA spacer sequence comprises, consists, or consists essentially of a spacer sequence of SEQ ID NO: 31-42.

In some aspects, the gRNA spacer sequence comprises, consists, or consists essentially of a spacer sequence comprising at least one, two, three, four or five nucleotide mismatches compared to a DNA sequence of any one of SEQ ID NOS: 31-42.

In some aspects, editing efficacy can be increased by targeting multiple location.

In some aspects, two gRNAs are complementary to and/or hybridize to sequences on the same strand of the NR4A gene. In some aspects, two gRNAs are complementary to and/or hybridize to sequences on the opposite strands of the NR4A gene. In some aspects, the two gRNAs are not complementary to and/or do not hybridize to sequences on the opposite strands of the NR4A gene. In some aspects, two gRNAs are complementary to and/or hybridize to overlapping target motifs of the NR4A gene. In some aspect, two gRNAs are complementary to and/or hybridize to offset target motifs of the NR4A gene.

In general, the gRNAs of the present disclosure can comprise any variant of its sequence or chemical modifications provided that it allows for the binding of the corresponding Cas protein, e.g., a Cas9 protein, to a target sequence, and subsequent ablation (total or partial) of the NR4A (NR4A1, NR4A2, and/or NR4A3) gene.

The Cas proteins, e.g., Cas9, used in the methods disclosed herein are endonucleases that cleave nucleic acids and are encoded by the CRISPR loci of numerous bacterial genomes and is involved in the Type II CRISPR system. Cas9 proteins are produced by numerous species of bacteria including *Streptococcus pyogenes, Staphylococcus aureus, Streptococcus thermophilus, Neisseria meningitidis*, etc. Accordingly, the Cas9 protein useful for the present disclosure can be derived from any suitable bacteria known in the art. Non-limiting examples of such bacteria include *Streptococcus pyogenes, Streptococcus mutans, Streptococcus pneumonia, Streptococcus aureus, Streptococcus thermophilus, Campylobacter jejuni, Neisseria meningitidis, Pasteurella multocida, Listeria innocua*, and *Francisella novicida*. The methods disclosed herein can be practiced with any Cas9 known in the art. In some aspects, the Cas9 is a wild type Cas9. In some aspects, the Cas9 is a mutated Cas9 with enhanced enzymatic activity or a fusion protein comprising a Cas9 moiety. In some aspects, the Cas9 nuclease protein is *Streptococcus pyogenes* Cas9 protein.

Because Cas9 nuclease proteins are normally expressed in bacteria, it can be advantageous to modify their nucleic acid sequences for optimal expression in eukaryotic cells (e.g., mammalian cells) when designing and preparing Cas9 recombinant proteins. Accordingly, in some aspects, the nucleic acid encoding a Cas9 used in the methods disclosed herein has been codon optimized for expression in eukaryotic cells, e.g., for expression in cell of a human subject in need thereof.

In some aspects, a Cas9 protein used in the methods disclosed herein comprises one or more amino acid substitutions or modifications. In some aspects, the one or more amino acid substitutions comprises a conservative amino acid substitution. In some instances, substitutions and/or modifications can prevent or reduce proteolytic degradation and/or extend the half-life of the polypeptide in a cell. In some aspects, the Cas9 protein can comprise a peptide bond replacement (e.g., urea, thiourea, carbamate, sulfonyl urea, etc.). In some aspects, the Cas9 protein can comprise a naturally occurring amino acid. In some aspects, the Cas9 protein can comprise an alternative amino acid (e.g., D-amino acids, beta-amino acids, homocysteine, phosphoserine, etc.). In some aspects, the Cas9 protein can comprise a modification to include a heterologous moiety (e.g., PEGylation, glycosylation, lipidation, acetylation, end-capping, etc.).

Although the methods disclosed herein are generally practiced using Cas9 proteins, it is envisioned that in some aspects, the Cas protein can be a Cas1, Cas2, Cas3, Cas4, Cas5, Cas6, Cas7, or Cas8. In some aspects, the Cas protein is Cas9 protein from any bacterial species or functional portion thereof. In some specific aspects, the Cas9 protein used in the methods disclosed herein is a *Streptococcus pyogenes* or *Staphylococcus aureus* Cas9 protein or a functional portion thereof, or a nucleic acid encoding such Cas9 or functional portion thereof. Non-limiting examples of other Cas nucleases that can be used are known in the art and described in, e.g., U.S. Pat. No. 9,970,001 B2; U.S. Pat. No. 10,221,398 B2; and US 2020/0190487 A1, each of which is incorporated herein by reference in its entirety. In some aspects, a Cas nuclease useful for the present disclosure comprises a Type I Cas protein. Non-limiting examples of Type I Cas proteins include Cas3, Cas5, Cas6, Cas7, Cas8a, Cas8b, Cas8c, Cas10d, Cse1, Cse2, Csy1, Csy2, Csy3, and variants thereof. In some aspects, a Cas nuclease useful for the present disclosure comprises a Type II Cas protein. Non-limiting examples of Type II Cas proteins include Cas9, Csn2, Cas4, and variants thereof. In some aspects, a Cas nuclease useful for the present disclosure comprises a Type III Cas protein. Non-limiting examples include Cas10, Csm2, Cmr5, Csx10, Csx11, and variants thereof. In some aspects, a Cas nuclease useful for the present disclosure comprises a Type IV Cas protein. Non-limiting example of such a Cas protein includes Csf1. In some aspects, a Cas nuclease useful for the present disclosure comprises a Type V Cas protein. Non-limiting examples include, Cas12, Cas12a (Cpf1), Cas12b (C2c1), Cas12c (C2c3), Cas12d (CasY), Cas12e (CasX), Cas12f (Cas14, C2c10), Cas12g, Cas12h, Cas12i, Cas12k (C2c5), C2c4, C2c8, C2c9, and variants thereof. In some aspects, a Cas nuclease useful for the present disclosure comprises a Type VI Cas protein. Non-limiting examples of Type VI Cas proteins include Cas13, Cas13a (C2c2), Cas13b, Cas13c, Cas13d, and variants thereof.

In some cases, a Cas protein useful for the present disclosure comprises orthologues or homologues of the above mentioned Cas proteins. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins can but need not be structurally related, or are only partially structurally related. An "orthologue" of a protein as used herein is a protein of a different species which performs the same or a similar function as the protein it is an orthologue of. Orthologous proteins can but need not be structurally related, or are only partially structurally related.

As used herein, "functional portion" refers to a portion of a peptide, e.g., Cas9, which retains its ability to complex with at least one gRNA and cleave a target sequence, resulting in reduced expression of the NR4A (NR4A1, NR4A2, and/or NR4A3) gene and/or protein. In some aspects, the functional portion comprises a combination of operably linked Cas9 protein functional domains selected from the group consisting of a DNA binding domain, at least one RNA binding domain, a helicase domain, and an endonuclease domain. In some aspects, the functional domains form a non-covalent complex. In some aspects, the functional domains form a fusion complex (e.g., a fusion protein). In some aspects, the functional domains are chemically linked (e.g., through one or more spacers or linkers). In some aspects, the functional domains are conjugated.

It should be appreciated that the present disclosure contemplates various ways of contacting the NR4A (NR4A1, NR4A2, and/or NR4A3) gene with at least one gRNA and at least one Cas protein, e.g., Cas9. In some aspects, exogenous Cas protein, e.g., Cas9, can be introduced into the cell in polypeptide form. In some aspects, a Cas protein, e.g., Cas9, can be conjugated to or fused to a cell-penetrating polypeptide or cell-penetrating peptide. As used herein, "cell-penetrating polypeptide" and "cell-penetrating peptide" refers to a polypeptide or peptide, respectively, which facilitates the uptake of molecule into a cell. The cell-penetrating polypeptides can contain a detectable label.

In some aspects, Cas protein, e.g., Cas9, can be conjugated to or fused to a charged protein, e.g., a protein that carries a positive, negative or overall neutral electric charge. Such linkage can be covalent. In some aspects, the Cas protein, e.g., Cas9, can be fused to a superpositively charged peptide to significantly increase the ability of the Cas protein, e.g., Cas9, to penetrate a cell. See Cronican et al. ACS Chem. Biol. 5(8):747-52 (2010). In some aspects, the Cas protein, e.g., Cas9, can be fused to a protein transduction domain (PTD) to facilitate its entry into a cell. Exemplary PTDs include, but are not limited to, Tat, oligoarginine, and penetratin. Thus, in some specific aspects, the methods disclosed herein can be practiced using a Cas protein, e.g., a Cas9 protein, comprising a Cas protein fused to a cell-penetrating peptide, a Cas protein fused to a PTD, a Cas protein fused to a tat domain, a Cas protein fused to an oligoarginine domain, a Cas protein fused to a penetratin domain, or a combination thereof.

In some aspects, the Cas protein, e.g., Cas9, can be introduced into a cell, e.g., an immune cell, such as an immune cell expressing a CAR or TCR and having an increased level of a c-Jun protein, containing the target polynucleotide sequence, e.g., the NR4A (NR4A1, NR4A2, and/or NR4A3) gene, in the form of a nucleic acid encoding the Cas protein, e.g., Cas9. The process of introducing the nucleic acids into cells can be achieved by any suitable technique. Suitable techniques include calcium phosphate or lipid-mediated transfection, electroporation, and transduction or infection using a viral vector. In some aspects, the nucleic acid comprises DNA. In some aspects, the nucleic acid comprises a modified DNA, as described herein. In some aspects, the nucleic acid comprises mRNA. In some aspects, the nucleic acid comprises a modified mRNA, as described herein (e.g., a synthetic, modified mRNA).

The gRNA sequences and/or nucleic sequences encoding Cas9 used in the methods disclosed herein can be chemically modified to enhance, for example, their stability (e.g., to increase their plasma half-life after administration to a subject in need thereof). Possible chemical modifications to the gRNAs disclosed herein and/or nucleic sequences encoding, e.g., Cas9, are discussed in detail below in this specification.

In some aspects, the entire gRNA is chemically modified. In some aspects, only the gRNA spacer is chemically modified. In some aspects, the gRNA spacer and gRNA frame sequence are chemically modified. Non-limiting examples of specific chemical modifications are disclosed in detail below.

Accordingly, in some aspects of the methods disclosed herein, the Cas protein (e.g., Cas9) and one or more gRNAs are provided to a target cell through expression from one or more delivery vectors coding therefor. In some aspects, the above-mentioned vector or vectors for introducing the gRNA or gRNAs and Cas9 in a target cell are viral vectors. In some aspects, the above-mentioned vector or vectors for introducing the gRNA or gRNAs and Cas9 in a target cell are non-viral vectors. In some aspects, the viral vector is an adeno-associated vector (AAV), a lentiviral vector (LV), a retroviral vector, an adenovirus vector, a herpes virus vector, or a combination thereof. The AAV vector or vectors can be based on one or more of several capsid types, including AAV1, AAV2, AAV5, AAV6, AAV8, and AAV9. In some aspects, the AAV vector is AAVDJ-8, AAV2DJ9, or a combination thereof.

In addition to the method disclosed above, the present disclosure further provides compositions to practice the disclosed methods. Accordingly, the present disclosure provides a nucleic acid encoding at least one the above-mentioned gRNAs.

Also provided is a composition and/or at least one Cas9. In some aspects, the nucleic acid encoding Cas9 encodes (i) a Cas9 from *S. aureus*, (ii) a Cas9 from *S. pyogenes*, (iii) a mutant Cas9 derived from Cas9 from *S. aureus* or from Cas9 from *S. pyogenes* wherein the mutant protein retains Cas9 activity, (iv) a fusion protein comprising a Cas9 moiety, or (v) a combination thereof.

In some aspects, one or more gene editing tools (e.g., those disclosed herein) can be used to modify the cells of the present disclosure.

IV.A.2. TALEN

In some aspects, a gene editing tool that can be used to edit (e.g., reduce or inhibit) the expression of a NR4A (NR4A1, NR4A2, and/or NR4A3) gene and/or protein is a nuclease agent, such as a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI.

The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al., (2010) *PNAS* 10.1073/pnas.1013133107; Scholze & Boch (2010) *Virulence* 1:428-432; Christian et al., *Genetics* (2010) 186:757-761; Li et al., (2010) *Nuc. Acids Res.* (2010) doi:10.1093/nar/gkg704; and Miller et al., (2011) *Nature Biotechnology* 29:143-148; all of which are herein incorporated by reference in their entirety.

Non-limiting examples of suitable TAL nucleases, and methods for preparing suitable TAL nucleases, are disclosed, e.g., in US Patent Application No. 2011/0239315 A1, 2011/0269234 A1, 2011/0145940 A1, 2003/0232410 A1, 2005/0208489 A1, 2005/0026157 A1, 2005/0064474 A1, 2006/0188987 A1, and 2006/0063231 A1 (each hereby incorporated by reference).

In various aspects, TAL effector nucleases are engineered that cut in or near a target nucleic acid sequence in, e.g., a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors as described herein.

In some aspects, each monomer of the TALEN comprises about 12-about 25 TAL repeats, wherein each TAL repeat binds a 1 bp subsite. In some aspects, the nuclease agent is a chimeric protein comprising a TAL repeat-based DNA binding domain operably linked to an independent nuclease. In some aspects, the independent nuclease is a FokI endo-nuclease. In some aspects, the nuclease agent comprises a first TAL-repeat-based DNA binding domain and a second TAL-repeat-based DNA binding domain, wherein each of the first and the second TAL-repeat-based DNA binding domain is operably linked to a FokI nuclease, wherein the first and the second TAL-repeat-based DNA binding domain recognize two contiguous target DNA sequences in each strand of the target DNA sequence separated by about 6 bp to about 40 bp cleavage site, and wherein the FokI nucleases dimerize and make a double strand break at a target sequence.

In some aspects, the nuclease agent comprises a first TAL-repeat-based DNA binding domain and a second TAL-repeat-based DNA binding domain, wherein each of the first and the second TAL-repeat-based DNA binding domain is operably linked to a FokI nuclease, wherein the first and the second TAL-repeat-based DNA binding domain recognize two contiguous target DNA sequences in each strand of the target DNA sequence separated by a 5 bp or 6 bp cleavage site, and wherein the FokI nucleases dimerize and make a double strand break.

IV.A.3. Zinc Finger Nuclease (ZFN)

In some aspects, a gene editing tool useful for the present disclosure includes a nuclease agent, such as a zinc-finger nuclease (ZFN) system. Zinc finger-based systems comprise a fusion protein comprising two protein domains: a zinc finger DNA binding domain and an enzymatic domain. A "zinc finger DNA binding domain", "zinc finger protein", or "ZFP" is a protein, or a domain within a larger protein, that binds DNA in a sequence-specific manner through one or more zinc fingers, which are regions of amino acid sequence within the binding domain whose structure is stabilized through coordination of a zinc ion. The zinc finger domain, by binding to a target DNA sequence (e.g., NR4A1, NR4A2, or NR4A3), directs the activity of the enzymatic domain to the vicinity of the sequence and, hence, induces modification of the endogenous target gene in the vicinity of the target sequence. A zinc finger domain can be engineered to bind to virtually any desired sequence. As disclosed herein, in some aspects, the zinc finger domain binds a DNA sequence that encodes the NR4A (NR4A1, NR4A2, and/or NR4A3) pro-tein. Accordingly, after identifying a target genetic locus containing a target DNA sequence at which cleavage or recombination is desired, one or more zinc finger binding domains can be engineered to bind to one or more target DNA sequences in the target genetic locus. Expression of a fusion protein comprising a zinc finger binding domain and an enzymatic domain in a cell, effects modification in the target genetic locus.

In some aspects, a zinc finger binding domain comprises one or more zinc fingers. Miller et al., (1985) EMBO J. 4:1609-1614; Rhodes (1993) *Scientific American* February: 56-65; U.S. Pat. No. 6,453,242. Typically, a single zinc finger domain is about 30 amino acids in length. An individual zinc finger binds to a three-nucleotide (i.e., triplet) sequence (or a four-nucleotide sequence which can overlap, by one nucleotide, with the four-nucleotide binding site of an adjacent zinc finger). Therefore, the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. Binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain. In some aspects, the DNA-binding domains of individual ZFNs comprise between three and six individual zinc finger repeats and can each recognize between about 9 and about 18 basepairs.

Zinc finger binding domains can be engineered to bind to a sequence of choice. See, for example, Beerli et al., (2002) *Nature Biotechnol.* 20:135-141; Pabo et al., (2001) *Ann. Rev. Biochem.* 70:313-340; Isalan et al., (2001) *Nature Biotechnol.* 19:656-660; Segal et al., (2001) *Curr. Opin. Biotechnol.* 12:632-637; Choo et al., (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection.

Selection of a target DNA sequence for binding by a zinc finger domain can be accomplished, for example, according to the methods disclosed in U.S. Pat. No. 6,453,242. It will be clear to those skilled in the art that simple visual inspection of a nucleotide sequence can also be used for selection of a target DNA sequence. Accordingly, any means for target DNA sequence selection can be used in the methods described herein. A target site generally has a length of at least about 9 nucleotides and, accordingly, is bound by a zinc finger binding domain comprising at least three zinc fingers. However, binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also possible.

The enzymatic domain portion of the zinc finger fusion proteins can be obtained from any endo- or exonuclease. Exemplary endonucleases from which an enzymatic domain can be derived include, but are not limited to, restriction endonucleases and homing endonucleases. See, for example, 2002-2003 Catalogue, New England Biolabs, Beverly, Mass.; and Belfort et al., (1997) *Nucleic Acids Res.* 25:3379-

3388. Additional enzymes which cleave DNA are known (e.g., 51 Nuclease; mung bean nuclease; pancreatic DNaseI; micrococcal nuclease; yeast HO endonuclease; see also Linn et al., (eds.) Nucleases, Cold Spring Harbor Laboratory Press, 1993). One or more of these enzymes (or functional fragments thereof) can be used as a source of cleavage domains.

Exemplary restriction endonucleases (restriction enzymes) suitable for use as an enzymatic domain of the ZFPs described herein are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487, 994; as well as Li et al., (1992) *Proc. Natl. Acad Sci. USA* 89:4275-4279; Li et al., (1993) *Proc. Natl. Acad Sci. USA* 90:2764-2768; Kim et al., (1994a) *Proc. Natl. Acad Sci. USA* 91:883-887; Kim et al., (1994b) *J. Biol. Chem.* 269: 31,978-31,982. Thus, in some aspects, fusion proteins comprise the enzymatic domain from at least one Type IIS restriction enzyme and one or more zinc finger binding domains.

An exemplary Type IIS restriction enzyme, whose cleavage domain is separable from the binding domain, is FokI. This particular enzyme is active as a dimer. Bitinaite et al., (1998) *Proc. Natl. Acad Sci. USA* 95: 10,570-10,575. Thus, for targeted double-stranded DNA cleavage using zinc finger-FokI fusions, two fusion proteins, each comprising a FokI enzymatic domain, can be used to reconstitute a catalytically active cleavage domain. Alternatively, a single polypeptide molecule containing a zinc finger binding domain and two FokI enzymatic domains can also be used. Exemplary ZFPs comprising FokI enzymatic domains are described in U.S. Pat. No. 9,782,437.

IV.A.3. Meganucleases

In some aspects, a gene editing tool that be used to regulate NR4A (NR4A1, NR4A2, and/or NR4A3) expression in a cell includes a nuclease agent such as a meganuclease system. Meganucleases have been classified into four families based on conserved sequence motifs, the families are the "LAGLIDADG," "GIY-YIG," "H-N-H," and "His-Cys box" families. These motifs participate in the coordination of metal ions and hydrolysis of phosphodiester bonds.

HEases are notable for their long recognition sites, and for tolerating some sequence polymorphisms in their DNA substrates. Meganuclease domains, structure and function are known, see, for example, Guhan and Muniyappa (2003) Crit Rev Biochem Mol Biol 38:199-248; Lucas et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure et al., (2002) *Nat Struct Biol* 9:764.

In some examples a naturally occurring variant, and/or engineered derivative meganuclease is used. Methods for modifying the kinetics, cofactor interactions, expression, optimal conditions, and/or recognition site specificity, and screening for activity are known, see for example, Epinat et al., (2003) *Nucleic Acids Res* 31:2952-62; Chevalier et al., (2002) *Mol Cell* 10:895-905; Gimble et al., (2003) *Mol Biol* 334:993-1008; Seligman et al., (2002) *Nucleic Acids Res* 30:3870-9; Sussman et al., (2004) *J Mol Biol* 342:31-41; Rosen et al., (2006) *Nucleic Acids Res* 34:4791-800;

Chames et al., (2005) *Nucleic Acids Res* 33:e178; Smith et al., (2006) *Nucleic Acids Res* 34:e149; Gruen et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346; each of which is herein incorporated by reference in its entirety.

Any meganuclease can be used herein, including, but not limited to, I-SceI, I-SceII, I-SceIII, I-SceIV, I-SceV, I-SecVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-Njal, I-Nsp236IP, I-PakI, I-PboIP, I-PcuIP, I-PcuAI, I-PcuVI, I-PgrIP, I-PobIP, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP, PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

In some aspects, the meganuclease recognizes double-stranded DNA sequences of 12 to 40 base pairs. In some aspects, the meganuclease recognizes one perfectly matched target sequence in the genome. In some aspects, the meganuclease is a homing nuclease. In some aspects, the homing nuclease is a "LAGLIDADG" family of homing nuclease. In some aspects, the "LAGLIDADG" family of homing nuclease is selected from I-SceI, I-CreI, I-Dmol, or combinations thereof.

IV.A.4. Restriction Endonucleases

In some aspects, a gene editing tool useful for the present disclosure includes a nuclease agent such as a restriction endonuclease, which includes Type I, Type II, Type III, and Type IV endonucleases. Type I and Type III restriction endonucleases recognize specific recognition sites, but typically cleave at a variable position from the nuclease binding site, which can be hundreds of base pairs away from the cleavage site (recognition site). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example in the REBASE database (webpage at rebase.neb.com; Roberts et al., (2003) *Nucleic Acids Res* 31:418-20), Roberts et al., (2003) *Nucleic Acids Res* 31:1805-12, and Belfort et al., (2002) in Mobile DNA II, pp. 761-783, Eds. Craigie et al., (ASM Press, Washington, D.C.).

As described herein, in some aspects, a gene editing tool (e.g., CRISPR, TALEN, meganuclease, restriction endonuclease, RNAi, antisense oligonucleotides) can be introduced into the cell by any means known in the art. In some aspects, the polypeptide encoding the particular gene editing tool can be directly introduced into the cell. Alternatively, a polynucleotide encoding the gene editing tool can be introduced into the cell. In some aspects, when a polynucleotide encoding the gene editing tool is introduced into the cell, the gene editing tool can be transiently, conditionally or constitutively expressed within the cell. Thus, the polynucleotide encoding the gene editing tool can be contained in an expression cassette and be operably linked to a conditional promoter, an inducible promoter, a constitutive promoter, or a tissue-specific promoter. Alternatively, the gene editing tool is introduced into the cell as an mRNA encoding or comprising the gene editing tool.

Active variants and fragments of nuclease agents (i.e., an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired recognition site and hence retain nick or double-strand-break-inducing activity. For example, any of the nuclease agents described herein can be modified from a native endonuclease sequence and designed to recognize and induce a nick or double-strand break at a recognition site that was not recognized by the native nuclease agent. Thus in some aspects, the engineered nuclease has a specificity to induce a nick or double-strand break at a recognition site that is different from the corresponding native nuclease agent recognition site. Assays for nick or double-strand-break-inducing activity are known and generally measure the overall activity and specificity of the endonuclease on DNA substrates containing the recognition site.

When the nuclease agent is provided to the cell through the introduction of a polynucleotide encoding the nuclease agent, such a polynucleotide encoding a nuclease agent can be modified to substitute codons having a higher frequency of usage in the cell of interest, as compared to the naturally occurring polynucleotide sequence encoding the nuclease agent. For example the polynucleotide encoding the nuclease agent can be modified to substitute codons having a higher frequency of usage in a given cell of interest.

IV.A.5. Interference RNA (RNAi)

In some aspects, a gene editing tool that can be used to reduce the expression of NR4A (NR4A1, NR4A2, and/or NR4A3) in a cell includes an RNA interference molecule ("RNAi"). As used herein, RNAi are RNA polynucleotide that mediates the decreased expression of an endogenous target gene product by degradation of a target mRNA through endogenous gene silencing pathways (e.g., Dicer and RNA-induced silencing complex (RISC)). Non-limiting examples of RNAi agents include micro RNAs (also referred to herein as "miRNAs"), short hairpin RNAs (shRNAs), small interfering RNAs (siRNAs), RNA aptamers, or combinations thereof.

In some aspects, the gene editing tools useful for the present disclosure comprises one or more miRNAs. "miRNAs" refer to naturally occurring, small non-coding RNA molecules of about 21-25 nucleotides in length. In some aspects, the miRNAs useful for the present disclosure are at least partially complementary to a NR4A (NR4A1, NR4A2, and/or NR4A3) mRNA molecule. miRNAs can downregulate (e.g., decrease) expression of an endogenous target gene product (i.e., NR4A protein) through translational repression, cleavage of the mRNA, and/or deadenylation.

In some aspects, a gene editing tool that can be used with the present disclosure comprises one or more shRNAs. "shRNAs" (or "short hairpin RNA" molecules) refer to an RNA sequence comprising a double-stranded region and a loop region at one end forming a hairpin loop, which can be used to reduce and/or silence a gene expression. The double-stranded region is typically about 19 nucleotides to about 29 nucleotides in length on each side of the stem, and the loop region is typically about three to about ten nucleotides in length (and 3'- or 5'-terminal single-stranded overhanging nucleotides are optional). shRNAs can be cloned into plasmids or in non-replicating recombinant viral vectors to be introduced intracellularly and result in the integration of the shRNA-encoding sequence into the genome. As such, an shRNA can provide stable and consistent repression of endogenous target gene (i.e., NR4A1, NR4A2, and/or NR4A3) translation and expression.

In some aspects, a gene editing tool disclosed herein comprises one or more siRNAs. "siRNAs" refer to double stranded RNA molecules typically about 21-23 nucleotides in length. The siRNA associates with a multi protein complex called the RNA-induced silencing complex (RISC), during which the "passenger" sense strand is enzymatically cleaved. The antisense "guide" strand contained in the activated RISC then guides the RISC to the corresponding mRNA because of sequence homology and the same nuclease cuts the target mRNA (e.g., NR4A (NR4A1, NR4A2, and/or NR4A3) mRNA), resulting in specific gene silencing. In some aspects, an siRNA is 18, 19, 20, 21, 22, 23 or 24 nucleotides in length and has a 2 base overhang at its 3' end. siRNAs can be introduced to an individual cell and/or culture system and result in the degradation of target mRNA sequence (i.e., NR4A (NR4A1, NR4A2, and/or NR4A3) mRNA). siRNAs and shRNAs are further described in Fire et al., *Nature* 391:19, 1998 and U.S. Pat. Nos. 7,732,417; 8,202,846; and 8,383,599; each of which is herein incorporated by reference in its entirety.

IV.A.6. Antisense Oligonucleotides (ASO)

In some aspects, a gene editing tool that can be used to reduce the expression of a NR4A (NR4A1, NR4A2, and/or NR4A3) gene and/or protein in a cell includes antisense oligonucleotides. As used herein, "antisense oligonucleotide" or "ASO" refer to an oligonucleotide capable of modulating expression of a target gene (e.g., NR4A1, NR4A2, and/or NR4A3) by hybridizing to a target nucleic acid, in particular to a contiguous sequence on a target nucleic acid. Antisense oligonucleotides are not essentially double stranded and are therefore not siRNAs or shRNAs.

In some aspects, ASOs useful for the present disclosure are single stranded. It is understood that single stranded oligonucleotides of the present disclosure can form hairpins or intermolecular duplex structures (duplex between two molecules of the same oligonucleotide), as long as the degree of intra or inter self-complementarity is less than approximately 50% across of the full length of the oligonucleotide. In some aspects, ASOs useful for the present disclosure can comprise one or more modified nucleosides or nucleotides, such as 2' sugar modified nucleosides. Additional modifications that can be made to an ASO (e.g., such as those that can be used to inhibit or reduce NR4A1, NR4A2, and/or NR4A3 gene expression) are provided in, e.g., US Publ. No. 2019/0275148 A1.

In some aspects, ASOs can reduce the expression of NR4A (NR4A1, NR4A2, or NR4A3) protein via nuclease mediated degradation of the NR4A transcript (e.g., mRNA), where the ASOs are capable of recruiting a nuclease, e.g., RNase H, such as RNaseH1. RNase H is a ubiquitous enzyme that hydrolyzes the RNA strand of an RNA/DNA duplex. Accordingly, in some aspects, once bound to the target sequence (e.g., NR4A1, NR4A2, and/or NR4A3 mRNA), ASOs can induce the degradation of the NR4A3mRNA and thereby, reduce the expression of NR4A protein.

As disclosed herein, the above examples of gene editing tools are not intended to be limiting and any gene editing tool available in the art can be used to reduce or inhibit the expression of NR4A (NR4A1, NR4A2, and/or NR4A3) gene and/or protein.

IV.A.7. Repressors

In some aspects, a gene editing tool that can be used with the present disclosure (e.g., to reduce the expression of NR4A1, NR4A2, and/or NR4A3 gene and/or protein) comprises a repressor. As used herein, the term "repressor" refers to any agent that is capable of binding to the following NR4A response elements without activating transcription: (i) NGFI-B response element (NBRE), (ii) Nur-response element (NurRE), or (iii) both (i) and (ii). Accordingly, by binding to NBRE and/or NurRE, the repressors described herein are capable of repressing (or reducing or inhibiting) the level of one or more NR4A family members in a cell (e.g., immune cell expressing a CAR or TCR). In some aspects, the binding of the repressor to NBRE and/or NurRE reduces the level of a NR4A1 gene and/or NR4A1 protein in a cell when the cell is contacted with the repressor. In some aspects, the binding of the repressor to NBRE and/or NurRE reduces the level of a NR4A2 gene and/or NR4A2 protein in a cell when the cell is contacted with the repressor. In some aspects, the binding of the repressor to NBRE and/or NurRE reduces the level of a NR4A3 gene and/or NR4A3 protein in a cell when the cell is contacted with the repressor. In some aspects, the binding of the repressor to NBRE and/or NurRE reduces the level of both (i) a NR4A1 gene and/or NR4A1 protein and (ii) a NR4A2 gene and/or NR4A2 protein. In some aspects, the binding of the repressor to NBRE and/or NurRE reduces the level of both (i) a NR4A1 gene and/or NR4A1 protein and (ii) a NR4A3 gene and/or NR4A3 protein. In some aspects, the binding of the repressor to NBRE and/or NurRE reduces the level of both (i) a NR4A2 gene and/or NR4A2 protein and (ii) a NR4A3 gene and/or NR4A3 protein. In some aspects, the binding of the repressor to NBRE and/or NurRE reduces the level of each of the following: (i) a NR4A1 gene and/or NR4A1 protein, (ii) a NR4A2 gene and/or NR4A2 protein, and (iii) a NR4A3 gene and/or NR4A3 protein. Repressors that are capable of reducing the level of all members of the NR4A family (i.e., NR4A1, NR4A2, and NR4A3) are also known as "NR4A super-repressors." See, e.g., WO2020237040A1, which is incorporated herein by reference in its entirety.

As is apparent from at least the above disclosure, repressors that are useful for the present disclosure comprises a DNA-binding domain that is capable of binding to the NBRE and/or NurRE response elements. In some aspects, such repressors comprise additional domains. Non-limiting examples of such additional domains include: NR4A ligand-binding domain, FLAG domain, Kruppel-associated box (KRAB) domain, NCOR domain, T2A domain, self-cleavage domain, nuclear localization signal, dimerization domain (e.g., diZIP dimerization domain), transcriptional repressor domain, chromatin compaction domain, an epitope tag, or any combination thereof. Additional disclosure relating to such additional domains can be found, e.g., in WO2020237040A1, which is incorporated herein by reference in its entirety. In some aspects, the additional domains do not comprise a transcriptional activation domain.

As described herein, in some aspects, in reducing the level of one or more members of the NR4A family, a cell can be contacted with a NR4A repressor protein described herein. In some aspects, a cell is contacted with a nucleic acid sequence encoding a NR4A repressor.

IV.B. Methods of Reducing Exhaustion/Dysfunction

The present disclosure provides methods of reducing, ameliorating, or inhibiting exhaustion or dysfunction of a cell comprising modifying the cell to: (i) overexpress a c-Jun protein and (ii) express reduced level of a NR4A (NR4A1, NR4A2, and/or NR4A3) gene and/or protein. In some aspects, the NR4A gene and/or protein comprises NR4A1 and/or NR4A1 protein. In some aspects, the NR4A gene and/or protein comprises NR4A2 and/or NR4A2 protein. In some aspects, the NR4A gene and/or protein comprises NR4A3 and/or NR4A3 protein. In some aspects, the NR4A gene and/or protein comprises both the NR4A1 gene and/or protein and the NR4A2 gene and/or protein. In some aspects, the NR4A gene and/or protein comprises both the NR4A1 gene and/or protein and the NR4A3 gene and/or protein. In some aspects, the NR4A gene and/or protein comprises both the NR4A2 gene and/or protein and the NR4A3 gene and/or protein. In some aspects, the NR4A gene and/or protein comprises the NR4A1 gene and/or protein, the NR4A2 gene and/or protein, and the NR4A3 gene and/or protein.

One of the various ways that tumor cells can evade a host immune response is by causing tumor-specific immune cells, e.g., T cells, to become exhausted. As used herein, the term "exhaustion," or more specifically, "T cell exhaustion," refers to the loss of T cell function, which can occur as a result of an infection or a disease (e.g., cancer). T cell exhaustion can be used interchangeably with "T cell dysfunction" or "T cell anergy" in the present disclosure. In some aspects, T cell exhaustion is associated with increased expression of various immune checkpoint inhibitory molecules (e.g., PD-1, TIM-3, and LAG-3), apoptosis, and reduced effector function (e.g., cytokine production and expression of cytotoxic molecules, such as perforin and granzymes). Accordingly, the terms "reduce T cell exhaustion," "ameliorate T cell exhaustion," "inhibit T cell exhaustion," and the like, refers to a condition of restored functionality of T cells characterized by one or more of the following: (i) decreased expression of one or more immune checkpoint inhibitory molecules (e.g., PD-1, TIM-3, and LAG-3), (ii) increased memory formation and/or maintenance of memory markers (e.g., CD45RO, CD62L, and/or CCR7), (iii) prevention of apoptosis, (iv) increased cytokine production (e.g., IL-2, IFN-γ, and/or TNF-α), (v) enhanced killing capacity, (vi) increased recognition of tumor targets with low surface antigen, (vii) enhanced proliferation in response to antigen, and (viii) any combination thereof.

In some aspects, modifying a cell, e.g., in a method disclosed herein, comprises modifying an immune cell, e.g., T cell, to have resistance or tolerance to exhaustion. Accordingly, in some aspects, the present disclosure relates to methods of reducing exhaustion in an immune cell, e.g., T cell (e.g., tumor-specific T cell) by reducing the expression level of a NR4A (NR4A1, NR4A2, and/or NR4A3) gene and/or protein in the cell. In some aspects, reducing exhaustion in an immune cell, e.g., T cell, comprises reversing the dysfunction that has already occurred in the immune cell, e.g., T cell, (i.e., making exhausted T cells become less exhausted). In some aspects, reducing exhaustion in an immune cell, e.g., T cell, comprises preventing a newly activated immune cell, e.g., T cell, from becoming exhausted. As is apparent from the present disclosure, in some aspects, the immune cell is previously, concurrently, or subsequently modified to: (i) express a ligand binding protein (e.g., CAR or TCR); (ii) have increased level of a c-Jun protein; or (iii) both (i) and (ii).

In some aspects, reducing exhaustion in an immune cell, e.g., T cell, comprises both reversing and preventing exhaustion in an immune cell, e.g., a T cell.

The exhaustion state of an immune cell, e.g., a T cell, can be determined by various methods known in the art. In some aspects, the exhaustion state of an immune cell, e.g., a T cell, can be measured by evaluating the resistance of the immune cell, e.g., a T cell, to apoptosis. Accordingly, in some aspects, the cell composition of the disclosure (i.e., overexpressing c-Jun and expressing reduced level of a NR4A (NR4A1, NR4A2, and/or NR4A3) gene and/or protein) exhibits increased resistance to apoptosis. In some aspects, the resistance to apoptosis in the cell composition of the disclosure is increased by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold or more as compared to that of a reference cell (e.g., corresponding cell that has not been modified to overexpress the c-Jun protein and to express lower levels of the NR4A gene and/or NR4A protein). In some aspects, increased resistance to apoptosis can promote the long-term persistence or survival of the immune cells described herein (e.g., T cell). Therefore, in some aspects, the cell composition of the disclosure (i.e., overexpressing a c-Jun protein and expressing reduced levels of a NR4A (NR4A1, NR4A2, and/or NR4A3) gene and/or protein) exhibits enhanced persistence or survival compared to a reference cell (e.g., corresponding cell that has not been modified to overexpress the c-Jun protein and express reduced levels of the NR4A (NR4A1, NR4A2, and/or NR4A3) gene and/or protein).

In some aspects, the persistence or survival of the cell composition provided herein is increased by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold or more as compared to that of the reference cell.

In some aspects, the exhaustion state of an immune cell, e.g., a T cell, can be measured by evaluating the resistance of the immune cell, e.g., a T cell, to immune checkpoint molecules. In some aspects, the resistance to immune checkpoint molecules is increased in the cell composition of the disclosure by at least 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold or more as compared to that of a reference cell (e.g., corresponding cell that has not been modified to overexpress the c-Jun protein and to express reduced levels of the NR4A (NR4A1, NR4A2, and/or NR4A3) gene and/or protein).

Not to be bound by any one theory, in some aspects, the increased resistance to immune checkpoint molecules is due to decreased expression of one or more immune checkpoint molecules on the immune cell, e.g., a T cell. Accordingly, in some aspects, the cell composition of the disclosure expresses reduced levels of one or more immune checkpoint molecules compared to a reference cell (e.g., corresponding cell, e.g., an immune cell such as a T cell, that has not been modified to overexpress the c-Jun protein and to express reduced levels of the NR4A (NR4A1, NR4A2, and/or NR4A3) gene and/or protein). In some aspects, the expression level of an immune checkpoint molecule is reduced in the cell composition of the disclosure by at least about 5%, at least about 10%, at least about 15%, at least about 30%, at least about 40%, at least about 50%, at least about 60%, at least about 70%, at least about 80%, at least about 90%, or at least about 100% compared to the reference cell. Examples of immune checkpoint molecules are known in the art and include, but are not limited to, PD-1, TIM-3, LAG-3, BTLA, SIGLEC7, CD200R, TIGIT, VISTA, and any combination thereof.

In some aspects, the exhaustion state of an immune cell, e.g., a T cell, can be measured by evaluating the ability of the immune cell, e.g., a T cell, to produce cytokines upon stimulation, e.g., T-cell receptor (TCR) stimulation. Accordingly, in some aspects, the cell composition of the disclosure (i.e., overexpressing a c-Jun protein and expressing reduced levels of a NR4A (NR4A1, NR4A2, and/or NR4A3) gene and/or protein) exhibits increased cytokine production as compared to that of a reference (e.g., cytokine production in a corresponding cell, e.g., an immune cell such as a T cell, that has not been modified to overexpress the c-Jun protein and express reduced levels of the NR4A (NR4A1, NR4A2, and/or NR4A3) gene and/or protein).

In some aspects, cytokine production in the cell composition of the disclosure is increased by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold or more as compared to that of a reference cell (e.g., corresponding cell that has not been modified to overexpress the c-Jun protein and to express reduced levels of the NR4A (NR4A1, NR4A2, and/or NR4A3) gene and/or protein). Non-limiting examples of cytokines include IFN-γ, IL-2, TNF-α, GM-CSF, IL-6, IL-10, IL-4, IL-5, IL-8, IL-9, IL-13, IL-17, IL-22, CCL2, CCL3, and any combination thereof.

In some aspects, the exhaustion state of an immune cell, e.g., a T cell, can be measured by evaluating the ability of the immune cell, e.g., a T cell, to kill tumor cells after repeated tumor challenge. In some aspects, the cell composition of the disclosure exhibits increased tumor cell killing compared to a reference cell (e.g., corresponding cell, e.g., an immune cell such as a T cell, that has not been modified to overexpress the c-Jun protein and to express reduced levels of the NR4A (NR4A1, NR4A2, and/or NR4A3) gene and/or protein) after two tumor challenges. In some aspects, the cell composition of the disclosure exhibits increased tumor cell killing compared to a reference cell (e.g., corresponding cell, e.g., an immune cell such as a T cell, that has not been modified to overexpress the c-Jun protein and to express reduced levels of the NR4A (NR4A1, NR4A2, and/or NR4A3) gene and/or protein) after three tumor challenges. In some aspects, the cell composition of the disclosure exhibits increased tumor cell killing compared to a reference cell (e.g., corresponding cell, e.g., an immune cell such as a T cell, that has not been modified to overexpress the c-Jun protein and express reduced levels of the NR4A gene and/or protein) after four tumor challenges. In some aspects, the cell composition of the disclosure exhibits increased tumor cell killing compared to a reference cell (e.g., corresponding cell, e.g., an immune cell such as a T cell, that has not been modified to overexpress the c-Jun protein and to express reduced levels of the NR4A gene and/or protein) after five tumor challenges. In some aspects, killing tumor cells comprises preventing the outgrowth of tumor cells.

In some aspects, after each of the tumor challenges, the ability to kill tumor cells of the cell composition of the disclosure is increased by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold or more as compared to that of a reference cell (e.g., corresponding cell that has not been modified to overexpress the c-Jun protein and to express reduced levels of the NR4A gene and/or protein).

IV.C. Method of Maintaining Anti-Tumor Function in Tumor Microenvironment

Tumorigenesis (i.e., the production or formation of a tumor) is a complex and dynamic process consisting of three stages: initiation, progression, and metastasis. Each of these stages is tightly regulated by tumor microenvironment (TME). See Wang, M., et al., *J Cancer* 8(5):761-773 (2017). As used herein, the term "tumor microenvironment" or "TME" refers to the environment around a tumor, including the surrounding blood vessels, immune cells, fibroblasts, signaling molecules, and the extracellular matrix. As described further below, tumors can influence the microenvironment by releasing extracellular signals, promoting tumor angiogenesis, and inducing peripheral immune tolerance, while the immune cells in the microenvironment can affect the growth and evolution of the tumor cells.

Tumor cells generally grow at very high speeds leading to insufficient blood supply to the tumor microenvironment. See Gouirand, V., et al., *Front Oncol* 8:117 (2018). This results in the tumor microenvironment to become hypoxic and increased generation of reactive oxygen species (ROS). Hypoxia and ROS can negatively affect immune cell function, and thereby, inhibit the anti-tumor immune response in a subject.

In some aspects, modifying a cell, e.g., in a method disclosed herein, results in enhancing the anti-tumor function of an immune cell (e.g., tumor-specific T cell) in a low oxygen environment, such as that found in tumor microenvironment. As used herein, the term "anti-tumor function" refers to the ability of an immune cell (e.g., tumor-specific T cell) to mount an immune response that results in the eradication and/or control of a tumor cell. Non-limiting examples of anti-tumor function comprises cytokine production, proliferation, reduced exhaustion, long-term survival, cytotoxicity (e.g., ability to kill tumor cells), or combinations thereof.

In some aspects, the anti-tumor function of the cell composition of the disclosure (e.g., comprising immune cells modified to: (i) express a ligand binding protein (e.g., CAR or TCR) (e.g., an anti-ROR1 binding protein), (ii) overexpress a c-Jun protein, and (iii) have reduced level of one or more members of the NR4A family) is enhanced (i.e., increased) in a low oxygen environment compared to a reference cell (e.g., corresponding cell that has not been modified to express reduced levels of the NR4A gene and/or protein and to overexpress the c-Jun protein).

The rapid proliferation of tumor cells can also result in the depletion of various nutrients (e.g., glucose) within a tumor microenvironment. See Gouirand, supra. As discussed herein, nutrients, such as glucose, are essential for normal immune cell function and development. In some aspects, the anti-tumor function of the cell composition of the disclosure (e.g., comprising immune cells modified to: (i) express a ligand binding protein (e.g., CAR or TCR), (ii) overexpress a c-Jun protein, and (iii) have reduced level of one or more members of the NR4A family) is enhanced (i.e., increased) in a low nutrient environment compared to a reference cell (e.g., corresponding cell, e.g., an immune cell such as a T cell, that has not been modified to express reduced levels of the NR4A gene and/or NR4A protein and to overexpress the c-Jun protein).

As described herein, one of the mechanisms by which tumor cells suppress host immune response is by releasing various immunosuppressive metabolites and/or cytokines into tumor microenvironment. The accumulation of such metabolites and/or cytokines within the tumor microenvironment can inhibit the normal function of immune cells (e.g., tumor-infiltrating lymphocytes). Non-limiting examples of such immunosuppressive metabolites and/or cytokines include indolamine-2-3-dioxygenase (IDO), arginase, inducible nitric oxide synthetase (iNOS), lactate dehydrogenase (LDH)-A, TGF-β, IL-10, VEGF, reactive oxygen species (ROS), adenosine, arginase, prostaglandin E2, and combinations thereof.

In some aspects, the anti-tumor function of the cell composition of the disclosure (e.g., comprising immune cells modified to: (i) express a ligand binding protein (e.g., CAR or TCR), (ii) overexpress a c-Jun protein, and (iii) have reduced level of one or more members of the NR4A family) is enhanced (i.e., increased) in the presence of immunosuppressive metabolites and/or cytokines by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 4 fold, at least about 5 fold, at least about 6 fold, at least about 7 fold, at least about 8 fold, at least about 9 fold, at least about 10 fold or more as compared to that of a reference cell (e.g., corresponding cell that has not been modified to overexpress the c-Jun protein and to express reduced levels of the NR4A gene and/or protein).

Another mechanism by which the tumor microenvironment can inhibit an anti-tumor immune response is through immune suppressive cells, such as myeloid-derived suppressor cells (MDSCs) and regulatory T ($T_{reg}$) cells.

As used herein, the term "myeloid-derived suppressor cells" or "MDSCs" refer to a heterogeneous population of immune cells that are defined by their myeloid origin, immature state, and ability to potently suppress T cell responses. MDSCs are generated in the bone marrow, and in tumor-bearing hosts, migrate to peripheral lymphoid organs and the tumor to contribute to the formation of the tumor microenvironment. In some aspects, the MDSCs are monocytic MDSCs (M-MDSCs), which are morphologically and phenotypically similar to monocytes. In some aspects, the MDSCs are polymorphonuclear MDSCs (PMN-MDSCs), which are morphologically and phenotypically similar to neutrophils. In some aspects, MDSCs comprise both M-MDSCs and PMN-MDSCs. MDSCs present within the tumor microenvironment generally exhibit poor phagocytic activity, continuous production of reactive oxygen species (ROS), nitric oxide (NO), and mostly anti-inflammatory cytokines (e.g., IL-10 and TGF-β).

As used herein, the term "regulatory T cells" or "$T_{reg}$ cells" refer to a specific population of T cells that have the ability to suppress the proliferation and/or function of other T cells (e.g., tumor-infiltrating lymphocytes). In some aspects, the regulatory T cells are CD4⁺ regulatory T cells. In some aspects, the regulatory T cells are Foxp3⁺. Regulatory T cells can exert their immunosuppressive activity through different contact-dependent and independent mechanisms. Non-limiting examples of such mechanisms include: (i) production of suppressive cytokines (e.g., TGF-β, IL-10, and IL-35); (ii) expression of immune checkpoint and inhibitory receptors (e.g., CTLA-4, PD-L1, Arginase, LAG-3, TIM-3, ICOS, TIGIT, IDO); (iii) direct cytotoxicity (perforin/granzyme-mediated or FasL-mediated); (iv) metabolic disruption of effector T cell activity (e.g., IL-2 consumption); (v) induction of tolerogenic dendritic cells, which can promote T cell exhaustion; (vi) adenosine production, and (vii) any combination thereof.

In some aspects, the anti-tumor function of the cell composition of the disclosure (e.g., comprising immune cells modified to: (i) express a ligand binding protein (e.g., CAR or TCR), (ii) overexpress a c-Jun protein, and (iii) have reduced level of one or more members of the NR4A family) is enhanced (i.e., increased) in the presence of suppressive cells compared to a reference cell (e.g., corresponding cell that has not been modified to overexpress the c-Jun protein and to express reduced levels of the NR4A gene and/or protein). In some aspects, the suppressive cells are MDSCs. In some aspects, the suppressive cells are $T_{reg}$ cells. In some aspects, the suppressive cells comprise both MDSCs and $T_{reg}$ cells.

While the above disclosure is provided largely in the context of T cells (e.g., tumor-infiltrating lymphocytes), those skilled in the art will recognize that the above disclosure can also apply to other types of immune cells. Accordingly, in some aspects, the methods disclosed herein can be used to enhance the activation, reduce the exhaustion/dysfunction, or maintain the anti-tumor function of any immune cells useful for the treatment of a tumor. Non-limiting examples of such immune cells include a lymphocyte, neutrophil, monocyte, macrophage, dendritic cell, or combinations thereof. In some aspects, a lymphocyte comprises a T cell, tumor-infiltrating lymphocyte (TIL), lymphokine-activated killer cell, natural (NK) cell, or combinations thereof. In some aspects, a lymphocyte is a T cell, e.g., CD4⁺ T cell or a CD8⁺ T cell. In some aspects, a lymphocyte is a tumor infiltrating lymphocyte (TIL). In some aspects, a TIL is a CD8⁺ TIL. In some aspects, a TIL is a CD4⁺ TIL. As described herein, in some aspects, an immune cell of the present disclosure comprises a chimeric antigen receptor (CAR), such as a CAR T cell or a CAR NK cell.

V. Nucleic Acids and Vectors

The present disclosure also provides one or more nucleic acid molecules that comprise a gene editing tool for reducing the expression of a NR4A (NR4A1, NR4A2, and/or NR4A3) gene and/or protein in a cell. Also provided herein are nucleic acid molecules comprising a guide RNA (e.g., synthetic guide RNA). As described herein, in some aspects, the nucleic acid molecule comprising the gene editing tool and the nucleic acid molecule comprising the guide RNA can be introduced into a cell as separate nucleic acid molecules (either concurrently or sequentially). In some aspects, the gene editing tool and the guide RNA can be part of a single nucleic acid molecule. For instance, in some aspects, the nucleic acid molecule that comprises a gene editing tool further comprises a guide RNA (e.g., synthetic guide RNA disclosed herein).

In some aspects, the nucleic acid molecule that comprises a gene editing tool further comprises a guide RNA (e.g., synthetic guide RNA disclosed herein) and a nucleic acid encoding a Cas nuclease, e.g., a Cas9 nuclease.

As described herein, some aspects of the present disclosure are directed to polynucleotides (e.g., isolated polynucleotides) comprising a nucleotide sequence that is capable of specifically binding to a target sequence within a NR4A gene (NR4A1, NR4A2, NR4A3, or a combination thereof). Not to be bound by any one theory, in some aspects, by binding to the target sequence within the NR4A gene, the polynucleotides of the present disclosure are capable of reducing the level of the NR4A gene and/or the encoded protein in a cell (e.g., immune cell).

As described herein, polynucleotides described herein comprise a nucleotide sequence that can specifically bind to a nucleic acid sequence within the NR4A gene. For instance, in some aspects, a polynucleotide of the present disclosure comprises a nucleotide sequence that specifically binds to a nucleic acid sequence within the NR4A1 gene. In some aspects, a polynucleotide of the present disclosure comprises a nucleotide sequence that specifically binds to a nucleic acid sequence within the NR4A2 gene. a polynucleotide of the present disclosure comprises a nucleotide sequence that specifically binds to a nucleic acid sequence within the NR4A3 gene. In some aspects, a polynucleotide of the present disclosure comprises a nucleotide sequence that specifically binds to a nucleic acid sequence within the NR4A1 gene and a nucleic acid sequence within the NR4A2 gene. In some aspects, a polynucleotide of the present disclosure comprises a nucleotide sequence that specifically binds to a nucleic acid sequence within the NR4A1 gene and a nucleic acid sequence within the NR4A3 gene. In some aspects, a polynucleotide of the present disclosure comprises a nucleotide sequence that specifically binds to a nucleic acid sequence within the NR4A2 gene and a nucleic acid sequence within the NR4A3 gene. In some aspects, a polynucleotide of the present disclosure comprises a nucleotide sequence that specifically binds to a nucleic acid sequence within the NR4A1 gene, a nucleic acid sequence within the NR4A2 gene, and a nucleic acid sequence within the NR4A3 gene. Such nucleotide sequences are also referred to herein as a "binding sequence" or a "guide sequence" or "guide RNA" (gRNA). Accordingly, the term "guide RNA" (gRNA), as used herein, is not particularly limited as long as it can specifically bind to a nucleic acid sequence within one or more members of the NR4A family, and thereby, reduce the level of the NR4A gene and/or NR4A protein.

In some aspects, the gRNA can be between about 5 and about 100 nucleotides long. In some aspects, the gRNA of a polynucleotide described herein is about 5, about 6, about 7, about 8, about 9, about 10, about 15, about 20, about 25, about 30, about 35, about 40, about 45, about 50, about 60, about 70, about 80, about 90, or about 100 nucleotides in length. In some aspects, the gRNA is between about 10 and about 30 nucleotides in length (e.g., about 10, about 11, about 12, about 13, about 14, about 15, about 16, about 17, about 18, about 19, about 20, about 21, about 22, about 23, about 24, about 25, about 26, about 27, about 28, about 29, or about 30 nucleotides). In some aspects, the gRNA is about 20 nucleotides in length. Additional disclosure relating to gRNAs that are useful for the present disclosure are provided elsewhere in the present application (see, e.g., Section IV.A.1. CRISPR/Cas System).

In some aspects, the gRNA of a polynucleotide described herein is designed to complement or substantially complement a nucleic sequence within the NR4A gene (also referred to herein as the "target sequence"). In some aspects, the gRNA can incorporate wobble or degenerate bases to bind multiple sequences (e.g., multiple target sequences within the NR4A gene; or a target sequence within the NR4A gene and a target sequence within other members of the NR4A family). In some cases, the gRNA can be altered to increase stability. For example, non-natural nucleotides can be incorporated to increase RNA resistance to degradation. In some aspects, the gRNA can be altered or designed to avoid or reduce secondary structure formation in the gRNA. In some aspects, the gRNA can be designed to optimize G-C content. In some aspects, G-C content is between about 40% and about 60% (e.g., about 40%, about 45%, about 50%, about 55%, about 60%). In some aspects, the gRNA can contain modified nucleotides such as, without limitation, methylated or phosphorylated nucleotides. Additional methods of modifying and thereby, improving one or more properties of the polynucleotides described herein are known in the art. Non-limiting examples of such modifications that can be added to a polynucleotide described herein include: a 5' cap, a 3' polyadenylated tail, a riboswitch sequence, a stability control sequence, a hairpin, a subcellular localization sequence, a detection or label sequence, a binding site for one or more proteins, a non-natural nucleotide, or combinations thereof. See, e.g., U.S. Publication No. 20210123046A1, which is incorporated herein by reference in its entirety. Additional disclosures relating to such modifications are provided elsewhere in the present disclosure.

As described herein, in some aspects, the nucleic acid molecule comprising the gene editing tool and the nucleic acid molecule comprising the guide RNA can be introduced into a cell as separate nucleic acid molecules (either concurrently or sequentially). In some aspects, the gene editing tool and the guide RNA can be part of a single nucleic acid molecule. For instance, in some aspects, the nucleic acid molecule that comprises a gene editing tool further comprises a guide RNA (e.g., synthetic guide RNA disclosed herein). In some aspects, the nucleic acid molecule that comprises a gene editing tool further comprises a guide RNA (e.g., synthetic guide RNA disclosed herein) and a nucleic acid encoding a Cas nuclease, e.g., a Cas9 nuclease.

The present disclosure also provides one or more nucleic acids that encode a ligand binding protein (e.g., chimeric antigen receptor or a T cell receptor). The present disclosure also provides one or more nucleic acids encoding a c-Jun protein, which can be used to overexpress c-Jun in the modified cell of the present disclosure. As described herein, in some aspects, one or more of the nucleic acids can be part of a single vector. In some aspects, each of the nucleic acids are on a separate vector. The nucleic acids can be present in whole cells, in a cell lysate, or in a partially purified or substantially pure form.

A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Inter-science, New York. A nucleic acid described herein can be, for example, DNA or RNA and can or cannot contain intronic sequences. In some aspects, the nucleic acid is a cDNA molecule. Nucleic acids described herein can be obtained using standard molecular biology techniques known in the art.

In some aspects, the present disclosure provides a vector comprising one or more of the following: (i) an isolated nucleic acid molecule comprising a gene editing tool for reducing the expression of a NR4A (NR4A1, NR4A2, and/or NR4A3) gene and/or protein in a cell, (ii) an isolated nucleic acid molecule that encodes a ligand binding protein (e.g., chimeric antigen receptor or a T cell receptor), (iii) an isolated nucleic acid molecule that encodes a c-Jun protein, or (iv) any combination thereof, and wherein each of the nucleic acids can be expressed in the modified cell of the present disclosure.

As described herein, such vectors can be used to modify a cell (e.g., CAR- or TCR-expressing cells) to overexpress a c-Jun protein and express reduced levels of a NR4A (NR4A1, NR4A2, and/or NR4A3) gene and/or protein, wherein such modified cells can be used to treat a disease or disorder, such as cancer. In some aspects, the vector comprises a polynucleotide encoding (i) a ligand binding protein (e.g., CAR or TCR, e.g., an anti-ROR1 CAR or an anti-ROR1 TCR) and (ii) a c-Jun protein, operably linked to a regulatory element. In some aspects, the vector comprises a polynucleotide encoding (i) a ligand binding protein (e.g., CAR or TCR, e.g., an anti-ROR1 CAR or an anti-ROR1 TCR), (ii) a c-Jun protein, and (iii) a truncated EGFR, operably linked to a regulatory element.

Suitable vectors for the disclosure include expression vectors, viral vectors, and plasmid vectors. In some aspects, the vector is a viral vector.

As used herein, the terms "vector" and "expression vector" refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

As used herein, viral vectors include, but are not limited to, nucleic acid sequences from the following viruses: retrovirus, such as Moloney murine leukemia virus, Harvey murine sarcoma virus, murine mammary tumor virus, and Rous sarcoma virus; lentivirus; adenovirus; adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA.

In some aspects, a vector is derived from an adeno-associated virus. In some aspects, a vector is derived from a lentivirus. Examples of the lentiviral vectors are disclosed in WO9931251, WO9712622, WO9817815, WO9817816, and WO9818934, each which is incorporated herein by reference in its entirety.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, CA.). Other plasmids are well-known to those of ordinary skill in the art. Additionally, plasmids can be custom designed using standard molecular biology techniques to remove and/or add specific fragments of DNA.

The present disclosure contemplates the use of any nucleic acid modification available to the skilled artisan to modify the nucleic acids disclosed herein, e.g., gRNAs and nucleic acids encoding gRNAs, nucleic acids encoding Cas9, vectors comprising nucleic acids encoding at least one gRNA or at least one gRNA and Cas9, nucleic acids encoding a CAR or a TCR, nucleic acids encoding any genome editing tool disclosed herein, nucleic acids encoding an RNAi, or an antisense oligonucleotide.

As used herein, "unmodified" or "natural" nucleosides or nucleobases include the purine bases adenine (A) and guanine (G), and the pyrimidine bases thymine (T), cytosine (C) and uracil (U). In some aspects, a synthetic, modified gRNA comprises at least one nucleoside ("base") modification or substitution.

The nucleic acids disclosed in the present application (e.g., gRNAs and nucleic acids encoding such gRNAs, as well as nucleic acids encoding Cas9) can comprise one or more modifications. In some aspects, a nucleotide sequence disclosed herein comprises at least one nucleotide analogue. In some aspects, at least one nucleotide analogue introduced by using in vitro translation (IVT) or chemical synthesis is selected from the group consisting of a 2'-O-methoxyethyl-RNA (2'-MOE-RNA) monomer, a 2'-fluoro-DNA monomer, a 2'-O-alkyl-RNA monomer, a 2'-amino-DNA monomer, a locked nucleic acid (LNA) monomer, a cEt monomer, a cMOE monomer, a 5'-Me-LNA monomer, a 2'-(3-hydroxy)propyl-RNA monomer, an arabino nucleic acid (ANA) monomer, a 2'-fluoro-ANA monomer, an anhydrohexitol nucleic acid (HNA) monomer, an intercalating nucleic acid (INA) monomer, and a combination of two or more of said nucleotide analogues. In some aspects, the optimized nucleic acid molecule, e.g., a gRNA, comprises at least one backbone modification, for example, a phosphorothioate internucleotide linkage.

In some aspects, nucleic acids disclosed in the present application (e.g., gRNAs and nucleic acids encoding such gRNAs, as well as nucleic acids encoding Cas9) can be chemically modified at terminal locations, for example by introducing M (2'-O-methyl), MS (2'-O-methyl 3' phosphorothioate), or MSP (2'-O-methy 3'thioPACE, phosphonoacetate) modifications, or combinations thereof at positions 1, 2, 3 respect to the 5' and/or 3' termini. For example, in one aspects, a gRNA of the present disclosure can comprise three M modifications at the three 5' nucleotides and three M modifications at the three 3' nucleotides. In some aspects, a gRNA of the present disclosure can comprise three MS modifications at the three 5' nucleotides and three MS modifications at the three 3' nucleotides. In some aspects, a gRNA of the present disclosure can comprise three MSP modifications at the three 5' nucleotides and three MSP modifications at the three 3' nucleotides.

In some aspects, at least 5%, 10%, 15%, 20%, 25%, 30%, 35%, 40%, 45%, 50%, 55%, 60%, 65%, 70%, 75%, 80%, 85%, 90%, or 95%, or 100% of the uridine, adenosine, guanosine, cytidine nucleosides in an nucleotide sequence disclosed herein, e.g., a gRNA, have been replaced with a nucleoside In some aspects, a nucleic acid disclosed in the present application (e.g., a gRNA) comprises a nucleotide sequence produced by IVT or chemical synthesis wherein (i) at least one uridine in the wild type nucleotide sequence has been replaced; and/or, (ii) at least one adenosine in the wild type nucleotide sequence has been; and/or, (iii) at least one guanosine in the wild type nucleotide sequence has been replaced; and/or, (iv) at least one cytidine in the wild type nucleotide sequence has been replaced.

Modified nucleic acids of the present disclosure (e.g., gRNAs) need not be uniformly modified along the entire length of the molecule. Different nucleotide modifications and/or backbone structures can exist at various positions in the nucleic acid. One of ordinary skill in the art will appreciate that the nucleotide analogs or other modification(s) can be located at any position(s) of a nucleic acid such that the function of the nucleic acid is not substantially decreased. A modification can also be a 5' or 3' terminal modification. The nucleic acids can contain at a minimum one and at maximum 100% modified nucleotides, or any intervening percentage, such as at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% modified nucleotides.

In some aspects, the nucleic acids provided herein are synthetic, modified DNA molecules encoding RNA (e.g., a gRNA) and/or polypeptides (e.g., Cas9), where the synthetic, modified DNA molecules comprise one or more modifications.

The synthetic, modified nucleic acids described herein (e.g., gRNAs) include modifications to prevent rapid degradation by endo- and exo-nucleases. Modifications include, but are not limited to, for example, (a) end modifications, e.g., 5' end modifications (phosphorylation dephosphorylation, conjugation, inverted linkages, etc.), 3' end modifications (conjugation, DNA nucleotides, inverted linkages, etc.), (b) base modifications, e.g., replacement with modified bases, stabilizing bases, destabilizing bases, or bases that base pair with an expanded repertoire of partners, or conjugated bases, (c) sugar modifications (e.g., at the 2' position or 4' position) or replacement of the sugar, as well as (d) internucleoside linkage modifications, including modification or replacement of the phosphodiester linkages.

Specific examples of synthetic, modified nucleic acids (e.g., gRNA) compositions useful with the methods described herein include, but are not limited to, modified nucleic acids (e.g., gRNA) containing modified or non-natural internucleoside linkages. Synthetic, modified nucleic acids (e.g., gRNA) having modified internucleoside linkages include, among others, those that do not have a phosphorus atom in the internucleoside linkage. In some aspects, the synthetic, modified nucleic acid (e.g., gRNA) has a phosphorus atom in its internucleoside linkage(s).

Non-limiting examples of modified internucleoside linkages include phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, T-5' linked analogs of these, and those) having inverted polarity wherein the adjacent pairs of nucleoside units are linked 3'-5' to 5'-3' or T-5' to 5'-T. Various salts, mixed salts and free acid forms are also included.

Modified internucleoside linkages that do not include a phosphorus atom therein have internucleoside linkages that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Some aspects of the synthetic, modified nucleic acids (e.g., gRNA) described herein include nucleic acids with phosphorothioate internucleoside linkages and oligonucleosides with heteroatom internucleoside linkage, and in particular —$CH_2$—NH—$CH_2$—, —$CH_2$—N($CH_3$)—O—$CH_2$— [known as a methylene (methylimino) or MMI], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester internucleoside linkage is represented as —O—P—O—$CH_2$—] of U.S. Pat. No. 5,489,677, and the amide backbones of U.S. Pat. No. 5,602,240, both of which are herein incorporated by reference in their entirety. In some aspects, the nucleic acid sequences featured herein have morpholino backbone structures of U.S. Pat. No. 5,034,506, herein incorporated by reference in its entirety.

Synthetic, modified nucleic acids (e.g., gRNA) described herein can also contain one or more substituted sugar moieties. The nucleic acids featured herein can include one of the following at the 2' position: H (deoxyribose); OH (ribose); F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary modifications include O[($CH_2$)nO]m$CH_3$, O($CH_2$)nO$CH_3$, O($CH_2$)nN$H_2$, O($CH_2$)n$CH_3$, O($CH_2$)nON$H_2$, and O($CH_2$)nON[($CH_2$)n$CH_3$)]$_2$, where n and m are from 1 to about 10. In some aspects, synthetic, modified RNAs include one of the following at the 2' position: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, a reporter group, an intercalator, a group for improving the pharmacokinetic properties of a certain nucleic acid (e.g., a gRNA), or a group for improving the pharmacodynamic properties of a synthetic, modified nucleic acid (e.g., gRNA), and other substituents having similar properties. In some aspects, the modification includes a 2' methoxyethoxy (2'-O—$CH_2CH_2OCH_3$, also known as 2'-O-(2-methoxyethyl) or -MOE) (Martin et al, Helv. Chim. Acta, 1995, 78:486-504), i.e., an alkoxy-alkoxy group. Another exemplary modification is 2'-dimethylaminooxyethoxy, i.e., a O($CH_2$)$_2$ON($CH_3$)$_2$ group, also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$.

Other modifications include 2'-methoxy (2'-O$CH_3$), 2'-aminopropoxy (2'-O$CH_2CH_2CH_2NH_2$) and 2'-fluoro (2'-F). Similar modifications can also be made at other positions on the nucleic acid sequence, particularly the 3' position of the sugar on the 3' terminal nucleotide or in 2'-5' linked nucleotides and the 5' position of 5' terminal nucleotide. A synthetic, modified gRNA can also have sugar mimetics such as cyclobutyl moieties in place of the pentofuranosyl sugar.

As non-limiting examples, synthetic, modified gRNAs described herein can include at least one modified nucleoside including a 2'-O-methyl modified nucleoside, a nucleoside comprising a 5' phosphorothioate group, a 2'-amino-modified nucleoside, 2'-alkyl-modified nucleoside, morpholino nucleoside, a phosphoramidate or a non-natural base comprising nucleoside, or any combination thereof.

In some aspects, the at least one modified nucleoside is selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxyuridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m2,7G), N2,N2,7-trimethylguanosine (m2,2,7G), and inosine (I).

Alternatively, a synthetic, modified gRNA can comprise at least two modified nucleosides, at least 3, at least 4, at least 5, at least 6, at least 7, at least 8, at least 9, at least 10, at least 15, at least 20 or more, up to the entire length of the nucleotide. At a minimum, a synthetic, modified gRNA molecule comprising at least one modified nucleoside comprises a single nucleoside with a modification as described herein. It is not necessary for all positions in a given synthetic, modified gRNA to be uniformly modified, and in fact more than one of the aforementioned modifications can be incorporated in a single synthetic, modified gRNA or even at a single nucleoside within a synthetic, modified gRNA. However, it is preferred, but not absolutely necessary, that each occurrence of a given nucleoside in a molecule is modified (e.g., each cytosine is a modified cytosine e.g., 5mC). However, it is also contemplated that different occurrences of the same nucleoside can be modified in a different way in a given synthetic, modified gRNA molecule (e.g., some cytosines modified as 5mC, others modified as 2'-O-methylcytidine or other cytosine analog). The modifications need not be the same for each of a plurality of modified nucleosides in a synthetic, modified gRNA. Furthermore, in some aspects of the aspects described herein, a synthetic, modified gRNA comprises at least two different modified nucleosides. In some aspects described herein, the at least two different modified nucleosides are 5-methylcytidine and pseudouridine. A synthetic, modified gRNA can also contain a mixture of both modified and unmodified nucleosides.

The gRNA and other nucleic acids disclosed herein, e.g., nucleic acids used for CRISPR gene editing, or a polynucleotide or set of polynucleotides encoding a CAR or a TCR, can be produced using chemical synthesis using an oligonucleotide synthesizer, host cell expression, in vitro translation (IVT), or any other methods known in the art. Naturally occurring nucleosides, non-naturally occurring nucleosides, or combinations thereof, replacing totally or partially naturally occurring nucleosides. Polynucleotide or nucleic acid synthesis reactions can be carried out by enzymatic methods utilizing polymerases. Polymerases catalyze the creation of phosphodiester bonds between nucleotides in a polynucleotide or nucleic acid chain.

Various tools in genetic engineering are based on the enzymatic amplification of a target nucleic acid which acts as a template. For the study of sequences of individual genes or specific regions of interest and other research needs, it is necessary to generate multiple copies of a target nucleic acid from a small sample of polynucleotides or nucleic acids. Such methods can be applied in the manufacture of the gRNAs and other nucleic acids disclosed herein (e.g., RNAi, an ASO, a polynucleotide encoding a Cas, or a polynucleotide or set of polynucleotides encoding a CAR or a TCR).

Polymerase chain reaction (PCR) has wide applications in rapid amplification of a target gene, as well as genome mapping and sequencing. The key components for synthesizing DNA comprise target DNA molecules as a template, primers complementary to the ends of target DNA strands, deoxynucleoside triphosphates (dNTPs) as building blocks, and a DNA polymerase. As PCR progresses through denaturation, annealing and extension steps, the newly produced DNA molecules can act as a template for the next circle of replication, achieving exponentially amplification of the target DNA. PCR requires a cycle of heating and cooling for denaturation and annealing. Variations of the basic PCR include asymmetric PCR (Innis et al., PNAS 85, 9436-9440 (1988)), inverse PCR (Ochman et al., Genetics 120(3), 621-623, (1988)), and reverse transcription PCR (RT-PCR) (Freeman et al., BioTechniques 26(1), 112-22, 124-5 (1999)), the contents of which are incorporated herein by reference in their entirety. In RT-PCR, a single stranded RNA is the desired target and is converted to a double stranded DNA first by reverse transcriptase. Any of the foregoing methods can be utilized in the manufacture of one or more regions of the polynucleotides of the present disclosure (e.g., a gRNA, a polynucleotide encoding a Cas, or a polynucleotide or set of polynucleotides encoding a CAR or a TCR).

Assembling polynucleotides or nucleic acids by a ligase is also widely used. DNA or RNA ligases promote intermolecular ligation of the 5' and 3' ends of polynucleotide chains through the formation of a phosphodiester bond. Accordingly, RNA ligases can be used for example to generate a gRNA by 3' to 5' intermolecular ligation of a gRNA spacer sequence and a gRNA frame sequence.

Standard methods can be applied to synthesize an isolated polynucleotide sequence encoding an isolated polypeptide of interest. For example, a single DNA or RNA oligomer containing a codon-optimized nucleotide sequence coding for the particular isolated polypeptide can be synthesized. In some aspects, several small oligonucleotides coding for portions of the desired polypeptide can be synthesized and then ligated. In some aspects, the individual oligonucleotides typically contain 5' or 3' overhangs for complementary assembly.

A polynucleotide disclosed herein (e.g., a gRNA, a polynucleotide encoding a Cas, or a polynucleotide or set of polynucleotides encoding a CAR or a TCR) can be chemically synthesized using chemical synthesis methods and potential nucleobase substitutions known in the art. See, for example, International Publication Nos. WO2014093924, WO2013052523; WO2013039857, WO2012135805, WO2013151671; U.S. Publ. No. US20130115272; or U.S. Pat. Nos. 8,999,380, 8,710,200, all of which are herein incorporated by reference in their entireties.

VI. Pharmaceutical Compositions

The present disclosure provides pharmaceutical compositions comprising a cell which has been modified as described herein to overexpress a c-Jun protein and to express reduced levels of an NR4A gene and/or NR4A protein, and a pharmaceutically acceptable carrier, excipient, or stabilizer. The present disclosure provides pharmaceutical compositions comprising a cell which has been modified to (i) overexpress a c-Jun protein, and (ii) express reduced levels of NR4A3 gene and/or NR4A3 protein, and that further have endogenous expression of NR4A1 and NR4A2 genes and NR4A1 and NR4A2 proteins (e.g., such as those cells described herein) and a pharmaceutically acceptable carrier, excipient, or stabilizer. In some aspects, the present disclosure provides pharmaceutical compositions comprising a cell which has been modified to (i) overexpress a c-Jun protein, and (ii) express reduced levels of NR4A2 gene and/or NR4A2 protein, and that further have endogenous expression of NR4A1 and NR4A3 genes and NR4A1 and NR4A3 proteins (e.g., such as those cells described herein) and a pharmaceutically acceptable carrier, excipient, or stabilizer. In some aspects, the present disclosure provides pharmaceutical compositions comprising a cell which has been modified to (i) overexpress a c-Jun protein, and (ii) express reduced levels of NR4A1 gene and/or NR4A1 protein, and that further have endogenous expression of NR4A2 and NR4A3 genes and NR4A2 and NR4A3 proteins (e.g., such as those cells described herein) and a pharmaceutically acceptable carrier, excipient, or stabilizer. In some aspects, the pharmaceutical compositions provided herein comprise: (1) a cell which has been modified to: (i) overexpress a c-Jun protein, and (ii) have reduced levels of both the NR4A1 gene and/or NR4A1 protein and the NR4A2 gene and/or NR4A2 protein but endogenous level of the NR4A3 gene and/or NR4A3 protein; and (2) a pharmaceutically acceptable carrier, excipient, or stabilizer. In some aspects, the pharmaceutical compositions provided herein comprise: (1) a cell which has been modified to: (i) overexpress a c-Jun protein, and (ii) have reduced levels of both the NR4A1 gene and/or NR4A1 protein and the NR4A3 gene and/or NR4A3 protein but endogenous level of the NR4A2 gene and/or NR4A2 protein; and (2) a pharmaceutically acceptable carrier, excipient, or stabilizer. In some aspects, the pharmaceutical compositions provided herein comprise: (1) a cell which has been modified to: (i) overexpress a c-Jun protein, and (ii) have reduced levels of both the NR4A2 gene and/or NR4A2 protein and the NR4A3 gene and/or NR4A3 protein but endogenous level of the NR4A1 gene and/or NR4A1 protein; and (2) a pharmaceutically acceptable carrier, excipient, or stabilizer. In some aspects, the pharmaceutical compositions provided herein comprise: (1) a cell which has been modified to: (i) overexpress a c-Jun protein, and (ii) have reduced levels of the NR4A1 gene and/or NR4A1 protein, the NR4A2 gene and/or NR4A2 protein, and the NR4A3 gene and/or NR4A3 protein; and (2) a pharmaceutically acceptable carrier, excipient, or stabilizer.

The present disclosure provides pharmaceutical compositions comprising a cell which has been modified to (i) overexpress a c-Jun protein, (ii) express reduced levels of NR4A3 gene and/or NR4A3 protein, and (iii) express a ligand binding protein (e.g., CAR or TCR) (e.g., specifically binds to ROR1), and that further have endogenous expression of NR4A1 and NR4A2 genes and NR4A1 and NR4A2 proteins (e.g., such as those cells described herein) and a pharmaceutically acceptable carrier, excipient, or stabilizer. In some aspects, the present disclosure provides pharmaceutical compositions comprising a cell which has been modified to (i) overexpress a c-Jun protein, (ii) express reduced levels of NR4A2 gene and/or NR4A2 protein, and (iii) a ligand binding protein (e.g., CAR or TCR) (e.g., specifically binds to ROR1), and that further have endogenous expression of NR4A1 and NR4A3 genes and NR4A1 and NR4A3 proteins (e.g., such as those cells described herein) and a pharmaceutically acceptable carrier, excipient, or stabilizer. In some aspects, the present disclosure provides pharmaceutical compositions comprising a cell which has been modified to (i) overexpress a c-Jun protein, (ii) express reduced levels of NR4A1 gene and/or NR4A1 protein, and (iii) express a ligand binding protein (e.g., CAR or TCR) (e.g., specifically binds to ROR1), and that further have endogenous expression of NR4A2 and NR4A3 genes and NR4A2 and NR4A3 proteins (e.g., such as those cells described herein) and a pharmaceutically acceptable carrier, excipient, or stabilizer. In some aspects, the pharmaceutical compositions provided herein comprise: (1) a cell which has been modified to: (i) express a ligand binding protein (e.g., CAR or TCR), (ii) overexpress a c-Jun protein, and (iii) have reduced levels of both the NR4A1 gene and/or NR4A1 protein and the NR4A2 gene and/or NR4A2 protein but endogenous level of the NR4A3 gene and/or NR4A3 protein; and (2) a pharmaceutically acceptable carrier, excipient, or stabilizer. In some aspects, the pharmaceutical compositions provided herein comprise: (1) a cell which has been modified to: (i) express a ligand binding protein (e.g., CAR or TCR), (ii) overexpress a c-Jun protein, and (iii) have reduced levels of both the NR4A1 gene and/or NR4A1 protein and the NR4A3 gene and/or NR4A3 protein but endogenous level of the NR4A2 gene and/or NR4A2 protein; and (2) a pharmaceutically acceptable carrier, excipient, or stabilizer. In some aspects, the pharmaceutical compositions provided herein comprise: (1) a cell which has been modified to: (i) express a ligand binding protein (e.g., CAR or TCR), (ii) overexpress a c-Jun protein, and (iii) have reduced levels of both the NR4A2 gene and/or NR4A2 protein and the NR4A3 gene and/or NR4A3 protein but endogenous level of the NR4A1 gene and/or NR4A1 protein; and (2) a pharmaceutically acceptable carrier, excipient, or stabilizer. In some aspects, the pharmaceutical compositions provided herein comprise: (1) a cell which has been modified to: (i) express a ligand binding protein (e.g., CAR or TCR), (ii) overexpress a c-Jun protein, and (iii) have reduced levels of the NR4A1 gene and/or NR4A1 protein, the NR4A2 gene and/or NR4A2 protein, and the NR4A3 gene and/or NR4A3 protein; and (2) a pharmaceutically acceptable carrier, excipient, or stabilizer.

As described herein, such pharmaceutical compositions can be used to prevent and/or treat a cancer. As described herein, in some aspects, the modified cell present in a pharmaceutical composition disclosed herein is an immune cell, such as a T cell (e.g., CAR or TCR-expressing T cells) or NK cells (e.g., CAR or TCR-expressing NK cells).

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

A pharmaceutical composition can be formulated for any route of administration to a subject. Specific examples of routes of administration include intramuscularly, subcutaneously, ophthalmic, intravenously, intraperitoneally, intradermally, intraorbitally, intracerebrally, intracranially, intraspinally, intraventricular, intrathecally, intracistemally, intracapsularly, or intratumorally. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN®80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutical compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874, each of which is herein incorporated by reference in its entirety.

The compositions to be used for in vivo administration can be sterile. This is readily accomplished by filtration through, e.g., sterile filtration membranes.

The present disclosure also provides a cell composition comprising a means for one or more methods described herein, e.g., promoting persistent memory and/or effector function in a population of immune cells. In some aspects, the present disclosure provides a cell composition comprising a means for reducing, ameliorating, or inhibiting exhaustion and/or dysfunction in a population of immune cells. In some aspects, the means comprises modifying an expression of a NR4A gene and/or a NR4A protein and expression of a c-Jun protein in the population of immune cells. In some aspects, the means comprises modifying an expression of a NR4A gene and/or a NR4A protein and expression of a c-Jun protein in the population of immune cells.

VII. Kits

The present disclosure also provides kits for practicing any of the methods of the present disclosure. In some aspects, the disclosure provides a kit comprising (i) a gene editing tool to reduce the expression of a NR4A gene and/or NR4A protein, and (ii) a nucleotide sequence encoding a c-Jun transcription factor, or (iii) a combination thereof, and optionally instructions for treating a tumor according to any of the methods disclosed herein. In some aspects, the kit comprises (i) a gene editing tool to reduce the expression of a NR4A gene and/or NR4A protein, (ii) a transcriptional activator which is capable of increasing the endogenous expression of c-Jun, or (iii) a combination thereof, and optionally instructions for treating a tumor according to any of the methods disclosed herein. Also provided is a kit comprising (i) a gene editing tool to reduce the expression of a NR4A gene and/or NR4A protein, (ii) a nucleotide sequence encoding a c-Jun transcription factor, or (iii) a combination thereof, and optionally instructions for preparing a cell composition according to the methods disclosed herein. In some aspects, the kit comprises (i) a gene editing tool to reduce the expression of a NR4A gene and/or NR4A protein, (ii) a transcriptional activator which is capable of increasing the endogenous expression of c-Jun, or (iii) a combination thereof, and optionally instructions for preparing a cell composition according to the methods disclosed herein.

The present disclosure also provides kits for practicing any of the methods of the present disclosure. In some aspects, the disclosure provides a kit comprising (i) a gene editing tool to reduce the expression of a NR4A gene and/or NR4A protein, (ii) a vector comprising a ligand binding protein (e.g., chimeric antigen receptor (CAR) (e.g., anti-ROR1 CAR) or a T cell receptor (TCR) (e.g., anti-ROR1 TCR), (iii) a nucleotide sequence encoding a c-Jun transcription factor, or (iv) a combination thereof, and optionally instructions for treating a tumor according to any of the methods disclosed herein. In some aspects, the kit comprises (i) a gene editing tool to reduce the expression of a NR4A gene and/or NR4A protein, (ii) a vector comprising a ligand binding protein (e.g., CAR or TCR), (iii) a transcriptional activator which is capable of increasing the endogenous expression of c-Jun, or (iv) a combination thereof, and optionally instructions for treating a tumor according to any of the methods disclosed herein. Also provided is a kit comprising (i) a gene editing tool to reduce the expression of a NR4A gene and/or NR4A protein, (ii) a vector comprising a ligand binding protein (e.g., chimeric antigen receptor (CAR) or a T cell receptor (TCR)), (iii) a nucleotide sequence encoding a c-Jun transcription factor, or (iv) a combination thereof, and optionally instructions for preparing a cell composition according to the methods disclosed herein. In some aspects, the kit comprises (i) a gene editing tool to reduce the expression of a NR4A gene and/or NR4A protein, (ii) a vector comprising a ligand binding protein (e.g., CAR or TCR), (iii) a transcriptional activator which is capable of increasing the endogenous expression of c-Jun, or (iv) a combination thereof, and optionally instructions for preparing a cell composition according to the methods disclosed herein.

In some aspects, the present disclosure provides kits comprising the compositions disclosed herein, for example, (i) a cell, e.g., an immune cell, that exhibits reduced expression of a NR4A gene and/or NR4A protein, (ii) at least one gRNA targeting the NR4A gene, (iii) a nucleic acid encoding at least one gRNA (e.g., a vector), (iv) at least one gRNA and a Cas protein (e.g., Cas9), (v) at least one nucleic acid encoding a gRNA (e.g. a vector) and a Cas protein (e.g., Cas9), (vi) at least one nucleic acid encoding a gRNA (e.g., a first vector) and a nucleic acid encoding a Cas protein such as Cas9 (e.g., a second vector), (vii) a single vector comprising a nucleic acid encoding at least one gRNA and at least one Cas protein, e.g., Cas9, (vii) a vector or set of vector encoding a ligand binding protein (e.g., CAR or a TCR). In some aspects, the kits comprise Cas9 RNPs targeting NR4A3 (e.g., Cas9 RNP including sgRNA GCUCGAGUAGCCCUCCACGA (SEQ ID NO: 30)). In some aspects, the sgRNA comprises those disclosed in Tables A, C, and D. In some aspects, the kits further comprise instructions for their use.

The present disclosure provides kits for the treatment of cancer comprising a modified cell (e.g., immune cell) disclosed herein, wherein the cell exhibits reduced expression of a NR4A gene and/or NR4A protein. The present disclosure provides kits for the treatment of cancer comprising a modified cell (e.g., immune cell) disclosed herein, wherein the cell exhibits reduced expression of a NR4A gene and/or NR4A protein, and wherein the cell expresses a ligand binding protein (e.g., CAR and/or TCR).

In some aspects, the kit comprises at least one gRNA disclosed herein, at least one isolated polynucleotide encoding a gRNA disclosed herein, at least one vector encoding a gRNA disclosed herein, a cell comprising at least one vector encoding a gRNA disclosed herein, or a combination thereof. In some aspects, the kit further comprises a Cas9 protein, an isolated polynucleotide encoding a Cas9 protein, or a vector comprising a polynucleotide encoding the Cas9 protein.

The present disclosure further provides a kit or package comprising at least one container means having disposed therein at least one of the above-mentioned gRNAs, Cas9; vectors, cells, or combinations thereof, together with instructions for reducing expression of NR4A gene and/or NR4A protein.

In some aspects, the kit comprises at least one upstream gRNA and a downstream gRNA. Accordingly, in some the kit comprises (i) at least one gRNA comprising a spacer sequence of any one of SEQ ID NOS: 34-41, and (ii) at least one gRNA comprising a spacer sequence of any one of SEQ ID NOS: 31-33.

In a specific aspect, the kit comprises a gRNA comprising a *S. pyogenes* spacer sequence of SEQ ID NO: 34-41 operably linked to a *S. aureus* chimeric frame, e.g., the sequence of SEQ ID NO: 42.

In some aspects, each kit comprising a gRNA for a specific bacterial species Cas9 (e.g., *S. pyogenes* Cas9) further comprises such Cas9.

In some aspects, the kit comprises one or more cells, cultures, or populations of cells expressing a CAR and/or a TCR targeting a cancer antigen.

EXAMPLES

Example 1—Guide RNA Screening and Generation of Modified T Cells

To assess whether reduced NR4A family gene and/or NR4A family protein expression and c-Jun overexpression are redundant or additive in their effects on reducing exhaustion and dysfunction, ROR1-R12 chimeric antigen receptor (CAR) T cell and NY-ESO-1 T cell receptor (TCR) T cell models were used. CRISPR-Cas9 guide RNAs (gRNAs) were identified that specifically reduced protein expression of each NR4A family member in human T cells transduced with a ROR1 CAR or NY-ESO-1 TCR overexpressing a c-Jun protein.

CRISPR-Cas9 guide RNAs for NR4A1 and NR4A2 are shown in Table A. In the experiments described in Examples 2-5, NR4A1 sgRNAs 5 and 6 were used in combination and NR4A2 sgRNAs 1, 2, and 3 were used in combination.

TABLE A

| NR4A1 and NR4A2 guide RNAs | |
| --- | --- |
| NR4A1 sgRNA5 (SEQ ID NO: 25) | GAAGUCCUCGAACUUGAAGG |
| NR4A1 sgRNA6 (SEQ ID NO: 26) | ACCUUCAUGGACGGCUACAC |
| NR4A2 sgRNA1 (SEQ ID NO: 27) | UUGGGAUGGUCAAAGAAGGU |
| NR4A2 sgRNA2 (SEQ ID NO: 28) | CAGCCAGGCACUUCUGAAAU |
| NR4A2 sgRNA3 (SEQ ID NO: 29) | UCCGGCGACGCUUGUCCACU |

Single gRNA specific for NR4A3 were designed and screened to identify gRNA with maximal editing efficiency and maximal protein reduction in three independent experiments (v0, v1, and v2). For all gRNA screening, isolated donor CD4+ and CD8+ T cells were purchased from All-Cells. CD4+ and CD8+ T cells were thawed and mixed at a 1:1 ratio for activation with 1% (v/v) TransAct (Miltenyi)

for 24 hours. The activated T cells were transduced 24 hours later with bi-cistronic (v0) or tri-cistronic lentiviral vectors encoding the anti-ROR1 CAR (v2) or left untransduced (v1). T cells were then electroporated with Cas9 RNPs targeting human NR4A3 utilizing modified guide RNAs (Synthego; v0—Table B, v1—Table C and v2—Table D) and the Lonza 4D Nucleofector unit. Electroporated T cells were transferred into G-Rex culture plates for expansion before cryopreservation in CryoStor media on day 7. One donor was used in Experiments v0 and v1 whereas two independent donors were used in Experiment v2. To evaluate efficiency of protein reduction by flow cytometry at day 7, $3\times10^5$ NR4A3-edited or control (electroporated without RNP) T cells were stimulated with CD3/CD28 Dynabeads (in v0 and v1) or PMA+ionomycin (in v2) for two hours in 200 pL of RPMI-1640 (Gibco)+10% fetal bovine serum (Gibco)+1% penicillin/streptomycin in 96 well round bottom plates (Corning) at 37 C to induce maximum NR4A3 expression. After stimulation, cells were stained with surface markers as described above. The cells were then fixed and permeabilized with the FoxP3 Transcription Factor staining buffer kit (eBiosciences) following manufacturer's instructions and intracellular staining was performed using custom fluorochrome conjugated NR4A3 antibody (R&D Systems).

None of the gRNA in v0 reduced NR4A3 protein expression compared to control non-edited cells (Table B). Confirmatory genomic editing efficiency by NGS was not performed. In vi, all 7 gRNA reduced NR4A3 protein expression compared to non-edited control and NGS editing efficiency was performed. Two guides (g4 and g8) had the highest genomic editing (as measured by total percent T cell variance). Despite high editing efficiency, indel characterization of the genomic variants revealed that g8 resulted in a high frequency of undesirable in-frame deletions (Table C. In v2, the top 14 gRNAs were selected based on KG conditions in which NR4A3 protein expression was reduced compared to non-edited controls and/or similar/better to benchmark g4 for both donors (Table D). Selected conditions are further evaluated to confirm genomic editing efficiency by NGS analysis.

TABLE B

| NR4A3 guide sequences from Experiment v0 in one donor. NR4A3 protein was not reduced compared to non-edited controls and editing efficiency determined by next-generation sequencing (NGS) in bulk T cells on day 7 of production was not performed. | | | | |
| --- | --- | --- | --- | --- |
| | 5' - 3' sequence | Protein Reduction (criteria met) | Tcell variance (%) | Type of Indel |
| g1 (SEQ ID NO: 48) | CAAUAUAGCC CUUCCCCUCC | No | N/A | N/A |
| g2 (SEQ ID NO: 49) | AACUGGAACC UGGAGGGGAA | No | N/A | N/A |
| g3 (SEQ ID NO: 50) | UAACUGGAAC CUGGAGGGGA | No | N/A | N/A |

N/A = not applicable.

TABLE C

NR4A3 guide sequences from Experiment v1 in one
donor. Shown are genomic editing efficiency by
NGS (measured by percent T cell variance) and
the indel characterization (percent of T cell
variance) in bulk T cells on day 7 of production.

| 5' - 3' sequence | Protein Reduction (criteria met) | T cell variance (%) | Type of Indel |
|---|---|---|---|
| g4 (SEQ ID NO: 30) GCUCGAGUAGCCCUCCACGA | Yes | 70.3 | Deletion - 42.3%<br>Insertion - 23.2%<br>Substitution - 11.2% |
| g5 (SEQ ID NO: 52) CCGCUGCAUUUGGUACACGC | Yes | 43.7 | Deletion - 20.8%<br>Insertion - 18.9%<br>Substitution - 7.4% |
| g6 (SEQ ID NO: 53) UGCGGCGCAGACAUACAGCU | Yes | 48.8 | Deletion - 17.9%<br>Insertion - 25.9%<br>Substitution - 6.8% |
| g7 (SEQ ID NO: 54) GCAGCGGCCCUUGAUCAAAG | Yes | 3.6 | Deletion - 0.5%<br>Insertion - 3%<br>Substitution - 0% |
| g8 (SEQ ID NO: 55) AUACAGCUCGGAAUACACCA | Yes | 71.7 | Deletion - 58.7%<br>Insertion - 11.5%<br>Substitution - 2.7% |
| g9 (SEQ ID NO: 56) CCUGCGUGUACCAAAUGCAG | Yes | 36.5 | Deletion - 32.9%<br>Insertion - 1.9%<br>Substitution - 2.3% |
| g10 (SEQ ID NO: 57) GCGGCCCUUGAUCAAAGUGG | Yes | 28 | Deletion - 25.9%<br>Insertion - 1.1%<br>Substitution - 1.7% |

TABLE D

NR4A3 guide sequences from Experiment v2 in two
donors. Shown are genomic editing efficiency by
NGS (measured by percent T cell variance) and
the indel characterization (percent of T cell
variance) in bulk T cells on day 7 of production.

| 5' - 3' sequence | Protein Reduction (criteria met) | Tcell variance (%) | Type of Indel |
|---|---|---|---|
| g11 (SEQ ID NO: 58) GGACUGCUUGAAGUACAUGG | Yes | TBD | TBD |
| g12 (SEQ ID NO: 59) CGGGUGGCUCUCAAGCGCGG | No | N/A | N/A |
| g13 (SEQ ID NO: 60) GACGACGAGCUCCUGCUGGG | No | N/A | N/A |
| g14 (SEQ ID NO: 61) GUCGGGGUUCAUGAUCUCCG | Yes | TBD | TBD |
| g15 (SEQ ID NO: 62) GAGGGCUUGAAGUGGAAGAG | No | N/A | N/A |
| g16 (SEQ ID NO: 63) GAUGAAGGCGGUCCCCACGG | No | N/A | N/A |
| g17 (SEQ ID NO: 64) GAAGGUACUGAUGCUGGGCA | No | N/A | N/A |
| g18 (SEQ ID NO: 65) UCCUCCAGCCUCCAGCCCGG | Yes | TBD | TBD |

TABLE D-continued

NR4A3 guide sequences from Experiment v2 in two
donors. Shown are genomic editing efficiency by
NGS (measured by percent T cell variance) and
the indel characterization (percent of T cell
variance) in bulk T cells on day 7 of production.

| 5' - 3' sequence | Protein Reduction (criteria met) | Tcell variance (%) | Type of Indel |
|---|---|---|---|
| g19 (SEQ ID NO: 66) AGCAUCAGUACCUUCGUGGA | No | N/A | N/A |
| g20 (SEQ ID NO: 67) CGACUACACCAAGCUGACCA | Yes | TBD | TBD |
| g21 (SEQ ID NO: 68) UGGUCAGCUUGGUGUAGUCG | Yes | TBD | TBD |
| g22 (SEQ ID NO: 69) GCUGGACCCGCCGAUGAAGG | No | N/A | N/A |
| g23 (SEQ ID NO: 70) UUGAAGUACAUGGAGGUGCU | Yes | TBD | TBD |
| g24 (SEQ ID NO: 71) GUACGGGUGGCUCUCAAGCG | Yes | TBD | TBD |
| g25 (SEQ ID NO: 72) CCGCAUAACUGGAACCUGGA | No | N/A | N/A |
| g26 (SEQ ID NO: 73) GGGCACGUGUGCCGUGUGCG | No | N/A | N/A |

TABLE D-continued

NR4A3 guide sequences from Experiment v2 in two
donors. Shown are genomic editing efficiency by
NGS (measured by percent T cell variance) and
the indel characterization (percent of T cell
variance) in bulk T cells on day 7 of production.

| 5' - 3' sequence | Protein Reduction (criteria met) | Tcell variance (%) | Type of Indel |
|---|---|---|---|
| g27 (SEQ ID NO: 74) UACGGCGUGCGAACCUGCGA | No | N/A | N/A |
| g28 (SEQ ID NO: 75) UGGGGACUGCUUGAAGUACA | Yes | TBD | TBD |
| g29 (SEQ ID NO: 76) CCUUGGCAGCACUGAGAUCA | Yes | TBD | TBD |
| g30 (SEQ ID NO: 77) CCUUGAUCAAAGUGGAGGAG | No | N/A | N/A |
| g31 (SEQ ID NO: 78) UGCAUUUGGUACACGCAGGA | No | N/A | N/A |
| g32 (SEQ ID NO: 79) UGAUCAAAGUGGAGGAGGGG | No | N/A | N/A |
| g33 (SEQ ID NO: 80) GUGGGGACCGCCUUCAUCGG | No | N/A | N/A |
| g34 (SEQ ID NO: 81) AGGAGCUCGUCGUCUGGCGA | No | N/A | N/A |
| g35 (SEQ ID NO: 82) CCACCUCGGCUACGACCCGA | Yes | TBD | TBD |
| g36 (SEQ ID NO: 83) GCGGCGGCGAGGGCUUGAAG | Yes | TBD | TBD |
| g37 (SEQ ID NO: 84) CAGCAUCAGUACCUUCGUGG | No | N/A | N/A |
| g38 (SEQ ID NO: 85) GCCGAUGAAGGCGGUCCCCA | No | N/A | N/A |
| g39 (SEQ ID NO: 86) CCGUCGGGUCGUAGCCGAGG | Yes | TBD | TBD |
| g40 (SEQ ID NO: 87) CUACGGCGUGCGAACCUGCG | No | N/A | N/A |
| g41 (SEQ ID NO: 88) CCAUAACGCCCCGCCUGCG | No | N/A | N/A |
| g42 (SEQ ID NO: 89) AUAACGCCCCGCCUGCGGG | No | N/A | N/A |
| g43 (SEQ ID NO: 90) GCCGCAUAACUGGAACCUGG | No | N/A | N/A |
| g44 (SEQ ID NO: 91) GAAAUCGACAGUACUGACAU | No | N/A | N/A |
| g45 (SEQ ID NO: 92) UUUCAGAAGUGUCUCAGUGU | No | N/A | N/A |
| g46 (SEQ ID NO: 93) GAAGUGUCUCAGUGUUGGAA | No | N/A | N/A |
| g47 (SEQ ID NO: 94) AGUGUUGGAAUGGUAAAAGA | Yes | TBD | TBD |
| g48 (SEQ ID NO: 95) GUACAGAUAGUCUGAAAGGG | No | N/A | N/A |
| g49 (SEQ ID NO: 96) GUGUUGAGUCUGUUAAAGCU | Yes | TBD | TBD |

TABLE D-continued

NR4A3 guide sequences from Experiment v2 in two
donors. Shown are genomic editing efficiency by
NGS (measured by percent T cell variance) and
the indel characterization (percent of T cell
variance) in bulk T cells on day 7 of production.

| 5' - 3' sequence | Protein Reduction (criteria met) | Tcell variance (%) | Type of Indel |
|---|---|---|---|
| g50 (SEQ ID NO: 97) GAUAGUCUGAAAGGGAGGAG | No | N/A | N/A |
| g51 (SEQ ID NO: 98) AGUCUGUUAAAGCUCGGACA | No | N/A | N/A |
| g52 (SEQ ID NO: 99) GUCCGUACAGAUAGUCUGAA | No | N/A | N/A |

N/A = not applicable;
TBD = to be determined.

As described in more detail in the Examples below, NR4A3-edited ROR1 CAR T cells overexpressing c-Jun displayed the greatest functional benefit, demonstrating significantly prolonged cytotoxicity, cytokine production, T cell persistence, and improved phenotype following continuous ROR1 antigen exposure compared to control ROR1 CAR T cells (e.g., not overexpressing c-Jun). NR4A3-edited NY-ESO-1 TCR T cells overexpressing c-Jun also displayed the greatest functional benefit, demonstrating prolonged cytotoxicity and cytokine production following continuous NY-ESO-1 antigen exposure compared to control NY-ESO-1 TCR T cells (e.g., not overexpressing c-Jun).

Example 2—Reduced NR4A3 Expression

Reduction of NR4A3 protein using NR4A3 sgRNA g4 (SEQ ID NO: 30) was validated in NR4A-edited ROR1 CAR T cells and NY-ESO-1 TCR T cells with and without c-Jun overexpression by flow cytometry. Stimulation with CD3/CD28 Dynabeads or PMA+ionomycin were used to induce maximum NR4A expression. For flow cytometry analyses, NR4A3-edited ROR1 CAR T cells and NY-ESO-1 TCR T cells with and without c-Jun overexpression were stained with a live dead dye for 10 minutes at room temperature (RT), blocked with TruStain FcX (Biolegend) for 5 minutes at RT, stained with CCR7 for 15 minutes at 37 C, and then stained with surface marker antibodies for 10 minutes at RT. All staining was performed in Biolegend cell staining buffer. The cells were then fixed and permeabilized with the FoxP3 Transcription Factor staining buffer kit (eBiosciences) following manufacturer's instructions. The cells were blocked with 10% normal mouse and rabbit serum for 10 minutes at room temperature and then stained with cParp (for day 0 of sequential stimulation only) and c-Jun.

$3 \times 10^5$ NR4A-edited or control ROR1 CAR T cells and NY-ESO-1 TCR T cells were stimulated with CD3/CD28 Dynabeads (Thermo Fisher) at a 3:1 bead-to-cell ratio or PMA+ionomycin (BioLegend) for two hours in 200 pL of RPMI-1640 (Gibco)+10% fetal bovine serum (Gibco)+1% penicillin/streptomycin in 96 well round bottom plates (Corning) at 37 C to induce maximum NR4A expression. After stimulation, Dynabeads were removed, and cells were stained with surface markers as described above. The cells were then fixed and permeabilized with the FoxP3 Transcription Factor staining buffer kit (eBiosciences) following manufacturer's instructions. Custom fluorochrome conjugated NR4A antibodies (R&D Systems) were used for staining.

NR4A3 protein expression was significantly reduced in NR4A3-edited ROR1 CD4$^+$ and CD8$^+$ CAR T cells and NY-ESO-1 CD4$^+$ and CD8$^+$ TCR T cells compared to non-edited controls irrespective of c-Jun expression (FIG. 1 and FIG. 12). Similarly, high efficiency NR4A1 and NR4A2 protein reduction was achieved using CRISPR-Cas9 gRNAs specific for the NR4A1 and NR4A2 genes (data not shown). Although the transduction efficiency of ROR1 CAR T cells (identified as % EGFR$^+$R12$^+$) was lower in control than c-Jun overexpressing CAR T cells, the mean geometric fluorescence (gMFI) of the ROR1-R12 CAR was not significantly different between the two ROR1 CAR constructs. The ROR1 CAR percentage and gMFI was similar across four donors tested and was not affected by NR4A editing (FIG. 2).

Although the transduction efficiency of NY-ESO-1 TCR T cells (identified as % TCRvβ13.1+ and gMFI) was significantly higher in control than c-Jun overexpressing TCR T cells, the NY-ESO-1 TCR percentages and gMFIs was similar across three donors tested and was not affected by NR4A editing (FIG. 13).

Example 3—Sustained Cytotoxicity and Cytokine Production in Sequential Stimulation The function of single NR4A-edited ROR1 CAR T cells (in which CAR T cells were edited at either NR4A1, NR4A2, or NR4A3) with and without c-Jun overexpression were evaluated in an in vitro exhaustion assay in which CAR T cells are sequentially exposed to antigen. Before setting up the assays, H1975-NucLight Red (NLR) tumor cells lines were cultured in RPMI-1640 (Gibco)+10% fetal bovine serum (Gibco)+1% penicillin/streptomycin for 2-3 passages. Cells were trypsinized with TrypLE Express enzyme (Gibco).

In the sequential stimulation assay, NR4A-edited ROR1 CAR T cells with and without c-Jun overexpression were subjected to five successive stimulations with the H1975 NSCLC ROR1-expressing tumor cell line. In particular, cryopreserved ROR1 CAR T cells were thawed and immediately cultured at a 1:1 E:T ratio of cParp$^-$CD3$^+$EGFR$^+$ R12$^+$ CAR T cells with H1975-NLR tumor cells in RPMI-1640 (Gibco)+10% fetal bovine serum (Gibco)+1% penicillin/streptomycin in triplicates in flat 24 well assay plates (Eppendorf). After 3 days of co-culture, wells were resuspended, and 25% of the culture was transferred onto new plates with the same initial number of fresh tumor cells per well. This was repeated for a total of 5 stimulations. Cytotoxicity was measured continuously in the Incucyte during the assay and supernatants were collected 24 hours after setting up each new stimulation to measure cytokine levels. Remaining cells from the triplicate co-culture wells were combined for phenotypic flow analyses as described above. c-Jun CAR T cells outperformed the non-c-Jun control CAR T cells. Unexpectedly, NR4A3 KO c-Jun overexpressing ROR1 CAR T cells remained the most cytotoxic against H1975 tumor cells, demonstrating a sustained ability to lyse target cells after five rounds of stimulation compared to all other conditions in 4 different donors (FIG. 3).

In addition to sustained cytotoxicity, NR4A3 KO c-Jun overexpressing ROR1 CAR T cells also produced the highest levels of IFN-γ, IL-2, and TNF-α compared to NR4A1, NR4A2, or non-edited control and c-Jun ROR1 CAR T cells (FIG. 4 and Tables 9-11) when stimulated with H1975 NSCLC RORK-expressing tumor cells. Cytokine levels were measured using Meso Scale Discovery V-Plex proinflammatory panel 1 human kits or custom human IFN-γ, IL-2, and TNF-α~ cytokine kits following the manufacturer's instructions.

TABLE 9

Unpaired t-test statistical analysis of secreted interferon-gamma (IFN-γ) produced from NR4A-edited and control non-edited R0R1 CAR T cells with or without c-Jun overexpression during the H1975 sequential stimulation assay corresponding to FIG. 4.

| | NR4A1 KO (−cJun) | NR4A2 KO (−cJun) | NR4A3 KO (−cJun) | Control ROR1 CAR (−cJun) | NR4A1 KO (+cJun) | NR4A2 KO (+cJun) | NR4A3 KO (+cJun) | Control ROR1 CAR (+cJun) |
|---|---|---|---|---|---|---|---|---|
| D6871 IFN-γ Stim 1 | | | | | | | | |
| NR4A1 KO (−cJun) | X | X | X | X | X | X | X | X |
| NR4A2 KO (−cJun) | * | X | X | X | X | X | X | X |
| NR4A3 KO (−cJun) | * | * | X | X | X | X | X | X |
| Control ROR1 CAR (−cJun) | *** | **** | ** | X | X | X | X | X |
| NR4A1 KO (+cJun) | ** | ns | **** | **** | X | X | X | X |
| NR4A2 KO (+cJun) | ns | * | * | ** | ** | X | X | X |
| NR4A3 KO (+cJun) | ns | ** | ** | *** | ** | ns | X | X |
| Control ROR1 CAR (+cJun) | ** | *** | ** | *** | ** | ns | * | X |
| D6871 IFN-γ Stim 2 | | | | | | | | |
| NR4A1 KO (−cJun) | X | X | X | X | X | X | X | X |
| NR4A2 KO (−cJun) | ns | X | X | X | X | X | X | X |

123 124

TABLE 9-continued

Unpaired t-test statistical analysis of secreted interferon-gamma
(IFN-γ) produced from NR4A-edited and control non-edited R0R1
CAR T cells with or without c-Jun overexpression during the H1975
sequential stimulation assay corresponding to FIG. 4.

| | NR4A1 KO (−cJun) | NR4A2 KO (−cJun) | NR4A3 KO (−cJun) | Control ROR1 CAR (−cJun) | NR4A1 KO (+cJun) | NR4A2 KO (+cJun) | NR4A3 KO (+cJun) | Control ROR1 CAR (+cJun) |
|---|---|---|---|---|---|---|---|---|
| NR4A3 KO (−cJun) | ns | * | X | X | X | X | X | X |
| Control ROR1 CAR (−cJun) | ** | *** | * | X | X | X | X | X |
| NR4A1 KO (+cJun) | **** | **** | **** | **** | X | X | X | X |
| NR4A2 KO (+cJun) | ** | **** | *** | **** | **** | X | X | X |
| NR4A3 KO (+cJun) | *** | *** | *** | **** | ** | *** | X | X |
| Control ROR1 CAR (+cJun) D6871 IFN-γ Stim 3 | ** | **** | ** | * | **** | **** | **** | X |
| NR4A1 KO (−cJun) | X | X | X | X | X | X | X | X |
| NR4A2 KO (−cJun) | ns | X | X | X | X | X | X | X |
| NR4A3 KO (−cJun) | ns | ns | X | X | X | X | X | X |
| Control ROR1 CAR (−cJun) | ** | ** | * | X | X | X | X | X |
| NR4A1 KO (+cJun) | ** | ** | *** | *** | X | X | X | X |
| NR4A2 KO (+cJun) | ** | *** | *** | **** | ** | X | X | X |
| NR4A3 KO (+cJun) | *** | *** | *** | *** | ** | *** | X | X |
| Control ROR1 CAR (+cJun) D7570 IFN-γ Stim 1 | ** | ** | ** | ns | *** | **** | *** | X |
| NR4A1 KO (−cJun) | X | X | X | X | X | X | X | X |
| NR4A2 KO (−cJun) | ** | X | X | X | X | X | X | X |
| NR4A3 KO (−cJun) | X | X | X | X | X | X | X | X |
| Control ROR1 CAR (−cJun) | *** | **** | X | X | X | X | X | X |
| NR4A1 KO (+cJun) | ** | ns | X | **** | X | X | X | X |
| NR4A2 KO (+cJun) | ** | *** | X | *** | *** | X | X | X |
| NR4A3 KO (+cJun) | * | ns | X | *** | ns | ** | X | X |
| Control ROR1 CAR (+cJun) D7570 IFN-γ Stim 2 | ** | *** | X | *** | **** | ns | ** | X |
| NR4A1 KO (−cJun) | X | X | X | X | X | X | X | X |
| NR4A2 KO (−cJun) | * | X | X | X | X | X | X | X |
| NR4A3 KO (−cJun) | X | X | X | X | X | X | X | X |
| Control ROR1 CAR (−cJun) | *** | *** | X | X | X | X | X | X |
| NR4A1 KO (+cJun) | * | ** | X | ** | X | X | X | X |
| NR4A2 KO (+cJun) | * | ** | X | ns | ns | X | X | X |

TABLE 9-continued

Unpaired t-test statistical analysis of secreted interferon-gamma
(IFN-γ) produced from NR4A-edited and control non-edited R0R1
CAR T cells with or without c-Jun overexpression during the H1975
sequential stimulation assay corresponding to FIG. 4.

| | NR4A1 KO (−cJun) | NR4A2 KO (−cJun) | NR4A3 KO (−cJun) | Control ROR1 CAR (−cJun) | NR4A1 KO (+cJun) | NR4A2 KO (+cJun) | NR4A3 KO (+cJun) | Control ROR1 CAR (+cJun) |
|---|---|---|---|---|---|---|---|---|
| NR4A3 KO (+cJun) | **** | ** | X | **** | **** | *** | X | X |
| Control ROR1 CAR (+cJun) | * | ** | X | ** | ns | ns | **** | X |
| D7570 IFN-γ Stim 3 | | | | | | | | |
| NR4A1 KO (−cJun) | X | X | X | X | X | X | X | X |
| NR4A2 KO (−cJun) | ns | X | X | X | X | X | X | X |
| NR4A3 KO (−cJun) | X | X | X | X | X | X | X | X |
| Control ROR1 CAR (−cJun) | *** | ** | X | X | X | X | X | X |
| NR4A1 KO (+cJun) | * | ns | X | ** | X | X | X | X |
| NR4A2 KO (+cJun) | ns | ns | X | *** | ** | X | X | X |
| NR4A3 KO (+cJun) | **** | *** | X | **** | *** | **** | X | X |
| Control ROR1 CAR (+cJun) | ** | * | X | **** | ** | ** | **** | X |
| D13570 IFN-γ Stim 1 | | | | | | | | |
| NR4A1 KO (−cJun) | X | X | X | X | X | X | X | X |
| NR4A2 KO (−cJun) | ns | X | X | X | X | X | X | X |
| NR4A3 KO (−cJun) | ns | ns | X | X | X | X | X | X |
| Control ROR1 CAR (−cJun) | ns | * | ns | X | X | X | X | X |
| NR4A1 KO (+cJun) | **** | ** | *** | *** | X | X | X | X |
| NR4A2 KO (+cJun) | ns | ns | ns | ns | *** | X | X | X |
| NR4A3 KO (+cJun) | **** | *** | **** | **** | * | **** | X | X |
| Control ROR1 CAR (+cJun) | ns | * | ns | ns | *** | ns | **** | X |
| D13570 IFN-γ Stim 2 | | | | | | | | |
| NR4A1 KO (−cJun) | X | X | X | X | X | X | X | X |
| NR4A2 KO (−cJun) | ns | X | X | X | X | X | X | X |
| NR4A3 KO (−cJun) | ** | ** | X | X | X | X | X | X |
| Control ROR1 CAR (−cJun) | ** | ** | ns | X | X | X | X | X |
| NR4A1 KO (+cJun) | *** | **** | **** | **** | X | X | X | X |
| NR4A2 KO (+cJun) | ns | ** | *** | *** | *** | X | X | X |
| NR4A3 KO (+cJun) | ** | *** | *** | *** | ns | ** | X | X |
| Control ROR1 CAR (+cJun) | * | ns | * | ** | **** | ** | *** | X |
| D13570 IFN-γ Stim 3 | | | | | | | | |
| NR4A1 KO (−cJun) | X | X | X | X | X | X | X | X |

TABLE 9-continued

Unpaired t-test statistical analysis of secreted interferon-gamma
(IFN-γ) produced from NR4A-edited and control non-edited R0R1
CAR T cells with or without c-Jun overexpression during the H1975
sequential stimulation assay corresponding to FIG. 4.

| | NR4A1 KO (−cJun) | NR4A2 KO (−cJun) | NR4A3 KO (−cJun) | Control ROR1 CAR (−cJun) | NR4A1 KO (+cJun) | NR4A2 KO (+cJun) | NR4A3 KO (+cJun) | Control ROR1 CAR (+cJun) |
|---|---|---|---|---|---|---|---|---|
| NR4A2 KO (−cJun) | ns | X | X | X | X | X | X | X |
| NR4A3 KO (−cJun) | * | * | X | X | X | X | X | X |
| Control ROR1 CAR (−cJun) | * | * | * | X | X | X | X | X |
| NR4A1 KO (+cJun) | ** | ** | *** | *** | X | X | X | X |
| NR4A2 KO (+cJun) | * | ** | *** | *** | * | X | X | X |
| NR4A3 KO (+cJun) | ** | *** | *** | *** | ** | ** | X | X |
| Control ROR1 CAR (+cJun) D14294 IFN-γ Stim 1 | ns | ns | ns | ns | * | ns | ** | X |
| NR4A1 KO (−cJun) | X | X | X | X | X | X | X | X |
| NR4A2 KO (−cJun) | ns | X | X | X | X | X | X | X |
| NR4A3 KO (−cJun) | ns | ** | X | X | X | X | X | X |
| Control ROR1 CAR (−cJun) | ** | *** | *** | X | X | X | X | X |
| NR4A1 KO (+cJun) | *** | **** | **** | **** | X | X | X | X |
| NR4A2 KO (+cJun) | ** | ** | *** | *** | ** | X | X | X |
| NR4A3 KO (+cJun) | *** | *** | *** | *** | ns | ** | X | X |
| Control ROR1 CAR (+cJun) D14294 IFN-γ Stim 2 | ** | ** | *** | *** | * | ns | ** | X |
| NR4A1 KO (−cJun) | X | X | X | X | X | X | X | X |
| NR4A2 KO (−cJun) | ns | X | X | X | X | X | X | X |
| NR4A3 KO (−cJun) | ** | **** | X | X | X | X | X | X |
| Control ROR1 CAR (−cJun) | *** | **** | **** | X | X | X | X | X |
| NR4A1 KO (+cJun) | ** | *** | **** | **** | X | X | X | X |
| NR4A2 KO (+cJun) | ns | ns | **** | **** | *** | X | X | X |
| NR4A3 KO (+cJun) | ** | ** | *** | *** | * | ** | X | X |
| Control ROR1 CAR (+cJun) D14294 IFN-γ Stim 3 | * | * | *** | **** | *** | ** | *** | X |
| NR4A1 KO (−cJun) | X | X | X | X | X | X | X | X |
| NR4A2 KO (−cJun) | * | X | X | X | X | X | X | X |
| NR4A3 KO (−cJun) | ** | * | X | X | X | X | X | X |
| Control ROR1 CAR (−cJun) | ** | **** | ** | X | X | X | X | X |
| NR4A1 KO (+cJun) | * | ** | ** | ** | X | X | X | X |

TABLE 9-continued

Unpaired t-test statistical analysis of secreted interferon-gamma
(IFN-γ) produced from NR4A-edited and control non-edited R0R1
CAR T cells with or without c-Jun overexpression during the H1975
sequential stimulation assay corresponding to FIG. 4.

| | NR4A1 KO (−cJun) | NR4A2 KO (−cJun) | NR4A3 KO (−cJun) | Control ROR1 CAR (−cJun) | NR4A1 KO (+cJun) | NR4A2 KO (+cJun) | NR4A3 KO (+cJun) | Control ROR1 CAR (+cJun) |
|---|---|---|---|---|---|---|---|---|
| NR4A2 KO (+cJun) | ns | ** | ** | **** | ** | X | X | X |
| NR4A3 KO (+cJun) | ** | ** | ** | ** | ** | ** | X | X |
| Control ROR1 CAR (+cJun) | ns | * |  | * |  | ns |  | X | ns—not significant, * p < 0.05,  p < 0.005, * p < 0.001, **** p < 0.0001.

TABLE 10

Unpaired t-test statistical analysis of secreted interleukin-2
(IL-2) produced from NR4A-edited and control non-edited ROR1
CAR T cells with or without c-Jun overexpression during the
H1975 sequential stimulation assay corresponding to FIG. 4.

| | NR4A1 KO (−cJun) | NR4A2 KO (−cJun) | NR4A3 KO (−cJun) | Control ROR1 CAR (−cJun) | NR4A1 KO (+cJun) | NR4A2 KO (+cJun) | NR4A3 KO (+cJun) | Control ROR1 CAR (+cJun) |
|---|---|---|---|---|---|---|---|---|
| D6871 IL-2 Stim 1 | | | | | | | | |
| NR4A1 KO (−cJun) | X | X | X | X | X | X | X | X |
| NR4A2 KO (−cJun) | ** | X | X | X | X | X | X | X |
| NR4A3 KO (−cJun) | *** | **** | X | X | X | X | X | X |
| Control ROR1 CAR (−cJun) | *** | **** | ns | X | X | X | X | X |
| NR4A1 KO (+cJun) | ** | ns | **** | **** | X | X | X | X |
| NR4A2 KO (+cJun) | ns | ns | ** | ** | ns | X | X | X |
| NR4A3 KO (+cJun) | ** | ns | **** | **** | * | ns | X | X |
| Control ROR1 CAR (+cJun) | ns | *** | **** | **** | **** | ns | *** | X |
| D6871 IL-2 Stim 2 | | | | | | | | |
| NR4A1 KO (−cJun) | X | X | X | X | X | X | X | X |
| NR4A2 KO (−cJun) | ns | X | X | X | X | X | X | X |
| NR4A3 KO (−cJun) | ns | ns | X | X | X | X | X | X |
| Control ROR1 CAR (−cJun) | ns | ns | ns | X | X | X | X | X |
| NR4A1 KO (+cJun) | ** | ** | ** | ** | X | X | X | X |
| NR4A2 KO (+cJun) | ** | *** | ** | ** | * | X | X | X |
| NR4A3 KO (+cJun) | *** | *** | *** | *** | * | ** | X | X |
| Control ROR1 CAR (+cJun) | ** | ** | ** | ns | *** | **** | *** | X |
| D6871 IL-2 Stim 3 | | | | | | | | |
| NR4A1 KO (−cJun) | X | X | X | X | X | X | X | X |
| NR4A2 KO (−cJun) | ns | X | X | X | X | X | X | X |

TABLE 10-continued

Unpaired t-test statistical analysis of secreted interleukin-2
(IL-2) produced from NR4A-edited and control non-edited ROR1
CAR T cells with or without c-Jun overexpression during the
H1975 sequential stimulation assay corresponding to FIG. 4.

| | NR4A1 KO (−cJun) | NR4A2 KO (−cJun) | NR4A3 KO (−cJun) | Control ROR1 CAR (−cJun) | NR4A1 KO (+cJun) | NR4A2 KO (+cJun) | NR4A3 KO (+cJun) | Control ROR1 CAR (+cJun) |
|---|---|---|---|---|---|---|---|---|
| NR4A3 KO (−cJun) | ns | ns | X | X | X | X | X | X |
| Control ROR1 CAR (−cJun) | * | ns | ** | X | X | X | X | X |
| NR4A1 KO (+cJun) | *** | ** | ** | *** | X | X | X | X |
| NR4A2 KO (+cJun) | *** | *** | *** | *** | * | X | X | X |
| NR4A3 KO (+cJun) | *** | *** | *** | *** | ** | *** | X | X |
| Control ROR1 CAR (+cJun) D7570 IL-2 Stim 1 | ns | ns | * | ns | *** | *** | *** | X |
| NR4A1 KO (−cJun) | X | X | X | X | X | X | X | X |
| NR4A2 KO (−cJun) | ** | X | X | X | X | X | X | X |
| NR4A3 KO (−cJun) | X | X | X | X | X | X | X | X |
| Control ROR1 CAR (−cJun) | *** | **** | X | X | X | X | X | X |
| NR4A1 KO (+cJun) | *** | ns | X | **** | X | X | X | X |
| NR4A2 KO (+cJun) | * | ns | X | *** | * | X | X | X |
| NR4A3 KO (+cJun) | *** | * | X | **** | ns | * | X | X |
| Control ROR1 CAR (+cJun) D7570 IL-2 Stim 2 | ns | **** | X | **** | *** | ** | *** | X |
| NR4A1 KO (−cJun) | X | X | X | X | X | X | X | X |
| NR4A2 KO (−cJun) | ns | X | X | X | X | X | X | X |
| NR4A3 KO (−cJun) | X | X | X | X | X | X | X | X |
| Control ROR1 CAR (−cJun) | *** | *** | X | X | X | X | X | X |
| NR4A1 KO (+cJun) | *** | ** | X | ns | X | X | X | X |
| NR4A2 KO (+cJun) | ns | ns | X | ns | ns | X | X | X |
| NR4A3 KO (+cJun) | *** | *** | X | **** | **** | ** | X | X |
| Control ROR1 CAR (+cJun) D7570 IL-2 Stim 3 | ns | ns | X | **** | *** | ns | *** | X |
| NR4A1 KO (−cJun) | X | X | X | X | X | X | X | X |
| NR4A2 KO (−cJun) | ns | X | X | X | X | X | X | X |
| NR4A3 KO (−cJun) | X | X | X | X | X | X | X | X |
| Control ROR1 CAR (−cJun) | ** | ** | X | X | X | X | X | X |
| NR4A1 KO (+cJun) | * | ns | X | ** | X | X | X | X |
| NR4A2 KO (+cJun) | ns | ns | X | ** | * | X | X | X |

TABLE 10-continued

Unpaired t-test statistical analysis of secreted interleukin-2
(IL-2) produced from NR4A-edited and control non-edited ROR1
CAR T cells with or without c-Jun overexpression during the
H1975 sequential stimulation assay corresponding to FIG. 4.

| | NR4A1 KO (−cJun) | NR4A2 KO (−cJun) | NR4A3 KO (−cJun) | Control ROR1 CAR (−cJun) | NR4A1 KO (+cJun) | NR4A2 KO (+cJun) | NR4A3 KO (+cJun) | Control ROR1 CAR (+cJun) |
|---|---|---|---|---|---|---|---|---|
| NR4A3 KO (+cJun) | *** | *** | X | **** | *** | *** | X | X |
| Control ROR1 CAR (+cJun) D13570 IL-2 Stim 1 | * | * | X | *** | ** | * | *** | X |
| NR4A1 KO (−cJun) | X | X | X | X | X | X | X | X |
| NR4A2 KO (−cJun) | ns | X | X | X | X | X | X | X |
| NR4A3 KO (−cJun) | * | ** | X | X | X | X | X | X |
| Control ROR1 CAR (−cJun) | *** | **** | *** | X | X | X | X | X |
| NR4A1 KO (+cJun) | ** | *** | **** | **** | X | X | X | X |
| NR4A2 KO (+cJun) | ns | ns | *** | *** | ns | X | X | X |
| NR4A3 KO (+cJun) | * | ** | *** | *** | ns | ns | X | X |
| Control ROR1 CAR (+cJun) D13570 IL-2 Stim 2 | ** | ** | ** | *** | **** | ** | *** | X |
| NR4A1 KO (−cJun) | X | X | X | X | X | X | X | X |
| NR4A2 KO (−cJun) | ns | X | X | X | X | X | X | X |
| NR4A3 KO (−cJun) | * | ** | X | X | X | X | X | X |
| Control ROR1 CAR (−cJun) | * | ** | * | X | X | X | X | X |
| NR4A1 KO (+cJun) | ns | * | **** | **** | X | X | X | X |
| NR4A2 KO (+cJun) | ns | * | **** | **** | ns | X | X | X |
| NR4A3 KO (+cJun) | ** | ** | ** | ** | ** | ** | X | X |
| Control ROR1 CAR (+cJun) D13570 IL-2 Stim 3 | ns | ns | ns | ns | ns | ns | * | X |
| NR4A1 KO (−cJun) | X | X | X | X | X | X | X | X |
| NR4A2 KO (−cJun) | ns | X | X | X | X | X | X | X |
| NR4A3 KO (−cJun) | * | ** | X | X | X | X | X | X |
| Control ROR1 CAR (−cJun) | * | ** | * | X | X | X | X | X |
| NR4A1 KO (+cJun) | ns | * | **** | **** | X | X | X | X |
| NR4A2 KO (+cJun) | ns | * | **** | **** | ns | X | X | X |
| NR4A3 KO (+cJun) | ** | ** | ** | ** | ** | ** | X | X |
| Control ROR1 CAR (+cJun) D14294 IL-2 Stim 1 | ns | ns | ns | ns | ns | ns | * | X |
| NR4A1 KO (−cJun) | X | X | X | X | X | X | X | X |

TABLE 10-continued

Unpaired t-test statistical analysis of secreted interleukin-2
(IL-2) produced from NR4A-edited and control non-edited ROR1
CAR T cells with or without c-Jun overexpression during the
H1975 sequential stimulation assay corresponding to FIG. 4.

| | NR4A1 KO (−cJun) | NR4A2 KO (−cJun) | NR4A3 KO (−cJun) | Control ROR1 CAR (−cJun) | NR4A1 KO (+cJun) | NR4A2 KO (+cJun) | NR4A3 KO (+cJun) | Control ROR1 CAR (+cJun) |
|---|---|---|---|---|---|---|---|---|
| NR4A2 KO (−cJun) | ns | X | X | X | X | X | X | X |
| NR4A3 KO (−cJun) | * | ** | X | X | X | X | X | X |
| Control ROR1 CAR (−cJun) | **** | **** | **** | X | X | X | X | X |
| NR4A1 KO (+cJun) | ** | **** | **** | **** | X | X | X | X |
| NR4A2 KO (+cJun) | ** | *** | **** | **** | * | X | X | X |
| NR4A3 KO (+cJun) | ns | ns | *** | *** | * | ns | X | X |
| Control ROR1 CAR (+cJun) D14294 IL-2 Stim 2 | ** | *** | *** | **** | **** | **** | ** | X |
| NR4A1 KO (−cJun) | X | X | X | X | X | X | X | X |
| NR4A2 KO (−cJun) | * | X | X | X | X | X | X | X |
| NR4A3 KO (−cJun) | * | * | X | X | X | X | X | X |
| Control ROR1 CAR (−cJun) |  |  | * | X | X | X | X | X |
| NR4A1 KO (+cJun) | ns | ** | *** | *** | X | X | X | X |
| NR4A2 KO (+cJun) | ns | * | ** | **** | ** | X | X | X |
| NR4A3 KO (+cJun) | * | ** | ** | ** | ns | * | X | X |
| Control ROR1 CAR (+cJun) D14294 IL-2 Stim 3 | ns | ns | * | *** | ** | ns | * | X |
| NR4A1 KO (−cJun) | X | X | X | X | X | X | X | X |
| NR4A2 KO (−cJun) | * | X | X | X | X | X | X | X |
| NR4A3 KO (−cJun) | * | ns | X | X | X | X | X | X |
| Control ROR1 CAR (−cJun) | *** | **** | ** | X | X | X | X | X |
| NR4A1 KO (+cJun) | * | ** | ** | *** | X | X | X | X |
| NR4A2 KO (+cJun) | ns | ** | * | **** | ** | X | X | X |
| NR4A3 KO (+cJun) | ** | ** | ** | ** | ** | ** | X | X |
| Control ROR1 CAR (+cJun) | ns | ns | ns | ** | * | ns | ** | X | ns—not significant, * p < 0.05,  p < 0.005, * p < 0.001, **** p < 0.0001.

TABLE 11

Unpaired t-test statistical analysis of secreted tumor necrosis factor alpha (TNF-α) produced from NR4A-edited and control non-edited ROR1 CAR T cells with or without c-Jun overexpression during the H1975 sequential stimulation assay corresponding to FIG. 4.

| | NR4A1 KO (−cJun) | NR4A2 KO (−cJun) | NR4A3 KO (−cJun) | Control ROR1 CAR (−cJun) | NR4A1 KO (+cJun) | NR4A2 KO (+cJun) | NR4A3 KO (+cJun) | Control ROR1 CAR (+cJun) |
|---|---|---|---|---|---|---|---|---|
| D6871 TNF-α Stim 1 | | | | | | | | |
| NR4A1 KO (−cJun) | X | X | X | X | X | X | X | X |
| NR4A2 KO (−cJun) | ns | X | X | X | X | X | X | X |
| NR4A3 KO (−cJun) | ** | *** | X | X | X | X | X | X |
| Control ROR1 CAR (−cJun) | *** | **** | ns | X | X | X | X | X |
| NR4A1 KO (+cJun) | ** | ** | *** | **** | X | X | X | X |
| NR4A2 KO (+cJun) | ns | ns | ** | *** | * | X | X | X |
| NR4A3 KO (+cJun) | * | ns | *** | **** | ** | ns | X | X |
| Control ROR1 CAR (+cJun) | ns | ** | ** | **** | *** | ns | ** | X |
| D6871 TNF-α Stim 2 | | | | | | | | |
| NR4A1 KO (−cJun) | X | X | X | X | X | X | X | X |
| NR4A2 KO (−cJun) | ns | X | X | X | X | X | X | X |
| NR4A3 KO (−cJun) | * | * | X | X | X | X | X | X |
| Control ROR1 CAR (−cJun) |  |  | * | X | X | X | X | X |
| NR4A1 KO (+cJun) | **** | **** | **** | **** | X | X | X | X |
| NR4A2 KO (+cJun) | *** | **** | **** | **** | *** | X | X | X |
| NR4A3 KO (+cJun) | *** | *** | *** | *** | * | ns | X | X |
| Control ROR1 CAR (+cJun) | ** | *** | ** | ns | **** | **** | *** | X |
| D6871 TNF-α Stim 3 | | | | | | | | |
| NR4A1 KO (−cJun) | X | X | X | X | X | X | X | X |
| NR4A2 KO (−cJun) | ns | X | X | X | X | X | X | X |
| NR4A3 KO (−cJun) | ns | ns | X | X | X | X | X | X |
| Control ROR1 CAR (−cJun) | *** | ** | ns | X | X | X | X | X |
| NR4A1 KO (+cJun) | **** | **** | *** | **** | X | X | X | X |
| NR4A2 KO (+cJun) | *** | *** | ** | *** | *** | X | X | X |
| NR4A3 KO (+cJun) | ** | ** | ** | ** | ** | ** | X | X |
| Control ROR1 CAR (+cJun) | ** | * | ns | ns | **** | *** | ** | X |
| D7570 TNF-α Stim 1 | | | | | | | | |
| NR4A1 KO (−cJun) | X | X | X | X | X | X | X | X |
| NR4A2 KO (−cJun) | * | X | X | X | X | X | X | X |
| NR4A3 KO (−cJun) | X | X | X | X | X | X | X | X |
| Control ROR1 CAR (−cJun) | ** | *** | X | X | X | X | X | X |

TABLE 11-continued

Unpaired t-test statistical analysis of secreted tumor necrosis factor
alpha (TNF-α) produced from NR4A-edited and control non-edited
ROR1 CAR T cells with or without c-Jun overexpression during the
H1975 sequential stimulation assay corresponding to FIG. 4.

| | NR4A1 KO (−cJun) | NR4A2 KO (−cJun) | NR4A3 KO (−cJun) | Control ROR1 CAR (−cJun) | NR4A1 KO (+cJun) | NR4A2 KO (+cJun) | NR4A3 KO (+cJun) | Control ROR1 CAR (+cJun) |
|---|---|---|---|---|---|---|---|---|
| NR4A1 KO (+cJun) | *** | *** | X | **** | X | X | X | X |
| NR4A2 KO (+cJun) | ns | ns | X | *** | **** | X | X | X |
| NR4A3 KO (+cJun) | *** | ** | X | **** | ns | *** | X | X |
| Control ROR1 CAR (+cJun) D7570 TNF-α Stim 2 | * | ns | X | *** | **** | ns | *** | X |
| NR4A1 KO (−cJun) | X | X | X | X | X | X | X | X |
| NR4A2 KO (−cJun) | * | X | X | X | X | X | X | X |
| NR4A3 KO (−cJun) | X | X | X | X | X | X | X | X |
| Control ROR1 CAR (−cJun) | **** | **** | X | X | X | X | X | X |
| NR4A1 KO (+cJun) | ** | **** | X | **** | X | X | X | X |
| NR4A2 KO (+cJun) | ns | * | X | ns | ns | X | X | X |
| NR4A3 KO (+cJun) | *** | *** | X | **** | **** | *** | X | X |
| Control ROR1 CAR (+cJun) D7570 TNF-α Stim 3 | ** | **** | X | **** | ns | ns | **** | X |
| NR4A1 KO (−cJun) | X | X | X | X | X | X | X | X |
| NR4A2 KO (−cJun) | ns | X | X | X | X | X | X | X |
| NR4A3 KO (−cJun) | X | X | X | X | X | X | X | X |
| Control ROR1 CAR (−cJun) | *** | ** | X | X | X | X | X | X |
| NR4A1 KO (+cJun) | * | ns | X | ** | X | X | X | X |
| NR4A2 KO (+cJun) | ns | ns | X | **** | * | X | X | X |
| NR4A3 KO (+cJun) | **** | **** | X | **** | **** | **** | X | X |
| Control ROR1 CAR (+cJun) D13570 TNF-α Stim 1 | * | * | X | **** | ** | *** | **** | X |
| NR4A1 KO (−cJun) | X | X | X | X | X | X | X | X |
| NR4A2 KO (−cJun) | * | X | X | X | X | X | X | X |
| NR4A3 KO (−cJun) | * | ns | X | X | X | X | X | X |
| Control ROR1 CAR (−cJun) | ns | * | ** | X | X | X | X | X |
| NR4A1 KO (+cJun) | **** | ** | *** | **** | X | X | X | X |
| NR4A2 KO (+cJun) | *** | ns | ** | **** | * | X | X | X |
| NR4A3 KO (+cJun) | *** | *** | *** | **** | ** | *** | X | X |
| Control ROR1 CAR (+cJun) D13570 TNF-α Stim 2 | * | ns | ns | ** | * | ns | *** | X |
| NR4A1 KO (−cJun) | X | X | X | X | X | X | X | X |

TABLE 11-continued

Unpaired t-test statistical analysis of secreted tumor necrosis factor alpha (TNF-α) produced from NR4A-edited and control non-edited ROR1 CAR T cells with or without c-Jun overexpression during the H1975 sequential stimulation assay corresponding to FIG. 4.

| | NR4A1 KO (−cJun) | NR4A2 KO (−cJun) | NR4A3 KO (−cJun) | Control ROR1 CAR (−cJun) | NR4A1 KO (+cJun) | NR4A2 KO (+cJun) | NR4A3 KO (+cJun) | Control ROR1 CAR (+cJun) |
|---|---|---|---|---|---|---|---|---|
| NR4A2 KO (−cJun) | ns | X | X | X | X | X | X | X |
| NR4A3 KO (−cJun) | ** | *** | X | X | X | X | X | X |
| Control ROR1 CAR (−cJun) | ** | *** | * | X | X | X | X | X |
| NR4A1 KO (+cJun) | * | ** | **** | **** | X | X | X | X |
| NR4A2 KO (+cJun) | ns | * | *** | *** | * | X | X | X |
| NR4A3 KO (+cJun) | ** | ** | *** | *** | ns | ** | X | X |
| Control ROR1 CAR (+cJun) D13570 TNF-α Stim 3 | ns | * | ** | ** | *** | ** | *** | X |
| NR4A1 KO (−cJun) | X | X | X | X | X | X | X | X |
| NR4A2 KO (−cJun) | ns | X | X | X | X | X | X | X |
| NR4A3 KO (−cJun) | ns | ** | X | X | X | X | X | X |
| Control ROR1 CAR (−cJun) | ns | ** | ns | X | X | X | X | X |
| NR4A1 KO (+cJun) | ns | ** | **** | **** | X | X | X | X |
| NR4A2 KO (+cJun) | ns | ** | **** | **** | * | X | X | X |
| NR4A3 KO (+cJun) | * | *** | **** | **** | *** | ** | X | X |
| Control ROR1 CAR (+cJun) D14294 TNF-α Stim 1 | ns | ns | ns | ns | ns | ns | ** | X |
| NR4A1 KO (−cJun) | X | X | X | X | X | X | X | X |
| NR4A2 KO (−cJun) | ns | X | X | X | X | X | X | X |
| NR4A3 KO (−cJun) | ns | ** | X | X | X | X | X | X |
| Control ROR1 CAR (−cJun) | * | ** | * | X | X | X | X | X |
| NR4A1 KO (+cJun) | *** | *** | **** | *** | X | X | X | X |
| NR4A2 KO (+cJun) | *** | *** | **** | *** | ** | X | X | X |
| NR4A3 KO (+cJun) | *** | *** | *** | *** | * | ** | X | X |
| Control ROR1 CAR (+cJun) D14294 TNF-α Stim 2 | ** | ** | *** | *** | ** | ns | ** | X |
| NR4A1 KO (−cJun) | X | X | X | X | X | X | X | X |
| NR4A2 KO (−cJun) | ns | X | X | X | X | X | X | X |
| NR4A3 KO (−cJun) | * | ** | X | X | X | X | X | X |
| Control ROR1 CAR (−cJun) | *** | **** | **** | X | X | X | X | X |
| NR4A1 KO (+cJun) | ** | *** | **** | **** | X | X | X | X |
| NR4A2 KO (+cJun) | ns | ns | **** | **** | *** | X | X | X |
| NR4A3 KO (+cJun) | ** | ** | *** | **** | ns | ** | X | X |

TABLE 11-continued

Unpaired t-test statistical analysis of secreted tumor necrosis factor
alpha (TNF-α) produced from NR4A-edited and control non-edited
ROR1 CAR T cells with or without c-Jun overexpression during the
H1975 sequential stimulation assay corresponding to FIG. 4.

| | NR4A1 KO (−cJun) | NR4A2 KO (−cJun) | NR4A3 KO (−cJun) | Control ROR1 CAR (−cJun) | NR4A1 KO (+cJun) | NR4A2 KO (+cJun) | NR4A3 KO (+cJun) | Control ROR1 CAR (+cJun) |
|---|---|---|---|---|---|---|---|---|
| Control ROR1 CAR (+cJun) D14294 TNF-α Stim 3 | ** | *** | ** | *** | **** | *** | *** | X |
| NR4A1 KO (−cJun) | X | X | X | X | X | X | X | X |
| NR4A2 KO (−cJun) | ** | X | X | X | X | X | X | X |
| NR4A3 KO (−cJun) | * | ns | X | X | X | X | X | X |
| Control ROR1 CAR (−cJun) | **** | *** | ** | X | X | X | X | X |
| NR4A1 KO (+cJun) | * | ** | ** | *** | X | X | X | X |
| NR4A2 KO (+cJun) | ns | ns | ns | **** | ** | X | X | X |
| NR4A3 KO (+cJun) | ** | ** | ** | *** | ** | ** | X | X |
| Control ROR1 CAR (+cJun) | * | ns | ns | * |  | ns | ** | X | ns—not significant,
* p < 0.05,
** p < 0.005,
*** p < 0.001,
**** p < 0.0001.

The differences in cytokine production were most notable following later rounds of stimulation, suggesting NR4A3 knockout and c-Jun overexpression contribute to sustained functional activity and/or improved CAR T cell survival following prolonged antigen stimulation. Indeed, higher maintenance of ROR1 CAR frequency in NR4A-edited c-Jun overexpressing ROR1 CAR T cells was observed (FIG. 5A). Consequently, this correlated to increased persistence of total NR4A3 KO c-Jun overexpressing ROR1 CAR T cell numbers at stimulation rounds 2-3 (FIG. 5B). NR4A3 KO c-Jun ROR1 CAR T cells demonstrated an altered cell surface phenotype consistent with reduced exhaustion after the second round of stimulation (FIG. 6). NR4A3 KO led to significantly lower expression of TIM3 and TIGIT in all 4 donors and lower PD-1 in 3 of 4 donors compared to non-edited c-Jun ROR1 CAR T cells. Interestingly, CD127 expression was significantly higher on NR4A3 KO c-Jun ROR1 CAR T cells compared to non-edited c-Jun ROR1 CAR T cells after the second round of stimulation even though CD127 expression was similar at baseline (day 0, data not shown). CD127 has been shown to be a marker for antigen-specific memory $CD8^+$ T cells in various viral infections (Huster et al., *PNAS*, 101, 5610-5615 (2004); Boettler et al., *J. Virol.* 80, 3532-3540 (2006); Xu et al., *Lab. Med.* 48, 57-64 (2017)), suggesting c-Jun overexpression in the absence of NR4A3 can synergize to maintain a more memory-like T cell state compared to c-Jun or KO alone.

The in vitro sequential stimulation model of T cell exhaustion revealed that NR4A3-edited c-Jun overexpressing ROR1 CAR T cells exhibited maximal enhancement and sustained cytotoxicity and cytokine production against ROR1-expressing H1975 tumor cells in four independent donors. The increased functional activity at later rounds of stimulation is likely at least partially due to the increased persistence of NR4A3-edited c-Jun ROR1 CAR T cells throughout the assay. Therefore, editing NR4A3 in combination with c-Jun overexpression in the context of ROR1-R12 CAR T cells can improve cellular immunotherapy against ROR1-expressing solid tumors.

Statistical analyses were performed using GraphPad Prism unpaired t-test and paired t-tests were used for statistical analysis. ns—not significant, *p<0.05,  p<0.005, *p<0.001, ****p<0.0001.

Example 4—Sustained Cytotoxicity and Cytokine Production of NR4A Triple KO (TKO) c-Jun CAR T Cells Upon Sequential Stimulation The function of c-Jun+NR4A triple KO (TKO) ROR1 CAR T cells (in which CAR T cells were edited at NR4A1, NR4A2, and NR4A3) with c-Jun overexpression were evaluated in an in vitro exhaustion assay in which CAR T cells are sequentially exposed to antigen. Before setting up the assays, H1975-NucLight Red (NLR) and A549-NLR tumor cells lines were cultured in RPMI-1640 (Gibco)+10% fetal bovine serum (Gibco)+1% penicillin/streptomycin for 2-3 passages. Cells were trypsinized with TrypLE Express enzyme (Gibco).

In the sequential stimulation assay, NR4A TKO or control (non-edited) c-Jun overexpressing ROR1 CAR T cells were subjected to five successive stimulations with the H1975 or A549 NSCLC ROR1-expressing tumor cell lines. In particular, cryopreserved ROR1 CAR T cells were thawed and immediately cultured at a 1:1 E:T ratio of cParp-CD3+ EGFR+R12+CAR T cells with H1975-NLR or A549-NLR tumor cells in RPMI-1640 (Gibco)+10% fetal bovine serum (Gibco)+1% penicillin/streptomycin in triplicates in flat 24 well assay plates (Eppendorf). After 3 days of co-culture, wells were resuspended, and 25% of the culture was transferred onto new plates with the same initial number of fresh tumor cells per well. This was repeated for a total of 5 stimulations. Cytotoxicity was measured continuously in the Incucyte during the assay and supernatants were collected 24 hours after setting up each new stimulation to measure cytokine levels. Remaining cells from the triplicate co-culture wells were combined for phenotypic flow analyses as described above. NR4A TKO c-Jun overexpressing ROR1 CAR T cells remained more cytotoxic against H1975 and/or A549 tumor cells compared to control c-Jun ROR1 CAR T cells, demonstrating a sustained ability to lyse target cells after five rounds of stimulation in 3 different donors (FIG. 7). In addition to sustained cytotoxicity, NR4A TKO c-Jun overexpressing ROR1 CAR T cells also produced higher levels of IFN-γ, IL-2, and TNF-α compared to control (non-edited) c-Jun overexpressing ROR1 CAR T cells (FIG. 8-10) after multiple stimulations with H1975 and/or A549. Cytokine levels were measured using Meso Scale Discovery V-Plex proinflammatory panel 1 human kits or custom human IFN-γ, IL-2, and TNF-α cytokine kits following the manufacturer's instructions. The increased cytotoxicity and cytokine secretion correlated with enhanced persistence of NR4A TKO compared to control c-Jun overexpressing ROR1 CAR T cells at later stimulations with H1975 in all 3 donors (FIG. 11).

Example 5—Sustained Cytotoxicity and Cytokine Production of Engineered TCR T Cells in Sequential Stimulation The function of single NR4A-edited NY-ESO-1 TCR T cells (in which TCR T cells were edited at either NR4A1, NR4A2, or NR4A3) with and without c-Jun overexpression were evaluated in an in vitro exhaustion assay in which TCR T cells are sequentially exposed to antigen. Before setting up the assays, A375-NucLight Red (NLR) tumor cells lines were cultured in RPMI-1640 (Gibco)+10% fetal bovine serum (Gibco)+1% penicillin/streptomycin for 2-3 passages. Cells were trypsinized with Accutase enzyme (StemCell Technologies).

In the sequential stimulation assay, NR4A-edited control and c-Jun overexpressing NY-ESO-1 TCR T cells were subjected to four successive stimulations with the A375 melanoma NY-ESO-1/LAGE-1a-expressing tumor cell line. In particular, cryopreserved NY-ESO-1 TCR T cells were thawed and immediately cultured at a 1:1 E:T ratio of $cParp^-CD3^+TCRv\beta13.1^+$ TCR T cells with A375-NLR tumor cells in RPMI-1640 (Gibco)+10% fetal bovine serum (Gibco)+1% penicillin/streptomycin in triplicates in flat 96 well assay plates (Eppendorf). After 3 or 4 days of co-culture, wells were resuspended, and 25% of the culture was transferred onto new plates with the same initial number of fresh tumor cells per well. This was repeated for a total of 4 stimulations. Cytotoxicity was measured continuously in the Incucyte during the assay and supernatants were collected 24 hours after setting up each new stimulation to measure cytokine levels. c-Jun overexpressing TCR T cells outperformed the non-c-Jun control TCR T cells. Unexpectedly, NR4A3 KO c-Jun overexpressing NY-ESO-1 TCR T cells remained the most cytotoxic against A375 tumor cells, demonstrating a sustained ability to lyse target cells after four rounds of stimulation compared to all other conditions in 3 different donors (FIG. 14).

In addition to sustained cytotoxicity, NR4A3 KO c-Jun overexpressing NY-ESO-1 TCR T cells also produced the highest levels of IFN-γ, IL-2, and TNF-α compared to NR4A1, NR4A2, or non-edited control and c-Jun NY-ESO-1 TCR T cells (FIG. 15 and Tables 12-14) when stimulated with A375 melanoma NY-ESO-1/LAGE-1a-expressing tumor cells. Similar results were observed when T cells were serially stimulated using a second NY-ESO-1/LAGE-1a-expressing tumor cell line H1703 (data not shown). Cytokine levels were measured using Meso Scale Discovery V-Plex proinflammatory panel 1 human kits or custom human IFN-γ, IL-2, and TNF-α cytokine kits following the manufacturer's instructions. The differences in cytokine production were most notable following later rounds of stimulation.

TABLE 12

Unpaired t-test statistical analysis of secreted interferon-gamma (IFN-γ) produced from NR4A-edited and control non-edited NY-ESO-1 TCR T cells with or without c-Jun overexpression during the A375 sequential stimulation assay corresponding to FIG. 15.

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| D33018 IFN-γ Stim 1 | | | | | | | | | |
| NR4A1 KO (−cJun) | X | X | X | X | X | X | X | X | X |
| NR4A2 KO (−cJun) | ** | X | X | X | X | X | X | X | X |
| NR4A3 KO (−cJun) | ** | ns | X | X | X | X | X | X | X |
| Control TCR (−cJun) | ns | ns | ns | X | X | X | X | X | X |
| NR4A1 KO (+cJun) | * | *** | *** | ** | X | X | X | X | X |
| NR4A2 KO (+cJun) | *** | **** | **** | *** | ** | X | X | X | X |
| NR4A3 KO (+cJun) | * | ** | ** | ** | ns | ns | X | X | X |
| Control TCR (+cJun) | ns | ** | ** | * | ns | * | * | X | X |
| Mock | **** | **** | **** | **** | **** | **** | *** | **** | X |
| D33018 IFN-γ Stim 2 | | | | | | | | | |
| NR4A1 KO (−cJun) | X | X | X | X | X | X | X | X | X |

TABLE 12-continued

Unpaired t-test statistical analysis of secreted interferon-gamma (IFN-γ) produced
from NR4A-edited and control non-edited NY-ESO-1 TCR T cells with or without c-Jun
overexpression during the A375 sequential stimulation assay corresponding to FIG. 15.

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| NR4A2 KO (−cJun) | ** | X | X | X | X | X | X | X | X |
| NR4A3 KO (−cJun) | ns | ** | X | X | X | X | X | X | X |
| Control TCR (−cJun) | ns | ns | ns | X | X | X | X | X | X |
| NR4A1 KO (+cJun) | *** | *** | ** | ** | X | X | X | X | X |
| NR4A2 KO (+cJun) | *** | *** | *** | *** | ns | X | X | X | X |
| NR4A3 KO (+cJun) | **** | **** | **** | **** | *** | ** | X | X | X |
| Control TCR (+cJun) | ** | *** | ** | ** | ns | ns | ** | X | X |
| Mock | **** | **** | *** | ** | **** | **** | **** | **** | X |

D33018 IFN-γ Stim 3

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| NR4A1 KO (−cJun) | X | X | X | X | X | X | X | X | X |
| NR4A2 KO (−cJun) | ** | X | X | X | X | X | X | X | X |
| NR4A3 KO (−cJun) | ns | * | X | X | X | X | X | X | X |
| Control TCR (−cJun) | ns | ns | ns | X | X | X | X | X | X |
| NR4A1 KO (+cJun) | *** | *** | *** | *** | X | X | X | X | X |
| NR4A2 KO (+cJun) | *** | *** | *** | *** | ns | X | X | X | X |
| NR4A3 KO (+cJun) | **** | **** | **** | **** | ** | * | X | X | X |
| Control TCR (+cJun) | **** | **** | **** | **** | * | ** | *** | X | X |
| Mock | *** | **** | *** | ** | *** | *** | **** | **** | X |

D33018 IFN-γ Stim 4

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| NR4A1 KO (−cJun) | X | X | X | X | X | X | X | X | X |
| NR4A2 KO (−cJun) | ** | X | X | X | X | X | X | X | X |
| NR4A3 KO (−cJun) | ns | * | X | X | X | X | X | X | X |
| Control TCR (−cJun) | * | ns | ns | X | X | X | X | X | X |
| NR4A1 KO (+cJun) | **** | **** | **** | **** | X | X | X | X | X |
| NR4A2 KO (+cJun) | **** | **** | **** | **** | ns | X | X | X | X |
| NR4A3 KO (+cJun) | *** | *** | *** | *** | * | * | X | X | X |
| Control TCR (+cJun) | **** | **** | **** | **** | ** | ** | ** | X | X |
| Mock | **** | **** | ** | ** | **** | **** | *** | **** | X |

D35108 IFN-γ Stim 1

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| NR4A1 KO (−cJun) | X | X | X | X | X | X | X | X | X |
| NR4A2 KO (−cJun) | ** | X | X | X | X | X | X | X | X |
| NR4A3 KO (−cJun) | ns | ** | X | X | X | X | X | X | X |
| Control TCR (−cJun) | ** | ns | ** | X | X | X | X | X | X |
| NR4A1 KO (+cJun) | ns | * | ns | * | X | X | X | X | X |
| NR4A2 KO (+cJun) | ns | ** | * | ** | ns | X | X | X | X |
| NR4A3 KO (+cJun) | * | *** | ** | *** | ns | ns | X | X | X |

TABLE 12-continued

Unpaired t-test statistical analysis of secreted interferon-gamma (IFN-γ) produced
from NR4A-edited and control non-edited NY-ESO-1 TCR T cells with or without c-Jun
overexpression during the A375 sequential stimulation assay corresponding to FIG. 15.

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| Control TCR (+cJun) | ** | *** | ** | *** | ns | * | * | X | X |
| Mock | **** | **** | **** | **** | *** | **** | **** | **** | X |
| D35108 IFN-γ Stim 2 | | | | | | | | | |
| NR4A1 KO (−cJun) | X | X | X | X | X | X | X | X | X |
| NR4A2 KO (−cJun) | *** | X | X | X | X | X | X | X | X |
| NR4A3 KO (−cJun) | ns | **** | X | X | X | X | X | X | X |
| Control TCR (−cJun) | *** | ns | *** | X | X | X | X | X | X |
| NR4A1 KO (+cJun) | ** | **** | ** | **** | X | X | X | X | X |
| NR4A2 KO (+cJun) | ** | **** | * | *** | ns | X | X | X | X |
| NR4A3 KO (+cJun) | *** | **** | *** | **** | ** | ** | X | X | X |
| Control TCR (+cJun) | ** | *** | ** | *** | * | * | ns | X | X |
| Mock | **** | **** | **** | **** | **** | **** | **** | *** | X |
| D35108 IFN-γ Stim 3 | | | | | | | | | |
| NR4A1 KO (−cJun) | X | X | X | X | X | X | X | X | X |
| NR4A2 KO (−cJun) | ** | X | X | X | X | X | X | X | X |
| NR4A3 KO (−cJun) | ns | *** | X | X | X | X | X | X | X |
| Control TCR (−cJun) | ** | ** | **** | X | X | X | X | X | X |
| NR4A1 KO (+cJun) | ** | ** | ** | ** | X | X | X | X | X |
| NR4A2 KO (+cJun) | ** | ** | ** | ** | * | X | X | X | X |
| NR4A3 KO (+cJun) | * | * | * | * | ns | ns | X | X | X |
| Control TCR (+cJun) | ** | ** | ** | ** | ns | ** | ns | X | X |
| Mock | *** | **** | **** | **** | ** | *** | * | ** | X |
| D35108 IFN-γ Stim 4 | | | | | | | | | |
| NR4A1 KO (−cJun) | X | X | X | X | X | X | X | X | X |
| NR4A2 KO (−cJun) | *** | X | X | X | X | X | X | X | X |
| NR4A3 KO (−cJun) | ns | *** | X | X | X | X | X | X | X |
| Control TCR (−cJun) | *** | * | *** | X | X | X | X | X | X |
| NR4A1 KO (+cJun) | * | * | * | ** | X | X | X | X | X |
| NR4A2 KO (+cJun) | ** | *** | ** | *** | * | X | X | X | X |
| NR4A3 KO (+cJun) | * | * | * | * | ns | ns | X | X | X |
| Control TCR (+cJun) | ** | ** | ** | ** | ns | * | ns | X | X |
| Mock | **** | **** | **** | **** | ** | *** | * | ** | X |
| D37244 IFN-γ Stim 1 | | | | | | | | | |
| NR4A1 KO (−cJun) | X | X | X | X | X | X | X | X | X |
| NR4A2 KO (−cJun) | ns | X | X | X | X | X | X | X | X |
| NR4A3 KO (−cJun) | ns | * | X | X | X | X | X | X | X |

TABLE 12-continued

Unpaired t-test statistical analysis of secreted interferon-gamma (IFN-γ) produced
from NR4A-edited and control non-edited NY-ESO-1 TCR T cells with or without c-Jun
overexpression during the A375 sequential stimulation assay corresponding to FIG. 15.

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| Control TCR (−cJun) | ** | ** | * | X | X | X | X | X | X |
| NR4A1 KO (+cJun) | ns | ns | ns | ** | X | X | X | X | X |
| NR4A2 KO (+cJun) | ** | ** | * | ns | ** | X | X | X | X |
| NR4A3 KO (+cJun) | ns | ns | * | *** | ns | *** | X | X | X |
| Control TCR (+cJun) | ns | ns | ns | * | ns | * | ns | X | X |
| Mock | **** | **** | **** | **** | **** | **** | **** | *** | X |

D37244 IFN-γ Stim 2

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| NR4A1 KO (−cJun) | X | X | X | X | X | X | X | X | X |
| NR4A2 KO (−cJun) | ns | X | X | X | X | X | X | X | X |
| NR4A3 KO (−cJun) | ** | * | X | X | X | X | X | X | X |
| Control TCR (−cJun) | *** | *** | **** | X | X | X | X | X | X |
| NR4A1 KO (+cJun) | *** | *** | *** | **** | X | X | X | X | X |
| NR4A2 KO (+cJun) | *** | *** | ** | *** | ns | X | X | X | X |
| NR4A3 KO (+cJun) | **** | **** | **** | **** | ns | * | X | X | X |
| Control TCR (+cJun) | **** | **** | **** | **** | ns | * | ns | X | X |
| Mock | **** | **** | **** | **** | **** | **** | **** | **** | X |

D37244 IFN-γ Stim 3

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| NR4A1 KO (−cJun) | X | X | X | X | X | X | X | X | X |
| NR4A2 KO (−cJun) | ** | X | X | X | X | X | X | X | X |
| NR4A3 KO (−cJun) | ** | ns | X | X | X | X | X | X | X |
| Control TCR (−cJun) | * | *** | *** | X | X | X | X | X | X |
| NR4A1 KO (+cJun) | **** | **** | **** | **** | X | X | X | X | X |
| NR4A2 KO (+cJun) | ** | ** | ** | ** | ns | X | X | X | X |
| NR4A3 KO (+cJun) | **** | **** | **** | **** | ** | ns | X | X | X |
| Control TCR (+cJun) | **** | **** | **** | **** | ns | ns | *** | X | X |
| Mock | **** | **** | **** | **** | **** | ** | **** | **** | X |

D37244 IFN-γ Stim 4

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| NR4A1 KO (−cJun) | X | X | X | X | X | X | X | X | X |
| NR4A2 KO (−cJun) | ns | X | X | X | X | X | X | X | X |
| NR4A3 KO (−cJun) | ns | ns | X | X | X | X | X | X | X |
| Control TCR (−cJun) | ** | *** | ** | X | X | X | X | X | X |
| NR4A1 KO (+cJun) | **** | **** | **** | **** | X | X | X | X | X |
| NR4A2 KO (+cJun) | **** | **** | **** | **** | ns | X | X | X | X |
| NR4A3 KO (+cJun) | **** | **** | **** | **** | *** | *** | X | X | X |

TABLE 12-continued

Unpaired t-test statistical analysis of secreted interferon-gamma (IFN-γ) produced
from NR4A-edited and control non-edited NY-ESO-1 TCR T cells with or without c-Jun
overexpression during the A375 sequential stimulation assay corresponding to FIG. 15.

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| Control TCR (+cJun) | **** | **** | **** | **** | ** | ns | **** | X | X |
| Mock | ** |  |  |  |  |  |  | ** | X | ns—not significant,
* p < 0.05,
** p < 0.005,
*** p < 0.001,
**** p < 0.0001.

TABLE 13

Unpaired t-test statistical analysis of secreted interleukin-2
(IL-2) produced from NR4A-edited and control non-edited NY-ESO-1
TCR T cells with or without c-Jun overexpression during the A375
sequential stimulation assay corresponding to FIG. 15.

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| D33018 IL-2 Stim 1 | | | | | | | | | |
| NR4A1 KO (−cJun) | X | X | X | X | X | X | X | X | X |
| NR4A2 KO (−cJun) | * | X | X | X | X | X | X | X | X |
| NR4A3 KO (−cJun) | ** | * | X | X | X | X | X | X | X |
| Control TCR (−cJun) | * | ns | * | X | X | X | X | X | X |
| NR4A1 KO (+cJun) | **** | *** | *** | *** | X | X | X | X | X |
| NR4A2 KO (+cJun) | *** | *** | *** | *** | * | X | X | X | X |
| NR4A3 KO (+cJun) | **** | **** | **** | **** | **** | *** | X | X | X |
| Control TCR (+cJun) | *** | *** | ** | ** | * | ns | ** | X | X |
| Mock | **** | **** | **** | **** | **** | **** | **** | **** | X |
| D33018 IL-2 Stim 2 | | | | | | | | | |
| NR4A1 KO (−cJun) | X | X | X | X | X | X | X | X | X |
| NR4A2 KO (−cJun) | ** | X | X | X | X | X | X | X | X |
| NR4A3 KO (−cJun) | * | ns | X | X | X | X | X | X | X |
| Control TCR (−cJun) | ** | ns | ns | X | X | X | X | X | X |
| NR4A1 KO (+cJun) | ns | ** | * | ** | X | X | X | X | X |
| NR4A2 KO (+cJun) | ns | * | ns | * | ns | X | X | X | X |
| NR4A3 KO (+cJun) | ns | ** | * | ** | ns | ns | X | X | X |
| Control TCR (+cJun) | * | ** | ** | ** | * | ns | * | X | X |
| Mock | *** | *** | ** | ** | *** | ** | *** | *** | X |
| D33018 IL-2 Stim 3 | | | | | | | | | |
| NR4A1 KO (−cJun) | X | X | X | X | X | X | X | X | X |
| NR4A2 KO (−cJun) | ns | X | X | X | X | X | X | X | X |
| NR4A3 KO (−cJun) | * | ns | X | X | X | X | X | X | X |

TABLE 13-continued

Unpaired t-test statistical analysis of secreted interleukin-2
(IL-2) produced from NR4A-edited and control non-edited NY-ESO-1
TCR T cells with or without c-Jun overexpression during the A375
sequential stimulation assay corresponding to FIG. 15.

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| Control TCR (−cJun) | ns | ns | * | X | X | X | X | X | X |
| NR4A1 KO (+cJun) | **** | **** | **** | **** | X | X | X | X | X |
| NR4A2 KO (+cJun) | **** | **** | **** | **** | * | X | X | X | X |
| NR4A3 KO (+cJun) | *** | *** | *** | *** | ** | ** | X | X | X |
| Control TCR (+cJun) | **** | **** | **** | **** | *** | *** | *** | X | X |
| Mock | ns | ns | * | ns | **** | **** | *** | **** | X |
| D33018 IL-2 Stim 4 | | | | | | | | | |
| NR4A1 KO (−cJun) | X | X | X | X | X | X | X | X | X |
| NR4A2 KO (−cJun) | * | X | X | X | X | X | X | X | X |
| NR4A3 KO (−cJun) | ns | ns | X | X | X | X | X | X | X |
| Control TCR (−cJun) | ns | * | ns | X | X | X | X | X | X |
| NR4A1 KO (+cJun) | ** | ** | ** | ** | X | X | X | X | X |
| NR4A2 KO (+cJun) | ** | ** | ** | ** | ns | X | X | X | X |
| NR4A3 KO (+cJun) | ** | ** | ** | ** | ** | ns | X | X | X |
| Control TCR (+cJun) | *** | *** | *** | *** | ns | ns | * | X | X |
| Mock | ns | * | ns | ns | ** | ** | ** | *** | X |
| D35108 IL-2 Stim 1 | | | | | | | | | |
| NR4A1 KO (−cJun) | X | X | X | X | X | X | X | X | X |
| NR4A2 KO (−cJun) | ** | X | X | X | X | X | X | X | X |
| NR4A3 KO (−cJun) | ** | ns | X | X | X | X | X | X | X |
| Control TCR (−cJun) | * | ns | ns | X | X | X | X | X | X |
| NR4A1 KO (+cJun) | **** | *** | **** | **** | X | X | X | X | X |
| NR4A2 KO (+cJun) | **** | **** | **** | **** | **** | X | X | X | X |
| NR4A3 KO (+cJun) | **** | *** | **** | **** | ** | ns | X | X | X |
| Control TCR (+cJun) | **** | **** | **** | **** | *** | ns | ns | X | X |
| Mock | *** | **** | **** | **** | **** | **** | **** | **** | X |
| D35108 IL-2 Stim 2 | | | | | | | | | |
| NR4A1 KO (−cJun) | X | X | X | X | X | X | X | X | X |
| NR4A2 KO (−cJun) | ** | X | X | X | X | X | X | X | X |
| NR4A3 KO (−cJun) | * | ** | X | X | X | X | X | X | X |
| Control TCR (−cJun) | ** | ** | *** | X | X | X | X | X | X |
| NR4A1 KO (+cJun) | *** | *** | *** | ** | X | X | X | X | X |
| NR4A2 KO (+cJun) | ** | * | ** | ns | ns | X | X | X | X |
| NR4A3 KO (+cJun) | ** | ** | ** | ns | ns | ns | X | X | X |

TABLE 13-continued

Unpaired t-test statistical analysis of secreted interleukin-2
(IL-2) produced from NR4A-edited and control non-edited NY-ESO-1
TCR T cells with or without c-Jun overexpression during the A375
sequential stimulation assay corresponding to FIG. 15.

|  | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| Control TCR (+cJun) | ** | ns | * | ns | * | ns | ns | X | X |
| Mock | *** | **** | **** | **** | *** | ** | ** | ** | X |
| D35108 IL-2 Stim 3 | | | | | | | | | |
| NR4A1 KO (−cJun) | X | X | X | X | X | X | X | X | X |
| NR4A2 KO (−cJun) | ns | X | X | X | X | X | X | X | X |
| NR4A3 KO (−cJun) | * | **** | X | X | X | X | X | X | X |
| Control TCR (−cJun) | ns | ** | **** | X | X | X | X | X | X |
| NR4A1 KO (+cJun) | ** | ** | ** | ** | X | X | X | X | X |
| NR4A2 KO (+cJun) | ** | ** | ** | ** | * | X | X | X | X |
| NR4A3 KO (+cJun) | ** | ** | * | ** | ns | ns | X | X | X |
| Control TCR (+cJun) | ** | ** | ** | ** | ns | * | ns | X | X |
| Mock | ns | ** | **** | ns | ** | ** | ** | ** | X |
| D35108 IL-2 Stim 4 | | | | | | | | | |
| NR4A1 KO (−cJun) | X | X | X | X | X | X | X | X | X |
| NR4A2 KO (−cJun) | ns | X | X | X | X | X | X | X | X |
| NR4A3 KO (−cJun) | * | ** | X | X | X | X | X | X | X |
| Control TCR (−cJun) | ns | * | ** | X | X | X | X | X | X |
| NR4A1 KO (+cJun) | **** | **** | **** | **** | X | X | X | X | X |
| NR4A2 KO (+cJun) | ** | ** | ** | ** | ns | X | X | X | X |
| NR4A3 KO (+cJun) | **** | **** | **** | **** | ** | ** | X | X | X |
| Control TCR (+cJun) | ** | ** | ** | ** | ns | ns | ** | X | X |
| Mock | * | ** | ** | * | **** | ** | **** | ** | X |
| D37244 IL-2 Stim 1 | | | | | | | | | |
| NR4A1 KO (−cJun) | X | X | X | X | X | X | X | X | X |
| NR4A2 KO (−cJun) | ns | X | X | X | X | X | X | X | X |
| NR4A3 KO (−cJun) | ns | ns | X | X | X | X | X | X | X |
| Control TCR (−cJun) | ns | ** | ** | X | X | X | X | X | X |
| NR4A1 KO (+cJun) | *** | *** | *** | *** | X | X | X | X | X |
| NR4A2 KO (+cJun) | **** | **** | **** | **** | ns | X | X | X | X |
| NR4A3 KO (+cJun) | **** | **** | **** | **** | ns | * | X | X | X |
| Control TCR (+cJun) | **** | **** | **** | **** | * | ** | * | X | X |

TABLE 13-continued

Unpaired t-test statistical analysis of secreted interleukin-2
(IL-2) produced from NR4A-edited and control non-edited NY-ESO-1
TCR T cells with or without c-Jun overexpression during the A375
sequential stimulation assay corresponding to FIG. 15.

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| Mock D37244 IL-2 Stim 2 | ** | **** | **** | **** | **** | **** | **** | **** | X |
| NR4A1 KO (−cJun) | X | X | X | X | X | X | X | X | X |
| NR4A2 KO (−cJun) | ns | X | X | X | X | X | X | X | X |
| NR4A3 KO (−cJun) | ns | ns | X | X | X | X | X | X | X |
| Control TCR (−cJun) | * | * | ns | X | X | X | X | X | X |
| NR4A1 KO (+cJun) | ** | ** | ** | ** | X | X | X | X | X |
| NR4A2 KO (+cJun) | ** | ** | ** | ** | ns | X | X | X | X |
| NR4A3 KO (+cJun) | ** | ** | ** | ** | * | ns | X | X | X |
| Control TCR (+cJun) | ** | ** | ** | *** | ns | * | ** | X | X |
| Mock D37244 IL-2 Stim 3 | *** | *** | ** | *** | *** | *** | *** | *** | X |
| NR4A1 KO (−cJun) | X | X | X | X | X | X | X | X | X |
| NR4A2 KO (−cJun) | * | X | X | X | X | X | X | X | X |
| NR4A3 KO (−cJun) | ** | ns | X | X | X | X | X | X | X |
| Control TCR (−cJun) | * | *** | *** | X | X | X | X | X | X |
| NR4A1 KO (+cJun) | **** | **** | **** | **** | X | X | X | X | X |
| NR4A2 KO (+cJun) | * | * | * | * | ns | X | X | X | X |
| NR4A3 KO (+cJun) | **** | **** | **** | **** | ** | ** | X | X | X |
| Control TCR (+cJun) | **** | **** | **** | **** | * | * | *** | X | X |
| Mock D37244 IL-2 Stim 4 | * | ** | ** | ** | *** | ** | *** | *** | X |
| NR4A1 KO (−cJun) | X | X | X | X | X | X | X | X | X |
| NR4A2 KO (−cJun) | ** | X | X | X | X | X | X | X | X |
| NR4A3 KO (−cJun) | ** | ** | X | X | X | X | X | X | X |
| Control TCR (−cJun) | ns | ** | ** | X | X | X | X | X | X |
| NR4A1 KO (+cJun) | **** | **** | **** | **** | X | X | X | X | X |
| NR4A2 KO (+cJun) | * | * | * | * | ns | X | X | X | X |
| NR4A3 KO (+cJun) | ns | ns | ns | ns | ns | ns | X | X | X |
| Control TCR (+cJun) | *** | ** | ** | *** | * | ns | ns | X | X |
| Mock | ns |  | * | ns | ** | ns | ns | * | X | ns—not significant,
* p < 0.05,
** p < 0.005,
*** p < 0.001,
**** p < 0.0001.

TABLE 14

Unpaired t-test statistical analysis of secreted tumor necrosis factor alpha (TNF-α) produced from NR4A-edited and control non-edited NY-ESO-1 TCR T cells with or without c-Jun overexpression during the A375 sequential stimulation assay corresponding to FIG. 15.

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| D33018 TNF-α Stim 1 | | | | | | | | | |
| NR4A1 KO (−cJun) | X | X | X | X | X | X | X | X | X |
| NR4A2 KO (−cJun) | ns | X | X | X | X | X | X | X | X |
| NR4A3 KO (−cJun) | ns | ns | X | X | X | X | X | X | X |
| Control TCR (−cJun) | ns | ns | ** | X | X | X | X | X | X |
| NR4A1 KO (+cJun) | *** | *** | **** | **** | X | X | X | X | X |
| NR4A2 KO (+cJun) | *** | *** | **** | **** | ** | X | X | X | X |
| NR4A3 KO (+cJun) | ** | ** | *** | ** | *** | *** | X | X | X |
| Control TCR (+cJun) | ** | ** | *** | ** | ns | ns | ** | X | X |
| Mock | **** | **** | **** | **** | **** | **** | **** | *** | X |
| D33018 TNF-α Stim 2 | | | | | | | | | |
| NR4A1 KO (−cJun) | X | X | X | X | X | X | X | X | X |
| NR4A2 KO (−cJun) | ns | X | X | X | X | X | X | X | X |
| NR4A3 KO (−cJun) | ns | ** | X | X | X | X | X | X | X |
| Control TCR (−cJun) | ns | ns | ** | X | X | X | X | X | X |
| NR4A1 KO (+cJun) | * | ns | ** | ns | X | X | X | X | X |
| NR4A2 KO (+cJun) | ns | ns | ** | ns | ns | X | X | X | X |
| NR4A3 KO (+cJun) | ns | ns | ** | ns | ** | ns | X | X | X |
| Control TCR (+cJun) | ns | ns | ** | ns | * | ns | ns | X | X |
| Mock | *** | *** | *** | ** | **** | *** | **** | **** | X |
| D33018 TNF-α Stim 3 | | | | | | | | | |
| NR4A1 KO (−cJun) | X | X | X | X | X | X | X | X | X |
| NR4A2 KO (−cJun) | ns | X | X | X | X | X | X | X | X |
| NR4A3 KO (−cJun) | * | * | X | X | X | X | X | X | X |
| Control TCR (−cJun) | ns | ns | * | X | X | X | X | X | X |
| NR4A1 KO (+cJun) | *** | *** | *** | *** | X | X | X | X | X |
| NR4A2 KO (+cJun) | ** | ** | ** | ** | ns | X | X | X | X |
| NR4A3 KO (+cJun) | **** | **** | **** | **** | *** | * | X | X | X |
| Control TCR (+cJun) | *** | *** | *** | *** | ** | * | *** | X | X |
| Mock | ** | *** | ** | ** | *** | ** | **** | *** | X |
| D33018 TNF-α Stim 4 | | | | | | | | | |
| NR4A1 KO (−cJun) | X | X | X | X | X | X | X | X | X |
| NR4A2 KO (−cJun) | ns | X | X | X | X | X | X | X | X |
| NR4A3 KO (−cJun) | ns | ns | X | X | X | X | X | X | X |
| Control TCR (−cJun) | ns | ns | ns | X | X | X | X | X | X |

TABLE 14-continued

Unpaired t-test statistical analysis of secreted tumor necrosis factor alpha (TNF-α)
produced from NR4A-edited and control non-edited NY-ESO-1 TCR T cells with or without
c-Jun overexpression during the A375 sequential stimulation assay corresponding to FIG. 15.

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| NR4A1 KO (+cJun) | ** | ** | ** | ** | X | X | X | X | X |
| NR4A2 KO (+cJun) | **** | **** | *** | **** | ns | X | X | X | X |
| NR4A3 KO (+cJun) | *** | *** | ** | *** | ** | * | X | X | X |
| Control TCR (+cJun) | *** | *** | ** | *** | ns | ** | ** | X | X |
| Mock D35108 TNF-α Stim 1 | *** | ** | * | ** | *** | **** | *** | *** | X |
| NR4A1 KO (−cJun) | X | X | X | X | X | X | X | X | X |
| NR4A2 KO (−cJun) | ns | X | X | X | X | X | X | X | X |
| NR4A3 KO (−cJun) | ** | * | X | X | X | X | X | X | X |
| Control TCR (−cJun) | ns | ** | *** | X | X | X | X | X | X |
| NR4A1 KO (+cJun) | **** | **** | **** | *** | X | X | X | X | X |
| NR4A2 KO (+cJun) | *** | **** | **** | *** | ** | X | X | X | X |
| NR4A3 KO (+cJun) | *** | **** | **** | *** | *** | ** | X | X | X |
| Control TCR (+cJun) | **** | **** | **** | *** | ns | ** | *** | X | X |
| Mock D35108 TNF-α Stim 2 | **** | **** | **** | **** | **** | **** | **** | **** | X |
| NR4A1 KO (−cJun) | X | X | X | X | X | X | X | X | X |
| NR4A2 KO (−cJun) | ** | X | X | X | X | X | X | X | X |
| NR4A3 KO (−cJun) | * | **** | X | X | X | X | X | X | X |
| Control TCR (−cJun) | *** | *** | **** | X | X | X | X | X | X |
| NR4A1 KO (+cJun) | *** | **** | **** | ** | X | X | X | X | X |
| NR4A2 KO (+cJun) | *** | **** | **** | ** | ns | X | X | X | X |
| NR4A3 KO (+cJun) | *** | *** | **** | * | ns | ns | X | X | X |
| Control TCR (+cJun) | *** | **** | **** | ** | ns | ns | ns | X | X |
| Mock D35108 TNF-α Stim 3 | **** | **** | **** | **** | **** | **** | *** | *** | X |
| NR4A1 KO (−cJun) | X | X | X | X | X | X | X | X | X |
| NR4A2 KO (−cJun) | ns | X | X | X | X | X | X | X | X |
| NR4A3 KO (−cJun) | ** | ns | X | X | X | X | X | X | X |
| Control TCR (−cJun) | *** | ** | *** | X | X | X | X | X | X |
| NR4A1 KO (+cJun) | * | * | * | ** | X | X | X | X | X |
| NR4A2 KO (+cJun) | ns | ns | ns | ** | ns | X | X | X | X |
| NR4A3 KO (+cJun) | * | * | * | * | ns | * | X | X | X |

TABLE 14-continued

Unpaired t-test statistical analysis of secreted tumor necrosis factor alpha (TNF-α)
produced from NR4A-edited and control non-edited NY-ESO-1 TCR T cells with or without
c-Jun overexpression during the A375 sequential stimulation assay corresponding to FIG. 15.

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| Control TCR (+cJun) | ** | ** | ** | *** | ns | ** | ns | X | X |
| Mock | **** | *** | **** | *** | ** | ** | * | *** | X |
| D35108 TNF-α Stim 4 | | | | | | | | | |
| NR4A1 KO (−cJun) | X | X | X | X | X | X | X | X | X |
| NR4A2 KO (−cJun) | ns | X | X | X | X | X | X | X | X |
| NR4A3 KO (−cJun) | ns | ns | X | X | X | X | X | X | X |
| Control TCR (−cJun) | * | ns | * | X | X | X | X | X | X |
| NR4A1 KO (+cJun) | ns | * | ns | * | X | X | X | X | X |
| NR4A2 KO (+cJun) | ns | ns | ns | * | ns | X | X | X | X |
| NR4A3 KO (+cJun) | ns | * | ns | * | ns | ns | X | X | X |
| Control TCR (+cJun) | * | * | ns | * | ns | * | ns | X | X |
| Mock | * | * | * | * | * | * | ns | * | X |
| D37244 TNF-α Stim 1 | | | | | | | | | |
| NR4A1 KO (−cJun) | X | X | X | X | X | X | X | X | X |
| NR4A2 KO (−cJun) | ** | X | X | X | X | X | X | X | X |
| NR4A3 KO (−cJun) | * | * | X | X | X | X | X | X | X |
| Control TCR (−cJun) | * | *** | *** | X | X | X | X | X | X |
| NR4A1 KO (+cJun) | ** | **** | **** | ** | X | X | X | X | X |
| NR4A2 KO (+cJun) | * | ** | ** | ns | ns | X | X | X | X |
| NR4A3 KO (+cJun) | * | *** | *** | ns | *** | ns | X | X | X |
| Control TCR (+cJun) | ** | **** | **** | ** | * | ns | *** | X | X |
| Mock | *** | **** | **** | **** | **** | ns | **** | **** | X |
| D37244 TNF-α Stim 2 | | | | | | | | | |
| NR4A1 KO (−cJun) | X | X | X | X | X | X | X | X | X |
| NR4A2 KO (−cJun) | * | X | X | X | X | X | X | X | X |
| NR4A3 KO (−cJun) | * | ns | X | X | X | X | X | X | X |
| Control TCR (−cJun) | *** | ** | ** | X | X | X | X | X | X |
| NR4A1 KO (+cJun) | ** | ns | ns | *** | X | X | X | X | X |
| NR4A2 KO (+cJun) | ns | ns | ns | ** | ns | X | X | X | X |
| NR4A3 KO (+cJun) | ** | ns | ns | *** | ns | ns | X | X | X |

TABLE 14-continued

Unpaired t-test statistical analysis of secreted tumor necrosis factor alpha (TNF-α) produced from NR4A-edited and control non-edited NY-ESO-1 TCR T cells with or without c-Jun overexpression during the A375 sequential stimulation assay corresponding to FIG. 15.

| | NR4A1 KO (−cJun) | NR4A2 KO (−cJun) | NR4A3 KO (−cJun) | Control TCR (−cJun) | NR4A1 KO (+cJun) | NR4A2 KO (+cJun) | NR4A3 KO (+cJun) | Control TCR (+cJun) | Mock |
|---|---|---|---|---|---|---|---|---|---|
| Control TCR (+cJun) | ** | * | * | *** | ns | * | ns | X | X |
| Mock D37244 TNF-α Stim 3 | **** | **** | **** | **** | **** | *** | **** | **** | X |
| NR4A1 KO (−cJun) | X | X | X | X | X | X | X | X | X |
| NR4A2 KO (−cJun) | ** | X | X | X | X | X | X | X | X |
| NR4A3 KO (−cJun) | * | ns | X | X | X | X | X | X | X |
| Control TCR (−cJun) | ** | *** | ** | X | X | X | X | X | X |
| NR4A1 KO (+cJun) | **** | **** | **** | **** | X | X | X | X | X |
| NR4A2 KO (+cJun) | ** | ** | ** | ** | ns | X | X | X | X |
| NR4A3 KO (+cJun) | **** | **** | **** | **** | *** | * | X | X | X |
| Control TCR (+cJun) | *** | *** | *** | *** | * | ns | *** | X | X |
| Mock D37244 TNF-α Stim 4 | **** | *** | ** | *** | **** | ** | **** | *** | X |
| NR4A1 KO (−cJun) | X | X | X | X | X | X | X | X | X |
| NR4A2 KO (−cJun) | * | X | X | X | X | X | X | X | X |
| NR4A3 KO (−cJun) | ** | ns | X | X | X | X | X | X | X |
| Control TCR (−cJun) | * | ** | ** | X | X | X | X | X | X |
| NR4A1 KO (+cJun) | **** | **** | **** | **** | X | X | X | X | X |
| NR4A2 KO (+cJun) | * | * | * | * | ns | X | X | X | X |
| NR4A3 KO (+cJun) | *** | *** | *** | *** | ** | ** | X | X | X |
| Control TCR (+cJun) | *** | *** | *** | *** | * | * | ** | X | X |
| Mock |  |  | *** | * | ** | * | * | * | X | ns—not significant,
* p < 0.05,
** p < 0.005,
*** p < 0.001,
**** p < 0.0001.

It is to be appreciated that the Detailed Description section, and not the Summary and Abstract sections, is intended to be used to interpret the claims. The Summary and Abstract sections can set forth one or more but not all exemplary aspects of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific aspects will so fully reveal the general nature of the disclosure that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

The contents of all cited references (including literature references, U.S. or foreign patents or patent applications, and websites) that are cited throughout this application are hereby expressly incorporated by reference as if written herein in their entireties for any purpose, as are the references cited therein. Where any inconsistencies arise, material literally disclosed herein controls.

What is claimed is:

1. A cell composition comprising a population of modified immune cells that have (i) a reduced expression level of a gene and/or protein of a member of a nuclear receptor subfamily 4 group A (NR4A) family and (ii) an increased expression level of a c-Jun protein, wherein the member of the NR4A family is selected from the group consisting of a NR4A member 1 (NR4A1), NR4A member 2 (NR4A2), and NR4A member 3 (NR4A3), wherein the modified immune cells are T cells.

2. The cell composition of claim 1, wherein the modified immune cells have a reduced expression level of the gene and/or protein of: (a) both NR4A1 and NR4A2; (b) both NR4A1 and NR4A3; (c) both NR4A2 and NR4A3; or (d) each of NR4A1, NR4A2, and NR4A3.

3. The cell composition of claim 1, wherein the modified immune cells comprise a chimeric antigen receptor (CAR) and/or a T cell receptor (TCR).

4. The cell composition of claim 1, wherein the population of modified immune cells comprises: (a) less than about 50% of effector T cells; (b) at least about 50% of naïve T (TN) cells, central memory T cells (TCM cells), stem memory T (TSCM) cells, or a combination thereof, or (c) both (a) and (b).

5. The cell composition of claim 1, wherein the modified immune cells have been contacted with:
(a) a gene editing tool which comprises a guide RNA comprising, consisting of, or consisting essentially of the sequence set forth in any one of SEQ ID NO: 25, SEQ ID NO: 26, SEQ ID NO: 27, SEQ ID NO: 28, SEQ ID NO: 29, SEQ ID NO: 30, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 61, SEQ ID NO: 65, SEQ ID NO: 67, SEQ ID NO: 68, SEQ ID NO: 70, SEQ ID NO: 71, SEQ ID NO: 75, SEQ ID NO: 76, SEQ ID NO: 82, SEQ ID NO: 83, SEQ ID NO: 86, SEQ ID NO: 94, and SEQ ID NO: 96,
(b) a nucleotide sequence encoding the c-Jun protein; or
(c) both (a) and (b).

6. The cell composition of claim 5, wherein the nucleotide sequence encoding the c-Jun protein comprises:

(a) a nucleic acid sequence having at least 89% sequence identity to the nucleic acid sequence as set forth in SEQ ID NO: 7;
(b) a nucleic acid sequence having at least 90% sequence identity to the nucleic acid sequence as set forth in SEQ ID NO: 8;
(c) a nucleic acid sequence having at least about 30% sequence identity to the nucleic acid sequence as set forth in SEQ ID NO: 10;
(d) a nucleic acid sequence having at least 79% sequence identity to the nucleic acid sequence as set forth in SEQ ID NO: 11;
(e) a nucleic acid sequence having at least 88% sequence identity to the nucleic acid sequence as set forth in SEQ ID NO: 12;
(f) a nucleic acid sequence having at least 82% sequence identity to the nucleic acid sequence as set forth in SEQ ID NO: 13;
(g) a nucleic acid sequence having at least 90% sequence identity to the nucleic acid sequence as set forth in SEQ ID NO: 14;
(h) a nucleic acid sequence having at least 55% sequence identity to the nucleic acid sequence as set forth in SEQ ID NO: 15; or
(i) a nucleic acid sequence having at least 85% sequence identity to the nucleic acid sequence as set forth in SEQ ID NO: 16.

7. A pharmaceutical composition comprising the cell composition of claim 1 and a pharmaceutically acceptable carrier.

8. A cell composition comprising a cell which (a) expresses a ligand binding protein, (b) has an increased expression level of a c-Jun protein, and (b) has a reduced expression level of a gene and/or protein of a member of a nuclear receptor subfamily 4 group A (NR4A) family, wherein the cell has been modified with a gRNA comprising, consisting of, or consisting essentially of the sequence set forth in any one of set forth in any one of SEQ ID NO: 25, SEQ ID NO: 26, SEQ ID NO: 27, SEQ ID NO: 28, SEQ ID NO: 29, SEQ ID NO: 30, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 61, SEQ ID NO: 65, SEQ ID NO: 67, SEQ ID NO: 68, SEQ ID NO: 70, SEQ ID NO: 71, SEQ ID NO: 75, SEQ ID NO: 76, SEQ ID NO: 82, SEQ ID NO: 83, SEQ ID NO: 86, SEQ ID NO: 94, and SEQ ID NO: 96, and wherein the cell is a T cell.

9. The cell composition of claim 2, wherein the modified immune cells have a reduced expression level of the gene and/or protein of both NR4A1 and NR4A2.

10. The cell composition of claim 2, wherein the modified immune cells have a reduced expression level of the gene and/or protein of both NR4A1 and NR4A3.

11. The cell composition of claim 2, wherein the modified immune cells have a reduced expression level of the gene and/or protein of both NR4A2 and NR4A3.

12. The cell composition of claim 2, wherein the modified immune cells have a reduced expression level of the gene and/or protein of each of NR4A1, NR4A2, and NR4A3.

13. The cell composition of claim 8, wherein the ligand binding protein comprises a chimeric antigen receptor (CAR) and/or a T cell receptor (TCR).

14. The cell composition of claim 8, wherein the cell has been contacted with a nucleotide sequence encoding the c-Jun protein.

15. The cell composition of claim 14, wherein the nucleotide sequence encoding the c-Jun protein comprises:

(a) a nucleic acid sequence having at least 89% sequence identity to the nucleic acid sequence as set forth in SEQ ID NO: 7;

(b) a nucleic acid sequence having at least 90% sequence identity to the nucleic acid sequence as set forth in SEQ ID NO: 8;

(c) a nucleic acid sequence having at least about 30% sequence identity to the nucleic acid sequence as set forth in SEQ ID NO: 10;

(d) a nucleic acid sequence having at least 79% sequence identity to the nucleic acid sequence as set forth in SEQ ID NO: 11;

(e) a nucleic acid sequence having at least 88% sequence identity to the nucleic acid sequence as set forth in SEQ ID NO: 12;

(f) a nucleic acid sequence having at least 82% sequence identity to the nucleic acid sequence as set forth in SEQ ID NO: 13;

(g) a nucleic acid sequence having at least 90% sequence identity to the nucleic acid sequence as set forth in SEQ ID NO: 14;

(h) a nucleic acid sequence having at least 55% sequence identity to the nucleic acid sequence as set forth in SEQ ID NO: 15; or a nucleic acid sequence having at least 85% sequence identity to the nucleic acid sequence as set forth in SEQ ID NO: 16.

16. The cell composition of claim 6, wherein the nucleotide sequence encoding the c-Jun protein comprises:

(a) the nucleic acid sequence set forth in SEQ ID NO: 7;

(b) the nucleic acid sequence set forth in SEQ ID NO: 8;

(c) the nucleic acid sequence set forth in SEQ ID NO: 10;

(d) the nucleic acid sequence set forth in SEQ ID NO: 11;

(e) the nucleic acid sequence set forth in SEQ ID NO: 12;

(f) the nucleic acid sequence set forth in SEQ ID NO: 13;

(g) the nucleic acid sequence set forth in SEQ ID NO: 14;

(h) the nucleic acid sequence set forth in SEQ ID NO: 15; or (i) the nucleic acid sequence set forth in SEQ ID NO: 16.

17. The cell composition of claim 15, wherein the nucleotide sequence encoding the c-Jun protein comprises:

(a) the nucleic acid sequence set forth in SEQ ID NO: 7;

(b) the nucleic acid sequence set forth in SEQ ID NO: 8;

(c) the nucleic acid sequence set forth in SEQ ID NO: 10;

(d) the nucleic acid sequence set forth in SEQ ID NO: 11;

(e) the nucleic acid sequence set forth in SEQ ID NO: 12;

(f) the nucleic acid sequence set forth in SEQ ID NO: 13;

(g) the nucleic acid sequence set forth in SEQ ID NO: 14;

(h) the nucleic acid sequence set forth in SEQ ID NO: 15; or (i) the nucleic acid sequence set forth in SEQ ID NO: 16.

18. A pharmaceutical composition comprising the cell composition of claim 8 and a pharmaceutically acceptable carrier.

19. The cell composition of claim 5, wherein the guide RNA consists of the sequence set forth in any one of SEQ ID NO: 25, SEQ ID NO: 26, SEQ ID NO: 27, SEQ ID NO: 28, SEQ ID NO: 29, SEQ ID NO: 30, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 61, SEQ ID NO: 65, SEQ ID NO: 67, SEQ ID NO: 68, SEQ ID NO: 70, SEQ ID NO: 71, SEQ ID NO: 75, SEQ ID NO: 76, SEQ ID NO: 82, SEQ ID NO: 83, SEQ ID NO: 86, SEQ ID NO: 94, and SEQ ID NO: 96.

20. The cell composition of claim 8, wherein the guide RNA consists of the sequence set forth in any one of SEQ ID NO: 25, SEQ ID NO: 26, SEQ ID NO: 27, SEQ ID NO: 28, SEQ ID NO: 29, SEQ ID NO: 30, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 61, SEQ ID NO: 65, SEQ ID NO: 67, SEQ ID NO: 68, SEQ ID NO: 70, SEQ ID NO: 71, SEQ ID NO: 75, SEQ ID NO: 76, SEQ ID NO: 82, SEQ ID NO: 83, SEQ ID NO: 86, SEQ ID NO: 94, and SEQ ID NO: 96.

* * * * *

SEQUENCE LISTING

```
<160> NUMBER OF SEQ ID NOS: 123

<210> SEQ ID NO 1
<211> LENGTH: 626
<212> TYPE: PRT
<213> ORGANISM: Artificial Sequence
<220> FEATURE:
<223> OTHER INFORMATION: NR4A3 Isoform Alpha

<400> SEQUENCE: 1

Met Pro Cys Val Gln Ala Gln Tyr Ser Pro Ser Pro Pro Gly Ser Ser
1               5                   10                  15

Tyr Ala Ala Gln Thr Tyr Ser Ser Glu Tyr Thr Thr Glu Ile Met Asn
            20                  25                  30

Pro Asp Tyr Thr Lys Leu Thr Met Asp Leu Gly Ser Thr Glu Ile Thr
        35                  40                  45

Ala Thr Ala Thr Thr Ser Leu Pro Ser Ile Ser Thr Phe Val Glu Gly
    50                  55                  60

Tyr Ser Ser Asn Tyr Glu Leu Lys Pro Ser Cys Val Tyr Gln Met Gln
65                  70                  75                  80

Arg Pro Leu Ile Lys Val Glu Glu Gly Arg Ala Pro Ser Tyr His His
                85                  90                  95

His His His His His His His His His His His Gln Gln Gln His
            100                 105                 110

Gln Gln Pro Ser Ile Pro Pro Ala Ser Ser Pro Glu Asp Glu Val Leu
        115                 120                 125

Pro Ser Thr Ser Met Tyr Phe Lys Gln Ser Pro Pro Ser Thr Pro Thr
    130                 135                 140

Thr Pro Ala Phe Pro Pro Gln Ala Gly Ala Leu Trp Asp Glu Ala Leu
145                 150                 155                 160

Pro Ser Ala Pro Gly Cys Ile Ala Pro Gly Pro Leu Leu Asp Pro Pro
                165                 170                 175

Met Lys Ala Val Pro Thr Val Ala Gly Ala Arg Phe Pro Leu Phe His
            180                 185                 190

Phe Lys Pro Ser Pro Pro His Pro Pro Ala Pro Ser Pro Ala Gly Gly
        195                 200                 205

His His Leu Gly Tyr Asp Pro Thr Ala Ala Ala Ala Leu Ser Leu Pro
    210                 215                 220

Leu Gly Ala Ala Ala Ala Ala Gly Ser Gln Ala Ala Ala Leu Glu Ser
225                 230                 235                 240

His Pro Tyr Gly Leu Pro Leu Ala Lys Arg Ala Ala Pro Leu Ala Phe
                245                 250                 255

Pro Pro Leu Gly Leu Thr Pro Ser Pro Thr Ala Ser Ser Leu Leu Gly
            260                 265                 270

Glu Ser Pro Ser Leu Pro Ser Pro Pro Ser Arg Ser Ser Ser Ser Gly
        275                 280                 285

Glu Gly Thr Cys Ala Val Cys Gly Asp Asn Ala Ala Cys Gln His Tyr
    290                 295                 300

Gly Val Arg Thr Cys Glu Gly Cys Lys Gly Phe Phe Lys Arg Thr Val
305                 310                 315                 320

Gln Lys Asn Ala Lys Tyr Val Cys Leu Ala Asn Lys Asn Cys Pro Val
                325                 330                 335

Asp Lys Arg Arg Arg Asn Arg Cys Gln Tyr Cys Arg Phe Gln Lys Cys
```

```
                 340              345              350
Leu Ser Val Gly Met Val Lys Glu Val Val Arg Thr Asp Ser Leu Lys
            355              360              365
Gly Arg Arg Gly Arg Leu Pro Ser Lys Pro Lys Ser Pro Leu Gln Gln
        370              375              380
Glu Pro Ser Gln Pro Ser Pro Pro Ser Pro Pro Ile Cys Met Met Asn
385              390              395              400
Ala Leu Val Arg Ala Leu Thr Asp Ser Thr Pro Arg Asp Leu Asp Tyr
            405              410              415
Ser Arg Tyr Cys Pro Thr Asp Gln Ala Ala Ala Gly Thr Asp Ala Glu
            420              425              430
His Val Gln Gln Phe Tyr Asn Leu Leu Thr Ala Ser Ile Asp Val Ser
            435              440              445
Arg Ser Trp Ala Glu Lys Ile Pro Gly Phe Thr Asp Leu Pro Lys Glu
        450              455              460
Asp Gln Thr Leu Leu Ile Glu Ser Ala Phe Leu Glu Leu Phe Val Leu
465              470              475              480
Arg Leu Ser Ile Arg Ser Asn Thr Ala Glu Asp Lys Phe Val Phe Cys
            485              490              495
Asn Gly Leu Val Leu His Arg Leu Gln Cys Leu Arg Gly Phe Gly Glu
        500              505              510
Trp Leu Asp Ser Ile Lys Asp Phe Ser Leu Asn Leu Gln Ser Leu Asn
        515              520              525
Leu Asp Ile Gln Ala Leu Ala Cys Leu Ser Ala Leu Ser Met Ile Thr
        530              535              540
Glu Arg His Gly Leu Lys Glu Pro Lys Arg Val Glu Glu Leu Cys Asn
545              550              555              560
Lys Ile Thr Ser Ser Leu Lys Asp His Gln Ser Lys Gly Gln Ala Leu
            565              570              575
Glu Pro Thr Glu Ser Lys Val Leu Gly Ala Leu Val Glu Leu Arg Lys
            580              585              590
Ile Cys Thr Leu Gly Leu Gln Arg Ile Phe Tyr Leu Lys Leu Glu Asp
        595              600              605
Leu Val Ser Pro Pro Ser Ile Ile Asp Lys Leu Phe Leu Asp Thr Leu
    610              615              620
Pro Phe
625

<210> SEQ ID NO 2
<211> LENGTH: 443
<212> TYPE: PRT
<213> ORGANISM: Artificial Sequence
<220> FEATURE:
<223> OTHER INFORMATION: NR4A3 Isoform Beta

<400> SEQUENCE: 2

Met Pro Cys Val Gln Ala Gln Tyr Ser Pro Ser Pro Pro Gly Ser Ser
1                5               10               15
Tyr Ala Ala Gln Thr Tyr Ser Ser Glu Tyr Thr Thr Glu Ile Met Asn
            20               25               30
Pro Asp Tyr Thr Lys Leu Thr Met Asp Leu Gly Ser Thr Glu Ile Thr
        35               40               45
Ala Thr Ala Thr Thr Ser Leu Pro Ser Ile Ser Thr Phe Val Glu Gly
    50               55               60
Tyr Ser Ser Asn Tyr Glu Leu Lys Pro Ser Cys Val Tyr Gln Met Gln
```

```
65              70              75              80

Arg Pro Leu Ile Lys Val Glu Glu Gly Arg Ala Pro Ser Tyr His His
                85              90              95

His His His His His His His His His His His His Gln Gln Gln His
            100             105             110

Gln Gln Pro Ser Ile Pro Pro Ala Ser Ser Pro Glu Asp Glu Val Leu
        115             120             125

Pro Ser Thr Ser Met Tyr Phe Lys Gln Ser Pro Pro Ser Thr Pro Thr
    130             135             140

Thr Pro Ala Phe Pro Pro Gln Ala Gly Ala Leu Trp Asp Glu Ala Leu
145             150             155             160

Pro Ser Ala Pro Gly Cys Ile Ala Pro Gly Pro Leu Leu Asp Pro Pro
                165             170             175

Met Lys Ala Val Pro Thr Val Ala Gly Ala Arg Phe Pro Leu Phe His
                180             185             190

Phe Lys Pro Ser Pro Pro His Pro Pro Ala Pro Ser Pro Ala Gly Gly
                195             200             205

His His Leu Gly Tyr Asp Pro Thr Ala Ala Ala Ala Leu Ser Leu Pro
    210             215             220

Leu Gly Ala Ala Ala Ala Ala Gly Ser Gln Ala Ala Ala Leu Glu Ser
225             230             235             240

His Pro Tyr Gly Leu Pro Leu Ala Lys Arg Ala Ala Pro Leu Ala Phe
                245             250             255

Pro Pro Leu Gly Leu Thr Pro Ser Pro Thr Ala Ser Ser Leu Leu Gly
                260             265             270

Glu Ser Pro Ser Leu Pro Ser Pro Pro Ser Arg Ser Ser Ser Ser Gly
    275             280             285

Glu Gly Thr Cys Ala Val Cys Gly Asp Asn Ala Ala Cys Gln His Tyr
    290             295             300

Gly Val Arg Thr Cys Glu Gly Cys Lys Gly Phe Phe Lys Arg Thr Val
305             310             315             320

Gln Lys Asn Ala Lys Tyr Val Cys Leu Ala Asn Lys Asn Cys Pro Val
                325             330             335

Asp Lys Arg Arg Arg Asn Arg Cys Gln Tyr Cys Arg Phe Gln Lys Cys
                340             345             350

Leu Ser Val Gly Met Val Lys Glu Val Val Arg Thr Asp Ser Leu Lys
    355             360             365

Gly Arg Arg Gly Arg Leu Pro Ser Lys Pro Lys Ser Pro Leu Gln Gln
    370             375             380

Glu Pro Ser Gln Pro Ser Pro Pro Ser Pro Pro Ile Cys Met Met Asn
385             390             395             400

Ala Leu Val Arg Ala Leu Thr Asp Ser Thr Pro Arg Asp Leu Asp Tyr
                405             410             415

Ser Arg Val Ser Phe Met Ile Ser Cys Phe Gln Met Asn Asp Gln Gly
                420             425             430

Leu Tyr Leu Trp Leu Leu Val Ile Arg Val Asp
        435             440
```

```
<210> SEQ ID NO 3
<211> LENGTH: 637
<212> TYPE: PRT
<213> ORGANISM: Artificial Sequence
<220> FEATURE:
<223> OTHER INFORMATION: NR4A3 Isoform 3
```

-continued

<400> SEQUENCE: 3

```
Met His Asp Ser Ile Arg Phe Gly Asn Val Asp Met Pro Cys Val Gln
1               5                   10                  15

Ala Gln Tyr Ser Pro Ser Pro Pro Gly Ser Ser Tyr Ala Ala Gln Thr
            20                  25                  30

Tyr Ser Ser Glu Tyr Thr Thr Glu Ile Met Asn Pro Asp Tyr Thr Lys
        35                  40                  45

Leu Thr Met Asp Leu Gly Ser Thr Glu Ile Thr Ala Thr Ala Thr Thr
    50                  55                  60

Ser Leu Pro Ser Ile Ser Thr Phe Val Glu Gly Tyr Ser Ser Asn Tyr
65                  70                  75                  80

Glu Leu Lys Pro Ser Cys Val Tyr Gln Met Gln Arg Pro Leu Ile Lys
                85                  90                  95

Val Glu Glu Gly Arg Ala Pro Ser Tyr His His His His His His His
            100                 105                 110

His His His His His His His Gln Gln Gln His Gln Gln Pro Ser Ile
        115                 120                 125

Pro Pro Ala Ser Ser Pro Glu Asp Glu Val Leu Pro Ser Thr Ser Met
    130                 135                 140

Tyr Phe Lys Gln Ser Pro Pro Ser Thr Pro Thr Thr Pro Ala Phe Pro
145                 150                 155                 160

Pro Gln Ala Gly Ala Leu Trp Asp Glu Ala Leu Pro Ser Ala Pro Gly
            165                 170                 175

Cys Ile Ala Pro Gly Pro Leu Leu Asp Pro Pro Met Lys Ala Val Pro
            180                 185                 190

Thr Val Ala Gly Ala Arg Phe Pro Leu Phe His Phe Lys Pro Ser Pro
            195                 200                 205

Pro His Pro Pro Ala Pro Ser Pro Ala Gly Gly His His Leu Gly Tyr
    210                 215                 220

Asp Pro Thr Ala Ala Ala Ala Leu Ser Leu Pro Leu Gly Ala Ala Ala
225                 230                 235                 240

Ala Ala Gly Ser Gln Ala Ala Ala Leu Glu Ser His Pro Tyr Gly Leu
            245                 250                 255

Pro Leu Ala Lys Arg Ala Ala Pro Leu Ala Phe Pro Pro Leu Gly Leu
            260                 265                 270

Thr Pro Ser Pro Thr Ala Ser Ser Leu Leu Gly Glu Ser Pro Ser Leu
    275                 280                 285

Pro Ser Pro Pro Ser Arg Ser Ser Ser Gly Glu Gly Thr Cys Ala
    290                 295                 300

Val Cys Gly Asp Asn Ala Ala Cys Gln His Tyr Gly Val Arg Thr Cys
305                 310                 315                 320

Glu Gly Cys Lys Gly Phe Phe Lys Arg Thr Val Gln Lys Asn Ala Lys
                325                 330                 335

Tyr Val Cys Leu Ala Asn Lys Asn Cys Pro Val Asp Lys Arg Arg Arg
            340                 345                 350

Asn Arg Cys Gln Tyr Cys Arg Phe Gln Lys Cys Leu Ser Val Gly Met
            355                 360                 365

Val Lys Glu Val Val Arg Thr Asp Ser Leu Lys Gly Arg Arg Gly Arg
    370                 375                 380

Leu Pro Ser Lys Pro Lys Ser Pro Leu Gln Gln Glu Pro Ser Gln Pro
385                 390                 395                 400

Ser Pro Pro Ser Pro Pro Ile Cys Met Met Asn Ala Leu Val Arg Ala
                405                 410                 415
```

```
Leu Thr Asp Ser Thr Pro Arg Asp Leu Asp Tyr Ser Arg Tyr Cys Pro
            420                 425                 430

Thr Asp Gln Ala Ala Ala Gly Thr Asp Ala Glu His Val Gln Gln Phe
            435                 440                 445

Tyr Asn Leu Leu Thr Ala Ser Ile Asp Val Ser Arg Ser Trp Ala Glu
            450                 455                 460

Lys Ile Pro Gly Phe Thr Asp Leu Pro Lys Glu Asp Gln Thr Leu Leu
465                 470                 475                 480

Ile Glu Ser Ala Phe Leu Glu Leu Phe Val Leu Arg Leu Ser Ile Arg
                485                 490                 495

Ser Asn Thr Ala Glu Asp Lys Phe Val Phe Cys Asn Gly Leu Val Leu
            500                 505                 510

His Arg Leu Gln Cys Leu Arg Gly Phe Gly Glu Trp Leu Asp Ser Ile
            515                 520                 525

Lys Asp Phe Ser Leu Asn Leu Gln Ser Leu Asn Leu Asp Ile Gln Ala
            530                 535                 540

Leu Ala Cys Leu Ser Ala Leu Ser Met Ile Thr Glu Arg His Gly Leu
545                 550                 555                 560

Lys Glu Pro Lys Arg Val Glu Glu Leu Cys Asn Lys Ile Thr Ser Ser
                565                 570                 575

Leu Lys Asp His Gln Ser Lys Gly Gln Ala Leu Glu Pro Thr Glu Ser
            580                 585                 590

Lys Val Leu Gly Ala Leu Val Glu Leu Arg Lys Ile Cys Thr Leu Gly
            595                 600                 605

Leu Gln Arg Ile Phe Tyr Leu Lys Leu Glu Asp Leu Val Ser Pro Pro
            610                 615                 620

Ser Ile Ile Asp Lys Leu Phe Leu Asp Thr Leu Pro Phe
625                 630                 635
```

```
<210> SEQ ID NO 4
<211> LENGTH: 331
<212> TYPE: PRT
<213> ORGANISM: Artificial Sequence
<220> FEATURE:
<223> OTHER INFORMATION: Wild-type human c-Jun

<400> SEQUENCE: 4
```

```
Met Thr Ala Lys Met Glu Thr Thr Phe Tyr Asp Asp Ala Leu Asn Ala
1               5                   10                  15

Ser Phe Leu Pro Ser Glu Ser Gly Pro Tyr Gly Tyr Ser Asn Pro Lys
            20                  25                  30

Ile Leu Lys Gln Ser Met Thr Leu Asn Leu Ala Asp Pro Val Gly Ser
            35                  40                  45

Leu Lys Pro His Leu Arg Ala Lys Asn Ser Asp Leu Leu Thr Ser Pro
            50                  55                  60

Asp Val Gly Leu Leu Lys Leu Ala Ser Pro Glu Leu Glu Arg Leu Ile
65                  70                  75                  80

Ile Gln Ser Ser Asn Gly His Ile Thr Thr Thr Pro Thr Pro Thr Gln
                85                  90                  95

Phe Leu Cys Pro Lys Asn Val Thr Asp Glu Gln Glu Gly Phe Ala Glu
            100                 105                 110

Gly Phe Val Arg Ala Leu Ala Glu Leu His Ser Gln Asn Thr Leu Pro
            115                 120                 125

Ser Val Thr Ser Ala Ala Gln Pro Val Asn Gly Ala Gly Met Val Ala
            130                 135                 140
```

-continued

```
Pro Ala Val Ala Ser Val Ala Gly Gly Ser Gly Ser Gly Gly Phe Ser
145                 150                 155                 160

Ala Ser Leu His Ser Glu Pro Pro Val Tyr Ala Asn Leu Ser Asn Phe
                165                 170                 175

Asn Pro Gly Ala Leu Ser Ser Gly Gly Gly Ala Pro Ser Tyr Gly Ala
            180                 185                 190

Ala Gly Leu Ala Phe Pro Ala Gln Pro Gln Gln Gln Gln Pro Pro
        195                 200                 205

His His Leu Pro Gln Gln Met Pro Val Gln His Pro Arg Leu Gln Ala
    210                 215                 220

Leu Lys Glu Glu Pro Gln Thr Val Pro Glu Met Pro Gly Glu Thr Pro
225                 230                 235                 240

Pro Leu Ser Pro Ile Asp Met Glu Ser Gln Glu Arg Ile Lys Ala Glu
                245                 250                 255

Arg Lys Arg Met Arg Asn Arg Ile Ala Ala Ser Lys Cys Arg Lys Arg
            260                 265                 270

Lys Leu Glu Arg Ile Ala Arg Leu Glu Glu Lys Val Lys Thr Leu Lys
        275                 280                 285

Ala Gln Asn Ser Glu Leu Ala Ser Thr Ala Asn Met Leu Arg Glu Gln
    290                 295                 300

Val Ala Gln Leu Lys Gln Lys Val Met Asn His Val Asn Ser Gly Cys
305                 310                 315                 320

Gln Leu Met Leu Thr Gln Gln Leu Gln Thr Phe
                325                 330

<210> SEQ ID NO 5
<211> LENGTH: 3257
<212> TYPE: DNA
<213> ORGANISM: Artificial Sequence
<220> FEATURE:
<223> OTHER INFORMATION: Wild-type human c-Jun

<400> SEQUENCE: 5
gctcagagtt gcactgagtg tggctgaagc agcgaggcgg gagtggaggt gcgcggagtc      60
aggcagacag acagacacag ccagccagcc aggtcggcag tatagtccga actgcaaatc     120
ttattttctt ttcaccttct ctctaactgc ccagagctag cgcctgtggc tcccgggctg     180
gtgtttcggg agtgtccaga gagcctggtc tccagccgcc cccgggagga gagccctgct     240
gcccaggcgc tgttgacagc ggcggaaagc agcggtaccc acgcgcccgc cggggggaagt     300 cggcgagcgg ctgcagcagc aaagaacttt cccggctggg aggaccggag acaagtggca     360
gagtcccgga gccaactttt gcaagccttt cctgcgtctt aggcttctcc acggcggtaa     420
agaccagaag gcggcggaga gccacgcaag agaagaagga cgtgcgctca gcttcgctcg     480
caccggttgt tgaacttggg cgagcgcgag ccgcggctgc cgggcgcccc ctccccctag     540
cagcggagga ggggacaagt cgtcggagtc cgggcggcca agacccgccg ccggccggcc     600
actgcagggt ccgcactgat ccgctccgcg gggagagccg ctgctctggg aagtgagttc     660
gcctgcggac tccgaggaac cgctgcgcac gaagagcgct cagtgagtga ccgcgacttt     720
tcaaagccgg gtagcgcgcg cgagtcgaca agtaagagtg cgggaggcat cttaattaac     780
cctgcgctcc ctggagcgag ctggtgagga gggcgcagcg gggacgacag ccagcgggtg     840
cgtgcgctct tagagaaact ttccctgtca aaggctccgg ggggcgcggg tgtccccgc      900 ttgccacagc cctgttgcgg ccccgaaact tgtgcgcgca gcccaaacta acctcacgtg     960
```

-continued

```
aagtgacgga ctgttctatg actgcaaaga tggaaacgac cttctatgac gatgccctca    1020
acgcctcgtt cctcccgtcc gagagcggac cttatggcta cagtaacccc aagatcctga    1080
aacagagcat gaccctgaac ctggccgacc cagtggggag cctgaagccg cacctccgcg    1140
ccaagaactc ggacctcctc acctcgcccg acgtgggggct gctcaagctg gcgtcgcccg    1200
agctggagcg cctgataatc cagtccagca acgggcacat caccaccacg ccgacccca     1260 cccagttcct gtgccccaag aacgtgacag atgagcagga gggcttcgcc gagggcttcg    1320
tgcgcgccct ggccgaactg cacagccaga acacgctgcc cagcgtcacg tcggcggcgc    1380
agccggtcaa cggggcaggc atggtggctc ccgcggtagc ctcggtggca gggggcagcg    1440
gcagcggcgg cttcagcgcc agcctgcaca gcgagccgcc ggtctacgca aacctcagca    1500
acttcaaccc aggcgcgctg agcagcggcg gcggggcgcc ctcctacggc gcggccggcc    1560 tggccttttcc cgcgcaaccc cagcagcagc agcagccgcc gcaccacctg ccccagcaga    1620
tgcccgtgca gcaccgcggg ctgcaggccc tgaaggagga gcctcagaca gtgcccgaga    1680
tgcccggcga gacaccgccc ctgtccccca tcgacatgga gtcccaggag cggatcaagg    1740
cggagaggaa gcgcatgagg aaccgcatcg ctgcctccaa gtgccgaaaa aggaagctgg    1800
agagaatcgc ccggctggag gaaaaagtga aaaccttgaa agctcagaac tcggagctgg    1860
cgtccacggc caacatgctc agggaacagg tggcacagct taaacagaaa gtcatgaacc    1920
acgttaacag tgggtgccaa ctcatgctaa cgcagcagtt gcaaacattt tgaagagaga    1980
ccgtcggggg ctgaggggca acgaagaaaa aaaataacac agagagacag acttgagaac    2040
ttgacaagtt gcgacggaga gaaaaaagaa gtgtccgaga actaaagcca agggtatcca    2100
agttggactg ggttgcgtcc tgacggcgcc cccagtgtgc acgagtggga aggacttggc    2160
gcgccctccc ttggcgtgga gccagggagc ggccgcctgc gggctgcccc gctttgcgga    2220
cgggctgtcc ccgcgcgaac ggaacgttgg acttttcgtt aacattgacc aagaactgca    2280
tggacctaac attcgatctc attcagtatt aaagggggga gggggagggg gttacaaact    2340
gcaatagaga ctgtagattg cttctgtagt actccttaag aacacaaagc gggggagggg    2400
ttggggaggg gcggcaggag ggaggtttgt gagagcgagg ctgagcctac agatgaactc    2460
tttctggcct gccttcgtta actgtgtatg tacatatata tatttttaa tttgatgaaa     2520 gctgattact gtcaataaac agcttcatgc ctttgtaagt tatttcttgt ttgtttgttt    2580
gggtatcctg cccagtgttg tttgtaaata agagatttgg agcactctga gtttaccatt    2640
tgtaataaag tatataattt ttttatgttt tgtttctgaa aattccagaa aggatattta    2700
agaaaataca ataaactatt ggaaagtact ccctaacct cttttctgca tcatctgtag     2760
atactagcta tctaggtgga gttgaaagag ttaagaatgt cgattaaaat cactctcagt    2820
gcttcttact attaagcagt aaaaactgtt ctctattaga ctttagaaat aaatgtacct    2880
gatgtacctg atgctatggt caggttatac tcctcctccc ccagctatct atatggaatt    2940
gcttaccaaa ggatagtgcg atgtttcagg aggctggagg aagggggggtt gcagtggaga    3000 gggacagccc actgagaagt caaacatttc aaagtttgga ttgtatcaag tggcatgtgc    3060
tgtgaccatt tataatgtta gtagaaattt tacaataggt gcttattctc aaagcaggaa    3120
ttggtggcag attttacaaa agatgtatcc ttccaatttg gaatcttctc tttgacaatt    3180
cctagataaa aagatggcct ttgcttatga atatttataa cagcattctt gtcacaataa    3240
atgtattcaa ataccaa                                                   3257
```

```
<210> SEQ ID NO 6
<211> LENGTH: 993
<212> TYPE: DNA
<213> ORGANISM: Artificial Sequence
<220> FEATURE:
<223> OTHER INFORMATION: Wild-type human c-Jun (coding region)

<400> SEQUENCE: 6
atgactgcaa agatggaaac gaccttctat gacgatgccc tcaacgcctc gttcctcccg      60
tccgagagcg gaccttatgg ctacagtaac cccaagatcc tgaaacagag catgaccctg     120
aacctggccg acccagtggg gagcctgaag ccgcacctcc gcgccaagaa ctcggacctc     180
ctcacctcgc ccgacgtggg gctgctcaag ctggcgtcgc ccgagctgga gcgcctgata     240
atccagtcca gcaacgggca catcaccacc acgccgaccc ccacccagtt cctgtgcccc     300
aagaacgtga cagatgagca ggagggcttc gccgagggct cgtgcgcgc cctggccgaa      360 ctgcacagcc agaacacgct gcccagcgtc acgtcggcgg cgcagccggt caacggggca     420
ggcatggtgg ctcccgcggt agcctcggtg gcaggggca gcggcagcgg cggcttcagc      480
gccagcctgc acagcgagcc gccggtctac gcaaacctca gcaacttcaa cccaggcgcg     540
ctgagcagcg gcggcgggc gccctcctac ggcgcggccg gcctggcctt tcccgcgcaa      600
ccccagcagc agcagcagcc gccgcaccac ctgcccagc agatgcccgt gcagcacccg      660
cggctgcagg ccctgaagga ggagcctcag acagtgcccg agatgcccgg cgagacaccg     720
cccctgtccc ccatcgacat ggagtcccag gagcggatca aggcggagag gaagcgcatg     780
aggaaccgca tcgctgcctc caagtgccga aaaaggaagc tggagagaat cgcccggctg     840
gaggaaaaag tgaaaacctt gaaagctcag aactcggagc tggcgtccac ggccaacatg     900
ctcagggaac aggtggcaca gcttaaacag aaagtcatga accacgttaa cagtgggtgc     960
caactcatgc taacgcagca gttgcaaaca ttt                                 993

<210> SEQ ID NO 7
<211> LENGTH: 993
<212> TYPE: DNA
<213> ORGANISM: Artificial Sequence
<220> FEATURE:
<223> OTHER INFORMATION: c-Jun codon optimized #1

<400> SEQUENCE: 7
atgacagcca agatggaaac cacattctac gacgacgccc tgaacgcctc attcctgcct      60
tctgagagcg gaccttacgg ctacagcaat cctaagatcc tgaaacagag catgaccctt     120
aacctggcta tcctgttgg aagcctgaaa cctcacctga gccaaaaaa cagcgacctg      180 ctcaccagcc ctgatgtggg cctgctgaag ctggcctctc cagagctgga cggctgatc      240 atccagagca gcaacggcca tcacaacc acccctaccc ctacacaatt cctgtgccct      300
aagaacgtga ccgacgagca ggagggcttc gccgaaggct ttgtgcgggc cctggcagaa     360
ctgcactctc agaacaccct gcctagcgtg acctccgccg cccagcctgt caacggcgcc     420
ggaatggtgg cccctgccgt ggcttctgtg gccggcggca gcggcagcgg cggattcagc     480
gcctctctgc actctgagcc tcctgtctac gccaatctgt ctaatttcaa ccccggagcc     540
ctgtccagcg gcggcgggagc tcctagctac ggcgctgctg gactggcctt ccccgcccag     600
ccccagcaac agcagcagcc tccacaccac ctgcccagc agatgcccgt gcagcaccct      660
agactgcagg ccctgaagga agaaccccaa acagtgcctg agatgcctgg cgagacacct     720
ccactgagcc ccatcgacat ggaaagccag gagcggatca aggccgagag aaagagaatg     780
```

-continued

```
cggaacagaa tcgccgctag caagtgcaga aagcggaagc tggaaagaat cgccagactg      840
gaagagaagg tgaagaccct gaaagcccaa aatagcgagc tggccagcac cgccaacatg      900
ctgcgggaac aggtggccca gctgaagcag aaggtgatga accacgtgaa ctctggttgt      960
cagctgatgc tgacccagca gctccagacc ttc                                  993
```

```
<210> SEQ ID NO 8
<211> LENGTH: 993
<212> TYPE: DNA
<213> ORGANISM: Artificial Sequence
<220> FEATURE:
<223> OTHER INFORMATION: c-Jun codon optimized #2

<400> SEQUENCE: 8
```

```
atgacagcca agatggaaac caccttctac gacgacgccc tcaacgcctc cttcctgcct       60
tctgagagcg gtccttacgg ctacagcaac cccaagatcc tgaagcaaag catgaccctg      120
aacctggccg accccgttgg ctccctgaaa cctcacctga gagccaaaaa cagcgacctg      180
ctgaccagcc ctgatgtggg cctgctgaag ctggcctctc cagagctgga aagactgatt      240
atccagagca gcaacggcca catcaccaca cacctaccc ctacacagtt cctgtgccct        300
aagaacgtga ctgatgagca ggagggcttt gccgagggct cgtgagagc cctggctgag        360 ctgcattctc agaacaccct gcctagcgtg acctctgccg cccagcctgt taatggcgcc      420
ggcatggtgg cccctgccgt ggcctctgtg gccggaggca gcggcagcgg cggattcagc       480
gcctctctgc acagcgagcc ccccgtctac gccaacctga gcaatttcaa ccctggcgcc       540
ctgtccagcg gcggcggcgc cccttcatat ggcgctgccg gctggccctt ccccgctcag       600
ccccagcagc agcaacagcc tccacaccac ctgccccagc agatgcccgt gcagcacccc       660
agactgcagg ccctgaagga agaacctcag accgtgcccg agatgcctgg cgagacccct      720
cctctgagcc ctatcgacat ggaaagccag gagagaatca aggccgagag gaagcggatg       780
cggaacagaa tcgccgccag caagtgcaga aaaagaaagc tggaacggat cgccagactg       840
gaggagaagg tgaagacact gaaagcccaa aattctgaac tggcctctac cgccaatatg       900
ctgcgcgagc aggtggctca actgaagcag aaggtgatga accacgtgaa cagcggatgt       960
cagctgatgc tgacacagca gctgcagact ttt                                  993
```

```
<210> SEQ ID NO 9
<211> LENGTH: 993
<212> TYPE: DNA
<213> ORGANISM: Artificial Sequence
<220> FEATURE:
<223> OTHER INFORMATION: c-Jun codon optimized #3

<400> SEQUENCE: 9
```

```
atgaccgcca agatggaaac caccttctac gacgacgccc tgaacgccag ctttctgcct       60
tctgagtctg gcccctacgg ctacagcaac cccaagatcc tgaagcagag catgaccctg      120
aacctggccg atcctgtggg cagcctgaaa cctcacctga gagccaagaa cagcgacctg      180
ctgacaagcc ctgatgtggg cctgctgaaa ctggcctctc ctgagctgga acggctgatc      240
atccagagca gcaacggcca catcaccacc acacctacac aaacacagtt tctgtgcccc      300
aagaacgtga ccgacgagca agagggattc gccgagggct tgttagagc cctggccgaa        360 ctgcacagcc agaatacccct gcctagcgtg acatctgccg ctcagcctgt taatggcgcc      420
ggaatggttg ctcctgccgt ggcttctgtt gctggcggat ctggatctgg cggctttagc       480
gcctctctgc actctgagcc tccagtgtac gccaacctga gcaacttcaa ccctggcgct       540
```

```
cttagctctg gtggcggagc accttcttat ggcgctgccg gattggcctt tcctgctcag     600
cctcagcagc agcaacagcc tcctcatcat ctgccccagc agatgcctgt gcagcaccct     660
agactgcagg ccctgaaaga ggaaccccag acagtccctg agatgcccgg cgaaacacct     720
cctctgagcc ccatcgacat ggaaagccaa gagcggatca aggccgagcg gaagcggatg     780
agaaatagaa tcgccgcctc caagtgccgg aagaggaagc tggaaagaat cgcccggctg     840
gaagagaaag tgaaaaccct gaaggcccag aactccgagc tggcctctac cgccaacatg     900
ctgagagaac aggtggccca gctgaaacag aaagtcatga accacgtgaa cagcggctgc     960
cagctgatgc tgacacagca gctgcagacc ttc                                 993

<210> SEQ ID NO 10
<211> LENGTH: 993
<212> TYPE: DNA
<213> ORGANISM: Artificial Sequence
<220> FEATURE:
<223> OTHER INFORMATION: c-Jun codon optimized #4

<400> SEQUENCE: 10
atgactgcca aaatggagac tacattctat gacgacgccc tcaatgccag ttttttgccg      60
agtgaatccg gccctacgg ctattcaaac cctaagatcc tcaagcaatc aatgaccctc     120
aatcttgctg acccagttgg ctccctgaaa ccccatctca gagctaaaaa tagtgacctc     180
cttacttccc ctgatgttgg actcctcaaa cttgcttctc ccgaactcga acgcttgatc     240
attcaatctt ccaacggcca catcacaaca acacccacac ccacccagtt tctttgccca     300
aaaaatgtca ccgatgaaca ggaaggtttc gcggaaggat tcgtccgcgc gctggccgaa     360
ctgcactccc agaatacact tccttcagtt acgtcagccg cccagccagt gaatggtgcg     420
ggaatggttg ctcctgcggt cgcttctgtc gcagggggct ccggttctgg cggatttagc     480
gcctctctgc attccgagcc acctgtatat gctaatcttt ctaattttaa ccccggagcc     540
ttgtctagcg gcggtggtgc ccccagctac ggtgctgcag gactcgcctt cccagctcaa     600
cctcagcagc agcaacaacc cccccatcac cttcccaac agatgccagt acaacatcca     660
aggctccagg ccctcaaaga ggaaccacag acggtgcccg aaatgcctgg cgaaactcca     720
ccactttccc ctattgatat ggaatcccaa gagcgcatca aggccgaaag aaagcgaatg     780
cggaatagaa tagcagcttc aaaatgtaga aaacggaaat tggaacgaat cgcacggttg     840
gaagaaaagg tgaagacctt gaaagcccag aacagtgagc tcgcctctac cgctaacatg     900
ctgcgcgagc aagtcgcaca acttaagcag aaggtgatga accatgtgaa tagcggatgt     960
caacttatgc tgactcaaca gttgcaaacc ttt                                 993

<210> SEQ ID NO 11
<211> LENGTH: 993
<212> TYPE: DNA
<213> ORGANISM: Artificial Sequence
<220> FEATURE:
<223> OTHER INFORMATION: c-Jun codon optimized #5

<400> SEQUENCE: 11
atgaccgcga aaatggagac aacatttttac gatgatgcac tgaacgcctc ttttctgcca      60
agtgaatccg gccctacgg atactcaaac cctaagattc tgaaacagtc tatgactctc     120
aacctggccg acccagttgg cagtctgaag cctcatttgc gagccaagaa tagtgatctg     180
ctgacctccc cagacgtggg actgctgaaa ctcgcctcac tgaacttga gcgcttgatt     240
```

-continued

```
atacagtcat ccaatgggca catcacaaca acacctactc ctacccagtt tctgtgcccc      300
aaaaacgtca ccgatgagca ggagggattc gcggaaggct ttgtgcgcgc cctggctgaa      360
ttgcatagtc agaacactct tcccagcgta accagcgccg cccaaccagt gaatggagcc      420
ggtatggtgg ctcccgcggt ggctagtgtt gcggggggggt caggctctgg tgggttcagt      480
gcttctcttc actctgaacc ccctgtgtat gccaatctgt ctaactttaa ccctgggggcc      540 ctctcctctg gtggggggtgc ccccagctac ggagcggccg gcctggcctt tcctgcccag      600
cctcagcagc agcagcaacc ccctcatcat cttccgcagc agatgccagt acagcatcca      660
cgcctgcagg ctcttaagga ggagccccag acggtgcccg aaatgcccgg ggaaactcca      720
cccttgtccc ccattgacat ggagtcccag gagcggatca aggctgaaag aaagaggatg      780
cggaatcgca tcgcagcctc taaatgccgc aagcggaaac ttgagaggat cgcgcgcgttg      840 gaggaaaaag taaaaacctt gaaggcacag aactctgagc tggcgagtac tgccaacatg      900
ctcagagaac aagtcgcaca gctgaagcag aaagtgatga accatgtgaa cagcggttgt      960
cagctgatgc tgactcagca gctgcagacc ttc                                   993
```

```
<210> SEQ ID NO 12
<211> LENGTH: 993
<212> TYPE: DNA
<213> ORGANISM: Artificial Sequence
<220> FEATURE:
<223> OTHER INFORMATION: c-Jun codon optimized #6

<400> SEQUENCE: 12
```

```
atgaccgcca agatggagac cacattctac gatgacgctc tgaacgcttc ctttctgcct       60
tccgagtccg gcccctacgg ctactccaat cccaagattc tgaagcagag catgacactg      120
aatctggctg atcccgtggg atctctgaag cctcatctga gagccaagaa ttccgatctg      180
ctgacaagcc ccgacgtggg actgctcaaa ctggccagcc ccgaactgga gaggctcatt      240
atccagagct ccaacggcca catcaccaca acacctaccc ctacccagtt tctctgtccc      300
aagaacgtga cagacgagca agagggattt gccgaaggct tcgtgagagc cctcgccgaa      360
ctgcatagcc agaacacact gccttccgtg accagcgctg ctcaacccgt gaacggcgct      420
ggcatggtcg ctcccgccgt cgccagcgtg gctggaggaa gcggatccgg aggcttcagc      480
gcttccctcc acagcgaacc tcccgtgtac gctaatctga gcaacttcaa ccccggcgct      540
ctgagcagcg gaggaggagc tcctagctat ggagctgccg gactggcttt tcccgcccag      600
ccccagcagc agcagcagcc cccccatcat ctgcctcagc agatgcccgt gcagcatccc      660
agactccaag ctctgaagga ggagcctcag accgtccccg agatgcccgg cgaaaccccc      720
cctctgtccc ccatcgacat ggaaagccaa gagaggatca aggccgagag gaagaggatg      780
aggaatagaa tcgccgccag caagtgtaga aagaggaagc tggagaggat cgccagactg      840
gaggagaagg tgaagaccct caaggctcag aattccgagc tggccagcac agccaacatg      900
ctgagagagc aagtggccca gctcaagcag aaggtgatga accacgtcaa cagcggatgc      960
cagctgatgc tcacccagca gctgcagacc ttc                                   993
```

```
<210> SEQ ID NO 13
<211> LENGTH: 993
<212> TYPE: DNA
<213> ORGANISM: Artificial Sequence
<220> FEATURE:
<223> OTHER INFORMATION: c-Jun codon optimized #7

<400> SEQUENCE: 13
```

-continued

```
atgaccgcta aaatggaaac cactttctat gacgatgccc tgaacgcctc cttccttccg        60
tccgagtccg gaccctacgg atactcaaat cctaagatcc tcaaacagtc gatgaccctc       120
aacctggccg accccgtggg atccctgaag ccgcacttgc gcgccaagaa ctccgacctc       180
ctgacgagcc cagacgtggg cctgctgaag ctcgcatcac ccgaacttga gcggttgatc       240
attcagtcct ccaacggaca tatcaccacc actcccaccc caactcagtt tctgtgtccg       300
aagaacgtga ccgatgagca agagggattc gccgagggat tcgtgcgggc cctggccgag       360
ctgcatagcc agaacaccct tccatccgtg acctcggcgg ctcagcctgt gaacggcgcg       420
ggaatggtcg cgcccgccgt ggcctcggtg gccgggggca gcggcagcgg gggattttcc       480
gcgtcgctgc actccgagcc gccggtgtac gccaacctgt caaacttcaa ccctggggcc       540
ctgagctccg gcggtggagc accttcgtac ggcgccgctg gcctggcgtt ccccgcgcaa       600
ccacagcagc aacagcagcc ccctcaccac ctcccccaac aaatgcctgt gcagcacccg       660
aggctgcagg ccctcaagga agaaccccag actgtgccgg aaatgccggg ggagactccg       720
ccgctgtccc ctatcgacat ggaatcacag gaacgcatta aggcagagcg gaagcgcatg       780
cggaaccgga ttgccgcctc caagtgccgc aagagaaagc tcgaaagaat cgccagattg       840
gaagaaaagg tcaagactct gaaggcccag aactctgagc tggcatccac cgctaatatg       900
ctgagggaac aagtggccca gctgaaacag aaggtcatga accacgtcaa cagcggttgc       960
cagctgatgc tgacccagca actccagaca ttc                                    993
```

```
<210> SEQ ID NO 14
<211> LENGTH: 993
<212> TYPE: DNA
<213> ORGANISM: Artificial Sequence
<220> FEATURE:
<223> OTHER INFORMATION: c-Jun codon optimized #8

<400> SEQUENCE: 14
```

```
atgaccgcca agatggagac caccttctac gacgacgccc tgaacgccag cttcctgccc        60
agcgagagcg acccctacgg ctactctaac cccaagatcc tgaaacagag catgacactg       120
aatctggccg accccgtggg cagcctgaag cctcacctta gagccaagaa cagcgacctg       180
ctgaccagcc ccgacgtggg cctgctgaag ctcgcctctc agagttaga gagactgatc       240 atccagtcca gcaacggcca catcacaacc accccaaccc ctacccagtt cctgtgcccc       300
aagaacgtga ccgacgagca ggagggcttc gccgagggct ttgtgagagc cctggccgag       360
ttgcactctc agaacaccct gccctccgtg accagcgccg ctcaacctgt gaacggcgca       420
ggaatggttg ctcctgccgt ggccagcgtt gcaggcggat ctggaagtgg aggcttctcc       480
gcctcccttc acagcgagcc tcccgtgtac gccaacctga gcaacttcaa ccccggcgcc       540
ctgagcagtg gaggaggcgc tcccagctat ggagcagctg gattagcctt ccccgcccag       600
ccacagcagc agcaacagcc tccccaccac ctgcctcagc aaatgcctgt gcagcaccct       660
cggctgcagg cccttaagga ggagccccag accgttcctg agatgcctgg cgagacccct       720
cccctgagcc ctatcgacat ggagtcccag gagcggatca aggccgagcg gaagcggatg       780
cggaaccgga tcgctgcttc caagtgccgg aagagaaagc tggagagaat cgcccggctg       840
gaggagaagg tgaagaccct gaaggcccag aactccgagc tggcctccac cgccaacatg       900
ctgcgggagc aggttgcaca gctgaagcag aaggtcatga accacgtgaa cagcggctgc       960
cagctgatgc tgacccagca gctgcagacc ttc                                    993
```

<210> SEQ ID NO 15
<211> LENGTH: 1059
<212> TYPE: DNA
<213> ORGANISM: Artificial Sequence
<220> FEATURE:
<223> OTHER INFORMATION: c-Jun codon optimized #9

<400> SEQUENCE: 15
atgacagcga agatggagac aaccttctat gacgatgctc ttaacgcctc cttcctgcct      60
tccgaaagcg ggccctacgg gtactctaat cctaagatac ttaagcaatc gatgactctc     120
aacctcgctg acccggttgg ctcactgaaa ccacacctga gagctaagaa tagtgacctg     180
ctcactagtc ccgatgtcgg gcttctgaag ctggcctctc ccgagctgga gaggcttatc     240
atccaatcat caaatggcca catcaccact accccaacac caactcaatt cctttgccct     300
aaaaacgtga ccgacgaaca ggaaggcttc gccgagggtt ttgtccgggc cttggccgag     360
ctgcattctc aaaatacact gccaagcgtc acttctgcgg cgcagccggt taacggagca     420
gggatggtgg ctcccgccgt tgctagcgtg gccggcggtt ccggctccgg cggtttctct     480
gcctccttgc attctgagcc accagtctac gcgaacctgt ccaactttaa tccggggggcg     540 ctgagtagcg gaggcggcgc ccctagctat ggggcagctg gactggcctt cccggcacaa     600
ccccaacaac aacagcaacc gccacaccat cttcctcaac aaatgccagt gcaacatcca     660
cgcttacaag ccctcaagga ggaaccccag accgtgcctg agatgcccgg cgaaaccccg     720
ccattgagcc ctattgacat ggaaagtcaa gagagaatta aggcagagcg caagagaatg     780
aggaaccgga tcgcagcatc taagtgccgc aaacggaaat tggagcggat cgctcgcttg     840
gaggagaagg tcaagactct caaggcccag aactccgagc ttgcgagcac agctaatatg     900
ctgcgcgagc aggtggccca gttaaaacaa aaggtcatga accatgtgaa cagcggctgt     960
cagctgatgc ttacgcaaca gctgcaaacc tttggctccg gtgcaacgaa cttcagcctg    1020
ctgaagcagg ccggagatgt tgaggaaaat ccaggtccc                          1059

<210> SEQ ID NO 16
<211> LENGTH: 993
<212> TYPE: DNA
<213> ORGANISM: Artificial Sequence
<220> FEATURE:
<223> OTHER INFORMATION: c-Jun codon optimized #10

<400> SEQUENCE: 16
atgacggcca aaatggagac tacgttctac gatgacgcac tcaacgcgtc cttcctgccc      60
tctgagagtg gaccctatgg ctactccaat ccaaagatcc tgaagcagtc tatgaccctc     120
aacctggcgg acccggtggg ctcccttaag ccgcacttgc gcgccaagaa ctccgacctg     180
ctgacctccc ctgatgtggg cctcctcaag ctcgctagcc ctgaattgga gaggctgatc     240
atccagagct caaatggcca catcaccacc acacctaccc caacccagtt cctgtgccca     300
aaaaacgtga ccgacgagca ggagggcttc gcggagggct tcgtcagagc tctggccgag     360
ctgcactcac agaacacgct cccttccgtg acctccgctg cccagccggt caatggcgct     420
ggaatggtgg ctccggctgt ggcctctgtt gccggcggct ccggctccgg aggcttttca     480
gcttctctgc attctgagcc cccagtgtac gctaacctga gcaacttcaa ccccgggggcg     540 ctcagctccg gtggcggtgc cccgagctac ggcgcggctg ggctggcgtt ccccgctcag     600
cctcagcagc aacagcaacc tccccaccac ctgccacagc agatgcctgt gcagcaccca     660
cgcctgcagg ccttgaagga ggaacctcag actgtgccag agatgcccgg cgagaccccca     720 cccctgtccc cgattgacat ggagagccag gagcgcatca aggcagagcg caagcgtatg          780
cgcaaccgca tcgcggcctc caagtgccga aagcgcaagc tggagcggat tgctcgcctg          840
gaggagaagg tgaagaccct gaaggcccag aattccgagc tggcctcgac cgccaacatg          900
ctacgagaac aggtcgcgca gctgaaacag aaggtcatga accatgtcaa cagcgggtgc          960
cagctgatgt tgacccagca gcttcagacc ttc                                       993

<210> SEQ ID NO 17
<211> LENGTH: 121
<212> TYPE: PRT
<213> ORGANISM: Artificial Sequence
<220> FEATURE:
<223> OTHER INFORMATION: R12 VH

<400> SEQUENCE: 17

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Thr Trp Val
    50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser
        115                 120

<210> SEQ ID NO 18
<211> LENGTH: 5
<212> TYPE: PRT
<213> ORGANISM: Artificial Sequence
<220> FEATURE:
<223> OTHER INFORMATION: R12 VH CDR1

<400> SEQUENCE: 18

Ala Tyr Tyr Met Ser
1               5

<210> SEQ ID NO 19
<211> LENGTH: 17
<212> TYPE: PRT
<213> ORGANISM: Artificial Sequence
<220> FEATURE:
<223> OTHER INFORMATION: R12 VH CDR2

<400> SEQUENCE: 19

Thr Ile Tyr Pro Ser Ser Gly Lys Thr Tyr Tyr Ala Thr Trp Val Asn
1               5                   10                  15

Gly

<210> SEQ ID NO 20
<211> LENGTH: 12
<212> TYPE: PRT
<213> ORGANISM: Artificial Sequence
<220> FEATURE:

<223> OTHER INFORMATION: R12 VH CDR3

<400> SEQUENCE: 20

```
Asp Ser Tyr Ala Asp Asp Gly Ala Leu Phe Asn Ile
1               5                   10
```

<210> SEQ ID NO 21
<211> LENGTH: 112
<212> TYPE: PRT
<213> ORGANISM: Artificial Sequence
<220> FEATURE:
<223> OTHER INFORMATION: R12 VL

<400> SEQUENCE: 21

```
Glu Leu Val Leu Thr Gln Ser Pro Ser Val Ser Ala Ala Leu Gly Ser
1               5                   10                  15

Pro Ala Lys Ile Thr Cys Thr Leu Ser Ser Ala His Lys Thr Asp Thr
            20                  25                  30

Ile Asp Trp Tyr Gln Gln Leu Gln Gly Glu Ala Pro Arg Tyr Leu Met
        35                  40                  45

Gln Val Gln Ser Asp Gly Ser Tyr Thr Lys Arg Pro Gly Val Pro Asp
    50                  55                  60

Arg Phe Ser Gly Ser Ser Ser Gly Ala Asp Arg Tyr Leu Ile Ile Pro
65                  70                  75                  80

Ser Val Gln Ala Asp Asp Glu Ala Asp Tyr Tyr Cys Gly Ala Asp Tyr
                85                  90                  95

Ile Gly Gly Tyr Val Phe Gly Gly Gly Thr Gln Leu Thr Val Thr Gly
            100                 105                 110
```

<210> SEQ ID NO 22
<211> LENGTH: 12
<212> TYPE: PRT
<213> ORGANISM: Artificial Sequence
<220> FEATURE:
<223> OTHER INFORMATION: R12 VL CDR1

<400> SEQUENCE: 22

```
Thr Leu Ser Ser Ala His Lys Thr Asp Thr Ile Asp
1               5                   10
```

<210> SEQ ID NO 23
<211> LENGTH: 7
<212> TYPE: PRT
<213> ORGANISM: Artificial Sequence
<220> FEATURE:
<223> OTHER INFORMATION: R12 VL CDR2

<400> SEQUENCE: 23

```
Gly Ser Tyr Thr Lys Arg Pro
1               5
```

<210> SEQ ID NO 24
<211> LENGTH: 9
<212> TYPE: PRT
<213> ORGANISM: Artificial Sequence
<220> FEATURE:
<223> OTHER INFORMATION: R12 VL CDR3

<400> SEQUENCE: 24

```
Gly Ala Asp Tyr Ile Gly Gly Tyr Val
1               5
```

<210> SEQ ID NO 25

-continued

```
<211> LENGTH: 20
<212> TYPE: RNA
<213> ORGANISM: Artificial Sequence
<220> FEATURE:
<223> OTHER INFORMATION: NR4A1 sgRNA 5

<400> SEQUENCE: 25
gaaguccucg aacuugaagg                                               20

<210> SEQ ID NO 26
<211> LENGTH: 20
<212> TYPE: RNA
<213> ORGANISM: Artificial Sequence
<220> FEATURE:
<223> OTHER INFORMATION: NR4A1 sgRNA 6

<400> SEQUENCE: 26
accuucaugg acggcuacac                                               20

<210> SEQ ID NO 27
<211> LENGTH: 20
<212> TYPE: RNA
<213> ORGANISM: Artificial Sequence
<220> FEATURE:
<223> OTHER INFORMATION: NR4A2 sgRNA 1

<400> SEQUENCE: 27
uugggauggu caaagaaggu                                               20

<210> SEQ ID NO 28
<211> LENGTH: 20
<212> TYPE: RNA
<213> ORGANISM: Artificial Sequence
<220> FEATURE:
<223> OTHER INFORMATION: NR4A2 sgRNA 2

<400> SEQUENCE: 28
cagccaggca cuucugaaau                                               20

<210> SEQ ID NO 29
<211> LENGTH: 20
<212> TYPE: RNA
<213> ORGANISM: Artificial Sequence
<220> FEATURE:
<223> OTHER INFORMATION: NR4A2 sgRNA 3

<400> SEQUENCE: 29
uccggcgacg cuuguccacu                                               20

<210> SEQ ID NO 30
<211> LENGTH: 20
<212> TYPE: RNA
<213> ORGANISM: Artificial Sequence
<220> FEATURE:
<223> OTHER INFORMATION: NR4A3 sgRNA 4

<400> SEQUENCE: 30
gcucgaguag cccuccacga                                               20

<210> SEQ ID NO 31
<211> LENGTH: 20
<212> TYPE: DNA
<213> ORGANISM: Artificial Sequence
<220> FEATURE:
<223> OTHER INFORMATION: gRNA 4

<400> SEQUENCE: 31
```

-continued

```
ggggtcccgt cggccgggtt                                           20

<210> SEQ ID NO 32
<211> LENGTH: 20
<212> TYPE: DNA
<213> ORGANISM: Artificial Sequence
<220> FEATURE:
<223> OTHER INFORMATION: gRNA 5

<400> SEQUENCE: 32
cccgtcggcc gggttcggcg                                           20

<210> SEQ ID NO 33
<211> LENGTH: 20
<212> TYPE: DNA
<213> ORGANISM: Artificial Sequence
<220> FEATURE:
<223> OTHER INFORMATION: gRNA 6

<400> SEQUENCE: 33
ctttaggggt cccgtcggcc                                           20

<210> SEQ ID NO 34
<211> LENGTH: 20
<212> TYPE: DNA
<213> ORGANISM: Artificial Sequence
<220> FEATURE:
<223> OTHER INFORMATION: gRNA 7

<400> SEQUENCE: 34
cagaacttta ggggtcccgt                                           20

<210> SEQ ID NO 35
<211> LENGTH: 20
<212> TYPE: DNA
<213> ORGANISM: Artificial Sequence
<220> FEATURE:
<223> OTHER INFORMATION: gRNA 8

<400> SEQUENCE: 35
actttagggg tcccgtcggc                                           20

<210> SEQ ID NO 36
<211> LENGTH: 20
<212> TYPE: DNA
<213> ORGANISM: Artificial Sequence
<220> FEATURE:
<223> OTHER INFORMATION: gRNA 9

<400> SEQUENCE: 36
agcgagcggg gggctgcccc                                           20

<210> SEQ ID NO 37
<211> LENGTH: 20
<212> TYPE: DNA
<213> ORGANISM: Artificial Sequence
<220> FEATURE:
<223> OTHER INFORMATION: gRNA 10

<400> SEQUENCE: 37
cgcctccgcc gccggagccc                                           20

<210> SEQ ID NO 38
<211> LENGTH: 20
<212> TYPE: DNA
```

-continued

```
<213> ORGANISM: Artificial Sequence
<220> FEATURE:
<223> OTHER INFORMATION: gRNA 11

<400> SEQUENCE: 38
cccgtcggcc gggttcggcg                                                  20

<210> SEQ ID NO 39
<211> LENGTH: 17
<212> TYPE: DNA
<213> ORGANISM: Artificial Sequence
<220> FEATURE:
<223> OTHER INFORMATION: S. aureus chimeric frame

<400> SEQUENCE: 39
taatacgact cactata                                                     17

<210> SEQ ID NO 40
<211> LENGTH: 20
<212> TYPE: DNA
<213> ORGANISM: Artificial Sequence
<220> FEATURE:
<223> OTHER INFORMATION: gRNA 1

<400> SEQUENCE: 40
gtcaataccg ccagaatcca                                                  20

<210> SEQ ID NO 41
<211> LENGTH: 20
<212> TYPE: DNA
<213> ORGANISM: Artificial Sequence
<220> FEATURE:
<223> OTHER INFORMATION: gRNA 2

<400> SEQUENCE: 41
caataccgcc agaatccatg                                                  20

<210> SEQ ID NO 42
<211> LENGTH: 20
<212> TYPE: DNA
<213> ORGANISM: Artificial Sequence
<220> FEATURE:
<223> OTHER INFORMATION: gRNA 3

<400> SEQUENCE: 42
tcaataccgc cagaatccat                                                  20

<210> SEQ ID NO 43
<211> LENGTH: 598
<212> TYPE: PRT
<213> ORGANISM: Artificial Sequence
<220> FEATURE:
<223> OTHER INFORMATION: NR4A2 Isoform 1

<400> SEQUENCE: 43

Met Pro Cys Val Gln Ala Gln Tyr Gly Ser Ser Pro Gln Gly Ala Ser
1               5                   10                  15

Pro Ala Ser Gln Ser Tyr Ser Tyr His Ser Ser Gly Glu Tyr Ser Ser
            20                  25                  30

Asp Phe Leu Thr Pro Glu Phe Val Lys Phe Ser Met Asp Leu Thr Asn
        35                  40                  45

Thr Glu Ile Thr Ala Thr Thr Ser Leu Pro Ser Phe Ser Thr Phe Met
    50                  55                  60

Asp Asn Tyr Ser Thr Gly Tyr Asp Val Lys Pro Pro Cys Leu Tyr Gln
```

-continued

```
65                  70                  75                  80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
               100                 105                 110

Met Met Pro His Ser Gly Ser Val Tyr Tyr Lys Pro Ser Ser Pro Pro
           115                 120                 125

Thr Pro Thr Thr Pro Gly Phe Gln Val Gln His Ser Pro Met Trp Asp
       130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
               165                 170                 175

Ser Phe Lys Gln Ser Pro Pro Gly Thr Pro Val Ser Ser Cys Gln Met
           180                 185                 190

Arg Phe Asp Gly Pro Leu His Val Pro Met Asn Pro Glu Pro Ala Gly
           195                 200                 205

Ser His His Val Val Asp Gly Gln Thr Phe Ala Val Pro Asn Pro Ile
       210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Pro Ser Arg Gly Ser
               245                 250                 255

Pro Ser Asn Glu Gly Leu Cys Ala Val Cys Gly Asp Asn Ala Ala Cys
           260                 265                 270

Gln His Tyr Gly Val Arg Thr Cys Glu Gly Cys Lys Gly Phe Phe Lys
           275                 280                 285

Arg Thr Val Gln Lys Asn Ala Lys Tyr Val Cys Leu Ala Asn Lys Asn
       290                 295                 300

Cys Pro Val Asp Lys Arg Arg Arg Asn Arg Cys Gln Tyr Cys Arg Phe
305                 310                 315                 320

Gln Lys Cys Leu Ala Val Gly Met Val Lys Glu Val Val Arg Thr Asp
           325                 330                 335

Ser Leu Lys Gly Arg Arg Gly Arg Leu Pro Ser Lys Pro Lys Ser Pro
           340                 345                 350

Gln Glu Pro Ser Pro Pro Ser Pro Pro Val Ser Leu Ile Ser Ala Leu
       355                 360                 365

Val Arg Ala His Val Asp Ser Asn Pro Ala Met Thr Ser Leu Asp Tyr
       370                 375                 380

Ser Arg Phe Gln Ala Asn Pro Asp Tyr Gln Met Ser Gly Asp Asp Thr
385                 390                 395                 400

Gln His Ile Gln Gln Phe Tyr Asp Leu Leu Thr Gly Ser Met Glu Ile
           405                 410                 415

Ile Arg Gly Trp Ala Glu Lys Ile Pro Gly Phe Ala Asp Leu Pro Lys
           420                 425                 430

Ala Asp Gln Asp Leu Leu Phe Glu Ser Ala Phe Leu Glu Leu Phe Val
           435                 440                 445

Leu Arg Leu Ala Tyr Arg Ser Asn Pro Val Glu Gly Lys Leu Ile Phe
       450                 455                 460

Cys Asn Gly Val Val Leu His Arg Leu Gln Cys Val Arg Gly Phe Gly
465                 470                 475                 480

Glu Trp Ile Asp Ser Ile Val Glu Phe Ser Ser Asn Leu Gln Asn Met
           485                 490                 495
```

Asn Ile Asp Ile Ser Ala Phe Ser Cys Ile Ala Ala Leu Ala Met Val
        500                 505                 510

Thr Glu Arg His Gly Leu Lys Glu Pro Lys Arg Val Glu Glu Leu Gln
        515                 520                 525

Asn Lys Ile Val Asn Cys Leu Lys Asp His Val Thr Phe Asn Asn Gly
        530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
        565                 570                 575

Lys Leu Glu Asp Leu Val Pro Pro Pro Ala Ile Ile Asp Lys Leu Phe
        580                 585                 590

Leu Asp Thr Leu Pro Phe
        595

<210> SEQ ID NO 44
<211> LENGTH: 535
<212> TYPE: PRT
<213> ORGANISM: Artificial Sequence
<220> FEATURE:
<223> OTHER INFORMATION: NR4A2 Isoform 2

<400> SEQUENCE: 44

Met Asp Asn Tyr Ser Thr Gly Tyr Asp Val Lys Pro Pro Cys Leu Tyr
1               5                   10                  15

Gln Met Pro Leu Ser Gly Gln Gln Ser Ser Ile Lys Val Glu Asp Ile
        20                  25                  30

Gln Met His Asn Tyr Gln Gln His Ser His Leu Pro Pro Gln Ser Glu
        35                  40                  45

Glu Met Met Pro His Ser Gly Ser Val Tyr Tyr Lys Pro Ser Ser Pro
        50                  55                  60

Pro Thr Pro Thr Thr Pro Gly Phe Gln Val Gln His Ser Pro Met Trp
65                  70                  75                  80

Asp Asp Pro Gly Ser Leu His Asn Phe His Gln Asn Tyr Val Ala Thr
                85                  90                  95

Thr His Met Ile Glu Gln Arg Lys Thr Pro Val Ser Arg Leu Ser Leu
        100                 105                 110

Phe Ser Phe Lys Gln Ser Pro Pro Gly Thr Pro Val Ser Ser Cys Gln
        115                 120                 125

Met Arg Phe Asp Gly Pro Leu His Val Pro Met Asn Pro Glu Pro Ala
        130                 135                 140

Gly Ser His His Val Val Asp Gly Gln Thr Phe Ala Val Pro Asn Pro
145                 150                 155                 160

Ile Arg Lys Pro Ala Ser Met Gly Phe Pro Gly Leu Gln Ile Gly His
                165                 170                 175

Ala Ser Gln Leu Leu Asp Thr Gln Val Pro Ser Pro Pro Ser Arg Gly
        180                 185                 190

Ser Pro Ser Asn Glu Gly Leu Cys Ala Val Cys Gly Asp Asn Ala Ala
        195                 200                 205

Cys Gln His Tyr Gly Val Arg Thr Cys Glu Gly Cys Lys Gly Phe Phe
        210                 215                 220

Lys Arg Thr Val Gln Lys Asn Ala Lys Tyr Val Cys Leu Ala Asn Lys
225                 230                 235                 240

Asn Cys Pro Val Asp Lys Arg Arg Arg Asn Arg Cys Gln Tyr Cys Arg
                245                 250                 255

-continued

```
Phe Gln Lys Cys Leu Ala Val Gly Met Val Lys Glu Val Val Arg Thr
        260             265             270

Asp Ser Leu Lys Gly Arg Arg Gly Arg Leu Pro Ser Lys Pro Lys Ser
        275             280             285

Pro Gln Glu Pro Ser Pro Pro Ser Pro Pro Val Ser Leu Ile Ser Ala
    290             295             300

Leu Val Arg Ala His Val Asp Ser Asn Pro Ala Met Thr Ser Leu Asp
305             310             315             320

Tyr Ser Arg Phe Gln Ala Asn Pro Asp Tyr Gln Met Ser Gly Asp Asp
                325             330             335

Thr Gln His Ile Gln Gln Phe Tyr Asp Leu Leu Thr Gly Ser Met Glu
        340             345             350

Ile Ile Arg Gly Trp Ala Glu Lys Ile Pro Gly Phe Ala Asp Leu Pro
        355             360             365

Lys Ala Asp Gln Asp Leu Leu Phe Glu Ser Ala Phe Leu Glu Leu Phe
    370             375             380

Val Leu Arg Leu Ala Tyr Arg Ser Asn Pro Val Glu Gly Lys Leu Ile
385             390             395             400

Phe Cys Asn Gly Val Val Leu His Arg Leu Gln Cys Val Arg Gly Phe
                405             410             415

Gly Glu Trp Ile Asp Ser Ile Val Glu Phe Ser Ser Asn Leu Gln Asn
        420             425             430

Met Asn Ile Asp Ile Ser Ala Phe Ser Cys Ile Ala Ala Leu Ala Met
        435             440             445

Val Thr Glu Arg His Gly Leu Lys Glu Pro Lys Arg Val Glu Glu Leu
        450             455             460

Gln Asn Lys Ile Val Asn Cys Leu Lys Asp His Val Thr Phe Asn Asn
465             470             475             480

Gly Gly Leu Asn Arg Pro Asn Tyr Leu Ser Lys Leu Leu Gly Lys Leu
                485             490             495

Pro Glu Leu Arg Thr Leu Cys Thr Gln Gly Leu Gln Arg Ile Phe Tyr
            500             505             510

Leu Lys Leu Glu Asp Leu Val Pro Pro Pro Ala Ile Ile Asp Lys Leu
        515             520             525

Phe Leu Asp Thr Leu Pro Phe
    530             535
```

```
<210> SEQ ID NO 45
<211> LENGTH: 598
<212> TYPE: PRT
<213> ORGANISM: Artificial Sequence
<220> FEATURE:
<223> OTHER INFORMATION: NR4A1 Isoform 1

<400> SEQUENCE: 45
```

```
Met Pro Cys Ile Gln Ala Gln Tyr Gly Thr Pro Ala Pro Ser Pro Gly
1               5               10              15

Pro Arg Asp His Leu Ala Ser Asp Pro Leu Thr Pro Glu Phe Ile Lys
                20              25              30

Pro Thr Met Asp Leu Ala Ser Pro Glu Ala Ala Pro Ala Ala Pro Thr
        35              40              45

Ala Leu Pro Ser Phe Ser Thr Phe Met Asp Gly Tyr Thr Gly Glu Phe
    50              55              60

Asp Thr Phe Leu Tyr Gln Leu Pro Gly Thr Val Gln Pro Cys Ser Ser
65              70              75              80
```

-continued

```
Ala Ser Ser Ser Ala Ser Ser Thr Ser Ser Ser Ser Ala Thr Ser Pro
                85              90              95

Ala Ser Ala Ser Phe Lys Phe Glu Asp Phe Gln Val Tyr Gly Cys Tyr
            100             105             110

Pro Gly Pro Leu Ser Gly Pro Val Asp Glu Ala Leu Ser Ser Ser Gly
            115             120             125

Ser Asp Tyr Tyr Gly Ser Pro Cys Ser Ala Pro Ser Pro Ser Thr Pro
    130             135             140

Ser Phe Gln Pro Pro Gln Leu Ser Pro Trp Asp Gly Ser Phe Gly His
145             150             155             160

Phe Ser Pro Ser Gln Thr Tyr Glu Gly Leu Arg Ala Trp Thr Glu Gln
            165             170             175

Leu Pro Lys Ala Ser Gly Pro Pro Gln Pro Pro Ala Phe Phe Ser Phe
            180             185             190

Ser Pro Pro Thr Gly Pro Ser Pro Ser Leu Ala Gln Ser Pro Leu Lys
    195             200             205

Leu Phe Pro Ser Gln Ala Thr His Gln Leu Gly Glu Gly Glu Ser Tyr
    210             215             220

Ser Met Pro Thr Ala Phe Pro Gly Leu Ala Pro Thr Ser Pro His Leu
225             230             235             240

Glu Gly Ser Gly Ile Leu Asp Thr Pro Val Thr Ser Thr Lys Ala Arg
            245             250             255

Ser Gly Ala Pro Gly Gly Ser Glu Gly Arg Cys Ala Val Cys Gly Asp
            260             265             270

Asn Ala Ser Cys Gln His Tyr Gly Val Arg Thr Cys Glu Gly Cys Lys
            275             280             285

Gly Phe Phe Lys Arg Thr Val Gln Lys Asn Ala Lys Tyr Ile Cys Leu
    290             295             300

Ala Asn Lys Asp Cys Pro Val Asp Lys Arg Arg Arg Asn Arg Cys Gln
305             310             315             320

Phe Cys Arg Phe Gln Lys Cys Leu Ala Val Gly Met Val Lys Glu Val
            325             330             335

Val Arg Thr Asp Ser Leu Lys Gly Arg Arg Gly Arg Leu Pro Ser Lys
            340             345             350

Pro Lys Gln Pro Pro Asp Ala Ser Pro Ala Asn Leu Leu Thr Ser Leu
            355             360             365

Val Arg Ala His Leu Asp Ser Gly Pro Ser Thr Ala Lys Leu Asp Tyr
    370             375             380

Ser Lys Phe Gln Glu Leu Val Leu Pro His Phe Gly Lys Glu Asp Ala
385             390             395             400

Gly Asp Val Gln Gln Phe Tyr Asp Leu Leu Ser Gly Ser Leu Glu Val
            405             410             415

Ile Arg Lys Trp Ala Glu Lys Ile Pro Gly Phe Ala Glu Leu Ser Pro
            420             425             430

Ala Asp Gln Asp Leu Leu Leu Glu Ser Ala Phe Leu Glu Leu Phe Ile
            435             440             445

Leu Arg Leu Ala Tyr Arg Ser Lys Pro Gly Glu Gly Lys Leu Ile Phe
    450             455             460

Cys Ser Gly Leu Val Leu His Arg Leu Gln Cys Ala Arg Gly Phe Gly
465             470             475             480

Asp Trp Ile Asp Ser Ile Leu Ala Phe Ser Arg Ser Leu His Ser Leu
            485             490             495
```

```
Leu Val Asp Val Pro Ala Phe Ala Cys Leu Ser Ala Leu Val Leu Ile
            500             505             510

Thr Asp Arg His Gly Leu Gln Glu Pro Arg Arg Val Glu Glu Leu Gln
            515             520             525

Asn Arg Ile Ala Ser Cys Leu Lys Glu His Val Ala Ala Val Ala Gly
            530             535             540

Glu Pro Gln Pro Ala Ser Cys Leu Ser Arg Leu Leu Gly Lys Leu Pro
545             550             555             560

Glu Leu Arg Thr Leu Cys Thr Gln Gly Leu Gln Arg Ile Phe Tyr Leu
            565             570             575

Lys Leu Glu Asp Leu Val Pro Pro Pro Ile Ile Asp Lys Ile Phe
            580             585             590

Met Asp Thr Leu Pro Phe
            595

<210> SEQ ID NO 46
<211> LENGTH: 611
<212> TYPE: PRT
<213> ORGANISM: Artificial Sequence
<220> FEATURE:
<223> OTHER INFORMATION: NR4A1 Isoform 2

<400> SEQUENCE: 46

Met Trp Leu Ala Lys Ala Cys Trp Ser Ile Gln Ser Glu Met Pro Cys
1               5               10              15

Ile Gln Ala Gln Tyr Gly Thr Pro Ala Pro Ser Pro Gly Pro Arg Asp
            20              25              30

His Leu Ala Ser Asp Pro Leu Thr Pro Glu Phe Ile Lys Pro Thr Met
            35              40              45

Asp Leu Ala Ser Pro Glu Ala Ala Pro Ala Ala Pro Thr Ala Leu Pro
            50              55              60

Ser Phe Ser Thr Phe Met Asp Gly Tyr Thr Gly Glu Phe Asp Thr Phe
65              70              75              80

Leu Tyr Gln Leu Pro Gly Thr Val Gln Pro Cys Ser Ser Ala Ser Ser
            85              90              95

Ser Ala Ser Ser Thr Ser Ser Ser Ala Thr Ser Pro Ala Ser Ala
            100             105             110

Ser Phe Lys Phe Glu Asp Phe Gln Val Tyr Gly Cys Tyr Pro Gly Pro
            115             120             125

Leu Ser Gly Pro Val Asp Glu Ala Leu Ser Ser Ser Gly Ser Asp Tyr
            130             135             140

Tyr Gly Ser Pro Cys Ser Ala Pro Ser Pro Ser Thr Pro Ser Phe Gln
145             150             155             160

Pro Pro Gln Leu Ser Pro Trp Asp Gly Ser Phe Gly His Phe Ser Pro
            165             170             175

Ser Gln Thr Tyr Glu Gly Leu Arg Ala Trp Thr Glu Gln Leu Pro Lys
            180             185             190

Ala Ser Gly Pro Pro Gln Pro Pro Ala Phe Phe Ser Phe Ser Pro Pro
            195             200             205

Thr Gly Pro Ser Pro Ser Leu Ala Gln Ser Pro Leu Lys Leu Phe Pro
            210             215             220

Ser Gln Ala Thr His Gln Leu Gly Glu Gly Glu Ser Tyr Ser Met Pro
225             230             235             240

Thr Ala Phe Pro Gly Leu Ala Pro Thr Ser Pro His Leu Glu Gly Ser
            245             250             255
```

```
Gly Ile Leu Asp Thr Pro Val Thr Ser Thr Lys Ala Arg Ser Gly Ala
            260             265             270

Pro Gly Gly Ser Glu Gly Arg Cys Ala Val Cys Gly Asp Asn Ala Ser
        275             280             285

Cys Gln His Tyr Gly Val Arg Thr Cys Glu Gly Cys Lys Gly Phe Phe
    290             295             300

Lys Arg Thr Val Gln Lys Asn Ala Lys Tyr Ile Cys Leu Ala Asn Lys
305             310             315             320

Asp Cys Pro Val Asp Lys Arg Arg Asn Arg Cys Gln Phe Cys Arg
            325             330             335

Phe Gln Lys Cys Leu Ala Val Gly Met Val Lys Glu Val Val Arg Thr
        340             345             350

Asp Ser Leu Lys Gly Arg Arg Gly Arg Leu Pro Ser Lys Pro Lys Gln
        355             360             365

Pro Pro Asp Ala Ser Pro Ala Asn Leu Leu Thr Ser Leu Val Arg Ala
    370             375             380

His Leu Asp Ser Gly Pro Ser Thr Ala Lys Leu Asp Tyr Ser Lys Phe
385             390             395             400

Gln Glu Leu Val Leu Pro His Phe Gly Lys Glu Asp Ala Gly Asp Val
        405             410             415

Gln Gln Phe Tyr Asp Leu Leu Ser Gly Ser Leu Glu Val Ile Arg Lys
        420             425             430

Trp Ala Glu Lys Ile Pro Gly Phe Ala Glu Leu Ser Pro Ala Asp Gln
        435             440             445

Asp Leu Leu Leu Glu Ser Ala Phe Leu Glu Leu Phe Ile Leu Arg Leu
    450             455             460

Ala Tyr Arg Ser Lys Pro Gly Glu Gly Lys Leu Ile Phe Cys Ser Gly
465             470             475             480

Leu Val Leu His Arg Leu Gln Cys Ala Arg Gly Phe Gly Asp Trp Ile
        485             490             495

Asp Ser Ile Leu Ala Phe Ser Arg Ser Leu His Ser Leu Leu Val Asp
        500             505             510

Val Pro Ala Phe Ala Cys Leu Ser Ala Leu Val Leu Ile Thr Asp Arg
        515             520             525

His Gly Leu Gln Glu Pro Arg Arg Val Glu Glu Leu Gln Asn Arg Ile
    530             535             540

Ala Ser Cys Leu Lys Glu His Val Ala Ala Val Ala Gly Glu Pro Gln
545             550             555             560

Pro Ala Ser Cys Leu Ser Arg Leu Leu Gly Lys Leu Pro Glu Leu Arg
        565             570             575

Thr Leu Cys Thr Gln Gly Leu Gln Arg Ile Phe Tyr Leu Lys Leu Glu
        580             585             590

Asp Leu Val Pro Pro Pro Ile Ile Asp Lys Ile Phe Met Asp Thr
    595             600             605

Leu Pro Phe
    610
```

```
<210> SEQ ID NO 47
<211> LENGTH: 325
<212> TYPE: PRT
<213> ORGANISM: Artificial Sequence
<220> FEATURE:
<223> OTHER INFORMATION: NR4A1 Isoform 3

<400> SEQUENCE: 47
```

-continued

```
Met Pro Cys Ile Gln Ala Gln Tyr Gly Thr Pro Ala Pro Ser Pro Gly
1               5                   10                  15

Pro Arg Asp His Leu Ala Ser Asp Pro Leu Thr Pro Glu Phe Ile Lys
                20                  25                  30

Pro Thr Met Asp Leu Ala Ser Pro Glu Ala Ala Pro Ala Ala Pro Thr
                35                  40                  45

Ala Leu Pro Ser Phe Ser Thr Phe Met Asp Gly Tyr Thr Gly Glu Phe
    50                  55                  60

Asp Thr Phe Leu Tyr Gln Leu Pro Gly Thr Val Gln Pro Cys Ser Ser
65                  70                  75                  80

Ala Ser Ser Ser Ala Ser Ser Thr Ser Ser Ser Ser Ala Thr Ser Pro
                85                  90                  95

Ala Ser Ala Ser Phe Lys Phe Glu Asp Phe Gln Val Tyr Gly Cys Tyr
                100                 105                 110

Pro Gly Pro Leu Ser Gly Pro Val Asp Glu Ala Leu Ser Ser Ser Gly
                115                 120                 125

Ser Asp Tyr Tyr Gly Ser Pro Cys Ser Ala Pro Ser Pro Ser Thr Pro
    130                 135                 140

Ser Phe Gln Pro Pro Gln Leu Ser Pro Trp Asp Gly Ser Phe Gly His
145                 150                 155                 160

Phe Ser Pro Ser Gln Thr Tyr Glu Gly Leu Arg Ala Trp Thr Glu Gln
                165                 170                 175

Leu Pro Lys Ala Ser Gly Pro Pro Gln Pro Pro Ala Phe Phe Ser Phe
                180                 185                 190

Ser Pro Pro Thr Gly Pro Ser Pro Ser Leu Ala Gln Ser Pro Leu Lys
                195                 200                 205

Leu Phe Pro Ser Gln Ala Thr His Gln Leu Gly Glu Gly Glu Ser Tyr
    210                 215                 220

Ser Met Pro Thr Ala Phe Pro Gly Leu Ala Pro Thr Ser Pro His Leu
225                 230                 235                 240

Glu Gly Ser Gly Ile Leu Asp Thr Pro Val Thr Ser Thr Lys Ala Arg
                245                 250                 255

Ser Gly Ala Pro Gly Gly Ser Glu Gly Arg Cys Ala Val Cys Gly Asp
                260                 265                 270

Asn Ala Ser Cys Gln His Tyr Gly Val Arg Thr Cys Glu Gly Cys Lys
                275                 280                 285

Gly Phe Phe Lys Val Pro Arg Ser Pro Arg Trp Gly Leu Leu Leu Glu
    290                 295                 300

Met Glu Arg Gly Trp Pro His Pro Ile Gly Thr Cys Gly Leu Pro Leu
305                 310                 315                 320

Gly Ser Pro Pro Ser
                325
```

```
<210> SEQ ID NO 48
<211> LENGTH: 20
<212> TYPE: RNA
<213> ORGANISM: Artificial Sequence
<220> FEATURE:
<223> OTHER INFORMATION: NR4A3 sgRNA 1

<400> SEQUENCE: 48
caauauagcc cuuccccucc                                                          20

<210> SEQ ID NO 49
<211> LENGTH: 20
<212> TYPE: RNA
```

<213> ORGANISM: Artificial Sequence
<220> FEATURE:
<223> OTHER INFORMATION: NR4A3 sgRNA 2

<400> SEQUENCE: 49
aacuggaacc uggaggggaa                                     20

<210> SEQ ID NO 50
<211> LENGTH: 20
<212> TYPE: RNA
<213> ORGANISM: Artificial Sequence
<220> FEATURE:
<223> OTHER INFORMATION: NR4A3 sgRNA 3

<400> SEQUENCE: 50
uaacuggaac cuggaggggga                                    20

<210> SEQ ID NO 51

<400> SEQUENCE: 51

000

<210> SEQ ID NO 52
<211> LENGTH: 20
<212> TYPE: RNA
<213> ORGANISM: Artificial Sequence
<220> FEATURE:
<223> OTHER INFORMATION: NR4A3 sgRNA 5

<400> SEQUENCE: 52
ccgcugcauu ugguacacgc                                     20

<210> SEQ ID NO 53
<211> LENGTH: 20
<212> TYPE: RNA
<213> ORGANISM: Artificial Sequence
<220> FEATURE:
<223> OTHER INFORMATION: NR4A3 sgRNA 6

<400> SEQUENCE: 53
ugcggcgcag acauacagcu                                     20

<210> SEQ ID NO 54
<211> LENGTH: 20
<212> TYPE: RNA
<213> ORGANISM: Artificial Sequence
<220> FEATURE:
<223> OTHER INFORMATION: NR4A3 sgRNA 7

<400> SEQUENCE: 54
gcagcggccc uugaucaaag                                     20

<210> SEQ ID NO 55
<211> LENGTH: 20
<212> TYPE: RNA
<213> ORGANISM: Artificial Sequence
<220> FEATURE:
<223> OTHER INFORMATION: NR4A3 sgRNA 8

<400> SEQUENCE: 55
auacagcucg gaauacacca                                     20

<210> SEQ ID NO 56
<211> LENGTH: 20
<212> TYPE: RNA

-continued

```
<213> ORGANISM: Artificial Sequence
<220> FEATURE:
<223> OTHER INFORMATION: NR4A3 sgRNA 9

<400> SEQUENCE: 56
ccugcgugua ccaaaugcag                                                        20

<210> SEQ ID NO 57
<211> LENGTH: 20
<212> TYPE: RNA
<213> ORGANISM: Artificial Sequence
<220> FEATURE:
<223> OTHER INFORMATION: NR4A3 sgRNA 10

<400> SEQUENCE: 57
gcggcccuug aucaaagugg                                                        20

<210> SEQ ID NO 58
<211> LENGTH: 20
<212> TYPE: RNA
<213> ORGANISM: Artificial Sequence
<220> FEATURE:
<223> OTHER INFORMATION: NR4A3 sgRNA 11

<400> SEQUENCE: 58
ggacugcuug aaguacaugg                                                        20

<210> SEQ ID NO 59
<211> LENGTH: 20
<212> TYPE: RNA
<213> ORGANISM: Artificial Sequence
<220> FEATURE:
<223> OTHER INFORMATION: NR4A3 sgRNA 12

<400> SEQUENCE: 59
cggguggcuc ucaagcgcgg                                                        20

<210> SEQ ID NO 60
<211> LENGTH: 20
<212> TYPE: RNA
<213> ORGANISM: Artificial Sequence
<220> FEATURE:
<223> OTHER INFORMATION: NR4A3 sgRNA 13

<400> SEQUENCE: 60
gacgacgagc uccugcuggg                                                        20

<210> SEQ ID NO 61
<211> LENGTH: 20
<212> TYPE: RNA
<213> ORGANISM: Artificial Sequence
<220> FEATURE:
<223> OTHER INFORMATION: NR4A3 sgRNA 14

<400> SEQUENCE: 61
gucgggguuc augaucuccg                                                        20

<210> SEQ ID NO 62
<211> LENGTH: 20
<212> TYPE: RNA
<213> ORGANISM: Artificial Sequence
<220> FEATURE:
<223> OTHER INFORMATION: NR4A3 sgRNA 15

<400> SEQUENCE: 62
gagggcuuga aguggaagag                                                        20
```

-continued

```
<210> SEQ ID NO 63
<211> LENGTH: 20
<212> TYPE: RNA
<213> ORGANISM: Artificial Sequence
<220> FEATURE:
<223> OTHER INFORMATION: NR4A3 sgRNA 16

<400> SEQUENCE: 63
gaugaaggcg guccccacgg                                               20

<210> SEQ ID NO 64
<211> LENGTH: 20
<212> TYPE: RNA
<213> ORGANISM: Artificial Sequence
<220> FEATURE:
<223> OTHER INFORMATION: NR4A3 sgRNA 17

<400> SEQUENCE: 64
gaagguacug augcugggca                                               20

<210> SEQ ID NO 65
<211> LENGTH: 20
<212> TYPE: RNA
<213> ORGANISM: Artificial Sequence
<220> FEATURE:
<223> OTHER INFORMATION: NR4A3 sgRNA 18

<400> SEQUENCE: 65
uccuccagcc uccagcccgg                                               20

<210> SEQ ID NO 66
<211> LENGTH: 20
<212> TYPE: RNA
<213> ORGANISM: Artificial Sequence
<220> FEATURE:
<223> OTHER INFORMATION: NR4A3 sgRNA 19

<400> SEQUENCE: 66
agcaucagua ccuucgugga                                               20

<210> SEQ ID NO 67
<211> LENGTH: 20
<212> TYPE: RNA
<213> ORGANISM: Artificial Sequence
<220> FEATURE:
<223> OTHER INFORMATION: NR4A3 sgRNA 20

<400> SEQUENCE: 67
cgacuacacc aagcugacca                                               20

<210> SEQ ID NO 68
<211> LENGTH: 20
<212> TYPE: RNA
<213> ORGANISM: Artificial Sequence
<220> FEATURE:
<223> OTHER INFORMATION: NR4A3 sgRNA 21

<400> SEQUENCE: 68
uggucagcuu gguguagucg                                               20

<210> SEQ ID NO 69
<211> LENGTH: 20
<212> TYPE: RNA
<213> ORGANISM: Artificial Sequence
<220> FEATURE:
```

-continued

<223> OTHER INFORMATION: NR4A3 sgRNA 22

<400> SEQUENCE: 69
gcuggacccg ccgaugaagg                                                      20

<210> SEQ ID NO 70
<211> LENGTH: 20
<212> TYPE: RNA
<213> ORGANISM: Artificial Sequence
<220> FEATURE:
<223> OTHER INFORMATION: NR4A3 sgRNA 23

<400> SEQUENCE: 70
uugaaguaca uggaggugcu                                                      20

<210> SEQ ID NO 71
<211> LENGTH: 20
<212> TYPE: RNA
<213> ORGANISM: Artificial Sequence
<220> FEATURE:
<223> OTHER INFORMATION: NR4A3 sgRNA 24

<400> SEQUENCE: 71
guacgggugg cucucaagcg                                                      20

<210> SEQ ID NO 72
<211> LENGTH: 20
<212> TYPE: RNA
<213> ORGANISM: Artificial Sequence
<220> FEATURE:
<223> OTHER INFORMATION: NR4A3 sgRNA 25

<400> SEQUENCE: 72
ccgcauaacu ggaaccugga                                                      20

<210> SEQ ID NO 73
<211> LENGTH: 20
<212> TYPE: RNA
<213> ORGANISM: Artificial Sequence
<220> FEATURE:
<223> OTHER INFORMATION: NR4A3 sgRNA 26

<400> SEQUENCE: 73
gggcacgugu gccgugugcg                                                      20

<210> SEQ ID NO 74
<211> LENGTH: 20
<212> TYPE: RNA
<213> ORGANISM: Artificial Sequence
<220> FEATURE:
<223> OTHER INFORMATION: NR4A3 sgRNA 27

<400> SEQUENCE: 74
uacggcgugc gaaccugcga                                                      20

<210> SEQ ID NO 75
<211> LENGTH: 20
<212> TYPE: RNA
<213> ORGANISM: Artificial Sequence
<220> FEATURE:
<223> OTHER INFORMATION: NR4A3 sgRNA 28

<400> SEQUENCE: 75
uggggacugc uugaaguaca                                                      20

```
<210> SEQ ID NO 76
<211> LENGTH: 20
<212> TYPE: RNA
<213> ORGANISM: Artificial Sequence
<220> FEATURE:
<223> OTHER INFORMATION: NR4A3 sgRNA 29

<400> SEQUENCE: 76
ccuuggcagc acugagauca                                                         20

<210> SEQ ID NO 77
<211> LENGTH: 20
<212> TYPE: RNA
<213> ORGANISM: Artificial Sequence
<220> FEATURE:
<223> OTHER INFORMATION: NR4A3 sgRNA 30

<400> SEQUENCE: 77
ccuugaucaa aguggaggag                                                         20

<210> SEQ ID NO 78
<211> LENGTH: 20
<212> TYPE: RNA
<213> ORGANISM: Artificial Sequence
<220> FEATURE:
<223> OTHER INFORMATION: NR4A3 sgRNA 31

<400> SEQUENCE: 78
ugcauuuggu acacgcagga                                                         20

<210> SEQ ID NO 79
<211> LENGTH: 20
<212> TYPE: RNA
<213> ORGANISM: Artificial Sequence
<220> FEATURE:
<223> OTHER INFORMATION: NR4A3 sgRNA 32

<400> SEQUENCE: 79
ugaucaaagu ggaggagggg                                                         20

<210> SEQ ID NO 80
<211> LENGTH: 20
<212> TYPE: RNA
<213> ORGANISM: Artificial Sequence
<220> FEATURE:
<223> OTHER INFORMATION: NR4A3 sgRNA 33

<400> SEQUENCE: 80 gugggggaccg ccuucaucgg                                                        20

<210> SEQ ID NO 81
<211> LENGTH: 20
<212> TYPE: RNA
<213> ORGANISM: Artificial Sequence
<220> FEATURE:
<223> OTHER INFORMATION: NR4A3 sgRNA 34

<400> SEQUENCE: 81
aggagcucgu cgucuggcga                                                         20

<210> SEQ ID NO 82
<211> LENGTH: 20
<212> TYPE: RNA
<213> ORGANISM: Artificial Sequence
<220> FEATURE:
<223> OTHER INFORMATION: NR4A3 sgRNA 35
```

<400> SEQUENCE: 82
ccaccucggc uacgacccga                                                        20

<210> SEQ ID NO 83
<211> LENGTH: 20
<212> TYPE: RNA
<213> ORGANISM: Artificial Sequence
<220> FEATURE:
<223> OTHER INFORMATION: NR4A3 sgRNA 36

<400> SEQUENCE: 83
gcggcggcga gggcuugaag                                                        20

<210> SEQ ID NO 84
<211> LENGTH: 20
<212> TYPE: RNA
<213> ORGANISM: Artificial Sequence
<220> FEATURE:
<223> OTHER INFORMATION: NR4A3 sgRNA 37

<400> SEQUENCE: 84
cagcaucagu accuucgugg                                                        20

<210> SEQ ID NO 85
<211> LENGTH: 20
<212> TYPE: RNA
<213> ORGANISM: Artificial Sequence
<220> FEATURE:
<223> OTHER INFORMATION: NR4A3 sgRNA 38

<400> SEQUENCE: 85
gccgaugaag gcggucccca                                                        20

<210> SEQ ID NO 86
<211> LENGTH: 20
<212> TYPE: RNA
<213> ORGANISM: Artificial Sequence
<220> FEATURE:
<223> OTHER INFORMATION: NR4A3 sgRNA 39

<400> SEQUENCE: 86
ccgucggguc guagccgagg                                                        20

<210> SEQ ID NO 87
<211> LENGTH: 20
<212> TYPE: RNA
<213> ORGANISM: Artificial Sequence
<220> FEATURE:
<223> OTHER INFORMATION: NR4A3 sgRNA 40

<400> SEQUENCE: 87
cuacggcgug cgaaccugcg                                                        20

<210> SEQ ID NO 88
<211> LENGTH: 20
<212> TYPE: RNA
<213> ORGANISM: Artificial Sequence
<220> FEATURE:
<223> OTHER INFORMATION: NR4A3 sgRNA 41

<400> SEQUENCE: 88
ccauaacgcc cccgccugcg                                                        20

<210> SEQ ID NO 89
<211> LENGTH: 20

```
<212> TYPE: RNA
<213> ORGANISM: Artificial Sequence
<220> FEATURE:
<223> OTHER INFORMATION: NR4A3 sgRNA 42

<400> SEQUENCE: 89
auaacgcccc cgccugcggg                                                 20

<210> SEQ ID NO 90
<211> LENGTH: 20
<212> TYPE: RNA
<213> ORGANISM: Artificial Sequence
<220> FEATURE:
<223> OTHER INFORMATION: NR4A3 sgRNA 43

<400> SEQUENCE: 90
gccgcauaac uggaaccugg                                                 20

<210> SEQ ID NO 91
<211> LENGTH: 20
<212> TYPE: RNA
<213> ORGANISM: Artificial Sequence
<220> FEATURE:
<223> OTHER INFORMATION: NR4A3 sgRNA 44

<400> SEQUENCE: 91
gaaaucgaca guacugacau                                                 20

<210> SEQ ID NO 92
<211> LENGTH: 20
<212> TYPE: RNA
<213> ORGANISM: Artificial Sequence
<220> FEATURE:
<223> OTHER INFORMATION: NR4A3 sgRNA 45

<400> SEQUENCE: 92
uuucagaagu gucucagugu                                                 20

<210> SEQ ID NO 93
<211> LENGTH: 20
<212> TYPE: RNA
<213> ORGANISM: Artificial Sequence
<220> FEATURE:
<223> OTHER INFORMATION: NR4A3 sgRNA 46

<400> SEQUENCE: 93
gaagugucuc aguguuggaa                                                 20

<210> SEQ ID NO 94
<211> LENGTH: 20
<212> TYPE: RNA
<213> ORGANISM: Artificial Sequence
<220> FEATURE:
<223> OTHER INFORMATION: NR4A3 sgRNA 47

<400> SEQUENCE: 94
aguguuggaa ugguaaaaga                                                 20

<210> SEQ ID NO 95
<211> LENGTH: 20
<212> TYPE: RNA
<213> ORGANISM: Artificial Sequence
<220> FEATURE:
<223> OTHER INFORMATION: NR4A3 sgRNA 48

<400> SEQUENCE: 95
```
guacagauag ucugaaaggg                                                      20

<210> SEQ ID NO 96
<211> LENGTH: 20
<212> TYPE: RNA
<213> ORGANISM: Artificial Sequence
<220> FEATURE:
<223> OTHER INFORMATION: NR4A3 sgRNA 49

<400> SEQUENCE: 96
guguugaguc uguuaaagcu                                                      20

<210> SEQ ID NO 97
<211> LENGTH: 20
<212> TYPE: RNA
<213> ORGANISM: Artificial Sequence
<220> FEATURE:
<223> OTHER INFORMATION: NR4A3 sgRNA 50

<400> SEQUENCE: 97
gauagucuga aagggaggag                                                      20

<210> SEQ ID NO 98
<211> LENGTH: 20
<212> TYPE: RNA
<213> ORGANISM: Artificial Sequence
<220> FEATURE:
<223> OTHER INFORMATION: NR4A3 sgRNA 51

<400> SEQUENCE: 98
agucuguuaa agcucggaca                                                      20

<210> SEQ ID NO 99
<211> LENGTH: 20
<212> TYPE: RNA
<213> ORGANISM: Artificial Sequence
<220> FEATURE:
<223> OTHER INFORMATION: NR4A3 sgRNA 52

<400> SEQUENCE: 99
guccguacag auagucugaa                                                      20

<210> SEQ ID NO 100
<211> LENGTH: 9
<212> TYPE: DNA
<213> ORGANISM: Artificial Sequence
<220> FEATURE:
<223> OTHER INFORMATION: NBRE

<400> SEQUENCE: 100 aaaaggtca                                                                  9

<210> SEQ ID NO 101

<400> SEQUENCE: 101

000

<210> SEQ ID NO 102

<400> SEQUENCE: 102

000

<210> SEQ ID NO 103

-continued

```
<400> SEQUENCE: 103

000

<210> SEQ ID NO 104

<400> SEQUENCE: 104

000

<210> SEQ ID NO 105

<400> SEQUENCE: 105

000

<210> SEQ ID NO 106
<211> LENGTH: 92
<212> TYPE: PRT
<213> ORGANISM: Artificial Sequence
<220> FEATURE:
<223> OTHER INFORMATION: NR4A1 DBD #1

<400> SEQUENCE: 106

Ser Glu Gly Arg Cys Ala Val Cys Gly Asp Asn Ala Ser Cys Gln His
1               5                   10                  15

Tyr Gly Val Arg Thr Cys Glu Gly Cys Lys Gly Phe Phe Lys Arg Thr
                20                  25                  30

Val Gln Lys Asn Ala Lys Tyr Ile Cys Leu Ala Asn Lys Asp Cys Pro
        35                  40                  45

Val Asp Lys Arg Arg Arg Asn Arg Cys Gln Phe Cys Arg Phe Gln Lys
    50                  55                  60

Cys Leu Ala Val Gly Met Val Lys Glu Val Val Arg Thr Asp Ser Leu
65                  70                  75                  80

Lys Gly Arg Arg Gly Arg Leu Pro Ser Lys Pro Lys
                85                  90

<210> SEQ ID NO 107
<211> LENGTH: 93
<212> TYPE: PRT
<213> ORGANISM: Artificial Sequence
<220> FEATURE:
<223> OTHER INFORMATION: NR4A1 DBD #2

<400> SEQUENCE: 107

Ser Glu Gly Arg Cys Ala Val Cys Gly Asp Asn Ala Ser Cys Gln His
1               5                   10                  15

Tyr Gly Val Arg Thr Cys Glu Gly Cys Lys Gly Phe Phe Lys Arg Thr
                20                  25                  30

Val Gln Lys Asn Ala Lys Tyr Ile Cys Leu Ala Asn Lys Asp Cys Pro
        35                  40                  45

Val Asp Lys Arg Arg Arg Asn Arg Cys Gln Phe Cys Arg Phe Gln Lys
    50                  55                  60

Cys Leu Ala Val Gly Met Val Lys Glu Val Val Arg Thr Asp Ser Leu
65                  70                  75                  80

Lys Gly Arg Arg Gly Arg Leu Pro Ser Lys Pro Lys Gln
                85                  90

<210> SEQ ID NO 108
<211> LENGTH: 92
<212> TYPE: PRT
<213> ORGANISM: Artificial Sequence
```

-continued

```
<220> FEATURE:
<223> OTHER INFORMATION: NR4A2 DBD #1

<400> SEQUENCE: 108

Asn Glu Gly Leu Cys Ala Val Cys Gly Asp Asn Ala Ala Cys Gln His
1               5                   10                  15

Tyr Gly Val Arg Thr Cys Glu Gly Cys Lys Gly Phe Phe Lys Arg Thr
            20                  25                  30

Val Gln Lys Asn Ala Lys Tyr Val Cys Leu Ala Asn Lys Asn Cys Pro
        35                  40                  45

Val Asp Lys Arg Arg Arg Asn Arg Cys Gln Tyr Cys Arg Phe Gln Lys
    50                  55                  60

Cys Leu Ala Val Gly Met Val Lys Glu Val Val Arg Thr Asp Ser Leu
65                  70                  75                  80

Lys Gly Arg Arg Gly Arg Leu Pro Ser Lys Pro Lys
                85                  90

<210> SEQ ID NO 109
<211> LENGTH: 93
<212> TYPE: PRT
<213> ORGANISM: Artificial Sequence
<220> FEATURE:
<223> OTHER INFORMATION: NR4A2 DBD #2

<400> SEQUENCE: 109

Asn Glu Gly Leu Cys Ala Val Cys Gly Asp Asn Ala Ala Cys Gln His
1               5                   10                  15

Tyr Gly Val Arg Thr Cys Glu Gly Cys Lys Gly Phe Phe Lys Arg Thr
            20                  25                  30

Val Gln Lys Asn Ala Lys Tyr Val Cys Leu Ala Asn Lys Asn Cys Pro
        35                  40                  45

Val Asp Lys Arg Arg Arg Asn Arg Cys Gln Tyr Cys Arg Phe Gln Lys
    50                  55                  60

Cys Leu Ala Val Gly Met Val Lys Glu Val Val Arg Thr Asp Ser Leu
65                  70                  75                  80

Lys Gly Arg Arg Gly Arg Leu Pro Ser Lys Pro Lys Ser
                85                  90

<210> SEQ ID NO 110
<211> LENGTH: 92
<212> TYPE: PRT
<213> ORGANISM: Artificial Sequence
<220> FEATURE:
<223> OTHER INFORMATION: NR4A3 DBD #1

<400> SEQUENCE: 110

Gly Glu Gly Thr Cys Ala Val Cys Gly Asp Asn Ala Ala Cys Gln His
1               5                   10                  15

Tyr Gly Val Arg Thr Cys Glu Gly Cys Lys Gly Phe Phe Lys Arg Thr
            20                  25                  30

Val Gln Lys Asn Ala Lys Tyr Val Cys Leu Ala Asn Lys Asn Cys Pro
        35                  40                  45

Val Asp Lys Arg Arg Arg Asn Arg Cys Gln Tyr Cys Arg Phe Gln Lys
    50                  55                  60

Cys Leu Ser Val Gly Met Val Lys Glu Val Val Arg Thr Asp Ser Leu
65                  70                  75                  80

Lys Gly Arg Arg Gly Arg Leu Pro Ser Lys Pro Lys
                85                  90
```

<210> SEQ ID NO 111
<211> LENGTH: 93
<212> TYPE: PRT
<213> ORGANISM: Artificial Sequence
<220> FEATURE:
<223> OTHER INFORMATION: NR4A3 DBD #2

<400> SEQUENCE: 111

Gly Glu Gly Thr Cys Ala Val Cys Gly Asp Asn Ala Ala Cys Gln His
1               5                   10                  15

Tyr Gly Val Arg Thr Cys Glu Gly Cys Lys Gly Phe Phe Lys Arg Thr
            20                  25                  30

Val Gln Lys Asn Ala Lys Tyr Val Cys Leu Ala Asn Lys Asn Cys Pro
        35                  40                  45

Val Asp Lys Arg Arg Arg Asn Arg Cys Gln Tyr Cys Arg Phe Gln Lys
    50                  55                  60

Cys Leu Ser Val Gly Met Val Lys Glu Val Val Arg Thr Asp Ser Leu
65                  70                  75                  80

Lys Gly Arg Arg Gly Arg Leu Pro Ser Lys Pro Lys Ser
                85                  90

<210> SEQ ID NO 112
<211> LENGTH: 232
<212> TYPE: PRT
<213> ORGANISM: Artificial Sequence
<220> FEATURE:
<223> OTHER INFORMATION: DBD with NBRE-binding TAL

<400> SEQUENCE: 112

Met Leu Thr Pro Glu Gln Val Val Ala Ile Ala Ser Asn His Gly Gly
1               5                   10                  15

Lys Gln Ala Leu Glu Thr Val Gln Arg Leu Leu Pro Val Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Arg Leu Leu Pro Val Cys Gln
    50                  55                  60

Ala His Gly Leu Thr Pro Glu Gln Val Val Ala Ile Ala Ser Asn Gly
65                  70                  75                  80

Gly Gly Lys Gln Ala Leu Glu Thr Val Gln Arg Leu Leu Pro Val Cys
                85                  90                  95

Gln Ala His Gly Leu Thr Pro Glu Gln Val Val Ala Ile Ala Ser Asn
            100                 105                 110

Ile Gly Gly Lys Gln Ala Leu Glu Thr Val Gln Arg Leu Leu Pro Val
        115                 120                 125

Cys Gln Ala His Gly Leu Thr Pro Glu Gln Val Val Ala Ile Ala Ser
    130                 135                 140

Asn Gly Gly Gly Lys Gln Ala Leu Glu Thr Val Gln Arg Leu Leu Pro
145                 150                 155                 160

Val Cys Gln Ala His Gly Leu Thr Pro Glu Gln Val Val Ala Ile Ala
            165                 170                 175

Ser Asn Gly Gly Gly Lys Gln Ala Leu Glu Thr Val Gln Arg Leu Leu
            180                 185                 190

Pro Val Cys Gln Ala His Gly Leu Thr Pro Glu Gln Val Val Ala Ile
        195                 200                 205

Ala Ser Asn Gly Gly Gly Lys Gln Ala Leu Glu Thr Val Gln Arg Leu
    210                 215                 220

-continued

```
Leu Pro Val Cys Gln Ala His Gly
225                 230

<210> SEQ ID NO 113
<211> LENGTH: 232
<212> TYPE: PRT
<213> ORGANISM: Artificial Sequence
<220> FEATURE:
<223> OTHER INFORMATION: DBD with NurRE-binding TAL #1

<400> SEQUENCE: 113

Met Leu Thr Pro Glu Gln Val Val Ala Ile Ala Ser Asn His Gly Gly
1               5                   10                  15

Lys Gln Ala Leu Glu Thr Val Gln Arg Leu Leu Pro Val Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Arg Leu Leu Pro Val Cys Gln
    50                  55                  60

Ala His Gly Leu Thr Pro Glu Gln Val Val Ala Ile Ala Ser Asn Gly
65                  70                  75                  80

Gly Gly Lys Gln Ala Leu Glu Thr Val Gln Arg Leu Leu Pro Val Cys
                85                  90                  95

Gln Ala His Gly Leu Thr Pro Glu Gln Val Val Ala Ile Ala Ser Asn
            100                 105                 110

Ile Gly Gly Lys Gln Ala Leu Glu Thr Val Gln Arg Leu Leu Pro Val
        115                 120                 125

Cys Gln Ala His Gly Leu Thr Pro Glu Gln Val Val Ala Ile Ala Ser
    130                 135                 140

Asn Gly Gly Gly Lys Gln Ala Leu Glu Thr Val Gln Arg Leu Leu Pro
145                 150                 155                 160

Val Cys Gln Ala His Gly Leu Thr Pro Glu Gln Val Val Ala Ile Ala
            165                 170                 175

Ser Asn Gly Gly Gly Lys Gln Ala Leu Glu Thr Val Gln Arg Leu Leu
        180                 185                 190

Pro Val Cys Gln Ala His Gly Leu Thr Pro Glu Gln Val Val Ala Ile
    195                 200                 205

Ala Ser Asn Gly Gly Gly Lys Gln Ala Leu Glu Thr Val Gln Arg Leu
    210                 215                 220

Leu Pro Val Cys Gln Ala His Gly
225                 230

<210> SEQ ID NO 114
<211> LENGTH: 231
<212> TYPE: PRT
<213> ORGANISM: Artificial Sequence
<220> FEATURE:
<223> OTHER INFORMATION: DBD with NurRE-binding TAL #2

<400> SEQUENCE: 114

Leu Thr Pro Glu Gln Val Val Ala Ile Ala Ser Asn Ile Gly Gly Lys
1               5                   10                  15

Gln Ala Leu Glu Thr Val Gln Arg Leu Leu Pro Val Cys Gln Ala His
            20                  25                  30

Gly Leu Thr Pro Glu Gln Val Val Ala Ile Ala Ser Asn Ile Gly Gly
        35                  40                  45

Lys Gln Ala Leu Glu Thr Val Gln Arg Leu Leu Pro Val Cys Gln Ala
```

-continued

```
       50                    55                    60

His Gly Leu Thr Pro Glu Gln Val Val Ala Ile Ala Ser Asn Ile Gly
65                    70                    75                    80

Gly Lys Gln Ala Leu Glu Thr Val Gln Arg Leu Leu Pro Val Cys Gln
                 85                    90                    95

Ala His Gly Leu Thr Pro Glu Gln Val Val Ala Ile Ala Ser Asn Gly
                 100                   105                   110

Gly Gly Lys Gln Ala Leu Glu Thr Val Gln Arg Leu Leu Pro Val Cys
                 115                   120                   125

Gln Ala His Gly Leu Thr Pro Glu Gln Val Val Ala Ile Ala Ser Asn
                 130                   135                   140

His Gly Gly Lys Gln Ala Leu Glu Thr Val Gln Arg Leu Leu Pro Val
145                   150                   155                   160

Cys Gln Ala His Gly Leu Thr Pro Glu Gln Val Val Ala Ile Ala Ser
                 165                   170                   175

His Asp Gly Gly Lys Gln Ala Leu Glu Thr Val Gln Arg Leu Leu Pro
                 180                   185                   190

Val Cys Gln Ala His Gly Leu Thr Pro Glu Gln Val Val Ala Ile Ala
                 195                   200                   205

Ser His Asp Gly Gly Lys Gln Ala Leu Glu Thr Val Gln Arg Leu Leu
                 210                   215                   220

Pro Val Cys Gln Ala His Gly
225                   230
```

<210> SEQ ID NO 115
<211> LENGTH: 9
<212> TYPE: DNA
<213> ORGANISM: Artificial Sequence
<220> FEATURE:
<223> OTHER INFORMATION: ZFP binding sequence #1

<400> SEQUENCE: 115 aaaggtcaa                                                                      9

<210> SEQ ID NO 116

<400> SEQUENCE: 116

000

<210> SEQ ID NO 117
<211> LENGTH: 6
<212> TYPE: DNA
<213> ORGANISM: Artificial Sequence
<220> FEATURE:
<223> OTHER INFORMATION: ZFP binding sequence #3

<400> SEQUENCE: 117 gatatt                                                                         6

<210> SEQ ID NO 118
<211> LENGTH: 6
<212> TYPE: DNA
<213> ORGANISM: Artificial Sequence
<220> FEATURE:
<223> OTHER INFORMATION: ZFP binding sequence #4

<400> SEQUENCE: 118 gccaat                                                                         6

```
<210> SEQ ID NO 119
<211> LENGTH: 92
<212> TYPE: PRT
<213> ORGANISM: Artificial Sequence
<220> FEATURE:
<223> OTHER INFORMATION: DBD with ZFP #1

<400> SEQUENCE: 119

Leu Glu Pro Gly Glu Lys Pro Tyr Lys Cys Pro Glu Cys Gly Lys Ser
1               5                   10                  15

Phe Ser Gln Ser Gly Asn Leu Thr Glu His Gln Arg Thr His Thr Gly
            20                  25                  30

Glu Lys Pro Tyr Lys Cys Pro Glu Cys Gly Lys Ser Phe Ser Thr Ser
        35                  40                  45

Gly His Leu Val Arg His Gln Arg Thr His Thr Gly Glu Lys Pro Tyr
    50                  55                  60

Lys Cys Pro Glu Cys Gly Lys Ser Phe Ser Gln Arg Ala Asn Leu Arg
65                  70                  75                  80

Ala His Gln Arg Thr His Thr Gly Lys Lys Thr Ser
                85                  90

<210> SEQ ID NO 120
<211> LENGTH: 64
<212> TYPE: PRT
<213> ORGANISM: Artificial Sequence
<220> FEATURE:
<223> OTHER INFORMATION: DBD with ZFP #2

<400> SEQUENCE: 120

Leu Glu Pro Gly Glu Lys Pro Tyr Lys Cys Pro Glu Cys Gly Lys Ser
1               5                   10                  15

Phe Ser His Lys Asn Ala Leu Gln Asn His Gln Arg Thr His Thr Gly
            20                  25                  30

Glu Lys Pro Tyr Lys Cys Pro Glu Cys Gly Lys Ser Phe Ser Thr Ser
        35                  40                  45

Gly Asn Leu Val Arg His Gln Arg Thr His Thr Gly Lys Lys Thr Ser
    50                  55                  60

<210> SEQ ID NO 121
<211> LENGTH: 64
<212> TYPE: PRT
<213> ORGANISM: Artificial Sequence
<220> FEATURE:
<223> OTHER INFORMATION: DBD with ZFP #3

<400> SEQUENCE: 121

Leu Glu Pro Gly Glu Lys Pro Tyr Lys Cys Pro Glu Cys Gly Lys Ser
1               5                   10                  15

Phe Ser Asp Cys Arg Asp Leu Ala Arg His Gln Arg Thr His Thr Gly
            20                  25                  30

Glu Lys Pro Tyr Lys Cys Pro Glu Cys Gly Lys Ser Phe Ser Thr Thr
        35                  40                  45

Gly Asn Leu Thr Val His Gln Arg Thr His Thr Gly Lys Lys Thr Ser
    50                  55                  60

<210> SEQ ID NO 122
<211> LENGTH: 246
<212> TYPE: PRT
<213> ORGANISM: Artificial Sequence
<220> FEATURE:
<223> OTHER INFORMATION: NR4A LBD #1
```

-continued

```
<400> SEQUENCE: 122

Pro Leu Gln Gln Glu Pro Ser Gln Pro Ser Pro Pro Ser Pro Pro Ile
1               5                   10                  15

Cys Met Met Asn Ala Leu Val Arg Ala Leu Thr Asp Ser Thr Pro Arg
                20                  25                  30

Asp Leu Asp Tyr Ser Arg Tyr Cys Pro Thr Asp Gln Ala Ala Ala Gly
            35                  40                  45

Thr Asp Ala Glu His Val Gln Gln Phe Tyr Asn Leu Leu Thr Ala Ser
    50                  55                  60

Ile Asp Val Ser Arg Ser Trp Ala Glu Lys Ile Pro Gly Phe Thr Asp
65                  70                  75                  80

Leu Pro Lys Glu Asp Gln Thr Leu Leu Ile Glu Ser Ala Phe Leu Glu
                85                  90                  95

Leu Phe Val Leu Arg Leu Ser Ile Arg Ser Asn Thr Ala Glu Asp Lys
                100                 105                 110

Phe Val Phe Cys Asn Gly Leu Val Leu His Arg Leu Gln Cys Leu Arg
            115                 120                 125

Gly Phe Gly Glu Trp Leu Asp Ser Ile Lys Asp Phe Ser Leu Asn Leu
    130                 135                 140

Gln Ser Leu Asn Leu Asp Ile Gln Ala Leu Ala Cys Leu Ser Ala Leu
145                 150                 155                 160

Ser Met Ile Thr Glu Arg His Gly Leu Lys Glu Pro Lys Arg Val Glu
                165                 170                 175

Glu Leu Cys Asn Lys Ile Thr Ser Ser Leu Lys Asp His Gln Ser Lys
                180                 185                 190

Gly Gln Ala Leu Glu Pro Thr Glu Ser Lys Val Leu Gly Ala Leu Val
    195                 200                 205

Glu Leu Arg Lys Ile Cys Thr Leu Gly Leu Gln Arg Ile Phe Tyr Leu
    210                 215                 220

Lys Leu Glu Asp Leu Val Ser Pro Pro Ser Ile Ile Asp Lys Leu Phe
225                 230                 235                 240

Leu Asp Thr Leu Pro Phe
                245

<210> SEQ ID NO 123
<211> LENGTH: 247
<212> TYPE: PRT
<213> ORGANISM: Artificial Sequence
<220> FEATURE:
<223> OTHER INFORMATION: NR4A LBD #2

<400> SEQUENCE: 123

Ser Pro Leu Gln Gln Glu Pro Ser Gln Pro Ser Pro Pro Ser Pro Pro
1               5                   10                  15

Ile Cys Met Met Asn Ala Leu Val Arg Ala Leu Thr Asp Ser Thr Pro
                20                  25                  30

Arg Asp Leu Asp Tyr Ser Arg Tyr Cys Pro Thr Asp Gln Ala Ala Ala
            35                  40                  45

Gly Thr Asp Ala Glu His Val Gln Gln Phe Tyr Asn Leu Leu Thr Ala
    50                  55                  60

Ser Ile Asp Val Ser Arg Ser Trp Ala Glu Lys Ile Pro Gly Phe Thr
65                  70                  75                  80

Asp Leu Pro Lys Glu Asp Gln Thr Leu Leu Ile Glu Ser Ala Phe Leu
                85                  90                  95

Glu Leu Phe Val Leu Arg Leu Ser Ile Arg Ser Asn Thr Ala Glu Asp
```

-continued

```
          100                105                110
Lys Phe Val Phe Cys Asn Gly Leu Val Leu His Arg Leu Gln Cys Leu
         115                120                125

Arg Gly Phe Gly Glu Trp Leu Asp Ser Ile Lys Asp Phe Ser Leu Asn
    130                135                140

Leu Gln Ser Leu Asn Leu Asp Ile Gln Ala Leu Ala Cys Leu Ser Ala
145                150                155                160

Leu Ser Met Ile Thr Glu Arg His Gly Leu Lys Glu Pro Lys Arg Val
             165                170                175

Glu Glu Leu Cys Asn Lys Ile Thr Ser Ser Leu Lys Asp His Gln Ser
         180                185                190

Lys Gly Gln Ala Leu Glu Pro Thr Glu Ser Lys Val Leu Gly Ala Leu
         195                200                205

Val Glu Leu Arg Lys Ile Cys Thr Leu Gly Leu Gln Arg Ile Phe Tyr
    210                215                220

Leu Lys Leu Glu Asp Leu Val Ser Pro Pro Ser Ile Ile Asp Lys Leu
225                230                235                240

Phe Leu Asp Thr Leu Pro Phe
             245
```